US009254319B2

(12) United States Patent
Robinson et al.

(10) Patent No.: US 9,254,319 B2
(45) **Date of Patent: *Feb. 9, 2016**

(54) COMPOSITIONS AND METHODS FOR GENERATING AN IMMUNE RESPONSE

(71) Applicant: EMORY UNIVERSITY, Atlanta, GA (US)

(72) Inventors: Harriet Robinson, Atlanta, GA (US); James Smith, Cumming, GA (US); Rama Amara, Atlanta, GA (US); Bernard Moss, Bethesda, MD (US); Salvatore T. Butera, Del Mar, CA (US); Dennis Ellenberger, Norcross, GA (US)

(73) Assignees: Emory University, Atlanta, GA (US); The United States of America as represented by The Department of Health and Human Services, Bethesda, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/137,095

(22) Filed: Dec. 20, 2013

(65) Prior Publication Data

US 2015/0004132 A1 Jan. 1, 2015

Related U.S. Application Data

(63) Continuation of application No. 10/336,566, filed on Jan. 3, 2003, now Pat. No. 8,623,379, which is a continuation-in-part of application No. 10/093,953, filed on Mar. 8, 2002, now abandoned, which is a continuation of application No. 09/798,675, filed on Mar. 2, 2001, now abandoned.

(60) Provisional application No. 60/186,364, filed on Mar. 2, 2000, provisional application No. 60/324,845, filed on Sep. 25, 2001, provisional application No. 60/325,004, filed on Sep. 26, 2001.

(51) Int. Cl.

| | |
|---|---|
| ***A61K 39/21*** | (2006.01) |
| ***C07K 14/005*** | (2006.01) |
| ***C12N 15/70*** | (2006.01) |
| ***C12N 15/85*** | (2006.01) |
| ***C12N 15/86*** | (2006.01) |
| ***A61K 39/39*** | (2006.01) |
| ***A61K 39/12*** | (2006.01) |
| *A61K 49/00* | (2006.01) |
| *A61K 39/00* | (2006.01) |

(52) U.S. Cl.

CPC ................ *A61K 39/21* (2013.01); *A61K 39/12* (2013.01); *A61K 39/39* (2013.01); *C07K 14/005* (2013.01); *C12N 15/70* (2013.01); *C12N 15/85* (2013.01); *C12N 15/86* (2013.01); *A61K 2039/5256* (2013.01); *A61K 2039/53* (2013.01); *A61K 2039/55511* (2013.01); *C12N 2710/24143* (2013.01); *C12N 2740/16022* (2013.01); *C12N 2740/16034* (2013.01); *C12N 2740/16122* (2013.01); *C12N 2740/16134* (2013.01); *C12N 2740/16222* (2013.01); *C12N 2740/16234* (2013.01); *C12N 2830/00* (2013.01); *C12N 2830/15* (2013.01); *C12N 2830/42* (2013.01); *C12N 2830/60* (2013.01)

(58) Field of Classification Search

CPC .. C07K 14/005; C07K 2319/00; C07K 14/47; C12N 2810/6054; A61K 39/21; G01N 33/56988; H01L 28/84

See application file for complete search history.

(56) References Cited

U.S. PATENT DOCUMENTS

| | | | | |
|---|---|---|---|---|
| 7,795,017 | B2 * | 9/2010 | Robinson et al. | 435/320.1 |
| 8,623,379 | B2 * | 1/2014 | Robinson et al. | 424/199.1 |

* cited by examiner

*Primary Examiner* — Bao Li

(74) *Attorney, Agent, or Firm* — King & Spalding

(57) ABSTRACT

We have developed DNA and viral vectors that can be used, alone or in combination, as a vaccine against one HIV clade, subtype, or recombinant form of HIV or against multiple HIV clades, subtypes, or recombinant forms. Moreover, the vectors can encode a variety of antigens, which may be obtained from one clade or from two or more different clades, and the antigens selected and/or the manner in which the vectors are formulated (e.g., mixed) can be manipulated to generate a protective immune response against a variety of clades (e.g., the clades to which a patient is most likely to be exposed; with the proportions of the components of the vaccine tailored to the extent of the patient's risk to a particular clade or clades).

22 Claims, 73 Drawing Sheets

Figure 2a. pGA1 Sequence

```
cgacaatattggctattggccattgcatacgttgtatctatatcataatatgtacatttatattggctcatgtccaatat
gaccgccatgttgacattgattattgactagttattaatagtaatcaattacggggtcattagttcatagcccatatatg
gagttccgcgttacataacttacggtaaatggcccgcctggctgaccgcccaacgacccccgcccattgacgtcaataat
gacgtatgttcccatagtaacgccaatagggactttccattgacgtcaatgggtggagtatttacggtaaactgcccact
tggcagtacatcaagtgtatcatatgccaagtccgccccctattgacgtcaatgacggtaaatggcccgcctggcattat
gcccagtacatgaccttacgggactttcctacttggcagtacatctacggtattagtcatcggctattaccatggtgatg
cggttttggcagtacaccaatgggcgtggatagcggtttgactcacggggatttccaagtctccaccccattgacgtcaa
tgggagtttgttttggcaccaaaatcaacgggactttccaaaatgtcgtaataaccccgccccgttgacgcaaatgggcg
gtaggcgtgtacggtgggaggtctatataagcagagctcgtttagtgaaccgtcagatcgcctggagacgccatccacgc
tgttttgacctccatagaagacaccgggaccgatccagcctccgcggccgggaacggtgcattggaacgcggattccccg
tgccaagagtgacgtaagtaccgcctatagactctataggcacacccctttggctcttatgcatgctatactgtttttgg
cttggggcctatacacccccgcttccttatgctataggtgatggtatagcttagcctataggtgtgggttattgaccatt
attgaccactcccctattggtgacgatactttccattactaatccataacatggctctttgccacaactatctctattgg
ctatatgccaatactctgtccttcagagactgacacggactctgtatttttacaggatggggtcccatttattatttaca
aattcacatatacaacaacgccgtcccccgtgcccgcagtttttattaaacatagcgtgggatctccacgcgaatctcgg
gtaccgtgttccggacatgggytcttctccggtagcggcggagcttccacatccgagccctggtcccatgcctccagcgg
ctcatggtcgctcggcagctccttgctcctaacagtggaggccagacttaggcacagcacaatgcccaccaccaccagtg
tgccgcacaaggccgtggcggtagggtatgtgtctgaaaatgagctcggagattgggctcgcaccgctgacgcagatgga
agacttaaggcagcggcagaagaagatgcaggcagctgagttgttgtattctgataagagtcagaggtaactcccgttgc
ggtgctgttaacggtggagggcagtgtagtctgagcagtactcgttgctgccgcgcgcgccaccagacataatagctgac
agactaacagactgttcctttccatgggtcttttctgcagtcaccatcgatgcttgcaatcatggatgcaatgaagagag
ggctctgctgtgtgctgctgctgtgtggagcagtcttcgtttcggctagccccgggtgataaacggaccgcgcaatccct
aggctgtgccttctagttgccagccatctgttgtttgcccctcccccgtgccttccttgaccctggaaggtgccactccc
actgtcctttcctaataaaatgaggaaattgcatcgcattgtctgagtaggtgtcattctattctggggggtggggtggg
gcaggacagcaagggggaggattgggaagacaatagcaggcatgctggggatgcggtgggctctatataaaaaacgcccg
gcggcaaccgagcgttctgaacgctagagtcgacaaattcagaagaactcgtcaagaaggcgatagaaggcgatgcgctg
cgaatcgggagcggcgataccgtaaagcacgaggaagcggtcagcccattcgccgccaagctcttcagcaatatcacggg
tagccaacgctatgtcctgatagcggtctgccacacccagccggccacagtcgatgaatccagaaaagcggccattttcc
accatgatattcggcaagcaggcatcgccatgggtcacgacgagatcctcgccgtcgggcatgctcgccttgagcctggc
gaacagttcggctggcgcgagcccctgatgctcttcgtccagatcatcctgatcgacaagaccggcttccatccgagtac
gtgctcgctcgatgcgatgtttcgcttggtggtcgaatgggcaggtagccggatcaagcgtatgcagccgccgcattgca
tcagccatgatggatactttctcggcaggagcaaggtgagatgacaggagatcctgccccggcacttcgcccaatagcag
ccagtcccttcccgcttcagtgacaacgtcgagcacagctgcgcaaggaacgcccgtcgtggccagccacgatagccgcg
ctgcctcgtcttgcagttcattcagggcaccggacaggtcggtcttgacaaaaagaaccgggcgcccctgcgctgacagc
cggaacacggcggcatcagagcagccgattgtctgttgtgcccagtcatagccgaatagcctctccacccaagcggccgg
agaacctgcgtgcaatccatcttgttcaatcatgcgaaacgatcctcatcctgtctcttgatcagatcttgatcccctgc
gccatcagatccttggcggcaagaaagccatccagtttactttgcagggcttcccaaccttaccagagggcgccccagct
ggcaattccggttcgcttgctgtccataaaaccgcccagtctagctatcgccatgtaagcccactgcaagctacctgctt
tctctttgcgcttgcgttttcccttgtccagatagcccagtagctgacattcatccggggtcagcaccgtttctgcggac
tggctttctacgtgaaaaggatctaggtgaagatcctttttgataatctcatgaccaaaatcccttaacgtgagttttcg
ttccactgagcgtcagaccccgtagaaaagatcaaaggatcttcttgagatcctttttttctgcgcgtaatctgctgctt
gcaaacaaaaaaaccaccgctaccagcggtggtttgtttgccggatcaagagctaccaactctttttccgaaggtaactg
gcttcagcagagcgcagataccaaatactgttcttctagtgtagccgtagttaggccaccacttcaagaactctgtagca
ccgcctacatacctcgctctgctaatcctgttaccagtggctgctgccagtggcgataagtcgtgtcttaccgggttgga
ctcaagacgatagttaccggataaggcgcagcggtcgggctgaacggggggttcgtgcacacagcccagcttggagcgaa
cgacctacaccgaactgagatacctacagcgtgagctatgagaaagcgccacgcttcccgaagggagaaaggcggacagg
tatccggtaagcggcagggtcggaacaggagagcgcacgagggagcttccagggggaaacgcctggtatctttatagtcc
tgtcgggtttcgccacctctgacttgagcgtcgatttttgtgatgctcgtcaggggggcggagcctatggaaaaacgcca
gcaacgcggcctttttacggttcctggccttttgctggccttttgctcacatgttgt
```

Figure 2b. pGA1 Functional Regions

| Functional region | Position within sequence (starting-and ending pos.) | Origin of sequence |
|---|---|---|
| CMVIE promoter | 1-690 | pJW4303 |
| CMV intron A | 691-1638 | pJW4303 |
| tPA leader | 1659-1721 | pJW4303 |
| Multiple cloning site | 1648-1758<br>Cla I-Avr II | pJW4303; mutation of Hind III and Bam HI sites and addition of Cla I and Rsr II sites to the multiple cloning site of pJW4303 |
| BGHpA | 1761-1983 | pJW4303 |
| Lambda T0 terminator | 1984-2018 | Synthetic oligonucleotide |
| Kanamycin resistance | 2039-2833 | pZErO-2 (Invitrogen) |
| ColE1 origin of replication | 3219-3892 | pZErO-2 (Invitrogen) |

Figure 3a. pGA1.1 Sequence cgacaatattggctattggccattgcatacgttgtatctatatcataatatgtacatttatattggctcatgtccaatat
gaccgccatgttgacattgattattgactagttattaatagtaatcaattacggggtcattagttcatagcccatatatg
gagttccgcgttacataacttacggtaaatggcccgcctggctgaccgcccaacgacccccgcccattgacgtcaataat
gacgtatgttcccatagtaacgccaatagggactttccattgacgtcaatgggtggagtatttacggtaaactgcccact
tggcagtacatcaagtgtatcatatgccaagtccgccccctattgacgtcaatgacggtaaatggcccgcctggcattat
gcccagtacatgaccttacgggactttcctacttggcagtacatctacggtattagtcatcggctattaccatggtgatg
cggttttggcagtacaccaatgggcgtggatagcggtttgactcacggggatttccaagtctccaccccattgacgtcaa
tgggagtttgttttggcaccaaaatcaacgggactttccaaaatgtcgtaataaccccgccccgttgacgcaaatgggcg
gtaggcgtgtacggtgggaggtctatataagcagagctcgtttagtgaaccgtcagatcgcctggagacgccatccacgc
tgttttgacctccatagaagacaccgggaccgatccagcctccgcggccgggaacggtgcattggaacgcggattccccg
tgccaagagtgacgtaagtaccgcctatagactctataggcacacccctttggctcttatgcatgctatactgtttttgg
cttggggcctatacacccccgcttccttatgctataggtgatggtatagcttagcctataggtgtgggttattgaccatt
attgaccactcccctattggtgacgatactttccattactaatccataacatggctctttgccacaactatctctattgg
ctatatgccaatactctgtccttcagagactgacacggactctgtatttttacaggatggggtcccatttattatttaca
aattcacatatacaacaacgccgtcccccgtgcccgcagtttttattaaacatagcgtgggatctccacgcgaatctcgg
gtaccgtgttccggacatgggytcttctccggtagcggcggagcttccacatccgagccctggtcccatgcctccagcgg
ctcatggtcgctcggcagctccttgctcctaacagtggaggccagacttaggcacagcacaatgcccaccaccaccagtg
tgccgcacaaggccgtggcggtagggtatgtgtctgaaaatgagctcggagattgggctcgcaccgctgacgcagatgga
agacttaaggcagcggcagaagaagatgcaggcagctgagttgttgtattctgataagagtcagaggtaactcccgttgc
ggtgctgttaacggtggagggcagtgtagtctgagcagtactcgttgctgccgcgcgcgccaccagacataatagctgac
agactaacagactgttcctttccatgggtcttttctgcagtcaccatcgatgcttgcaatcatggatgcaatgaagagag
ggctctgctgtgtgctgctgctgtgtggagaattcttcgtttctgctgctgtgtggagaattcttcgtttcggctagccc
cgggtgataaacggaccgcgcaatccctaggctgtgccttctagttgccagccatctgttgtttgcccctcccccgtgcc
ttccttgaccctggaaggtgccactcccactgtcctttcctaataaaatgaggaaattgcatcgcattgtctgagtaggt
gtcattctattctggggggtggggtggggcaggacagcaagggggaggattgggaagacaatagcaggcatgctggggat
gcggtgggctctatataaaaaacgcccggcggcaaccgagcgttctgaacgctagagtcgacaaattcagaagaactcgt
caagaaggcgatagaaggcgatgcgctgcgaatcgggagcggcgataccgtaaagcacgaggaagcggtcagcccattcg
ccgccaagctcttcagcaatatcacgggtagccaacgctatgtcctgatagcggtctgccacacccagccggccacagtc
gatgaatccagaaaagcggccattttccaccatgatattcggcaagcaggcatcgccatgggtcacgacgagatcctcgc
cgtcgggcatgctcgccttgagcctggcgaacagttcggctggcgcgagcccctgatgctcttcgtccagatcatcctga
tcgacaagaccggcttccatccgagtacgtgctcgctcgatgcgatgtttcgcttggtggtcgaatgggcaggtagccgg
atcaagcgtatgcagccgccgcattgcatcagccatgatggatactttctcggcaggagcaaggtgagatgacaggagat
cctgccccggcacttcgcccaatagcagccagtcccttcccgcttcagtgacaacgtcgagcacagctgcgcaaggaacg
cccgtcgtggccagccacgatagccgcgctgcctcgtcttgcagttcattcagggcaccggacaggtcggtcttgacaaa
aagaaccgggcgcccctgcgctgacagccggaacacggcggcatcagagcagccgattgtctgttgtgcccagtcatagc
cgaatagcctctccacccaagcggccggagaacctgcgtgcaatccatcttgttcaatcatgcgaaacgatcctcatcct
gtctcttgatcagatcttgatcccctgcgccatcagatccttggcggcaagaaagccatccagtttactttgcagggctt
cccaaccttaccagagggcgccccagctggcaattccggttcgcttgctgtccataaaaccgcccagtctagctatcgcc
atgtaagcccactgcaagctacctgctttctctttgcgcttgcgttttcccttgtccagatagcccagtagctgacattc
atccggggtcagcaccgtttctgcggactggctttctacgtgaaaaggatctaggtgaagatcctttttgataatctcat
gaccaaaatcccttaacgtgagttttcgttccactgagcgtcagaccccgtagaaaagatcaaaggatcttcttgagatc
ctttttttctgcgcgtaatctgctgcttgcaaacaaaaaaaccaccgctaccagcggtggtttgtttgccggatcaagag
ctaccaactctttttccgaaggtaactggcttcagcagagcgcagataccaaatactgttcttctagtgtagccgtagtt
aggccaccacttcaagaactctgtagcaccgcctacatacctcgctctgctaatcctgttaccagtggctgctgccagtg
gcgataagtcgtgtcttaccgggttggactcaagacgatagttaccggataaggcgcagcggtcgggctgaacggggggt
tcgtgcacacagcccagcttggagcgaacgacctacaccgaactgagatacctacagcgtgagctatgagaaagcgccac
gcttcccgaagggagaaaggcggacaggtatccggtaagcggcagggtcggaacaggagagcgcacgagggagcttccag
ggggaaacgcctggtatctttatagtcctgtcgggtttcgccacctctgacttgagcgtcgatttttgtgatgctcgtca
ggggggcggagcctatggaaaaacgccagcaacgcggcctttttacggttcctggccttttgctggccttttgctcacat
gttgt

Figure 3b. pGA1.1 Functional Regions

| Functional region | Position within sequence (starting-and ending pos.) | Origin of sequence |
|---|---|---|
| CMVIE promoter | 1-690 | pGA1 |
| CMV intron A | 691-1638 | pGA1 |
| tPA leader | none | |
| Multiple cloning site | 1648-1786<br>(Cla I-Avr II) | pGA1, addition of two EcoR I sites to pGA1 multiple cloning site |
| BGHpA | 1789-2011 | pGA1 |
| Lambda T0 terminator | 2012-2046 | pGA1 |
| Kanamycin resistance | 2067-2861 | pGA1 |
| ColE1 origin of replication | 3247-3920 | pGA1 |

Figure 4a. pGA1.2 Sequence cgacaatattggctattggccattgcatacgttgtatctatatcataatatgtacatttatattggctcatgtccaatat
gaccgccatgttgacattgattattgactagttattaatagtaatcaattacgggttcattagttcatagcccatatatg
gagttccgcgttacataacttacggtaaatggcccgcctggctgaccgcccaacgacccccgcccattgacgtcaataat
gacgtatgttcccatagtaacgccaatagggactttccattgacgtcaatgggtggagtatttacggtaaactgcccact
tggcagtacatcaagtgtatcatatgccaagtccgccccctattgacgtcaatgacggtaaatggcccgcctggcattat
gcccagtacatgaccttacgggactttcctacttggcagtacatctacggtattagtcatcggctattaccatggtgatg
cggttttggcagtacaccaatgggcgtggatagcggtttgactcacggggatttccaagtctccaccccattgacgtcaa
tgggagtttgttttggcaccaaaatcaacgggactttccaaaatgtcgtaataaccccgccccgttgacgcaaatgggcg
gtaggcgtgtacggtgggaggtctatataagcagagctcgtttagtgaaccgtcagatcgcctggagacgccatccacgc
tgttttgacctccatagaagacaccgggaccgatccagcctccgcggccgggaacggtgcattggaacgcggattccccg
tgccaagagtgacgtaagtaccgcctatagactctataggcacacccctttggctcttatgcatgctatactgtttttgg
cttggggcctatacacccccgcttccttatgctataggtgatggtatagcttagcctataggtgtgggttattgaccatt
attgaccactcccctattggtgacgatactttccattactaatccataacatggctctttgccacaactatctctattgg
ctatatgccaatactctgtccttcagagactgacacggactctgtatttttacaggatggggtcccatttattatttaca
aattcacatatacaacaacgccgtcccccgtgcccgcagtttttattaaacatagcgtgggatctccacgcgaatctcgg
gtaccgtgttccggacatgggytcttctccggtagcggcggagcttccacatccgagccctggtcccatgcctccagcgg
ctcatggtcgctcggcagctccttgctcctaacagtggaggccagacttaggcacagcacaatgcccaccaccaccagtg
tgccgcacaaggccgtggcggtagggtatgtgtctgaaaatgagctcggagattgggctcgcaccgctgacgcagatgga
agacttaaggcagcggcagaagaagatgcaggcagctgagttgttgtattctgataagagtcagaggtaactcccgttgc
ggtgctgttaacggtggagggcagtgtagtctgagcagtactcgttgctgccgcgcgcgccaccagacataatagctgac
agactaacagactgttcctttccatgggtcttttctgcagtcaccatggatccttgcactcgaggatgcaatgaagagag
ggctctgctgtgtgctgctgctgtgtggagaattcttcgtttctgctgctgtgtggagaattcttcgtttcggctagccc
cgggtgataaacggaccgcgcaatccctaggctgtgccttctagttgccagccatctgttgtttgcccctcccccgtgcc
ttccttgaccctggaaggtgccactcccactgtcctttcctaataaaatgaggaaattgcatcgcattgtctgagtaggt
gtcattctattctggggggtggggtggggcaggacagcaagggggaggattgggaagacaatagcaggcatgctggggat
gcggtgggctctatataaaaaacgcccggcggcaaccgagcgttctgaacgctagagtcgacaaattcagaagaactcgt
caagaaggcgatagaaggcgatgcgctgcgaatcgggagcggcgataccgtaaagcacgaggaagcggtcagcccattcg
ccgccaagctcttcagcaatatcacgggtagccaacgctatgtcctgatagcggtctgccacacccagccggccacagtc
gatgaatccagaaaagcggccattttccaccatgatattcggcaagcaggcatcgccatgggtcacgacgagatcctcgc
cgtcgggcatgctcgccttgagcctggcgaacagttcggctggcgcgagcccctgatgctcttcgtccagatcatcctga
tcgacaagaccggcttccatccgagtacgtgctcgctcgatgcgatgtttcgcttggtggtcgaatgggcaggtagccgg
atcaagcgtatgcagccgccgcattgcatcagccatgatggatactttctcggcaggagcaaggtgagatgacaggagat
cctgccccggcacttcgcccaatagcagccagtcccttcccgcttcagtgacaacgtcgagcacagctgcgcaaggaacg
cccgtcgtggccagccacgatagccgcgctgcctcgtcttgcagttcattcagggcaccggacaggtcggtcttgacaaa
aagaaccgggcgcccctgcgctgacagccggaacacggcggcatcagagcagccgattgtctgttgtgcccagtcatagc
cgaatagcctctccacccaagcggccggagaacctgcgtgcaatccatcttgttcaatcatgcgaaacgatcctcatcct
gtctcttgatcagatcttgatcccctgcgccatcagatccttggcggcaagaaagccatccagtttactttgcagggctt
cccaaccttaccagagggcgccccagctggcaattccggttcgcttgctgtccataaaaccgcccagtctagctatcgcc
atgtaagcccactgcaagctacctgctttctctttgcgcttgcgttttcccttgtccagatagcccagtagctgacattc
atccggggtcagcaccgtttctgcggactggctttctacgtgaaaggatctaggtgaagatcctttttgataatctcat
gaccaaaatcccttaacgtgagttttcgttccactgagcgtcagaccccgtagaaaagatcaaaggatcttcttgagatc
ctttttttctgcgcgtaatctgctgcttgcaaacaaaaaaaccaccgctaccagcggtggtttgtttgccggatcaagag
ctaccaactctttttccgaaggtaactggcttcagcagagcgcagataccaaatactgttcttctagtgtagccgtagtt
aggccaccacttcaagaactctgtagcaccgcctacatacctcgctctgctaatcctgttaccagtggctgctgccagtg
gcgataagtcgtgtcttaccgggttggactcaagacgatagttaccggataaggcgcagcggtcgggctgaacggggggt
tcgtgcacacagcccagcttggagcgaacgacctacaccgaactgagatacctacagcgtgagctatgagaaagcgccac
gcttcccgaagggagaaaggcggacaggtatccggtaagcggcagggtcggaacaggagagcgcacgagggagcttccag
ggggaaacgcctggtatctttatagtcctgtcgggtttcgccacctctgacttgagcgtcgatttttgtgatgctcgtca
ggggggcggagcctatggaaaaacgccagcaacgcggcctttttacggttcctggccttttgctggccttttgctcacat
gttgt

Figure 4b. pGA1.2 Functional Regions

| Functional region | Position within sequence (starting-and ending pos.) | Origin of sequence |
|---|---|---|
| CMVIE promoter | 1-690 | pGA1.1 |
| CMV intron A | 691-1638 | pGA1.1 |
| tPA leader | none | |
| Multiple cloning site | 1648-1786 (Bam HI-Avr II) | pGA1.1, addition of Bam HI and Xho I sites to pGA1.1 multiple cloning site |
| BGHpA | 1789-2011 | pGA1.1 |
| Lambda T0 terminator | 2012-2046 | pGA1.1 |
| Kanamycin resistance | 2067-2861 | pGA1.1 |
| ColE1 origin of replication | 3247-3920 | pGA1.1 |

Figure 6a. pGA2 Sequence

```
cgacaatattggctattggccattgcatacgttgtatctatatcataatatgtacatttatattggctcatgtccaatat
gaccgccatgttgacattgattattgactagttattaatagtaatcaattacggggtcattagttcatagcccatatatg
gagttccgcgttacataacttacggtaaatggcccgcctggctgaccgcccaacgacccccgcccattgacgtcaataat
gacgtatgttcccatagtaacgccaatagggactttccattgacgtcaatgggtggagtatttacggtaaactgcccact
tggcagtacatcaagtgtatcatatgccaagtccgcccctattgacgtcaatgacggtaaatggcccgcctggcattat
gcccagtacatgaccttacgggactttcctacttggcagtacatctacgtattagtcatcgctattaccatggtgatgcg
gttttggcagtacaccaatgggcgtggatagcggtttgactcacggggatttccaagtctccaccccattgacgtcaatg
ggagtttgttttggcaccaaaatcaacgggactttccaaaatgtcgtaataaccccgccccgttgacgcaaatgggcggt
aggcgtgtacggtgggaggtctatataagcagagctcgtttagtgaactcattctatcgatgcttgcaatcatggatgca
atgaagagagggctctgctgtgtgctgctgctgtgtggagcagtcttcgtttcggctagccccgggtgataaacggaccg
cgcaatccctaggctgtgccttctagttgccagccatctgttgtttgcccctcccccgtgccttccttgaccctggaagg
tgccactcccactgtcctttcctaataaaatgaggaaattgcatcgcattgtctgagtaggtgtcattctattctgggg
gtggggtggggcaggacagcaagggggaggattgggaagacaatagcaggcatgctggggatgcggtgggctctatataa
aaaacgcccggcggcaaccgagcgttctgaacgctagagtcgacaaattcagaagaactcgtcaagaaggcgatagaagg
cgatgcgctgcgaatcgggagcggcgataccgtaaagcacgaggaagcggtcagcccattcgccgccaagctcttcagca
atatcacgggtagccaacgctatgtcctgatagcggtctgccacacccagccggccacagtcgatgaatccagaaaagcg
gccattttccaccatgatattcggcaagcaggcatcgccatgggtcacgacgagatcctcgccgtcgggcatgctcgcct
tgagcctggcgaacagttcggctggcgcgagcccctgatgctcttcgtccagatcatcctgatcgacaagaccggcttcc
atccgagtacgtgctcgctcgatgcgatgtttcgcttggtggtcgaatgggcaggtagccggatcaagcgtatgcagccg
ccgcattgcatcagccatgatggatactttctcggcaggagcaaggtgagatgacaggagatcctgccccggcacttcgc
ccaatagcagccagtcccttcccgcttcagtgacaacgtcgagcacagctgcgcaaggaacgcccgtcgtggccagccac
gatagccgcgctgcctcgtcttgcagttcattcagggcaccggacaggtcggtcttgacaaaaagaaccgggcgcccctg
cgctgacagccggaacacggcggcatcagagcagccgattgtctgttgtgcccagtcatagccgaatagcctctccaccc
aagcggccggagaacctgcgtgcaatccatcttgttcaatcatgcgaaacgatcctcatcctgtctcttgatcagatctt
gatcccctgcgccatcagatccttggcggcaagaaagccatccagtttactttgcagggcttcccaaccttaccagaggg
cgccccagctggcaattccggttcgcttgctgtccataaaaccgcccagtctagctatcgccatgtaagcccactgcaag
ctacctgctttctctttgcgcttgcgtttcccttgtccagatagcccagtagctgacattcatccggggtcagcaccgt
ttctgcggactggctttctacgtgaaaaggatctaggtgaagatcctttttgataatctcatgaccaaaatcccttaacg
tgagttttcgttccactgagcgtcagaccccgtagaaaagatcaaaggatcttcttgagatcctttttttctgcgcgtaa
tctgctgcttgcaaacaaaaaaaccaccgctaccagcggtggtttgtttgccggatcaagagctaccaactctttttccg
aaggtaactggcttcagcagagcgcagataccaaatactgttcttctagtgtagccgtagttaggccaccacttcaagaa
ctctgtagcaccgcctacatacctcgctctgctaatcctgttaccagtggctgctgccagtggcgataagtcgtgtctta
ccgggttggactcaagacgatagttaccggataaggcgcagcggtcgggctgaacggggggttcgtgcacacagcccagc
ttggagcgaacgacctacaccgaactgagatacctacagcgtgagctatgagaaagcgccacgcttcccgaagggagaaa
ggcggacaggtatccggtaagcggcagggtcggaacaggagagcgcacgagggagcttccagggggaaacgcctggtatc
tttatagtcctgtcgggtttcgccacctctgacttgagcgtcgatttttgtgatgctcgtcaggggggcggagcctatgg
aaaaacgccagcaacgcggcctttttacggttcctggccttttgctggccttttgctcacatgttgt
```

Figure 6b. PGA2 functional regions

| Functional region | Position within sequence (starting-and ending pos.) | Origin of sequence |
|---|---|---|
| CMVIE promoter | 1-687 | pGA1 |
| tPA leader | 712-774 | pGA1 |
| Multiple cloning site | 698-808<br>Cla I-Avr II | pGA1 |
| BGHpA | 814-1036 | pGA1 |
| Lambda T0 terminator | 1037-1071 | pGA1 |
| Kanamycin resistance | 1089-1883 | pGA1 |
| ColE1 origin of replication | 2269-2942 | pGA1 |

Figure 7a. pGA2.1 Sequence

```
cgacaatattggctattggccattgcatacgttgtatctatatcataatatgtacatttatattggctcatgtccaatat
gaccgccatgttgacattgattattgactagttattaatagtaatcaattacggggtcattagttcatagcccatatatg
gagttccgcgttacataacttacggtaaatggcccgcctggctgaccgcccaacgacccccgcccattgacgtcaataat
gacgtatgttcccatagtaacgccaatagggactttccattgacgtcaatgggtggagtatttacggtaaactgcccact
tggcagtacatcaagtgtatcatatgccaagtccgccccctattgacgtcaatgacggtaaatggcccgcctggcattat
gcccagtacatgaccttacgggactttcctacttggcagtacatctacgtattagtcatcgctattaccatggtgatgcg
gttttggcagtacaccaatgggcgtggatagcggtttgactcacggggatttccaagtctccaccccattgacgtcaatg
ggagtttgttttggcaccaaaatcaacgggactttccaaaatgtcgtaataaccccgccccgttgacgcaaatgggcggt
aggcgtgtacggtgggaggtctatataagcagagctcgtttagtgaactcattctatcgatgcttgcaatcatggatgca
atgaagagagggctctgctgtgtgctgctgctgtgtggagaattcttcgtttcggctgctgctgtgtggagaattcttcg
tttcggctagccccgggtgataaacggaccgcgcaatccctaggctgtgccttctagttgccagccatctgttgtttgcc
cctcccccgtgccttccttgaccctggaaggtgccactcccactgtcctttcctaataaaatgaggaaattgcatcgcat
tgtctgagtaggtgtcattctattctggggggtggggtggggcaggacagcaagggggaggattgggaagacaatagcag
gcatgctggggatgcggtgggctctatataaaaaacgcccggcggcaaccgagcgttctgaacgctagagtcgacaaatt
cagaagaactcgtcaagaaggcgatagaaggcgatgcgctgcgaatcgggagcggcgataccgtaaagcacgaggaagcg
gtcagcccattcgccgccaagctcttcagcaatatcacgggtagccaacgctatgtcctgatagcggtctgccacaccca
gccggccacagtcgatgaatccagaaaagcggccattttccaccatgatattcggcaagcaggcatcgccatgggtcacg
acgagatcctcgccgtcgggcatgctcgccttgagcctggcgaacagttcggctggcgcgagcccctgatgctcttcgtc
cagatcatcctgatcgacaagaccggcttccatccgagtacgtgctcgctcgatgcgatgtttcgcttggtggtcgaatg
ggcaggtagccggatcaagcgtatgcagccgccgcattgcatcagccatgatggatactttctcggcaggagcaaggtga
gatgacaggagatcctgccccggcacttcgcccaatagcagccagtcccttcccgcttcagtgacaacgtcgagcacagc
tgcgcaaggaacgcccgtcgtggccagccacgatagccgcgctgcctcgtcttgcagttcattcagggcaccggacaggt
cggtcttgacaaaaagaaccgggcgcccctgcgctgacagccggaacacggcggcatcagagcagccgattgtctgttgt
gcccagtcatagccgaatagcctctccacccaagcggccggagaacctgcgtgcaatccatcttgttcaatcatgcgaaa
cgatcctcatcctgtctcttgatcagatcttgatcccctgcgccatcagatccttggcggcaagaaagccatccagttta
ctttgcagggcttcccaaccttaccagagggcgccccagctggcaattccggttcgcttgctgtccataaaaccgcccag
tctagctatcgccatgtaagcccactgcaagctacctgctttctctttgcgcttgcgttttcccttgtccagatagccca
gtagctgacattcatccggggtcagcaccgtttctgcggactggctttctacgtgaaaaggatctaggtgaagatccttt
ttgataatctcatgaccaaaatcccttaacgtgagttttcgttccactgagcgtcagaccccgtagaaaagatcaaagga
tcttcttgagatcctttttttctgcgcgtaatctgctgcttgcaaacaaaaaaaccaccgctaccagcggtggtttgttt
gccggatcaagagctaccaactctttttccgaaggtaactggcttcagcagagcgcagataccaaatactgttcttctag
tgtagccgtagttaggccaccacttcaagaactctgtagcaccgcctacatacctcgctctgctaatcctgttaccagtg
gctgctgccagtggcgataagtcgtgtcttaccgggttggactcaagacgatagttaccggataaggcgcagcggtcggg
ctgaacggggggttcgtgcacacagcccagcttggagcgaacgacctacaccgaactgagatacctacagcgtgagctat
gagaaagcgccacgcttcccgaagggagaaaggcggacaggtatccggtaagcggcagggtcggaacaggagagcgcacg
agggagcttccagggggaaacgcctggtatctttatagtcctgtcgggtttcgccacctctgacttgagcgtcgattttt
gtgatgctcgtcaggggggcggagcctatggaaaaacgccagcaacgcggcctttttacggttcctggccttttgctggc
cttttgctcacatgttgt
```

Figure 7b. PGA2.1 functional regions

| Functional region | Position within sequence (starting-and ending pos.) | Origin of sequence |
|---|---|---|
| CMVIE promoter | 1-687 | PGA2 |
| tPA leader | None | |
| Multiple cloning site | 698-839<br>Cla I-Avr II | PGA2, addition of two EcoR I sites to pGA2 multiple cloning site |
| BGHpA | 842-1064 | PGA2 |
| Lambda T0 terminator | 1065-1099 | PGA2 |
| Kanamycin resistance | 1914-1120 | PGA2 |
| ColE1 origin of replication | 2300-2973 | PGA2 |

Figure 8a. pGA2.2 Sequence cgacaatattggctattggccattgcatacgttgtatctatatcataatatgtacatttatattggctcatgtccaatat
gaccgccatgttgacattgattattgactagttattaatagtaatcaattacggggtcattagttcatagcccatatatg
gagttccgcgttacataacttacggtaaatggcccgcctggctgaccgcccaacgacccccgcccattgacgtcaataat
gacgtatgttcccatagtaacgccaatagggactttccattgacgtcaatgggtggagtatttacggtaaactgcccact
tggcagtacatcaagtgtatcatatgccaagtccgccccctattgacgtcaatgacggtaaatggcccgcctggcattat
gcccagtacatgaccttacgggactttcctacttggcagtacatctacgtattagtcatcgctattaccatggtgatgcg
gttttggcagtacaccaatgggcgtggatagcggtttgactcacggggatttccaagtctccaccccattgacgtcaatg
ggagtttgttttggcaccaaaatcaacgggactttccaaaatgtcgtaataaccccgccccgttgacgcaaatgggcggt
aggcgtgtacggtgggaggtctatataagcagagctcgtttagtgaactcattctatggatccttgctcgagtggatgca
atgaagagagggctctgctgtgtgctgctgctgtgtggagaattcttcgtttcggctgctgctgtgtggagaattcttcg
tttcggctagcccgggtgataaacggaccgcgcaatccctaggctgtgccttctagttgccagccatctgttgtttgcc
cctcccccgtgccttccttgaccctggaaggtgccactcccactgtcctttcctaataaaatgaggaaattgcatcgcat
tgtctgagtaggtgtcattctattctggggggtggggtggggcaggacagcaagggggaggattgggaagacaatagcag
gcatgctggggatgcggtgggctctatataaaaaacgcccggcggcaaccgagcgttctgaacgctagagtcgacaaatt
cagaagaactcgtcaagaaggcgatagaaggcgatgcgctgcgaatcgggagcggcgataccgtaaagcacgaggaagcg
gtcagcccattcgccgccaagctcttcagcaatatcacgggtagccaacgctatgtcctgatagcggtctgccacaccca
gccggccacagtcgatgaatccagaaaagcggccattttccaccatgatattcggcaagcaggcatcgccatgggtcacg
acgagatcctcgccgtcgggcatgctcgccttgagcctggcgaacagttcggctggcgcgagcccctgatgctcttcgtc
cagatcatcctgatcgacaagaccggcttccatccgagtacgtgctcgctcgatgcgatgtttcgcttggtggtcgaatg
ggcaggtagccggatcaagcgtatgcagccgccgcattgcatcagccatgatggatactttctcggcaggagcaaggtga
gatgacaggagatcctgccccggcacttcgcccaatagcagccagtcccttcccgcttcagtgacaacgtcgagcacagc
tgcgcaaggaacgcccgtcgtggccagccacgatagccgcgctgcctcgtcttgcagttcattcagggcaccggacaggt
cggtcttgacaaaaagaaccgggcgcccctgcgctgacagccggaacacggcggcatcagagcagccgattgtctgttgt
gcccagtcatagccgaatagcctctccacccaagcggccggagaacctgcgtgcaatccatcttgttcaatcatgcgaaa
cgatcctcatcctgtctcttgatcagatcttgatcccctgcgccatcagatccttggcggcaagaaagccatccagttta
ctttgcagggcttcccaaccttaccagagggcgccccagctggcaattccggttcgcttgctgtccataaaaccgcccag
tctagctatcgccatgtaagcccactgcaagctacctgctttctctttgcgcttgcgttttcccttgtccagatagccca
gtagctgacattcatccggggtcagcaccgtttctgcggactggctttctacgtgaaaaggatctaggtgaagatccttt
ttgataatctcatgaccaaaatcccttaacgtgagttttcgttccactgagcgtcagaccccgtagaaaagatcaaagga
tcttcttgagatcctttttttctgcgcgtaatctgctgcttgcaaacaaaaaaaccaccgctaccagcggtggtttgttt
gccggatcaagagctaccaactctttttccgaaggtaactggcttcagcagagcgcagataccaaatactgttcttctag
tgtagccgtagttaggccaccacttcaagaactctgtagcaccgcctacatacctcgctctgctaatcctgttaccagtg
gctgctgccagtggcgataagtcgtgtcttaccgggttggactcaagacgatagttaccggataaggcgcagcggtcggg
ctgaacggggggttcgtgcacacagcccagcttggagcgaacgacctacaccgaactgagatacctacagcgtgagctat
gagaaagcgccacgcttcccgaagggagaaaggcggacaggtatccggtaagcggcagggtcggaacaggagagcgcacg
agggagcttccagggggaaacgcctggtatctttatagtcctgtcgggtttcgccacctctgacttgagcgtcgattttt
gtgatgctcgtcaggggggcggagcctatggaaaaacgccagcaacgcggcctttttacggttcctggccttttgctggc
cttttgctcacatgttgt

Figure 8b. PGA2.2 functional regions

| Functional region | Position within sequence (starting-and ending pos.) | Origin of sequence |
|---|---|---|
| CMVIE promoter | 1-687 | PGA2.1 |
| tPA leader | None | |
| Multiple cloning site | 698-839<br>Bam HI-Avr II | PGA2.1, addition of Bam HI and Xho I sites to pGA2.1 multiple cloning site |
| BGHpA | 842-1064 | PGA2.1 |
| Lambda T0 terminator | 1065-1099 | PGA2.1 |
| Kanamycin resistance | 1914-1120 | PGA2.1 |
| ColE1 origin of replication | 2300-2973 | PGA2.1 |

FIG. 10A pGA2/JS2 sequence

```
atcgatgcaggactcggcttgctgaagcgcgcacggcaagaggcgaggggcggcgactggtgggtacgccaaaaattttg
actagcggaggctagaaggagagagatgggtgcgagagcgtcagtattaagcgggggagaattagatcgatgggaaaaa
ttcggttaaggccagggggaaagaaaaaatataaattaaaacatatagtatgggcaagcagggagctagaacgattcgca
gttaatcctggcctgttagaaacatcagaaggctgtagacaaatactgggacagctacaaccatcccttcagacaggatc
agaagaacttagatcattatataatacagtagcaaccctctattgtgtgcatcaaaggatagagataaaagacaccaagg
aagctttagacaagatagaggaagagcaaaacaaaagtaagaaaaaagcacagcaagcagcagctgacacaggacacagc
agtcaggtcagccaaaattaccctatagtgcagaacatccaggggcaaatggtacatcaggccatatcacctagaacttt
aaatgcatgggtaaaagtagtagaagagaaggctttcagcccagaagtaatacccatgttttcagcattatcagaaggag
ccaccccacaagatttaaacaccatgctaaacacagtgggggacatcaagcagccatgcaaatgttaaaagagaccatc
aatgaggaagctgcagaatgggatagagtacatccagtgcatgcagggcctattgcaccaggccagatgagagaaccaag
gggaagtgacatagcaggaactactagtacccttcaggaacaaataggatggatgacaaataatccacctatcccagtag
gagaaatttataaaagatggataatcctgggattaaataaaatagtaagaatgtatagccctaccagcattctggacata
agacaaggaccaaaagaaccttttagagactatgtagaccggttctataaaactctaagagccgagcaagcttcacagga
ggtaaaaaattggatgacagaaaccttgttggtccaaaatgcgaacccagattgtaagactattttaaaagcattgggac
cagcggctacactagaagaaatgatgacagcatgtcagggagtaggaggacccggccataaggcaagagttttggctgaa
gcaatgagccaagtaacaaatacagctaccataatgatgcagagaggcaattttaggaaccaaagaaagatggttaagag
cttcaatagcggcaaagaagggcacacagccagaaattgcagggcccctaggaaaaagggcagctggaaaagcggaaagg
aaggacaccaaatgaaagattgtactgagagacaggctaatttttagggaagatctggccttcctacaagggaaggcca
gggaattttcttcagagcagaccagagccaacagccccaccatttcttcagagcagaccagagccaacagccccaccaga
agagagcttcaggtctggggtagagacaacaactccccctcagaagcaggagccgatagacaaggaactgtatcctttaa
cttccctcagatcactctttggcaacgacccctcgtcacaataaagataggggggcaactaaaggaagctctattagata
caggagcagatgatacagtattagaagaaatgagtttgccaggaagatggaaaccaaaaatgataggggggaattggaggt
tttatcaaagtaagacagtatgatcagatactcatagaaatctgtggacataaagctataggtacagtattagtaggacc
tacacctgtcaacataattggaagaaatctgttgactcagattggttgcactttaaattttcccattagccctattgaga
ctgtaccagtaaaattaaagccaggaatggatggcccaaaagttaaacaatggccattgacagaagaaaaaataaaagca
ttagtagaaatttgtacagaaatggaaaaggaagggaaaatttcaaaaattgggcctgagaatccatacaatactccagt
atttgccataaagaaaaaagacagtactaaatggagaaaattagtagatttcagagaacttaataagagaactcaagact
tctgggaagttcaattaggaataccacatcccgcagggttaaaaaagaaaaaatcagtaacagtactggatgtgggtgat
gcatatttttcagttcccttagatgaagacttcaggaagtatactgcatttaccatacctagtataaacaatgagacacc
agggattagatatcagtacaatgtgcttccacagggatggaaaggatcaccagcaatattccaaagtagcatgacaaaaa
tcttagagccttttaaaaaacaaaatccagacatagttatctatcaatacatgaacgatttgtatgtaggatctgactta
gaaatagggcagcatagaacaaaaatagaggagctgagacaacatctgttgaggtggggacttaccacaccagacaaaaa
acatcagaaagaacctccattcctttggatgggttatgaactccatcctgataaatggacagtacagcctatagtgctgc
cagaaaaagacagctggactgtcaatgacatacagaagttagtggggaaattgaataccgcaagtcagatttacccaggg
attaaagtaaggcaattatgtaaactccttagaggaaccaaagcactaacagaagtaataccactaacagaagaagcaga
gctagaactggcagaaaacagagagattctaaaagaaccagtacatggagtgtattatgacccatcaaaagacttaatag
cagaaatacagaagcaggggcaaggccaatggacatatcaaatttatcaagagccatttaaaaatctgaaaacaggaaaa
tatgcaagaatgaggggtgcccacactaatgatgtaaaacaattaacagaggcagtgcaaaaaataaccacagaaagcat
agtaatatggggaaagactcctaaatttaaactacccatacaaaaggaaacatgggaaacatggtggacagagtattggc
aagccacctggattcctgagtgggagtttgttaatacccctcctttagtgaaattatggtaccagttagagaaagaaccc
atagtaggagcagaaaccttctatgtagatggggcagctaacagggagactaaattaggaaaagcaggatatgttactaa
caaaggaagacaaaaggttgtccccctaactaacacaacaaatcagaaaactcagttacaagcaatttatctagctttgc
aggattcaggattagaagtaaacatagtaacagactcacaatatgcattaggaatcattcaagcacaaccagataaaagt
gaatcagagttagtcaatcaaataatagagcagttaataaaaaggaaaaggtctatctggcatgggtaccagcacacaa
aggaattggaggaaatgaacaagtagataaattagtcagtgctggaatcaggaaaatactatttttagatggaatagata
aggcccaagatgaacattagaattctgcaacaactgctgtttatccatttcagaattgggtgtcgacatagcagaatag
gcgttactcgacagaggagagcaagaaatggagccagtagatcctagactagagccctggaagcatccaggaagtcagcc
taaaactgcttgtaccaattgctattgtaaaaagtgttgctttcattgccaagtttgtttcataacaaaagccttaggca
tctcctatggcaggaagaagcggagacagcgacgaagacctcctcaagacagtcagactcatcaagtttctctatcaaag
cagtaagtagtaaatgtaatgcaacctttacaaatattagcaatagtagcattagtagtagcagcaataatagcaatagt
tgtgtggaccatagtattcatagaatataggaaatattaagacaaagaaaaatagacaggttaattgataggataacag
aaagagcagaagacagtggcaatgaaagtgaaggggatcaggaagaattatcagcacttgtggaaatggggcatcatgct
ccttgggatgttgatgatctgtagtgctgtagaaaatttgtgggtcacagtttattatggggtacctgtgtggaaagaag
caaccaccactctattttgtgcatcagatgctaaagcatatgatacagaggtacataatgtttgggccacacatgcctgt
gtacccacagaccccaacccacaagaagtagtattggaaaatgtgacagaaaatttaacatgtggaaaaataacatggt
agaacagatgcatgaggatataatcagtttatgggatcaaagcctaaagccatgtgtaaaattaaccccactctgtgtta
ctttaaattgcactgatttgaggaatgttactaatatcaataatagtagtgagggaatgagaggagaaataaaaaactgc
tctttcaatatcaccacaagcataagagataaggtgaagaaagactatgcactttttatagacttgatgtagtaccaat
agataatgataatactagctataggttgataaattgtaatacctcaaccattacacaggcctgtccaaaggtatcctttg
agccaattcccatacattattgtaccccggctggttttgcgattctaaagtgtaaagacaagaagttcaatggaacaggg
ccatgtaaaaatgtcagcacagtacaatgtacacatggaattaggccagtagtgtcaactcaactgctgttaaatggcag
```

FIG. 10B tctagcagaagaagaggtagtaattagatctagtaatttcacagacaatgcaaaaaacataatagtacagttgaaagaat
ctgtagaaattaattgtacaagacccaacaacaatacaaggaaaagtatacatataggaccaggaagagcattttataca
acaggagaaataataggagatataagacaagcacattgcaacattagtagaacaaaatggaataacactttaaatcaaat
agctacaaaattaaaagaacaatttgggaataataaaacaatagtctttaatcaatcctcaggaggggacccagaaattg
taatgcacagttttaattgtggaggggaatttttctactgtaattcaacacaactgtttaatagtacttggaattttaat
ggtacttggaatttaacacaatcgaatggtactgaaggaaatgacactatcacactcccatgtagaataaaacaaattat
aaatatgtggcaggaagtaggaaaagcaatgtatgcccctcccatcagaggacaaattagatgctcatcaaatattacag
ggctaatattaacaagagatggtggaactaacagtagtgggtccgagatcttcagacctggggaggagatatgagggac
aattggagaagtgaattatataaatataaagtagtaaaaattgaaccattaggagtagcacccaccaaggcaaaaagaag
agtggtgcagagagaaaaaagagcagtgggaacgataggagctatgttccttgggttcttgggagcagcaggaagcacta
tgggcgcagcgtcaataacgctgacggtacaggccagactattattgtctggtatagtgcaacagcagaacaatttgctg
agggctattgaggcgcaacagcatctgttgcaactcacagtctggggcatcaagcagctccaggcaagagtcctggctct
ggaaagatacctaagggatcaacagctcctagggatttggggttgctctggaaaactcatctgcaccactgctgtgcctt
ggaatgctagttggagtaataaaactctggatatgatttgggataacatgacctggatggagtgggaaagagaaatcgaa
aattacacaggcttaatatacaccttaattgaagaatcgcagaaccaacaagaaaagaatgaacaagacttattagcatt
agataagtgggcaagtttgtggaattggtttgacatatcaaattggctgtggtgtataaaaatcttcataatgatagtag
gaggcttgataggtttaagaatagtttttactgtactttctatagtaaatagagttaggcagggatactcaccattgtca
tttcagacccacctcccagccccgaggggacccgacaggcccgaaggaatcgaagaagaaggtggagacagagacagaga
cagatccgtgcgattagtggatggatccttagcacttatctgggacgatctgcggagcctgtgcctcttcagctaccacc
gcttgagagacttactcttgattgtaacgaggattgtggaacttctgggacgcagggggtgggaagccctcaaatattgg
tggaatctcctacagtattggagtcaggagctaaagaatagtgctgttagcttgctcaatgccacagctatagcagtagc
tgaggggacagatagggttatagaagtagtacaaggagcttatagagctattcgccacatacctagaagaataagacagg
gcttggaaaggattttgctataagatgggtggctagccccgggtgataaacggaccgcgcaatccctaggctgtgccttc
tagttgccagccatctgttgtttgcccctcccccgtgccttccttgaccctggaaggtgccactcccactgtcctttcct
aataaaatgaggaaattgcatcgcattgtctgagtaggtgtcattctattctggggggtggggtggggcaggacagcaag
ggggaggattgggaagacaatagcaggcatgctggggatgcggtgggctctatataaaaaacgcccggcggcaaccgagc
gttctgaacgctagagtcgacaaattcagaagaactcgtcaagaaggcgatagaaggcgatgcgctgcgaatcgggagcg
gcgataccgtaaagcacgaggaagcggtcagcccattcgccgccaagctcttcagcaatatcacgggtagccaacgctat
gtcctgatagcggtctgccacacccagccggccacagtcgatgaatccagaaaagcggccattttccaccatgatattcg
gcaagcaggcatcgccatgggtcacgacgagatcctcgccgtcgggcatgctcgccttgagcctggcgaacagttcggct
ggcgcgagcccctgatgctcttcgtccagatcatcctgatcgacaagaccggcttccatccgagtacgtgctcgctcgat
gcgatgtttcgcttggtggtcgaatgggcaggtagccggatcaagcgtatgcagccgccgcattgcatcagccatgatgg
atactttctcggcaggagcaaggtgagatgacaggagatcctgccccggcacttcgcccaatagcagccagtcccttccc
gcttcagtgacaacgtcgagcacagctgcgcaaggaacgcccgtcgtggccagccacgatagccgcgctgcctcgtcttg
cagttcattcagggcaccggacaggtcggtcttgacaaaaagaaccgggcgcccctgcgctgacagccggaacacggcgg
catcagagcagccgattgtctgttgtgcccagtcatagccgaatagcctctccacccaagcggccggagaacctgcgtgc
aatccatcttgttcaatcatgcgaaacgatcctcatcctgtctcttgatcagatcttgatcccctgcgccatcagatcct
tggcggcgagaaagccatccagtttactttgcagggcttcccaaccttaccagagggcgccccagctggcaattccggtt
cgcttgctgtccataaaaccgcccagtctagctatcgccatgtaagcccactgcaagctacctgctttctctttgcgctt
gcgttttcccttgtccagatagcccagtagctgacattcatccggggtcagcaccgtttctgcggactggctttctacgt
gaaaaggatctaggtgaagatcctttttgataatctcatgaccaaaatcccttaacgtgagttttcgttccactgagcgt
cagaccccgtagaaaagatcaaaggatcttcttgagatcctttttttctgcgcgtaatctgctgcttgcaaacaaaaaaa
ccaccgctaccagcggtggtttgtttgccggatcaagagctaccaactctttttccgaaggtaactggcttcagcagagc
gcagataccaaatactgtccttctagtgtagccgtagttaggccaccacttcaagaactctgtagcaccgcctacatacc
tcgctctgctaatcctgttaccagtggctgctgccagtggcgataagtcgtgtcttaccgggttggactcaagacgatag
ttaccggataaggcgcagcggtcgggctgaacggggggttcgtgcacacagcccagcttggagcgaacgacctacaccga
actgagatacctacagcgtgagctatgagaaagcgccacgcttcccgaagggagaaaggcggacaggtatccggtaagcg
gcagggtcggaacaggagagcgcacgagggagcttccagggggaaacgcctggtatctttatagtcctgtcgggtttcgc
cacctctgacttgagcgtcgatttttgtgatgctcgtcaggggggcggagcctatggaaaacgccagcaacgcggccttt
ttacggttcctggccttttgctggccttttgctcacatgttgtcgaccgacaatattggctattggccattgcatacgtt
gtatctatatcataatatgtacatttatattggctcatgtccaatatgaccgccatgttgacattgattattgactagtt
attaatagtaatcaattacggggtcattagttcatagcccatatatggagttccgcgttacataacttacggtaaatggc
ccgcctcgtgaccgcccaacgacccccgcccattgacgtcaataatgacgtatgttcccatagtaacgccaatagggact
ttccattgacgtcaatgggtggagtatttacggtaaactgcccacttggcagtacatcaagtgtatcatatgccaagtcc
gcccctattgacgtcaatgacggtaaatggcccgcctggcattatgcccagtacatgaccttacggactttcctacttg
gcagtacatctacgtattagtcatcgctattaccatggtgatgcggttttggcagtacaccaatgggcgtggatagcggt
ttgactcacggggatttccaagtctccaccccattgacgtcaatgggagtttgttttggcaccaaaatcaacgggacttt
ccaaaatgtcgtaataaccccgccccgttgacgcaaatgggcggtaggcgtgtacggtgggaggtctatataagcagagc
tcgtttagtgaaccgtcagatcgc FIG. 10C pGA2/JS2 Functional Regions

| **Position within sequence (starting and ending pos.)** | **Gene/ORF (indicate complete name of the gen and the expressed gene product)** | **Origin of sequence (organism)** |
|---|---|---|
| 106-1644 | Gag, inactivating point mutations in zinc finger packaging sequences for viral RNA | HIV-1 IIIb (BH10) |
| 1401-3620 | Pol, inactivating point mutations in reverse transcriptase, deletion of integrase | HIV-1 IIIb (BH10) |
| 3708-3922 and 6247-6337 | Tat exons #1 and #2 | |
| 3847-3922 and 6247-6521 | Rev exons #1 and #2 | |
| 3939-4184 | Vpu | |
| 4102-6663 | Env | HIV-ADA |
| 6664-9544 | Plasmid vector | pGA2, GenBank accession # AF425298 |

FIG. 10D JS2 Mutation Chart

| Codon Change | Amino acid change | Region | Function |
|---|---|---|---|
| to AGC Position 1279-1281 | C392S | Gag | Ablation of zinc finger used in packaging |
| to AGC Position 1288-1290 | C395S | Gag | Ablation of zinc finger used in packaging |
| to AGC Position 1342-1344 | C413S | Gag | Ablation of zinc finger used in packaging |
| to AGC Position 1351-1353 | C416S | Gag | Ablation of zinc finger used in packaging |
| to AAC Position 2454-2456 | D185N | Reverse Transcriptase | Inactivation of Polymerase active site |
| to ACC Position 2697-2699 | W266T | Reverse Transcriptase | Ablation of strand transfer activity |
| to CAG Position 3333-3335 | E478Q | RNase H | Inactivation of RNase H activity |

FIG. 11A pGA2/JS7 Sequence

ATCGATGCAGGACTCGGCTTGCTGAAGCGCGCACGGCAAGAGGCGAGGGGCGGCGACTGGTGAGTACGCCAAAAATTTTG
ACTAGCGGAGGCTAGAAGGAGAGAGATGGGTGCGAGAGCGTCAGTATTAAGCGGGGGAGAATTAGATCGATGGGAAAAAA
TTCGGTTAAGGCCAGGGGGAAAGAAAAAATATAAATTAAAACATATAGTATGGGCAAGCAGGGAGCTAGAACGATTCGCA
GTTAATCCTGGCCTGTTAGAAACATCAGAAGGCTGTAGACAAATACTGGGACAGCTACAACCATCCCTTCAGACAGGATC
AGAAGAACTTAGATCATTATATAATACAGTAGCAACCCTCTATTGTGTGCATCAAAGGATAGAGATAAAAGACACCAAGG
AAGCTTTAGACAAGATAGAGGAAGAGCAAAACAAAAGTAAGAAAAAAGCACAGCAAGCAGCAGCTGACACAGGACACAGC
AATCAGGTCAGCCAAAATTACCCTATAGTGCAGAACATCCAGGGGCAAATGGTACATCAGGCCATATCACCTAGAACTTT
AAATGCATGGGTAAAAGTAGTAGAAGAGAAGGCTTTCAGCCCAGAAGTGATACCCATGTTTTCAGCATTATCAGAAGGAG
CCACCCCACAAGATTTAAACACCATGCTAAACACAGTGGGGGGACATCAAGCAGCCATGCAAATGTTAAAAGAGACCATC
AATGAGGAAGCTGCAGAATGGGATAGAGTGCATCCAGTGCATGCAGGGCCTATTGCACCAGGCCAGATGAGAGAACCAAG
GGGAAGTGACATAGCAGGAACTACTAGTACCCTTCAGGAACAAATAGGATGGATGACAAATAATCCACCTATCCCAGTAG
GAGAAATTTATAAAAGATGGATAATCCTGGGATTAAATAAAATAGTAAGAATGTATAGCCCTACCAGCATTCTGGACATA
AGACAAGGACCAAAAGAACCCTTTAGAGACTATGTAGACCGGTTCTATAAAACTCTAAGAGCCGAGCAAGCTTCACAGGA
GGTAAAAAATTGGATGACAGAAACCTTGTTGGTCCAAAATGCGAACCCAGATTGTAAGACTATTTTAAAAGCATTGGGAC
CAGCGGCTACACTAGAAGAAATGATGACAGCATGTCAGGGAGTAGGAGGACCCGGCCATAAGGCAAGAGTTTTGGCTGAA
GCAATGAGCCAAGTAACAAATTCAGCTACCATAATGATGCAGAGAGGCAATTTTAGGAACCAAAGAAAGATTGTTAAGAG
CTTCAATAGCGGCAAAGAAGGGCACACAGCCAGAAATTGCAGGGCCCCTAGGAAAAAGGGCAGCTGGAAAAGCGGAAAGG
AAGGACACCAAATGAAAGATTGTACTGAGAGACAGGCTAATTTTTTAGGGAAGATCTGGCCTTCCTACAAGGGAAGGCCA
GGGAAtTTTCTTCAGAGCAGACCAGAGCCAACAGCCCCACCAGAAGAGAGCTTCAGGTCTGGGGTAGAGACAACAACTCC
CCCTCAGAAGCAGGAGCCGATAGACAAGGAACTGTATCCTTTAACTTCCCTCAGATCACTCTTTGGCAACGACCCCTCGT
CACAATAAAGATAGGGGGGCAACTAAAGGAAGCTCTATTAGCCACAGGAGCAGATGATACAGTATTAGAAGAAATGAGTT
TGCCAGGAAGATGGAAACCAAAAATGATAGGGGGAATTGGAGGTTTTATCAAAGTAAGACAGTATGATCAGATACTCATA
GAAATCTGTGGACATAAAGCTATAGGTACAGTATTAGTAGGACCTACACCTGTCAACATAATTGGAAGAAATCTGTTGAC
TCAGATTGGTTGCACTTTAAATTTTCCCATTAGCCCTATTGAGACTGTACCAGTAAAATTAAAGCCAGGAATGGATGGCC
CAAAAGTTAAACAATGGCCATTGACAGAAGAAAAGATAAAAGCATTAGTAGAAATTTGTACAGAGATGGAAAAGGAAGGG
AAAATTTCAAAAATTGGGCCTGAAAATCCATACAATACTCCAGTATTTGCCATAAAGAAAAAAGACAGTACTAAATGGAG
AAAATTAGTAGATTTCAGAGAACTTAATAAGAGAACTCAAGACTTCTGGGAAGTTCAATTAGGAATACCACATCCCGCAG
GGTTAAAAAAGAAAAAATCAGTAACAGTACTGGATGTGGGTGATGCATATTTTTCAGTTCCCTTAGATGAAGACTTCAGG
AAATATACTGCATTTACCATACCTAGTATAAACAATGAGACACCAGGGATTAGATATCAGTACAATGTGCTTCCACAGGG
ATGGAAAGGATCACCAGCAATATTCCAAAGTAGCATGACAAAAATCTTAGAGCCTTTTAGAAAACAAAATCCAGACATAG
TTATCTATCAATACATGAACGATTTGTATGTAGGATCTGACTTAGAAATAGGGCAGCATAGAACAAAAATAGAGGAGCTG
AGACAACATCTGTTGAGGTGGGGACTTACCACACCAGACAAAAAACATCAGAAAGAACCTCCATTCCTTTGGATGGGTTA
TGAACTCCATCCTGATAAATGGACAGTACAGCCTATAGTGCTGCCAGAAAAAGACAGCTGGACTGTCAATGACATACAGA
AGTTAGTGGGGAAATTGAATACCGCAAGTCAGATTTACCCAGGGATTAAAGTAAGGCAATTATGTAAACTCCTTAGAGGA
aCCAAAGCACTAACAGAAGTAATACCACTAACAGAAGAAGCAGAGCTAGAACTGGCAGAAAACAGAGAGATTCTAAAAGA
ACCAGTACATGGAGTGTATTATGACCCATCAAAAGACTTAATAGCAGAAATACAGAAGCAGGGGCAAGGCCAATGGACAT
ATCAAATTTATCAAGAGCCATTTAAAAATCTGAAAACAGGAAAATATGCAAGAATGAGGGGTGCCCACACTAATGATGTA
AAACAATTAACAGAGGCAGTGCAAAAAATAACCACAGAAAGCATAGTAATATGGGGAAAGACTCCTAAATTTAAACTGCC
CATACAAAAGGAAACATGGGAAACATGGTGGACAGAGTATTGGCAAGCCACCTGGATTCCTGAGTGGGAGTTTGTTAATA
CCCCTCCTTTAGTGAAATTATGGTACCAGTTAGAGAAAGAACCCATAGTAGGAGCAGAAACCTTCTATGTAGATGGGGCA
GCTAACAGGGAGACTAAATTAGGAAAAGCAGGATATGTTACTAATAGAGGAAGACAAAAAGTTGTCACCCTAACTAACAC
AACAAATCAGAAAACTCAGTTACAAGCAATTTATCTAGCTTTGCAGGATTCGGGATTAGAAGTAAACATAGTAACAGACT
CACAATATGCATTAGGAATCATTCAAGCACAACCAGATCAAAGTGAATCAGAGTTAGTCAATCAAATAATAGAGCAGTTA
ATAAAAAAGGAAAAGGTCTATCTGGCATGGGTACCAGCACACAAAGGAATTGGAGGAAATGAACAAGTAGATAAATTAGT
CAGTGCTGGAATCAGGAAAGTACTATTTTTAGATGGAATAGATAAGGCCCAAGATGAACATTAGAATTCTGCAACAACTG
CTGTTTATCCATTTCAGAATTGGGTGTCGACATAGCAGAATAGGCGTTACTCGACAGAGGAGAGCAAGAAATGGAGCCAG
TAGATCCTAGACTAGAGCCCTGGAAGCATCCAGGAAGTCAGCCTAAAACTGCTTGTACCAATTGCTATTGTAAAAAGTGT
TGCTTTCATTGCCAAGTTTGTTTCATAACAAAAGCCTTAGGCATCTCCTATGGCAGGAAGAAGCGGAGACAGCGACGAAG
AGCTCCTCAAGACAGTCAGACTCATCAAGTTTCTCTATCAAAGCAGTAAGTAGTAAATGTAATGCAACCTTTACAAATAT
TAGCAATAGTAGCATTAGTAGTAGCAGCAATAATAGCAATAGTTGTGTGGACCATAGTATTCATAGAATATAGGAAAATA
TTAAGACAAAGAAAAATAGACAGGTTAATTGATAGGATAACAGAAAGAGCAGAAGACAGTGGCAATGAAAGTGAAGGGGA
TCAGGAAGAATTATCAGCACTTGTGGAAATGGGGCATCATGCTCCTTGGGATGTTGATGATCTGTAGTGCTGTAGAAAAT
TTGTGGGTCACAGTTTATTATGGGGTACCTGTGTGGAAAGAAGCAACCACCACTCTATTTTGTGCATCAGATGCTAAAGC
ATATGATACAGAGGTACATAATGTTTGGGCCACACATGCCTGTGTACCCACAGACCCCAACCCACAAGAAGTAGTATTGG
AAAATGTGACAGAAAATTTTAACATGTGGAAAAATAACATGGTAGAACAGATGCATGAGGATATAATCAGTTTATGGGAT
CAAAGCCTAAAGCCATGTGTAAAATTAACCCCACTCTGTGTTACTTTAAATTGCACTGATTTGAGGAATGTTACTAATAT
CAATAATAGTAGTGAGGGAATGAGAGGAGAAATAAAAAACTGCTCTTTCAATATCACCACAAGCATAAGAGATAAGGTGA
AGAAAGACTATGCACTTTTTTATAGACTTGATGTAGTACCAATAGATAATGATAATACTAGCTATAGGTTGATAAATTGT
AATACCTCAACCATTACACAGGCCTGTCCAAAGGTATCCTTTGAGCCAATTCCCATACATTATTGTACCCCGGCTGGTTT
TGCGATTCTAAAGTGTAAAGACAAGAAGTTCAATgGAACAGGGCCATGTAAAAATGTCAGCACAGTACAATGTACACATG
GAATTAGGCCAGTAGTGTCAACTCAACTGCTGTTAAATGGCAGTCTAGCAGAAGAAGAGGTAGTAATTAGATCTAGTAAT

FIG. 11B

TTCACAGACAATGCAAAAAACATAATAGTACAGTTGAAAGAATCTGTAGAAATTAATTGTACAAGACCCAACAACAATAC
AAGGAAAAGTATACATATAGGACCAGGAAGAGCATTTTATACAACAGGAGAAATAATAGGAGATATAAGACAAGCACATT
GCAACATTAGTAGAACAAAATGGAATAACACTTTAAATCAAATAGCTACAAAATTAAAAGAACAATTTGGGAATAATAAA
ACAATAGTCTTTAATCAATCCTCAGGAGGGGACCCAGAAATTGTAATGCACAGTTTTAATTGTGGAGGGGAATTTTTCTA
CTGTAATTCAACACAACTGTTTAATAGTACTTGGAATTTTAATGGTACTTGGAATTTAACACAATCGAATGGTACTGAAG
GAAATGACACTATCACACTCCCATGTAGAATAAAACAAATTATAAATATGTGGCAGGAAGTAGGAAAAGCAATGTATGCC
CCTCCCATCAGAGGACAAATTAGATGCTCATCAAATATTACAGGGCTAATATTAACAAGAGATGGTGGAACTAACAGTAG
TGGGTCCGAGATCTTCAGACCTGGGGGAGGAGATATGAGGGACAATTGGAGAAGTGAATTATATAAATATAAAGTAGTAA
AAATTGAACCATTAGGAGTAGCACCCACCAAGGCAAAAAGAAGAGTGGTGCAGAGAGAAAAAAGAGCAGTGGGAACGATA
GGAGCTATGTTCCTTGGGTTCTTGGGAGCAGCAGGAAGCACTATGGGCGCAGCGTCAATAACGCTGACGGTACAGGCCAG
ACTATTATTGTCTGGTATAGTGCAACAGCAGAACAATTTGCTGAGGGCTATTGAGGCGCAACAGCATCTGTTGCAACTCA
CAGTCTGGGGCATCAAGCAGCTCCAGGCAAGAGTCCTGGCTGTGGAAAGATACCTAAGGGATCAACAGCTCCTAGGGATT
TGGGGTTGCTCTGGAAAACTCATCTGCACCACTGCTGTGCCTTGGAATGCTAGTTGGAGTAATaAAACTCTGGATATGAT
TTGGGATAACATGACCTGGATGGAGTGGGAAAGAGAAATCGAAAATTACACAGGCTTAATATACACCTTAATTGAAGAAT
CGCAGAACCAACAAGAAAAGAATGAACAAGACTTATTAGCATTAGATAAGTGGGCAAGTTTGTGGAATTGGTTTGACATA
TCAAATTGGCTGTGGTATGTAAAAATCTTCATAATGATAGTAGGAGGCTTGATAGGTTTAAGAATAGTTTTTACTGTACT
TTCTATAGTAAATAGAGTTAGGCAGGGATACTCACCATTGTCATTTCAGACCCACCTCCCAGCCCCGAGGGGACCCGACA
GGCCCGAAGGAATCGAAGAAGAAGGTGGAGACAGAGACAGAGACAGATCCGTGCGATTAGTGGATGGATCCTTAGCACTT
ATCTGGGACGATCTGCGGAGCCTGTGCCTCTTCAGCTACCACCGCTTGAGAGACTTACTCTTGATTGTAACGAGGATTGT
GGAACTTCTGGGACGCAGGGGGTGGGAAGCCCTCAAATATTGGTGGAATCTCCTACAGTATTGGAGTCAGGAGCTAAAGA
ATAGTGCTGTTAGCTTGCTCAATGCCACAGCTATAGCAGTAGCTGAGGGGACAGATAGGGTTATAGAAGTAGTACAAGGA
GCTTATAGAGCTATTCGCCACATACCTAGAAGAATAAGACAGGGCTTGGAAAGGATTTTGCTATAAGATGGGTGGCTAGC
CCCGGGTGATAAACGGACCGCGCAATCCCTAGGCTGTGCCTTCTAGTTGCCAGCCATCTGTTGTTTGCCCCTCCCCCGTG
CCTTCCTTGACCCTGGAAGGTGCCACTCCCACTGTCCTTTCCTAATAAAATGAGGAAATTGCATCGCATTGTCTGAGTAG
GTGTCATTCTATTCTGGGGGGTGGGGTGGGGCAGGACAGCAAGGGGGAGGATTGGGAAGACAATAGCAGGCATGCTGGGG
ATGCGGTGGGCTCTATATAAAAAACGCCCGGCGGCAACCGAGCGTTCTGAACGCTAGAGTCGACAAATTCAGAAGAACTC
GGCAAGAAGGCGATAGAAGGCGATGCGCTGCGAATCGGGAGCGGCGATACCGTAAAGCACGAGGAAGCGGTCAGCCCATT
CGCCGCCAAGCTCTTCAGCAATATCACGGGTAGCCAACGCTATGTCCTGATAGCGGTCTGCCACACCCAGCCGGCCACAG
TCGATGAATCCAGAAAAGCGGCCATTTTCCACCATGATATTCGGCAAGCAGGCATCGCCATGGGTCACGACGAGATCCTC
GCCGTCGGGCATGCTCGCCTTGAGCCTGGCGAACAGTTCGGCTGGCGCGAGCCCCTGATGCTCTTCGTCCAGATCATCCT
GATCGACAAGACCGGCTTCCATCCGAGTACGTGCTCGCTCGATGCGATGTTTCGCTTGGTGGTCGAATGGGCAGGTAGCC
GGATCAAGCGTATGCAGCCGCCGCATTGCATCAGCCATGATGGATACTTTCTCGGCAGGAGCAAGGTGAGATGACAGGAG
ATCCTGCCCCGGCACTTCGCCCAATAGCAGCCAGTCCCTTCCCGCTTCAGTGACAACGTCGAGCACAGCTGCGCAAGGAA
CGCCCGTCGTGGCCAGCCACGATAGCCGCGCTGCCTCGTCTTGCAGTTCATTCAGGGCACCGGACAGGTCGGTCTTGACA
AAAAGAACCGGGCGCCCCTGCGCTGACAGCCGGAACACGGCGGCATCAGAGCAGCCGATTGTCTGTTGTGCCCAGTCATA
GCCGAATAGCCTCTCCACCCAAGCGGCCGGAGAACCTGCGTGCAATCCATCTTGTTCAATCATGCGAAACGATCCTCATC
CTGTCTCTTGATCAGATCTTGATCCCCTGCGCCATCAGATCCTTGGCGGCAAGAAAGCCATCCAGTTTACTTTGCAGGGC
TTCCCAACCTTACCAGAGGGCGCCCCAGCTGGCAATTCCGGTTCGCTTGCTGTCCATAAAACCGCCCAGTCTAGCTATCG
CCATGTAAGCCCACTGCAAGCTACCTGCTTTCTCTTTGCGCTTGCGTTTTCCCTTGTCCAGATAGCCCAGTAGCTGACAT
TCATCCGGGGTCAGCACCGTTTCTGCGGACTGGCTTTCTACGTGAAAAGGATCTAGGTGAAGATCCTTTTTGATAATCTC
ATGACCAAAATCCCTTAACGTGAGTTTTCGTTCCACTGAGCGTCAGACCCCGTAGAAAAGATCAAAGGATCTTCTTGAGA
TCCTTTTTTTCTGCGCGTAATCTGCTGCTTGCAAACAAAAAAACCACCGCTACCAGCGGTGGTTTGTTTGCCGGATCAAG
AGCTACCAACTCTTTTTCCGAAGGTAACTGGCTTCAGCAGAGCGCAGATACCAAATACTGTTCTTCTAGTGTAGCCGTAG
TTAGGCCACCACTTCAAGAACTCTGTAGCACCGCCTACATACCTCGCTCTGCTAATCCTGTTACCAGTGGCTGCTGCCAG
TGGCGATAAGTCGTGTCTTACCGGGTTGGACTCAAGACGATAGTTACCGGATAAGGCGCAGCGGTCGGGCTGAACGGGGG
GTTCGTGCACACAGCCCAGCTTGGAGCGAACGACCTACACCGAACTGAGATACCTACAGCGTGAGCTATGAGAAAGCGCC
ACGCTTCCCGAAGGGAGAAAGGCGGACAGGTATCCGGTAAGCGGCAGGGTCGGAACAGGAGAGCGCACGAGGGAGCTTCC
AGGGGGAAACGCCTGGTATCTTTATAGTCCTGTCGGGTTTCGCCACCTCTGACTTGAGCGTCGATTTTTGTGATGCTCGT
CAGGGGGGCGGAGCCTATGGAAAAACGCCAGCAACGCGGCCCTTTTTACGGTTCCTGGCCTTTTGCTGGCCTTTTGCTCAC
ATGTTGTCGACAATATTGGCTATTGGCCATTGCATACGTTGTATCTATATCATAATATGTACATTTATATTGGCTCATGT
CCAATATGACCGCCATGTTGACATTGATTATTGACTAGTTATTAATAGTAATCAATTACGGGTTCATTAGTTCATAGCCC
ATATATGGAGTTCCGCGTTACATAACTTACGGTAAATGGCCCGCCTGGcTGACCGCCCAACGACCCCCGCCCATTGACGT
CAATAATGACGTATGTTCCCATAGTAACGCCAATAGGGACTTTCCATTGACGTCAATGGGTGGAGTATTTACGGTAAACT
GCCCACTTGGCAGTACATCAAGTGTATCATATGCCAAGTCCGCCCCCTATTGACGTCAATGACGGTAAATGGCCCGCCTG
GCATTATGCCCAGTACATGACCTTACGGGACTTTCCTACTTGGCAGTACATCTACGTATTAGTCATCGCTATTACCATGG
TGATGCGGTTTTGGCAGTACACCAATGGGCGTGGATAGCGGTTTGACTCACGGGGATTTCCAAGTCTCCACCCCATTGAC
GTCAATGGGAGTTTGTTTTGGCACCAAAATCAACGGGACTTTCCAAAATGTCGTAATAACCCCGCCCCGTTGACGCAAAT
GGGCGGTAGGCGTGTACGGTGGGAGGTCTATATAAGCAGAGCTCGTTTAGTGAACCGTCAGATCGC

FIG. 11C pGA2/JS7 Functional Regions

| **Position within sequence (starting and ending pos.)** | **Gene/ORF (indicate complete name of the gen and the expressed gene product)** | **Origin of sequence (organism)** |
|---|---|---|
| 106-1608 | Gag, inactivating point mutations in zinc finger packaging sequences for viral RNA | HIV-1 HXB2 |
| 1401-3584 | Pol, inactivating point mutations in reverse transcriptase, deletion of integrase | HIV-1 HXB2 |
| 3671-3885 and 6210-6300 | Tat exons #1 and #2 | |
| 3810-3885 and 6210-6884 | Rev exons #1 and #2 | |
| 3902-4147 | Vpu | |
| 4165-6626 | Env | HIV-ADA |
| 6627-9506 | Plasmid vector | pGA2, GenBank accession # AF425298 |

FIG. 11D JS7 Mutation Chart

| Codon Change | Amino acid change | Region | Function |
|---|---|---|---|
| to AGC Position 1279-1281 | C392S | Gag | Ablation of zinc finger used in packaging |
| to AGC Position 1288-1290 | C395S | Gag | Ablation of zinc finger used in packaging |
| to AGC Position 1342-1344 | C413S | Gag | Ablation of zinc finger used in packaging |
| to AGC Position 1351-1353 | C416S | Gag | Ablation of zinc finger used in packaging |
| to ACA Position 1641-1643 | D25A | Protease | Inactivation of Protease active site |
| to AAC Position 2418-2420 | D185N | Reverse Transcriptase | Inactivation of Polymerase active site |
| to ACC Position 2661-2663 | W266T | Reverse Transcriptase | Ablation of strand transfer activity |
| to CAG Position 3297-3299 | E478Q | RNase H | Inactivation of RNase H activity |

FIG. 12A pGA2/JS7.1 Sequence atcgatgcaggactcggcttgctgaagcgcgcacggcaagaggcgaggggcggcgactggtgagtacgccaaaatt
ttgactagcggaggctagaaggagagagatgggtgcgagagcgtcagtattaagcgggggagaattagatcgatggg
aaaaaattcggttaaggccagggggaaagaaaaaatataaattaaaacatatagtatgggcaagcagggagctagaa
cgattcgcagttaatcctggcctgttagaaacatcagaaggctgtagacaaatactgggacagctacaaccatccct
tcagacaggatcagaagaacttagatcattatataatacagtagcaaccctctattgtgtgcatcaaaggatagaga
taaaagacaccaaggaagctttagacaagatagaggaagagcaaaacaaaagtaagaaaaaagcacagcaagcagca
gctgacacaggacacagcaatcaggtcagccaaaattaccctatagtgcagaacatccaggggcaaatggtacatca
ggccatatcacctagaactttaaatgcatgggtaaaagtagtagaagagaaggctttcagcccagaagtgataccca
tgttttcagcattatcagaaggagccaccccacaagatttaaacaccatgctaaacacagtgggggggacatcaagca
gccatgcaaatgttaaaagagaccatcaatgaggaagctgcagaatgggatagagtgcatccagtgcatgcagggcc
tattgcaccaggccagatgagagaaccaaggggaagtgacatagcaggaactactagtacccttcaggaacaaatag
gatggatgacaaataatccacctatcccagtaggagaaatttataaaagatggataatcctgggattaaataaaata
gtaagaatgtatagccctaccagcattctggacataagacaaggaccaaaagaaccctttagagactatgtagaccg
gttctataaaactctaagagccgagcaagcttcacaggaggtaaaaaattggatgacagaaaccttgttggtccaaa
atgcgaacccagattgtaagactattttaaaagcattgggaccagcggctacactagaagaaatgatgacagcatgt
cagggagtaggaggacccggccataaggcaagagttttggctgaagcaatgagccaagtaacaaattcagctaccat
aatgatgcagagaggcaattttaggaaccaaagaaagattgttaagagcttcaatagcggcaaagaagggcacacag
ccagaaattgcagggcccctaggaaaaagggcagctggaaaagcggaaaggaaggacaccaaatgaaagattgtact
gagagacaggctaatttttttagggaagatctggccttcctacaagggaaggccagggaattttcttcagagcagacc
agagccaacagccccaccagaagagagcttcaggtctggggtagagacaacaactccccctcagaagcaggagccga
tagacaaggaactgtatcctttaacttccctcagatcactctttggcaacgacccctcgtcacaataaagatagggg
ggcaactaaaggaagctctattagccacaggagcagatgatacagtattagaagaaatgagtttgccaggaagatgg
aaaccaaaaatgatagggggaattggaggttttatcaaagtaagacagtatgatcagatactcatagaaatctgtgg
acataaagctataggtacagtattagtaggacctacacctgtcaacataattggaagaaatctgttgactcagattg
gttgcactttaaattttcccattagccctattgagactgtaccagtaaaattaaagccaggaatggatggcccaaaa
gttaaacaatggccattgacagaagaaaagataaaagcattagtagaaatttgtacagagatggaaaaggaagggaa
aatttcaaaaattgggcctgaaaatccatacaatactccagtatttgccataaagaaaaaagacagtactaaatgga
gaaaattagtagatttcagagaacttaataagagaactcaagacttctgggaagttcaattaggaataccacatccc
gcagggttaaaaaagaaaaaatcagtaacagtactggatgtgggtgatgcatatttttcagttcccttagatgaaga
cttcaggaaatatactgcatttaccatacctagtataaacaatgagacaccagggattagatatcagtacaatgtgc
ttccacagggatggaaaggatcaccagcaatattccaaagtagcatgacaaaaatcttagagccttttagaaaacaa
aatccagacatagttatctatcaatacatgaacgatttgtatgtaggatctgacttagaaatagggcagcatagaac
aaaaatagaggagctgagacaacatctgttgaggtggggacttaccacaccagacaaaaaacatcagaaagaacctc
cattcctttggatgggttatgaactccatcctgataaatggacagtacagcctatagtgctgccagaaaaagacagc
tggactgtcaatgacatacagaagttagtggggaaattgaataccgcaagtcagatttacccagggattaaagtaag
gcaattatgtaaactccttagaggaaccaaagcactaacagaagtaataccactaacagaagaagcagagctagaac
tggcagaaaacagagagattctaaaagaaccagtacatggagtgtattatgacccatcaaaagacttaatagcagaa
atacagaagcaggggcaaggccaatggacatatcaaatttatcaagagccatttaaaaatctgaaaacaggaaaata
tgcaagaatgaggggtgcccacactaatgatgtaaaacaattaacagaggcagtgcaaaaaataaccacagaaagca
tagtaatatggggaaagactcctaaatttaaactgcccatacaaaaggaaacatgggaaacatggtggacagagtat
tggcaagccacctggattcctgagtgggagtttgttaatacccctcctttagtgaaattatggtaccagttagagaa
agaacccatagtaggagcagaaaccttctatgtagatggggcagctaacagggagactaaattaggaaaagcaggat
atgttactaatagaggaagacaaaaagttgtcaccctaactaacacaacaaatcagaaaactcagttacaagcaatt
tatctagctttgcaggattcgggattagaagtaaacatagtaacagactcacaatatgcattaggaatcattcaagc
acaaccagatcaaagtgaatcagagttagtcaatcaaataatagagcagttaataaaaaaggaaaaggtctatctgg
catgggtaccagcacacaaaggaattggaggaaatgaacaagtagataaattagtcagtgctggaatcaggaaagta
ctatttttagatggaatagataaggcccaagatgaacattagaattctgcaacaactgctgtttatccatttcagaa
ttgggtgtcgacatagcagaataggcgttactcgacagaggagagcaagaaatggagccagtagatcctagactaga
gccctggaagcatccaggaagtcagcctaaaactgcttgtaccaattgctattgtaaaaagtgttgctttcattgcc
aagtttgtttcataacaaaagccttaggcatctcctatggcaggaagaagcggagacagcgacgaagagctcctcaa
gacagtcagactcatcaagtttctctatcaaagcagtaagtagtaaatctaatccaacctttacaatattagcaat
agtagcattagtagtagcagcaataatagcaatagttgtgtggaccatagtattcatagaatataggaaaatattaa
gacaaagaaaaatagacaggttaattgataggataacagaaagagcagaagacagtggcaatgaaagtgaaggggat
caggaagaattatcagcacttgtggaaatggggcatcatgctccttgggatgttgatgatctgtagtgctgtagaaa
atttgtgggtcacagtttattatggggtacctgtgtggaaagaagcaaccaccactctattttgtgcatcagatgct

FIG. 12B aaagcatatgatacagaggtacataatgtttgggccacacatgcctgtgtacccacagaccccaacccacaagaagt
agtattggaaaatgtgacagaaattttaacatgtggaaaaataacatggtagaacagatgcatgaggatataatca
gtttatgggatcaaagcctaaagccatgtgtaaaattaaccccactctgtgttactttaaattgcactgatttgagg
aatgttactaatatcaataatagtagtgagggaatgagaggagaaataaaaaactgctctttcaatatcaccacaag
cataagagataaggtgaagaaagactatgcactttttttatagacttgatgtagtaccaatagataatgataatacta
gctataggttgataaattgtaatacctcaaccattacacaggcctgtccaaaggtatcctttgagccaattcccata
cattattgtaccccggctggttttgcgattctaaagtgtaaagacaagaagttcaatggaacagggccatgtaaaaa
tgtcagcacagtacaatgtacacatggaattaggccagtagtgtcaactcaactgctgttaaatggcagtctagcag
aagaagaggtagtaattagatctagtaatttcacagacaatgcaaaaaacataatagtacagttgaaagaatctgta
gaaattaattgtacaagacccaacaacaatacaaggaaaagtatacatataggaccaggaagagcattttatacaac
aggagaaataataggagatataagacaagcacattgcaacattagtagaacaaaatggaataacactttaaatcaaa
tagctacaaaattaaaagaacaatttgggaataataaaacaatagtctttaatcaatcctcaggaggggacccagaa
attgtaatgcacagttttaattgtggaggggaattttctactgtaattcaacacaactgtttaatagtacttggaa
ttttaatggtacttggaatttaacacaatcgaatggtactgaaggaaatgacactatcacactcccatgtagaataa
aacaaattataaatatgtggcaggaagtaggaaaagcaatgtatgcccctcccatcagaggacaaattagatgctca
tcaaatattacagggctaatattaacaagagatggtggaactaacagtagtgggtccgagatcttcagacctgggg
aggagatatgagggacaattggagaagtgaattatataaatataaagtagtaaaaattgaaccattaggagtagcac
ccaccaaggcaaaaagaagagtggtgcagagagaaaaaagagcagtgggaacgataggagctatgttccttgggttc
ttgggagcagcaggaagcactatgggcgcagcgtcaataacgctgacggtacaggccagactattattgtctggtat
agtgcaacagcagaacaatttgctgagggctattgaggcgcaacagcatctgttgcaactcacagtctggggcatca
agcagctccaggcaagagtcctggctgtggaaagatacctaagggatcaacagctcctagggatttggggttgctct
ggaaaactcatctgcaccactgctgtgccttggaatgctagttggagtaataaaactctggatatgatttgggataa
catgacctggatggagtgggaaagagaaatcgaaaattacacaggcttaatatacaccttaattgaagaatcgcaga
accaacaagaaaagaatgaacaagacttattagcattagataagtgggcaagtttgtggaattggtttgacatatca
aattggctgtggtatgtaaaaatcttcataatgatagtaggaggcttgataggtttaagaatagtttttactgtact
ttctatagtaaatagagttaggcagggatactcaccattgtcatttcagacccacctcccagccccgaggggacccg
acaggcccgaaggaatcgaagaagaaggtggagacagagacagagacagatccgtgcgattagtggatggatcctta
gcacttatctgggacgatctgcggagcctgtgcctcttcagctaccaccgcttgagagacttactcttgattgtaac
gaggattgtggaacttctgggacgcagggggtgggaagccctcaaatattggtggaatctcctacagtattggagtc
aggagctaaagaatagtgctgttagcttgctcaatgccacagctatagcagtagctgaggggacagatagggttata
gaagtagtacaaggagcttatagagctattcgccacatacctagaagaataagacagggcttggaaaggattttgct
ataagatgggtggctagccccgggtgataaacggaccgcgcaatccctaggctgtgccttctagttgccagccatct
gttgtttgcccctcccccgtgccttccttgaccctggaaggtgccactcccactgtcctttcctaataaaatgagga
aattgcatcgcattgtctgagtaggtgtcattctattctggggggtggggtggggcaggacagcaagggggaggatt
gggaagacaatagcaggcatgctggggatgcggtgggctctatataaaaaacgcccggcggcaaccgagcgttctga
acgctagagtcgacaaattcagaagaactcgtcaagaaggcgatagaaggcgatgcgctgcgaatcgggagcggcga
taccgtaaagcacgaggaagcggtcagcccattcgccgccaagctcttcagcaatatcacgggtagccaacgctatg
tcctgatagcggtctgccacacccagccggccacagtcgatgaatccagaaaagcggccattttccaccatgatatt
cggcaagcaggcatcgccatgggtcacgacgagatcctcgccgtcgggcatgctcgccttgagcctggcgaacagtt
cggctggcgcgagcccctgatgctcttcgtccagatcatcctgatcgacaagaccggcttccatccgagtacgtgct
cgctcgatgcgatgtttcgcttggtggtcgaatgggcaggtagccggatcaagcgtatgcagccgccgcattgcatc
agccatgatggatactttctcggcaggagcaaggtgagatgacaggagatcctgccccggcacttcgcccaatagca
gccagtcccttcccgcttcagtgacaacgtcgagcacagctgcgcaaggaacgcccgtcgtggccagccacgatagc
cgcgctgcctcgtcttgcagttcattcagggcaccggacaggtcggtcttgacaaaaagaaccgggcgcccctgcgc
tgacagccggaacacggcggcatcagagcagccgattgtctgttgtgcccagtcatagccgaatagcctctccaccc
aagcggccggagaacctgcgtgcaatccatcttgttcaatcatgcgaaacgatcctcatcctgtctcttgatcagat
cttgatcccctgcgccatcagatccttggcggcragaaagccatccagtttactttgcagggcttcccaaccttacc
agagggcgccccagctggcaattccggttcgcttgctgtccataaaaccgcccagtctagctatcgccatgtaagcc
cactgcaagctacctgctttctctttgcgcttgcgtttcccttgtccagatagcccagtagctgacattcatccgg
ggtcagcaccgtttctgcggactggctttctacgtgaaaaggatctaggtgaagatcctttttgataatctcatgac
caaaatcccttaacgtgagttttcgttccactgagcgtcagaccccgtagaaaagatcaaaggatcttcttgagatc
ctttttttctgcgcgtaatctgctgcttgcaaacaaaaaaaccaccgctaccagcggtggtttgtttgccggatcaa
gagctaccaactctttttccgaaggtaactggcttcagcagagcgcagataccaaatactgttcttctagtgtagcc
gtagttaggccaccacttcaagaactctgtagcaccgcctacatacctcgctctgctaatcctgttaccagtggctg
ctgccagtggcgataagtcgtgtcttaccgggttggactcaagacgatagttaccggataaggcgcagcggtcgggc
tgaacggggggttcgtgcacacagcccagcttggagcgaacgacctacaccgaactgagatacctacagcgtgagct
atgagaaagcgccacgcttcccgaagggagaaaggcggacaggtatccggtaagcggcagggtcggaacaggagagc

FIG. 12C gcacgagggagcttccagggggaaacgcctggtatctttatagtcctgtcgggtttcgccacctctgacttgagcgt
cgatttttgtgatgctcgtcaggggggcggagcctatggaaaaacgccagcaacgcggcctttttacggttcctggc
cttttgctggccttttgctcacatgttgtcgacaatattggctattggccattgcatacgttgtatctatatcataa
tatgtacatttatattggctcatgtccaatatgaccgccatgttgacattgattattgactagttattaatagtaat
caattacgggktcattagttcatagcccatatatggagttccgcgttacataacttacggtaaatggcccgcctggc
tgaccgcccaacgacccccgcccattgacgtcaataatgacgtatgttcccatagtaacgccaatagggactttcca
ttgacgtcaatgggtggagtatttacggtaaactgcccacttggcagtacatcaagtgtatcatatgccaagtccgc
ccctattgacgtcaatgacggtaaatggcccgcctggcattatgcccagtacatgaccttacgggactttcctactt
ggcagtacatctacgtattagtcatcgctattaccatggtgatgcggttttggcagtacaccaatgggcgtggatag
cggtttgactcacggggatttccaagtctccaccccattgacgtcaatgggagtttgttttkgscaccaaaatcaacg
ggactttccaaaatgtcgtaataaccccgccccgttgacgcaaatgggcggtaggcgtgtacggtgggaggtctata
taagcagagctcgtttagtgaaccgtcagatcgc FIG. 12D pGA2/JS7.1 Functional Regions

| **Position within sequence (starting and ending pos.)** | **Gene/ORF (indicate complete name of the gen and the expressed gene product)** | **Origin of sequence (organism)** |
|---|---|---|
| 106-1608 | Gag, inactivating point mutations in zinc finger packaging sequences for viral RNA | HIV-1 HXB2 |
| 1401-3584 | Pol, inactivating point mutations in reverse transcriptase, deletion of integrase | HIV-1 HXB2 |
| 3671-3885 and 6210-6300 | Tat exons #1 and #2 | HIV-1 ADA |
| 3810-3885 and 6210-6884 | Rev exons #1 and #2 | HIV-1 ADA |
| 3902-4147 | Vpu start site mutated (G3904C) and upstream ATG mutated (G3899C) | HIV-1 ADA |
| 4165-6626 | Env | HIV-1 ADA |
| 6627-9506 | Plasmid vector | pGA2, GenBank accession # AF425298 |

FIG. 12E JS7.1 Mutation Chart

| Codon Change | Amino acid change | Region | Function |
|---|---|---|---|
| to AGC Position 1279-1281 | C392S | Gag | Ablation of zinc finger used in packaging |
| to AGC Position 1288-1290 | C395S | Gag | Ablation of zinc finger used in packaging |
| to AGC Position 1342-1344 | C413S | Gag | Ablation of zinc finger used in packaging |
| to AGC Position 1351-1353 | C416S | Gag | Ablation of zinc finger used in packaging |
| to ACA Position 1641-1643 | D25A | Protease | Inactivation of Protease active site |
| to AAC Position 2418-2420 | D185N | Reverse Transcriptase | Inactivation of Polymerase active site |
| to ACC Position 2661-2663 | W266T | Reverse Transcriptase | Ablation of strand transfer activity |
| to CAG Position 3297-3299 | E478Q | RNase H | Inactivation of RNase H activity |
| to ATC Position 3902-3904 | NA | Vpu | Vpu start site mutated |
| to ATC 3299 Position 3897-3899 | NA | Non-coding region | ATG upstream of Vpu mutated |

FIG. 13A pGA1/IC25 Sequence atcgatgcaaggactcggcttgctgaggtgcacacagcaagaggcgagagcgacgactggtgagtacgccaattttgac
tagcggaggctagaaggagagagatgggtgcgagagcgtcagtgttaacgggggaaaattagattcatgggagaaaatt
aggttaaggccagggggaaagaaaagatatagactaaaacacctagtatgggcaagcagggagctggagagattcgcact
taaccctggcctattagaaacagcagaaggatgtcaacaactaatgggacagttacaaccagctctcaggacaggatcag
aagagtttaaatcattatataatatagtagcaaccctttggtgcgtacatcaaagaatagacataaaagacacccaggag
gccttagataaagtagaggaaaaacaaaataagagcaagcaaaaggcacagcaggcagcagctgcaacagccgccacagg
aagcagcagccaaaattaccctatagtgcaaaatgcacaagggcaaatggtacatcagtccatgtcacctaggactttaa
atgcatgggtgaaggtaatagaagaaaaggcttttagcccagaggtaatacccatgttttcagcattatcagagggagcc
accccacaagatttaaatatgatgctaaacatagtgggggacaccaggcagcaatgcagatgttaaaagataccatcaa
tgatgaagctgcagaatgggacagagtacatccagtacatgcagggcctattccaccaggccaaatgagggaaccaaggg
gaagtgacatagcaggaactactagtacccttcaagaacaaataggatggatgacaagtaatccacctatcccagtggga
gaaatctataaaagatggatagtcctgggattaaataaaatagtaagaatgtatagccctaccagcattttggacataag
acaagggccaaaagaaccctttagagattatgtagacaggttctttaaaactttgagagctgaacaagctacgcaggagg
taaaaaactggatgacagaaaccttgttggtccaaaatgcgaatccagactgcaagtccattttaagagcattaggacca
ggggctacattagaagaaatgatgacatcatgtcagggagtgggaggacctggccataaagcaagggttttggctgaggc
aatgagtcaagtacaacagaccaatgtaatgatgcagagaggcaattttagaggccagagaataataaagagcttcaaca
gcggcaaagaaggacacctagccagaaattgcaaggctcctagaaagagaggcagctggaaaagcggaaaggaaggacac
caaatgaaagactgtactgaaagacaggctaattttttagggaaaatttggccttcccacaaggggaggccaggaaattt
tcctcagagcagaccagaaccaacagccccgccagcagagagctttggagtgggggaagagataccctcctctccgaagc
aggagccgagggacaagggactatatcctcccttaacttccctcaaatcactctttggcaacgaccagtagtcacagtaa
gaataggggggacagccaatagaagccctattaaacacaggagcagatgatacagtattagaagaaataagtttaccagga
aaatggaaaccaaaaatgatagggggaattggaggttttatcaaagtaagacagtatgatcagatatctatagaaatttg
tggaaaaagggccataggtacagtattagtaggacctacacctgtcaacataattggacgaaatatgttgactcagattg
gttgtactttaaattttccaattagtcctattgaaactgtgccagtaaaattaaagtcaggaatggatggcccaaaggtt
aaacaatggccattgacagaagaaaaaataaaagcattaaaagaaatttgtgcagagatggaaaaggaaggaaaaatttc
aaaaattgggcctgaaaacccatacaatactccaatatttgccataaagaaaaaagatagtactaaatggagaaaattag
tagatttcagagaactcaataagagaactcaagacttctgggaggtccaattaggaatacctcatcctgcgggattaaaa
aagaaaaaatcagtaacagtactagatgtgggggatgcatatttttcagttcccttagatgaagactttagaaaatatac
tgcattcaccatacctagtttaaataatgagacaccagggattagatatcagtacaatgtactcccacagggatggaaag
gatcaccagcaatatttcaggcaagcatgacaaaaatcttagagccctttagagcaaaaaatccagagatagtgatctac
caatatatgaacgatttatatgtaggatctgacttagaaatagggcagcatagagcaaaaatagaggagttgagagaaca
tctattgaaatggggatttaccacaccagacaaaaaacatcagaaagaacctccatttctttggatgggatatgaactcc
atcctgacaaatggacagtccagcctatacagctgccagaaaaagacagctggactgtcaatgatatacaaaaattagtg
ggaaaactaaataccgcaagtcagatttatgcaggaattaaagtaaagcaattgtgtagactcctcaggggagccaaagc
gctaacagatgtagtaacactgactgaggaagcagaattagaattggcagagaacagggaaattctaaaagaacctgtac
atggagtatattatgacccaacaaaagacttagtggcagaaatacagaaacaagggcaagatcaatggacatatcaaatt
tatcaagagccatttaaaaatctaaagacaggaaaatatgcaaaaagaggtcggcccacactaatgatgtaaaacaatt
aacagaggtagtgcagaaaatagccatagaaagcatagtaatatggggaaagacccctaaatttagactacccatacaaa
gagaaacatggaagcatggtggatggagtattggcaggctacctggattcctgaatgggagtttgtcaatacccctcct
ctagtaaaattatggtaccagttagagaaggaccccataatgggagcagaaactttctatgtagatggggcagctaatag
ggagactaagctaggaaaagcagggtatgtcactgacagaggaagacaaaaggttgtttccctaattcagacaacaaatc
aaaagactcagttacatgcaattcatctagccttgcaggattcaggatcagaagtaaatatagtaacagactcacagtat
gcattaggaatcattcaggcacaaccagacaggagtgaatcagagttagtcaatcaaataatagagaaactaatagaaaa
ggacaaagtctacctgtcatgggtaccagcacacaaagggattggaggaaatgaacaagtagataaattagtcagtagtg
gaatcagaaaggtactatttttagatggaatagataaagcccaagatgaacattagaattctgcaacagctactgtttgt
tcatttcagaattgggtgtcaacatagcagaataggcattattccagggagaagaggcaggaatggagctggtagatcct
agcctagagccctggaaccacccgggaagtcagcctacaactgcttgtagcaagtgttactgtaaaaaatgctgctggca
ttgccaattgtgctttctgaacaagggcttaggcatctcctatggcaggaagaagcggagacgccgacgaggaactcctc
aggaccgtcaggttcatcaaaatcctgtaccaaaacagtaagtagtagtaattagtatatgtgatgcaatctttacaaat
agctgcaatagtaggactagtagtagcatccatagtagccatagttgtgtggtccatagtatttatagaatatagaaaaa
taaggaaacagaagaaaatagacaggttacttgagagaataagagaaagagcagaagatagtggcaatgagagtgatggg
gatacagaagaattatccactcttatggagagggggtatgacaatatttggttaatgatgatttgtaatgctgaaaagt
tgtgggtcacagtctactatggggtacctgtgtggagagacgcagagaccaccctattctgtgcatcagatgctaaagca
tatgacaaagaagcacacaatgtctgggctacgcatgcctgcgtacccacagaccctgacccacaagaattacctttggt
aaatgtaacagaagagtttaacatgtggaaaaataatatggtagaacagatgcatgaagatataattagtctatgggacc
aaagcttaaagccatgtgtacagctaacccctctctgcgttactttagggtgtgctgacgctcaaaacgtcaccgacacc
aacaccaccatatctaatgaaatgcaaggggaaataaaaaactgctctttcaatatgaccacagaattaagagataagaa
gcagaaagtgtatgcactttttatagacctgatgtaatagaaattaataaaactaagattaacaatagtaatagtagtc
agtatatgttaataaattgtaatacctcaaccattacacagacttgtccaaaggtatcctttgagccaattcccatacat
tattgtgccccagctggttttgcaattctaaagtgtaatgatacggagttcagtggaaaagggacatgcaagagtgtcag
cacagtacaatgcacacatggaatcaagccagtagtatcaactcaactgctgttaaatggcagtctagcagaaggaaaga

FIG. 13B tagcgattagatctgagaatatctcaaacaatgccaaaactataatagtacaattgactgagcctgtagaaattaattgt
atcagacctggcaacaatacaagaaaaagtgtacgcataggaccaggacaaacattctatgcaacaggtgacataatagg
agatataagacaagcacactgtaatgttagtaaaatagcatgggaagaaactttacaaaaggtagctgcacaattaagga
agcactttcagaatgccacaataaaatttactaaacactcaggaggggatttagaaattacaacaaatagttttaattgt
ggaggagaatttttctattgcaatacaacaaagctgtttaatagcacttggaataatgataactcaaacctcacagagga
aaagagaaaggaaaacataactctccactgcagaataaagcaaattgtaaatatgtggccaagagtaggacaagcaatat
atgcccctcccatcccaggaaacataacttgtggatcaaacattactgggctactattaacaagagatggagggaataat
ggtacaaatgatactgagaccttcaggcctggaggaggagatatgagggacaattggagaagtgaattatataaatataa
agtagtaaaaattgaaccactaggtgtagcaccaacccctgcaaaaagaagagtggtggaaagagaaaaaagagcagttg
gaatgggagctttgatctttgagttcttaggagcagcaggaagcactatgggcgcggcgtcaatggcgctgacggtacag
gccagacaattattgtctggtatagtgcaacagcagagcaatctgctgaaggctatagaggctcaacaacatctgttgag
actcacggtctggggcattaaacagctccaggcaagagtcctggctctggaaagatacctaaaggatcaacagctcctag
gaatttggggctgctctggaaaactcatttgcaccactgctgtaccttggaactctagctggagtaataaaagttataat
gacatatgggataacatgacctggctgcaatgggataaagaaattaacaattacacatacataatatataatctacttga
aaaatcgcagaaccagcaggaaattaatgaacaagacttattggcattagacaagtgggcaagtctgtggaattggtttg
acataacaagctggctatggtatataagattaggtataatgatagtaggaggcgtaataggcttaagaataatttttgct
gtgcttactatagtgaatagagttaggcagggatactcacctttgtcattccagacccttgcccaccaccagagggaacc
cgacaggcccgaaagaatcgaagaaggaggtggcgagcaagacagagagagatccgtgcgcttagtgagcggattcttag
cacttgcctgggaagatctgcggagcctgtgcctcttcagctaccgccgattgagagacttagtcttgattgcagcaagg
actgtggaactcctgggacacagcagtctcaagggactgagactggggtgggaagccctcaaatatctgtggaaccttct
atcatactggggtcaggaactaaagaatagtgctattaatttgcttgatacaatagcaatagcagtagctaactggacag
atagagttataaaaatagtacaaagaactggtagagctattcttaacatacctagaaggatcagatagggctagccccgg
gtgataaacggaccgcgcaatccctaggctgtgccttctagttgccagccatctgttgtttgcccctcccccgtgccttc
cttgaccctggaaggtgccactcccactgtcctttcctaataaaatgaggaaattgcatcgcattgtctgagtaggtgtc
attctattctggggggtggggtggggcaggacagcaagggggaggattgggaagacaatagcaggcatgctggggatgcg
gtgggctctatataaaaaacgcccggcggcaaccgagcgttctgaacgctagagtcgacaaattcagaagaactcgtcaa
gaaggcgatagaaggcgatgcgctgcgaatcgggagcggcgataccgtaaagcacgaggaagcggtcagcccattcgccg
ccaagctcttcagcaatatcacgggtagccaacgctatgtcctgatagcggtctgccacacccagccggccacagtcgat
gaatccagaaaagcggccattttccaccatgatattcggcaagcaggcatcgccatgggtcacgacgagatcctcgccgt
cgggcatgctcgccttgagcctggcgaacagttcggctggcgcgagcccctgatgctcttcgtccagatcatcctgatcg
acaagaccggcttccatccgagtacgtgctcgctcgatgcgatgtttcgcttggtggtcgaatgggcaggtagccggatc
aagcgtatgcagccgccgcattgcatcagccatgatggatactttctcggcaggagcaaggtgagatgacaggagatcct
gccccggcacttcgcccaatagcagccagtcccttcccgcttcagtgacaacgtcgagcacagctgcgcaaggaacgccc
gtcgtggccagccacgatagccgcgctgcctcgtcttgcagttcattcagggcaccggacaggtcggtcttgacaaaaag
aaccgggcgcccctgcgctgacagccggaacacggcggcatcagagcagccgattgtctgttgtgcccagtcatagccga
atagcctctccacccaagcggccggagaacctgcgtgcaatccatcttgttcaatcatgcgaaacgatcctcatcctgtc
tcttgatcagatcttgatcccctgcgccatcagatccttggcggcaagaaagccatccagtttactttgcagggcttccc
aaccttaccagagggcgccccagctggcaattccggttcgcttgctgtccataaaaccgcccagtctagctatcgccatg
taagcccactgcaagctacctgctttctctttgcgcttgcgttttcccttgtccagatagcccagtagctgacattcatc
cggggtcagcaccgtttctgcggactggctttctacgtgaaaaggatctaggtgaagatcctttttgataatctcatgac
caaaatcccttaacgtgagttttcgttccactgagcgtcagaccccgtagaaaagatcaaaggatcttcttgagatcctt
tttttctgcgcgtaatctgctgcttgcaaacaaaaaaaccaccgctaccagcggtggtttgtttgccggatcaagagcta
ccaactctttttccgaaggtaactggcttcagcagagcgcagataccaaatactgttcttctagtgtagccgtagttagg
ccaccacttcaagaactctgtagcaccgcctacatacctcgctctgctaatcctgttaccagtggctgctgccagtggcg
ataagtcgtgtcttaccgggttggactcaagacgatagttaccggataaggcgcagcggtcgggctgaacggggggttcg
tgcacacagcccagcttggagcgaacgacctacaccgaactgagatacctacagcgtgagctatgagaaagcgccacgct
tcccgaagggagaaaggcggacaggtatccggtaagcggcagggtcggaacaggagagcgcacgagggagcttccagggg
gaaacgcctggtatctttatagtcctgtcgggtttcgccacctctgacttgagcgtcgatttttgtgatgctcgtcaggg
gggcggagcctatggaaaaacgccagcaacgcggcctttttacggttcctggccttttgctggccttttgctcacatgtt
gtcgacaatattggctattggccattgcatacgttgtatctatatcataatatgtacatttatattggctcatgtccaat
atgaccgccatgttgacattgattattgactagttattaatagtaatcaattacgggttcattagttcatagcccatata
tggagttccgcgttacataacttacggtaaatggcccgcctggctgaccgcccaacgacccccgcccattgacgtcaata
atgacgtatgttcccatagtaacgccaatagggactttccattgacgtcaatgggtggagtatttacggtaaactgccca
cttggcagtacatcaagtgtatcatatgccaagtccgccccctattgacgtcaatgacggtaaatggcccgcctggcatt
atgcccagtacatgaccttacgggactttcctacttggcagtacatctacggtattagtcatcggctattaccatggtga
tgcggttttggcagtacaccaatgggcgtggatagcggtttgactcacggggatttccaagtctccaccccattgacgtc
aatgggagtttgttttggcaccaaaatcaacgggactttccaaaatgtcgtaataaccccgccccgttgacgcaaatggg
cggtaggcgtgtacggtgggaggtctatataagcagagctcgtttagtgaaccgtcagatcgcctggagacgccatccac
gctgttttgacctccatagaagacaccgggaccgatccagcctccgcggccgggaacggtgcattggaacgcggattccc
cgtgccaagagtgacgtaagtaccgcctatagactctataggcacacccctttggctcttatgcatgctatactgttttt
ggcttggggcctatacacccccgcttccttatgctataggtgatggtatagcttagcctataggtgtgggttattgacca
ttattgaccactcccctattggtgacgatactttccattactaatccataacatggctctttgccacaactatctctatt
ggctatatgccaatactctgtccttcagagactgacacggactctgtatttttacaggatggggtcccatttattattta

FIG. 13C caaattcacatatacaacaacgccgtcccccgtgcccgcagtttttattaaacatagcgtgggatctccacgcgaatctc
gggtaccgtgttccggacatgggytcttctccggtagcggcggagcttccacatccgagccctggtcccatgcctccagc
ggctcatggtcgctcggcagctccttgctcctaacagtggaggccagacttaggcacagcacaatgcccaccaccaccag
tgtgccgcacaaggccgtggcggtagggtatgtgtctgaaaatgagctcggagattgggctcgcaccgctgacgcagatg
gaagacttaaggcagcggcagaagaagatgcaggcagctgagttgttgtattctgataagagtcagaggtaactcccgtt
gcggtgctgttaacggtggagggcagtgtagtctgagcagtactcgttgctgccgcgcgcgccaccagacataatagctg
acagactaacagactgttcctttccatgggtcttttctgcagtcacc FIG. 13D pGA1/IC25 Functional Regions

| **Position within sequence (starting and ending pos.)** | **Gene/ORF (indicate complete name of the gen and the expressed gene product)** | **Origin of sequence (organism)** |
|---|---|---|
| 104-1591 | Gag, inactivating point mutations in zinc finger packaging sequences for viral RNA | AG HIV-1 isolate 928 |
| 1393-3576 | Pol, inactivating point mutations in reverse transcriptase, deletion of integrase | AG HIV-1 isolate 928 |
| 3663-3877 and 6215-6305 | Tat exons #1 and #2 | AG HIV-1 isolate 928 |
| 3802-3877 and 6215-3510 | Rev exons #1 and #2 | AG HIV-1 isolate 928 |
| 3904-4149 | Vpu | AG HIV-1 isolate 928 |
| 4067-6628 | Env | AG HIV-1 isolate 928 |
| 6629-10447 | Plasmid vector | pGA1, GenBank accession # AF425297 |

FIG. 13E IC25 Mutation Chart

| Codon Change | Amino acid change | Region | Function |
|---|---|---|---|
| to AGC Position 1271-1273 | C390S | Gag | Ablation of zinc finger used in packaging |
| to AGC Position 1280-1282 | C393S | Gag | Ablation of zinc finger used in packaging |
| to AGC Position 1334-1336 | C411S | Gag | Ablation of zinc finger used in packaging |
| to AGC Position 1343-1345 | C414S | Gag | Ablation of zinc finger used in packaging |
| to ACA Position 1633-1635 | R25N | Protease | Inactivation of Protease active site |
| to AAC Position 2410-2412 | D185N | Reverse Transcriptase | Inactivation of Polymerase active site |
| to ACC Position 2653-2655 | W266T | Reverse Transcriptase | Ablation of strand transfer activity |
| to CAG Position 3289-3291 | E478Q | RNase H | Inactivation of RNase H activity |

FIG. 14A pGA1/IC2 Sequence atcgatgcaaggactcggcttgctgaggtgcacacagcaagaggcgagagcgacgactggtgagtacgccaattttgac
tagcggaggctagaaggagagagatgggtgcgagagcgtcagtgttaacgggggaaaattagattcatgggagaaaatt
aggttaaggccagggggaaagaaaagatatagactaaaacacctagtatgggcaagcagggagctggagagattcgcact
taaccctggcctattagaaacagcagaaggatgtcaacaactaatggacagttacaaccagctctcaggacaggatcag
aagagtttaaatcattatataatatagtagcaaccctttggtgcgtacatcaaagaatagacataaaagacacccaggag
gccttagataaagtagaggaaaaacaaaataagagcaagcaaaaggcacagcaggcagcagctgcaacagccgccacagg
aagcagcagccaaaattaccctatagtgcaaaatgcacaagggcaaatggtacatcagtccatgtcacctaggactttaa
atgcatgggtgaaggtaatagaagaaaaggcttttagcccagaggtaatacccatgttttcagcattatcagagggagcc
accccacaagatttaaatatgatgctaaacatagtgggggacaccaggcagcaatgcagatgttaaaagataccatcaa
tgatgaagctgcagaatgggacagagtacatccagtacatgcagggcctattccaccaggccaaatgagggaaccaaggg
gaagtgacatagcaggaactactagtacccttcaagaacaaataggatggatgacaagtaatccacctatcccagtggga
gaaatctataaaagatggatagtcctgggattaaataaaatagtaagaatgtatagccctaccagcattttggacataag
acaagggccaaaagaaccctttagagattatgtagacaggttctttaaaactttgagagctgaacaagctacgcaggagg
taaaaaactggatgacagaaaccttgttggtccaaaatgcgaatccagactgcaagtccattttaagagcattaggacca
ggggctacattagaagaaatgatgacatcatgtcagggagtgggaggacctggccataaagcaagggttttggctgaggc
aatgagtcaagtacaacagaccaatgtaatgatgcagagaggcaatttagaggccagagaataataaagagcttcaaca
gcggcaaagaaggacacctagccagaaattgcaaggctcctagaaagagaggcagctggaaaagcggaaaggaaggacac
caaatgaaagactgtactgaaagacaggctaatttttttagggaaaatttggccttcccacaaggggaggccaggaaattt
tcctcagagcagaccagaaccaacagccccgccagcagagagctttggagtgggggaagagataccctcctctccgaagc
aggagccgagggacaagggactatatcctcccttaacttccctcaaatcactctttggcaacgaccagtagtcacagtaa
gaataggggggacagccaatagaagccctattagacacaggagcagatgatacagtattagaagaaataagtttaccagga
aaatggaaaccaaaaatgatagggggaattggaggttttatcaaagtaagacagtatgatcagatatctatagaaatttg
tggaaaaagggccataggtacagtattagtaggacctacacctgtcaacataattggacgaaatatgttgactcagattg
gttgtactttaaattttccaattagtcctattgaaactgtgccagtaaaattaaagtcaggaatggatggcccaaaggtt
aaacaatggccattgacagaagaaaaaataaaagcattaaaagaaatttgtgcagagatggaaaaggaaggaaaaatttc
aaaaattgggcctgaaaacccatacaatactccaatatttgccataaagaaaaaagatagtactaaatggagaaaattag
tagatttcagagaactcaataagagaactcaagacttctgggaggtccaattaggaatacctcatcctgcgggattaaaa
aagaaaaaatcagtaacagtactagatgtgggggatgcatatttttcagttcccttagatgaagactttagaaaatatac
tgcattcaccatacctagtttaaataatgagacaccagggattagatatcagtacaatgtactcccacagggatggaaag
gatcaccagcaatatttcaggcaagcatgacaaaaatcttagagccctttagagcaaaaaatccagagatagtgatctac
caatatatgaacgatttatatgtaggatctgacttagaaatagggcagcatagagcaaaaatagaggagttgagagaaca
tctattgaaatggggatttaccacaccagacaaaaaacatcagaaagaacctccatttctttggatgggatatgaactcc
atcctgacaaatggacagtccagcctatacagctgccagaaaaagacagctggactgtcaatgatatacaaaaattagtg
ggaaaactaaataccgcaagtcagatttatgcaggaattaaagtaaagcaattgtgtagactcctcaggggagccaaagc
gctaacagatgtagtaacactgactgaggaagcagaattagaattggcagagaacagggaaattctaaaagaacctgtac
atggagtatattatgacccaacaaaagacttagtggcagaaatacagaaacaagggcaagatcaatggacatatcaaatt
tatcaagagccatttaaaaatctaaagacaggaaaatatgcaaaaaagaggtcggcccacactaatgatgtaaaacaatt
aacagaggtagtgcagaaaatagccatagaaagcatagtaatatggggaaagacccctaaatttagactacccatacaaa
gagaaacatgggaagcatggtggatggagtattggcaggctacctggattcctgaatgggagtttgtcaatacccctcct
ctagtaaaattatggtaccagttagagaaggaccccataatgggagcagaaactttctatgtagatggggcagctaatag
ggagactaagctaggaaaagcagggtatgtcactgacagaggaagacaaaaggttgtttccctaattcagacaacaaatc
aaaagactcagttacatgcaattcatctagccttgcaggattcaggatcagaagtaaatatagtaacagactcacagtat
gcattaggaatcattcaggcacaaccagacaggagtgaatcagagttagtcaatcaaataatagagaaactaatagaaaa
ggacaaagtctacctgtcatgggtaccagcacacaaagggattggaggaaatgaacaagtagataaattagtcagtagtg
gaatcagaaaggtactatttttagatggaatagataaagcccaagatgaacattagaattctgcaacagctactgtttgt
tcatttcagaattgggtgtcaacatagcagaataggcattattccagggagaagaggcaggaatggagctggtagatcct
agcctagagccctggaaccacccgggaagtcagcctacaactgcttgtagcaagtgttactgtaaaaaatgctgctggca
ttgccaattgtgctttctgaacaagggcttaggcatctcctatggcaggaagaagcggagacgccgacgaggaactcctc
aggaccgtcaggttcatcaaaatcctgtaccaaaacagtaagtagtagtaattagtatatgtgatgcaatctttacaaat
agctgcaatagtaggactagtagtagcatccatagtagccatagttgtgtggtccatagtatttatagaatatagaaaaa
taaggaaacagaagaaaatagacaggttacttgagagaataagagaaagagcagaagatagtggcaatgagagtgatggg
gatacagaagaattatccactcttatggagagggggtatgacaatattttggttaatgatgatttgtaatgctgaaaagt
tgtgggtcacagtctactatggggtacctgtgtggagagacgcagagaccaccctattctgtgcatcagatgctaaagca
tatgacaaagaagcacacaatgtctgggctacgcatgcctgcgtacccacagaccctgacccacaagaattacctttggt
aaatgtaacagaagagtttaacatgtggaaaaataatatggtagaacagatgcatgaagatataattagtctatgggacc
aaagcttaaagccatgtgtacagctaacccctctctgcgttactttagggtgtgctgacgctcaaaacgtcaccgacacc
aacaccaccatatctaatgaaatgcaaggggaaataaaaaactgctctttcaatatgaccacagaattaagagataagaa
gcagaaagtgtatgcactttttatagacctgatgtaatagaaattaataaaactaagattaacaatagtaatagtagtc
agtatatgttaataaattgtaatacctcaaccattacacagacttgtccaaaggtatcctttgagccaattcccatacat
tattgtgccccagctggttttgcaattctaaagtgtaatgatacggagttcagtggaaaagggacatgcaagagtgtcag
cacagtacaatgcacacatggaatcaagccagtagtatcaactcaactgctgttaaatggcagtctagcagaaggaaaga

FIG. 14B tagcgattagatctgagaatatctcaaacaatgccaaaactataatagtacaattgactgagcctgtagaaattaattgt
atcagacctggcaacaatacaagaaaaagtgtacgcataggaccaggacaaacattctatgcaacaggtgacataatagg
agatataagacaagcacactgtaatgttagtaaaatagcatgggaagaaactttacaaaaggtagctgcacaattaagga
agcactttcagaatgccacaataaaatttactaaacactcaggaggggatttagaaattacaacaaatagttttaattgt
ggaggagaatttttctattgcaatacaacaaagctgtttaatagcacttggaataatgataactcaaacctcacagagga
aaagagaaaggaaaacataactctccactgcagaataaagcaaattgtaaatatgtggccaagagtaggacaagcaatat
atgcccctcccatcccaggaaacataacttgtggatcaaacattactgggctactattaacaagagatggagggaataat
ggtacaaatgatactgagaccttcaggcctggaggaggagatatgagggacaattggagaagtgaattatataaatataa
agtagtaaaaattgaaccactaggtgtagcaccaacccctgcaaaaagaagagtggtggaaagagaaaaaagagcagttg
gaatgggagctttgatctttgagttcttaggagcagcaggaagcactatgggcgcggcgtcaatggcgctgacggtacag
gccagacaattattgtctggtatagtgcaacagcagagcaatctgctgaaggctatagaggctcaacaacatctgttgag
actcacggtctggggcattaaacagctccaggcaagagtcctggctctggaaagatacctaaaggatcaacagctcctag
gaatttggggctgctctggaaaactcatttgcaccactgctgtaccttggaactctagctggagtaataaaagttataat
gacatatgggataacatgacctggctgcaatgggataaagaaattaacaattacacatacataatatataatctacttga
aaaatcgcagaaccagcaggaaattaatgaacaagacttattggcattagacaagtgggcaagtctgtggaattggtttg
acataacaagctggctatggtatataagattaggtataatgatagtaggaggcgtaataggcttaagaataatttttgct
gtgcttactatagtgaatagagttaggcagggatactcacctttgtcattccagacccttgcccaccaccagagggaacc
cgacaggcccgaaagaatcgaagaaggaggtggcgagcaagacagagagagatccgtgcgcttagtgagcggattcttag
cacttgcctgggaagatctgcggagcctgtgcctcttcagctaccgccgattgagagacttagtcttgattgcagcaagg
actgtggaactcctgggacacagcagtctcaagggactgagactggggtgggaagccctcaaatatctgtggaaccttct
atcatactggggtcaggaactaaagaatagtgctattaatttgcttgatacaatagcaatagcagtagctaactggacag
atagagttataaaaatagtacaaagaactggtagagctattcttaacatacctagaaggatcagatagggctagccccgg
gtgataaacggaccgcgcaatccctaggctgtgccttctagttgccagccatctgttgtttgcccctcccccgtgccttc
cttgaccctggaaggtgccactcccactgtcctttcctaataaaatgaggaaattgcatcgcattgtctgagtaggtgtc
attctattctggggggtggggtggggcaggacagcaagggggaggattgggaagacaatagcaggcatgctggggatgcg
gtgggctctatataaaaaacgcccggcggcaaccgagcgttctgaacgctagagtcgacaaattcagaagaactcgtcaa
gaaggcgatagaaggcgatgcgctgcgaatcgggagcggcgataccgtaaagcacgaggaagcggtcagcccattcgccg
ccaagctcttcagcaatatcacgggtagccaacgctatgtcctgatagcggtctgccacacccagccggccacagtcgat
gaatccagaaaagcggccattttccaccatgatattcggcaagcaggcatcgccatgggtcacgacgagatcctcgccgt
cgggcatgctcgccttgagcctggcgaacagttcggctggcgcgagcccctgatgctcttcgtccagatcatcctgatcg
acaagaccggcttccatccgagtacgtgctcgctcgatgcgatgtttcgcttggtggtcgaatgggcaggtagccggatc
aagcgtatgcagccgccgcattgcatcagccatgatggatactttctcggcaggagcaaggtgagatgacaggagatcct
gccccggcacttcgcccaatagcagccagtcccttcccgcttcagtgacaacgtcgagcacagctgcgcaaggaacgccc
gtcgtggccagccacgatagccgcgctgcctcgtcttgcagttcattcagggcaccggacaggtcggtcttgacaaaaag
aaccgggcgcccctgcgctgacagccggaacacggcggcatcagagcagccgattgtctgttgtgcccagtcatagccga
atagcctctccacccaagcggccggagaacctgcgtgcaatccatcttgttcaatcatgcgaaacgatcctcatcctgtc
tcttgatcagatcttgatcccctgcgccatcagatccttggcggcaagaaagccatccagtttactttgcagggcttccc
aaccttaccagagggcgccccagctggcaattccggttcgcttgctgtccataaaaccgcccagtctagctatcgccatg
taagcccactgcaagctacctgctttctctttgcgcttgcgttttcccttgtccagatagcccagtagctgacattcatc
cggggtcagcaccgtttctgcggactggctttctacgtgaaaaggatctaggtgaagatcctttttgataatctcatgac
caaaatcccttaacgtgagttttcgttccactgagcgtcagaccccgtagaaaagatcaaaggatcttcttgagatcctt
tttttctgcgcgtaatctgctgcttgcaaacaaaaaaaccaccgctaccagcggtggtttgtttgccggatcaagagcta
ccaactctttttccgaaggtaactggcttcagcagagcgcagataccaaatactgttcttctagtgtagccgtagttagg
ccaccacttcaagaactctgtagcaccgcctacatacctcgctctgctaatcctgttaccagtggctgctgccagtggcg
ataagtcgtgtcttaccgggttggactcaagacgatagttaccggataaggcgcagcggtcgggctgaacggggggttcg
tgcacacagcccagcttggagcgaacgacctacaccgaactgagatacctacagcgtgagctatgagaaagcgccacgct
tcccgaagggagaaaggcggacaggtatccggtaagcggcagggtcggaacaggagagcgcacgagggagcttccagggg
gaaacgcctggtatctttatagtcctgtcgggtttcgccacctctgacttgagcgtcgatttttgtgatgctcgtcaggg
gggcggagcctatggaaaaacgccagcaacgcggcctttttacggttcctggccttttgctggccttttgctcacatgtt
gtcgacaatattggctattggccattgcatacgttgtatctatatcataatatgtacatttatattggctcatgtccaat
atgaccgccatgttgacattgattattgactagttattaatagtaatcaattacgggttcattagttcatagcccatata
tggagttccgcgttacataacttacggtaaatggcccgcctggctgaccgcccaacgacccccgcccattgacgtcaata
atgacgtatgttcccatagtaacgccaatagggactttccattgacgtcaatgggtggagtatttacggtaaactgccca
cttggcagtacatcaagtgtatcatatgccaagtccgccccctattgacgtcaatgacggtaaatggcccgcctggcatt
atgcccagtacatgaccttacgggactttcctacttggcagtacatctacggtattagtcatcggctattaccatggtga
tgcggttttggcagtacaccaatgggcgtggatagcggtttgactcacggggatttccaagtctccaccccattgacgtc
aatgggagtttgttttggcaccaaaatcaacgggactttccaaaatgtcgtaataaccccgccccgttgacgcaaatggg
cggtaggcgtgtacggtgggaggtctatataagcagagctcgtttagtgaaccgtcagatcgcctggagacgccatccac
gctgttttgacctccatagaagacaccgggaccgatccagcctccgcggccgggaacggtgcattggaacgcggattccc
cgtgccaagagtgacgtaagtaccgcctatagactctataggcacacccctttggctcttatgcatgctatactgttttt
ggcttggggcctatacacccccgcttccttatgctataggtgatggtatagcttagcctataggtgtgggttattgacca
ttattgaccactcccctattggtgacgatactttccattactaatccataacatggctctttgccacaactatctctatt
ggctatatgccaatactctgtccttcagagactgacacggactctgtatttttacaggatggggtcccatttattattta

FIG. 14C caaattcacatatacaacaacgccgtcccccgtgcccgcagttttattaaacatagcgtgggatctccacgcgaatctc
gggtaccgtgttccggacatgggytcttctccggtagcggcggagcttccacatccgagccctggtcccatgcctccagc
ggctcatggtcgctcggcagctccttgctcctaacagtggaggccagacttaggcacagcacaatgcccaccaccaccag
tgtgccgcacaaggccgtggcggtagggtatgtgtctgaaaatgagctcggagattgggctcgcaccgctgacgcagatg
gaagacttaaggcagcggcagaagaagatgcaggcagctgagttgttgtattctgataagagtcagaggtaactcccgtt
gcggtgctgttaacggtggagggcagtgtagtctgagcagtactcgttgctgccgcgcgcgccaccagacataatagctg
acagactaacagactgttcctttccatgggtcttttctgcagtcacc FIG. 14D pGA1/IC2 Functional Regions

| **Position within sequence (starting and ending pos.)** | **Gene/ORF (indicate complete name of the gen and the expressed gene product)** | **Origin of sequence (organism)** |
|---|---|---|
| 104-1591 | Gag, inactivating point mutations in zinc finger packaging sequences for viral RNA | AG HIV-1 isolate 928 |
| 1393-3576 | Pol, inactivating point mutations in reverse transcriptase, deletion of integrase | AG HIV-1 isolate 928 |
| 3663-3877 and 6215-6305 | Tat exons #1 and #2 | AG HIV-1 isolate 928 |
| 3802-3877 and 6215-3510 | Rev exons #1 and #2 | AG HIV-1 isolate 928 |
| 3904-4149 | Vpu | AG HIV-1 isolate 928 |
| 4067-6628 | Env | AG HIV-1 isolate 928 |
| 6629-10447 | Plasmid vector | pGA1, GenBank accession # AF425297 |

FIG. 14E IC2 Mutation Chart

| Codon Change | Amino acid change | Region | Function |
|---|---|---|---|
| to AGC Position 1271-1273 | C390S | Gag | Ablation of zinc finger used in packaging |
| to AGC Position 1280-1282 | C393S | Gag | Ablation of zinc finger used in packaging |
| to AGC Position 1334-1336 | C411S | Gag | Ablation of zinc finger used in packaging |
| to AGC Position 1343-1345 | C414S | Gag | Ablation of zinc finger used in packaging |
| to AAC Position 2410-2412 | D185N | Reverse Transcriptase | Inactivation of Polymerase active site |
| to ACC Position 2653-2655 | W266T | Reverse Transcriptase | Ablation of strand transfer activity |
| to CAG Position 3289-3291 | E478Q | RNase H | Inactivation of RNase H activity |

FIG. 15A pGA1/IC48 sequence

```
atcgatgcaaggactcggcttgctgaggtgcacacagcaagaggcgagagcgacgactggtgagtacgccaattttgac
tagcggaggctagaaggagagagatgggtgcgagagcgtcagtgttaacgggggaaaattagattcatgggagaaaatt
aggttaaggccagggggaaagaaaagatatagactaaaacacctagtatgggcaagcagggagctggagagattcgcact
taaccctggcctattagaaacagcagaaggatgtcaacaactaatgggacagttacaaccagctctcaggacaggatcag
aagagtttaaatcattatataatatagtagcaaccctttggtgcgtacatcaaagaatagacataaaagacacccaggag
gccttagataaagtagaggaaaaacaaaataagagcaagcaaaaggcacagcaggcagcagctgcaacagccgccacagg
aagcagcagccaaaattaccctatagtgcaaaatgcacaagggcaaatggtacatcagtccatgtcacctaggactttaa
atgcatgggtgaaggtaatagaagaaaaggcttttagcccagaggtaatacccatgttttcagcattatcagagggagcc
accccacaagatttaaatatgatgctaaacatagtgggggacaccaggcagcaatgcagatgttaaaagataccatcaa
tgatgaagctgcagaatgggacagagtacatccagtacatgcagggcctattccaccaggccaaatgagggaaccaaggg
gaagtgacatagcaggaactactagtacccttcaagaacaaataggatggatgacaagtaatccacctatcccagtggga
gaaatctataaaagatggatagtcctgggattaaataaaatagtaagaatgtatagccctaccagcattttggacataag
acaagggccaaaagaaccctttagagattatgtagacaggttctttaaaactttgagagctgaacaagctacgcaggagg
taaaaaactggatgacagaaaccttgttggtccaaaatgcgaatccagactgcaagtccattttaagagcattaggacca
ggggctacattagaagaaatgatgacatcatgtcagggagtgggaggacctggccataaagcaagggttttggctgaggc
aatgagtcaagtacaacagaccaatgtaatgatgcagagaggcaattttagaggccagagaataataaagagcttcaaca
gcggcaaagaaggacacctagccagaaattgcaaggctcctagaaagagaggcagctggaaaagcggaaaggaaggacac
caaatgaaagactgtactgaaagacaggctaattttttagggaaaatttggccttcccacaaggggaggccaggaaattt
tcctcagagcagaccagaaccaacagccccgccagcagagagctttggagtggggaagagatacccctcctctccgaagc
aggagccgagggacaagggactatatcctcccttaacttccctcaaatcactctttggcaacgaccagtagtcacagtaa
gaataggggacagccaatagaagccctattagacacaggagcagatgatacagtattagaagaaataagtttaccagga
aaatggaaaccaaaaatgataggtggaattggaggttttatcaaagtaagacagtatgatcagatatctatagaaatttg
tggaaaagggccataggtacagtattagtaggacctacacctgtcaacataattggacgaaatatgttgactcagattg
gttgtactttaaattttccaattagtcctattgaaactgtgccagtaaaattaaagtcaggaatggatggcccaaaggtt
aaacaatggccattgacagaagaaaaaataaaagcattaaaagaaatttgtgcagagatggaaaaggaaggaaaaatttc
aaaaattgggcctgaaaacccatacaatactccaatatttgccataaagaaaaaagatagtactaaatggagaaaattag
tagatttcagagaactcaataagagaactcaagacttctgggaggtccaattaggaatacctcatcctgcgggattaaaa
aagaaaaaatcagtaacagtactagatgtggggdatgcatatttttcagttcccttagatgaagacttagaaaatatac
tgcattcaccatacctagtttaaataatgagacaccagggattagatatcagtacaatgtactcccacagggatggaaag
gatcaccagcaatatttcaggcaagcatgacaaaaatcttagagccctttagagcaaaaaatccagagatagtgatctac
caatatatgaacgatttatatgtaggatctgacttagaaatagggcagcatagagcaaaaatagaggagttgagagaaca
tctattgaaatggggatttaccacaccagacaaaaaacatcagaaagaacctccatttctttggatgggatatgaactcc
atcctgacaaatggacagtccagcctatacagctgccagaaaaagacagctggactgtcaatgatatacaaaaattagtg
ggaaaactaaataccgcaagtcagatttatgcaggaattaaagtaaagcaattgtgtagactcctcaggggagccaaagc
gctaacagatgtagtaacactgactgaggaagcagaattagaattggcagagaacagggaaattctaaaagaacctgtac
atggagtatattatgacccaacaaaagacttagtggcagaaatacagaaacaagggcaagatcaatggacatatcaaatt
tatcaagagccatttaaaaatctaaagacaggaaaatatgcaaaaaagaggtcggcccacactaatgatgtaaaacaatt
aacagaggtagtgcagaaaatagccatagaaagcatagtaatatggggaaagacccctaaatttagactacccatacaaa
gagaaacatgggaagcatggtggatggagtattggcaggctacctggattcctgaatgggagtttgtcaatacccctcct
ctagtaaaattatggtaccagttagagaaggaccccataatgggagcagaaactttctatgtagatggggcagctaatag
ggagactaagctaggaaaagcagggtatgtcactgacagaggaagacaaaaggttgtttccctaattcagacaacaaatc
aaaagactcagttacatgcaattcatctagccttgcaggattcaggatcagaagtaaatatagtaacagactcacagtat
gcattaggaatcattcaggcacaaccagacaggagtgaatcagagttagtcaatcaaataatagagaaactaatagaaaa
ggacaaagtctacctgtcatgggtaccagcacacaaagggattggaggaaatgaacaagtagataaattagtcagtagtg
gaatcagaaaggtactatttttagatggaatagataaagcccaagatgaacattagaattctgcaacagctactgtttgt
tcatttcagaattgggtgtcaacatagcagaataggcattattccagggagaagaggcaggaatggagctggtagatcct
agcctagagccctggaaccacccgggaagtcagcctacaactgcttgtagcaagtgttactgtaaaaaatgctgctggca
ttgccaattgtgctttctgaacaagggcttaggcatctcctatggcaggaagaagcggagacgccgacgaggaactcctc
aggaccgtcaggttcatcaaaatcctgtaccaaaacagtaagtagtagtaattagtatatgtgatgcaatctttacaaat
agctgcaatagtaggactagtagtagcatccatagtagccatagttgtgtggtccatagtatttatagaatatagaaaaa
taaggaaacagaagaaaatagacaggttacttgagagaataagagaaagagcagaagatagtggcaatgagagtgatggg
gatacagaagaattatccactcttatggagaggggggtatgacaatatttggttaatgatgatttgtaatgctgaaaagt
tgtgggtcacagtctactatggggtacctgtgtggagagacgcagagaccaccctattctgtgcatcagatgctaaagca
tatgacaaagaagcacacaatgtctgggctacgcatgcctgcgtacccacagaccctgacccacaagaattacctttggt
aaatgtaacagaagagtttaacatgtggaaaaataatatggtagaacagatgcatgaagatataattagtctatggacc
aaagcttaaagccatgtgtacagctaacccctctctgcgttactttagggtgtgctgacgctcaaaacgtcaccgacacc
aacaccaccatatctaatgaaatgcaaggggaaataaaaaactgctctttcaatatgaccacagaattaagagataagaa
gcagaaagtgtatgcactttttatagacctgatgtaatagaaattaataaaactaagattaacaatagtaatagtagtc
agtatatgttaataaattgtaatacctcaaccattacacagacttgtccaaaggtatcctttgagccaattcccatacat
tattgtgccccagctggttttgcaattctaaagtgtaatgatacggagttcagtggaaaagggacatgcaagagtgtcag
cacagtacaatgcacacatggaatcaagccagtagtatcaactcaactgctgttaaatggcagtctagcagaaggaaaga
```

FIG. 15B tagcgattagatctgagaatatctcaaacaatgccaaaactataatagtacaattgactgagcctgtagaaattaattgt
atcagacctggcaacaatacaagaaaaagtgtacgcataggaccaggacaaacattctatgcaacaggtgacataatagg
agatataagacaagcacactgtaatgttagtaaaatagcatgggaagaaactttacaaaaggtagctgcacaattaagga
agcactttcagaatgccacaataaaatttactaaacactcaggaggggatttagaaattacaacaaatagttttaattgt
ggaggagaatttttctattgcaatacaacaaagctgtttaatagcacttggaataatgataactcaaacctcacagagga
aaagagaaaggaaaacataactctccactgcagaataaagcaaattgtaaatatgtggccaagagtaggacaagcaatat
atgcccctcccatcccaggaaacataacttgtggatcaaacattactgggctactattaacaagagatggagggaataat
ggtacaaatgatactgagaccttcaggcctggaggaggagatatgagggacaattggagaagtgaattatataaatataa
agtagtaaaaattgaaccactaggtgtagcaccaacccctgcaaaaagaagagtggtggaaagagaaaaaagagcagttg
gaatgggagctttgatctttgagttcttaggagcagcaggaagcactatgggcgcggcgtcaatggcgctgacggtacag
gccagacaattattgtctggtatagtgcaacagcagagcaatctgctgaaggctatagaggctcaacaacatctgttgag
actcacggtctggggcattaaacagctccaggcaagagtcctggctctggaaagatacctaaaggatcaacagctcctag
gaatttggggctgctctggaaaactcatttgcaccactgctgtaccttggaactctagctggagtaataaaagttataat
gacatatgggataacatgacctggctgcaatgggataaagaaattaacaattacacatacataatatataatctacttga
aaaatcgcagaaccagcaggaaattaatgaacaagacttattggcattagacaagtgggcaagtctgtggaattggtttg
acataacaagctggctatggtatataagattaggtataatgatagtaggaggcgtaataggcttaagaataatttttgct
gtgcttactatagtgaatagagttaggcagggatactcacctttgtcattccagacccttgcccaccaccagagggaacc
cgacaggcccgaaagaatcgaagaaggaggtggcgagcaagacagagagagatccgtgcgcttagtgagcggattcttag
cacttgcctgggaagatctgcggagcctgtgcctcttcagctaccgccgattgagagacttagtcttgattgcagcaagg
actgtggaactcctgggacacagcagtctcaagggactgagactggggtgggaagccctcaaatatctgtggaaccttct
atcatactggggtcaggaactaaagaatagtgctattaatttgcttgatacaatagcaatagcagtagctaactggacag
atagagttataaaaatagtacaaagaactggtagagctattcttaacatacctagaaggatcagatagggctagccccgg
gtgataaacggaccgcgcaatccctaggctgtgccttctagttgccagccatctgttgtttgcccctcccccgtgccttc
cttgaccctggaaggtgccactcccactgtcctttcctaataaaatgaggaaattgcatcgcattgtctgagtaggtgtc
attctattctggggggtggggtggggcaggacagcaagggggaggattgggaagacaatagcaggcatgctggggatgcg
gtgggctctatataaaaaacgcccggcggcaaccgagcgttctgaacgctagagtcgacaaattcagaagaactcgtcaa
gaaggcgatagaaggcgatgcgctgcgaatcgggagcggcgataccgtaaagcacgaggaagcggtcagcccattcgccg
ccaagctcttcagcaatatcacgggtagccaacgctatgtcctgatagcggtctgccacacccagccggccacagtcgat
gaatccagaaaagcggccattttccaccatgatattcggcaagcaggcatcgccatgggtcacgacgagatcctcgccgt
cgggcatgctcgccttgagcctggcgaacagttcggctggcgcgagcccctgatgctcttcgtccagatcatcctgatcg
acaagaccggcttccatccgagtacgtgctcgctcgatgcgatgtttcgcttggtggtcgaatgggcaggtagccggatc
aagcgtatgcagccgccgcattgcatcagccatgatggatactttctcggcaggagcaaggtgagatgacaggagatcct
gccccggcacttcgcccaatagcagccagtcccttcccgcttcagtgacaacgtcgagcacagctgcgcaaggaacgccc
gtcgtggccagccacgatagccgcgctgcctcgtcttgcagttcattcagggcaccggacaggtcggtcttgacaaaaag
aaccgggcgcccctgcgctgacagccggaacacggcggcatcagagcagccgattgtctgttgtgcccagtcatagccga
atagcctctccacccaagcggccggagaacctgcgtgcaatccatcttgttcaatcatgcgaaacgatcctcatcctgtc
tcttgatcagatcttgatcccctgcgccatcagatccttggcggcaagaaagccatccagtttactttgcagggcttccc
aaccttaccagagggcgccccagctggcaattccggttcgcttgctgtccataaaaccgcccagtctagctatcgccatg
taagcccactgcaagctacctgctttctctttgcgcttgcgttttcccttgtccagatagcccagtagctgacattcatc
cggggtcagcaccgtttctgcggactggctttctacgtgaaaaggatctaggtgaagatcctttttgataatctcatgac
caaaatcccttaacgtgagttttcgttccactgagcgtcagaccccgtagaaaagatcaaaggatcttcttgagatcctt
tttttctgcgcgtaatctgctgcttgcaaacaaaaaaaccaccgctaccagcggtggtttgtttgccggatcaagagcta
ccaactctttttccgaaggtaactggcttcagcagagcgcagataccaaatactgttcttctagtgtagccgtagttagg
ccaccacttcaagaactctgtagcaccgcctacatacctcgctctgctaatcctgttaccagtggctgctgccagtggcg
ataagtcgtgtcttaccgggttggactcaagacgatagttaccggataaggcgcagcggtcgggctgaacggggggttcg
tgcacacagcccagcttggagcgaacgacctacaccgaactgagatacctacagcgtgagctatgagaaagcgccacgct
tcccgaagggagaaaggcggacaggtatccggtaagcggcagggtcggaacaggagagcgcacgagggagcttccagggg
gaaacgcctggtatctttatagtcctgtcgggtttcgccacctctgacttgagcgtcgatttttgtgatgctcgtcaggg
gggcggagcctatggaaaaacgccagcaacgcggcctttttacggttcctggccttttgctggccttttgctcacatgtt
gtcgacaatattggctattggccattgcatacgttgtatctatatcataatatgtacatttatattggctcatgtccaat
atgaccgccatgttgacattgattattgactagttattaatagtaatcaattacggggtcattagttcatagcccatata
tggagttccgcgttacataacttacggtaaatggcccgcctggctgaccgcccaacgacccccgcccattgacgtcaata
atgacgtatgttcccatagtaacgccaatagggactttccattgacgtcaatgggtggagtatttacggtaaactgccca
cttggcagtacatcaagtgtatcatatgccaagtccgccccctattgacgtcaatgacggtaaatggcccgcctggcatt
atgcccagtacatgaccttacgggactttcctacttggcagtacatctacggtattagtcatcgctattaccatggtga
tgcggttttggcagtacaccaatgggcgtggatagcggtttgactcacggggatttccaagtctccaccccattgacgtc
aatgggagtttgttttggcaccaaaatcaacgggactttccaaaatgtcgtaataaccccgccccgttgacgcaaatggg
cggtaggcgtgtacggtgggaggtctatataagcagagctcgtttagtgaaccgtcagatcgcctggagacgccatccac
gctgttttgacctccatagaagacaccgggaccgatccagcctccgcggccgggaacggtgcattggaacgcggattccc
cgtgccaagagtgacgtaagtaccgcctatagactctataggcacacccctttggctcttatgcatgctatactgttttt
ggcttggggcctatacacccccgcttccttatgctataggtgatggtatagcttagcctataggtgtgggttattgacca
ttattgaccactcccctattggtgacgatactttccattactaatccataacatggctctttgccacaactatctctatt
ggctatatgccaatactctgtccttcagagactgacacggactctgtatttttacaggatggggtcccatttattatta

FIG. 15C caaattcacatatacaacaacgccgtcccccgtgcccgcagttttattaaacatagcgtgggatctccacgcgaatctc
gggtaccgtgttccggacatgggytcttctccggtagcggcggagcttccacatccgagccctggtcccatgcctccagc
ggctcatggtcgctcggcagctccttgctcctaacagtggaggccagacttaggcacagcacaatgcccaccaccaccag
tgtgccgcacaaggccgtggcggtagggtatgtgtctgaaaatgagctcggagattgggctcgcaccgctgacgcagatg
gaagacttaaggcagcggcagaagaagatgcaggcagctgagttgttgtattctgataagagtcagaggtaactcccgtt
gcggtgctgttaacggtggagggcagtgtagtctgagcagtactcgttgctgccgcgcgcgccaccagacataatagctg
acagactaacagactgttcctttccatgggtcttttctgcagtcacc FIG. 15D pGA1/IC48 Functional Regions

| Position within sequence (starting and ending pos.) | Gene/ORF (indicate complete name of the gen and the expressed gene product) | Origin of sequence (organism) |
|---|---|---|
| 104-1591 | Gag, inactivating point mutations in zinc finger packaging sequences for viral RNA | AG HIV-1 isolate 928 |
| 1393-3576 | Pol, inactivating point mutations in reverse transcriptase, deletion of integrase | AG HIV-1 isolate 928 |
| 3663-3877 and 6215-6305 | Tat exons #1 and #2 | AG HIV-1 isolate 928 |
| 3802-3877 and 6215-3510 | Rev exons #1 and #2 | AG HIV-1 isolate 928 |
| 3904-4149 | Vpu | AG HIV-1 isolate 928 |
| 4067-6628 | Env | AG HIV-1 isolate 928 |
| 6629-10447 | Plasmid vector | pGA1, GenBank accession # AF425297 |

FIG. 15E IC48 Mutation Chart

| Codon Change | Amino acid change | Region | Function |
|---|---|---|---|
| to AGC Position 1271-1273 | C390S | Gag | Ablation of zinc finger used in packaging |
| to AGC Position 1280-1282 | C393S | Gag | Ablation of zinc finger used in packaging |
| to AGC Position 1334-1336 | C411S | Gag | Ablation of zinc finger used in packaging |
| to AGC Position 1343-1345 | C414S | Gag | Ablation of zinc finger used in packaging |
| to GTG Position 1703-1705 | G48V | Protease | Partial inactivation of Protease |
| to AAC Position 2410-2412 | D185N | Reverse Transcriptase | Inactivation of Polymerase active site |
| to ACC Position 2653-2655 | W266T | Reverse Transcriptase | Ablation of strand transfer activity |
| to CAG Position 3289-3291 | E478Q | RNase H | Inactivation of RNase H activity |

FIG. 16A pGA1/IC90 sequence atcgatgcaaggactcggcttgctgaggtgcacacagcaagaggcgagagcgacgactggtgagtacgccaatttttgac
tagcggaggctagaaggagagagatgggtgcgagagcgtcagtgttaacgggggaaaattagattcatgggagaaaatt
aggttaaggccagggggaaagaaaagatatagactaaaacacctagtatgggcaagcagggagctggagagattcgcact
taaccctggcctattagaaacagcagaaggatgtcaacaactaatgggacagttacaaccagctctcaggacaggatcag
aagagtttaaatcattatataatatagtagcaaccctttggtgcgtacatcaaagaatagacataaaagacacccaggag
gccttagataaagtagaggaaaaacaaaataagagcaagcaaaaggcacagcaggcagcagctgcaacagccgccacagg
aagcagcagccaaaattaccctatagtgcaaaatgcacaagggcaaatggtacatcagtccatgtcacctaggactttaa
atgcatgggtgaaggtaatagaagaaaaggcttttagcccagaggtaatacccatgttttcagcattatcagagggagcc
accccacaagatttaaatatgatgctaaacatagtgggggacaccaggcagcaatgcagatgttaaaagataccatcaa
tgatgaagctgcagaatgggacagagtacatccagtacatgcagggcctattccaccaggccaaatgagggaaccaaggg
gaagtgacatagcaggaactactagtacccttcaagaacaaataggatggatgacaagtaatccacctatcccagtggga
gaaatctataaaagatggatagtcctgggattaaataaaatagtaagaatgtatagccctaccagcattttggacataag
acaagggccaaaagaaccctttagagattatgtagacaggttctttaaaactttgagagctgaacaagctacgcaggagg
taaaaaactggatgacagaaaccttgttggtccaaaatgcgaatccagactgcaagtccattttaagagcattaggacca
ggggctacattagaagaaatgatgacatcatgtcagggagtgggaggacctggccataaagcaagggttttggctgaggc
aatgagtcaagtacaacagaccaatgtaatgatgcagagaggcaattttagaggccagagaataataaagagcttcaaca
gcggcaaagaaggacacctagccagaaattgcaaggctcctagaaagagaggcagctggaaaagcggaaaggaaggacac
caaatgaaagactgtactgaaagacaggctaattttttagggaaaatttggccttcccacaaggggaggccaggaaattt
tcctcagagcagaccagaaccaacagccccgccagcagagagctttggagtgggggaagagataccctcctctccgaagc
aggagccgagggacaagggactatatcctcccttaacttccctcaaatcactctttggcaacgaccagtagtcacagtaa
gaataggggggacagccaatagaagccctattagacacaggagcagatgatacagtattagaagaaataagtttaccagga
aaatggaaaccaaaaatgataggggggaattggaggttttatcaaagtaagacagtatgatcagatatctatagaaatttg
tggaaaaagggccataggtacagtattagtaggacctacacctgtcaacataattggacgaaatatgatgactcagattg
gttgtactttaaattttccaattagtcctattgaaactgtgccagtaaaattaaagtcaggaatggatggcccaaaggtt
aaacaatggccattgacagaagaaaaaataaaagcattaaaagaaatttgtgcagagatggaaaaggaaggaaaaatttc
aaaaattgggcctgaaaacccatacaatactccaatatttgccataaagaaaaaagatagtactaaatggagaaaattag
tagatttcagagaactcaataagagaactcaagacttctgggaggtccaattaggaatacctcatcctgcgggattaaaa
aagaaaaaatcagtaacagtactagatgtgggggatgcatatttttcagttcccttagatgaagactttagaaaatatac
tgcattcaccatacctagtttaaataatgagacaccagggattagatatcagtacaatgtactcccacagggatggaaag
gatcaccagcaatatttcaggcaagcatgacaaaaatcttagagccctttagagcaaaaaatccagagatagtgatctac
caatatatgaacgatttatatgtaggatctgacttagaaatagggcagcatagagcaaaaatagaggagttgagagaaca
tctattgaaatggggatttaccacaccagacaaaaaacatcagaaagaacctccatttctttggatgggatatgaactcc
atcctgacaaatggacagtccagcctatacagctgccagaaaaagacagctggactgtcaatgatatacaaaaattagtg
ggaaaactaaataccgcaagtcagatttatgcaggaattaaagtaaagcaattgtgtagactcctcaggggagccaaagc
gctaacagatgtagtaacactgactgaggaagcagaattagaattggcagagaacagggaaattctaaaagaacctgtac
atggagtatattatgacccaacaaaagacttagtggcagaaatacagaaacaagggcaagatcaatggacatatcaaatt
tatcaagagccatttaaaaatctaaagacaggaaaatatgcaaaaaagaggtcggcccacactaatgatgtaaaacaatt
aacagaggtagtgcagaaaatagccatagaaagcatagtaatatggggaaagacccctaaatttagactacccatacaaa
gagaaacatggaagcatggtggatggagtattggcaggctacctggattcctgaatgggagtttgtcaatacccctcct
ctagtaaaattatggtaccagttagagaaggaccccataatgggagcagaaactttctatgtagatggggcagctaatag
ggagactaagctaggaaaagcagggtatgtcactgacagaggaagacaaaaggttgtttccctaattcagacaacaaatc
aaaagactcagttacatgcaattcatctagccttgcaggattcaggatcagaagtaaatatagtaacagactcacagtat
gcattaggaatcattcaggcacaaccagacaggagtgaatcagagttagtcaatcaaataatagagaaactaatagaaaa
ggacaaagtctacctgtcatgggtaccagcacacaaagggattggaggaaatgaacaagtagataaattagtcagtagtg
gaatcagaaaggtactatttttagatggaatagataaagcccaagatgaacattagaattctgcaacagctactgtttgt
tcatttcagaattgggtgtcaacatagcagaataggcattattccagggagaagaggcaggaatggagctggtagatcct
agcctagagccctggaaccacccgggaagtcagcctacaactgcttgtagcaagtgttactgtaaaaaatgctgctggca
ttgccaattgtgctttctgaacaagggcttaggcatctcctatggcaggaagaagcggagacgccgacgaggaactcctc
aggaccgtcaggttcatcaaaatcctgtaccaaaacagtaagtagtagtaattagtatatgtgatgcaatctttacaaat
agctgcaatagtaggactagtagtagcatccatagtagccatagttgtgtggtccatagtatttatagaatatagaaaaa
taaggaaacagaagaaaatagacaggttacttgagagaataagagaaagagcagaagatagtggcaatgagagtgatggg
gatacagaagaattatccactcttatggagagggggtatgacaatatttggttaatgatgatttgtaatgctgaaaagt
tgtgggtcacagtctactatggggtacctgtgtggagagacgcagagaccaccctattctgtgcatcagatgctaaagca
tatgacaaagaagcacacaatgtctgggctacgcatgcctgcgtacccacagaccctgacccacaagaattacctttggt
aaatgtaacagaagagtttaacatgtggaaaaataatatggtagaacagatgcatgaagatataattagtctatgggacc
aaagcttaaagccatgtgtacagctaacccctctctgcgttactttagggtgtgctgacgctcaaaacgtcaccgacacc
aacaccaccatatctaatgaaatgcaaggggaaataaaaaactgctctttcaatatgaccacagaattaagagataagaa
gcagaaagtgtatgcactttttTatagacctgatgtaatagaaattaataaaactaagattaacaatagtaatagtagtc
agtatatgttaataaattgtaatacctcaaccattacacagacttgtccaaaggtatcctttgagccaattcccatacat
tattgtgccccagctggttttgcaattctaaagtgtaatgatacggagttcagtggaaaaggacatgcaagagtgtcag
cacagtacaatgcacacatggaatcaagccagtagtatcaactcaactgctgttaaatggcagtctagcagaaggaaaga

FIG. 16B tagcgattagatctgagaatatctcaaacaatgccaaaactataatagtacaattgactgagcctgtagaaattaattgt
atcagacctggcaacaatacaagaaaaagtgtacgcataggaccaggacaaacattctatgcaacaggtgacataatagg
agatataagacaagcacactgtaatgttagtaaaatagcatgggaagaaactttacaaaggtagctgcacaattaagga
agcactttcagaatgccacaataaaatttactaaacactcaggaggggatttagaaattacaacaaatagttttaattgt
ggaggagaatttttctattgcaatacaacaaagctgtttaatagcacttggaataatgataactcaaacctcacagagga
aaagagaaaggaaaacataactctccactgcagaataaagcaaattgtaaatatgtggccaagagtaggacaagcaatat
atgcccctcccatcccaggaaacataacttgtggatcaaacattactgggctactattaacaagagatggagggaataat
ggtacaaatgatactgagaccttcaggcctggaggaggagatatgagggacaattggagaagtgaattatataaatataa
agtagtaaaaattgaaccactaggtgtagcaccaacccctgcaaaaagaagagtggtggaaagagaaaaaagagcagttg
gaatgggagctttgatctttgagttcttaggagcagcaggaagcactatgggcgcggcgtcaatggcgctgacggtacag
gccagacaattattgtctggtatagtgcaacagcagagcaatctgctgaaggctatagaggctcaacaacatctgttgag
actcacggtctggggcattaaacagctccaggcaagagtcctggctctggaaagatacctaaaggatcaacagctcctag
gaatttggggctgctctggaaaactcatttgcaccactgctgtaccttggaactctagctggagtaataaaagttataat
gacatatgggataacatgacctggctgcaatgggataaagaaattaacaattacacatacataatatataatctacttga
aaaatcgcagaaccagcaggaaattaatgaacaagacttattggcattagacaagtgggcaagtctgtggaattggtttg
acataacaagctggctatggtatataagattaggtataatgatagtaggaggcgtaataggcttaagaataattttgct
gtgcttactatagtgaatagagttaggcagggatactcacctttgtcattccagacccttgcccaccaccagagggaacc
cgacaggcccgaaagaatcgaagaaggaggtggcgagcaagacagagagagatccgtgcgcttagtgagcggattcttag
cacttgcctgggaagatctgcggagcctgtgcctcttcagctaccgccgattgagagacttagtcttgattgcagcaagg
actgtggaactcctgggacacagcagtctcaagggactgagactggggtgggaagccctcaaatatctgtggaaccttct
atcatactggggtcaggaactaaagaatagtgctattaatttgcttgatacaatagcaatagcagtagctaactggacag
atagagttataaaaatagtacaaagaactggtagagctattcttaacatacctagaaggatcagatagggctagccccgg
gtgataaacggaccgcgcaatccctaggctgtgccttctagttgccagccatctgttgtttgcccctcccccgtgccttc
cttgaccctggaaggtgccactcccactgtcctttcctaataaaatgaggaaattgcatcgcattgtctgagtaggtgtc
attctattctggggggtggggtggggcaggacagcaagggggaggattgggaagacaatagcaggcatgctggggatgcg
gtgggctctatataaaaaacgcccggcggcaaccgagcgttctgaacgctagagtcgacaaattcagaagaactcgtcaa
gaaggcgatagaaggcgatgcgctgcgaatcgggagcggcgataccgtaaagcacgaggaagcggtcagcccattcgccg
ccaagctcttcagcaatatcacgggtagccaacgctatgtcctgatagcggtctgccacacccagccggccacagtcgat
gaatccagaaaagcggccattttccaccatgatattcggcaagcaggcatcgccatgggtcacgacgagatcctcgccgt
cgggcatgctcgccttgagcctggcgaacagttcggctggcgcgagcccctgatgctcttcgtccagatcatcctgatcg
acaagaccggcttccatccgagtacgtgctcgctcgatgcgatgtttcgcttggtggtcgaatgggcaggtagccggatc
aagcgtatgcagccgccgcattgcatcagccatgatggatactttctcggcaggagcaaggtgagatgacaggagatcct
gccccggcacttcgcccaatagcagccagtcccttcccgcttcagtgacaacgtcgagcacagctgcgcaaggaacgccc
gtcgtggccagccacgatagccgcgctgcctcgtcttgcagttcattcagggcaccggacaggtcggtcttgacaaaaag
aaccgggcgcccctgcgctgacagccggaacacggcggcatcagagcagccgattgtctgttgtgcccagtcatagccga
atagcctctccacccaagcggccggagaacctgcgtgcaatccatcttgttcaatcatgcgaaacgatcctcatcctgtc
tcttgatcagatcttgatcccctgcgccatcagatccttggcggcaagaaagccatccagtttactttgcagggcttccc
aaccttaccagagggcgccccagctggcaattccggttcgcttgctgtccataaaaccgcccagtctagctatcgccatg
taagcccactgcaagctacctgctttctctttgcgcttgcgttttcccttgtccagatagcccagtagctgacattcatc
cggggtcagcaccgtttctgcggactggctttctacgtgaaaaggatctaggtgaagatcctttttgataatctcatgac
caaaatcccttaacgtgagttttcgttccactgagcgtcagaccccgtagaaaagatcaaaggatcttcttgagatcctt
tttttctgcgcgtaatctgctgcttgcaaacaaaaaaaccaccgctaccagcggtggtttgtttgccggatcaagagcta
ccaactctttttccgaaggtaactggcttcagcagagcgcagataccaaatactgttcttctagtgtagccgtagttagg
ccaccacttcaagaactctgtagcaccgcctacatacctcgctctgctaatcctgttaccagtggctgctgccagtggcg
ataagtcgtgtcttaccgggttggactcaagacgatagttaccggataaggcgcagcggtcgggctgaacggggggttcg
tgcacacagcccagcttggagcgaacgacctacaccgaactgagatacctacagcgtgagctatgagaaagcgccacgct
tcccgaagggagaaaggcggacaggtatccggtaagcggcagggtcggaacaggagagcgcacgagggagcttccagggg
gaaacgcctggtatctttatagtcctgtcgggtttcgccacctctgacttgagcgtcgatttttgtgatgctcgtcaggg
gggcggagcctatggaaaaacgccagcaacgcggcctttttacggttcctggccttttgctggccttttgctcacatgtt
gtcgacaatattggctattggccattgcatacgttgtatctatatcataatatgtacatttatattggctcatgtccaat
atgaccgccatgttgacattgattattgactagttattaatagtaatcaattacgggttcattagttcatagcccatata
tggagttccgcgttacataacttacggtaaatggcccgcctggctgaccgcccaacgacccccgcccattgacgtcaata
atgacgtatgttcccatagtaacgccaatagggactttccattgacgtcaatgggtggagtatttacggtaaactgccca
cttggcagtacatcaagtgtatcatatgccaagtccgccccctattgacgtcaatgacggtaaatggcccgcctggcatt
atgcccagtacatgaccttacgggactttcctacttggcagtacatctacgtattagtcatcgctattaccatggtga
tgcggttttggcagtacaccaatgggcgtggatagcggtttgactcacggggatttccaagtctccaccccattgacgtc
aatgggagtttgttttggcaccaaaatcaacgggactttccaaaatgtcgtaataaccccgccccgttgacgcaaatggg
cggtaggcgtgtacggtgggaggtctatataagcagagctcgtttagtgaaccgtcagatcgcctggagacgccatccac
gctgttttgacctccatagaagacaccgggaccgatccagcctccgcggccgggaacggtgcattggaacgcggattccc
cgtgccaagagtgacgtaagtaccgcctatagactctataggcacacccctttggctcttatgcatgctatactgttttt
ggcttggggcctatacacccccgcttccttatgctataggtgatggtatagcttagcctataggtgtgggttattgacca
ttattgaccactcccctattggtgacgatactttccattactaatccataacatggctctttgccacaactatctctatt
ggctatatgccaatactctgtccttcagagactgacacggactctgtatttttacaggatggggtcccatttattattta

FIG. 16C caaattcacatatacaacaacgccgtcccccgtgcccgcagtttttattaaacatagcgtgggatctccacgcgaatctc
gggtaccgtgttccggacatgggytcttctccggtagcggcggagcttccacatccgagccctggtcccatgcctccagc
ggctcatggtcgctcggcagctccttgctcctaacagtggaggccagacttaggcacagcacaatgcccaccaccaccag
tgtgccgcacaaggccgtggcggtagggtatgtgtctgaaaatgagctcggagattgggctcgcaccgctgacgcagatg
gaagacttaaggcagcggcagaagaagatgcaggcagctgagttgttgtattctgataagagtcagaggtaactcccgtt
gcggtgctgttaacggtggagggcagtgtagtctgagcagtactcgttgctgccgcgcgcgccaccagacataatagctg
acagactaacagactgttcctttccatgggtcttttctgcagtcacc FIG. 16D pGA1/IC90 Functional Regions

| **Position within sequence (starting and ending pos.)** | **Gene/ORF (indicate complete name of the gen and the expressed gene product)** | **Origin of sequence (organism)** |
|---|---|---|
| 104-1591 | Gag, inactivating point mutations in zinc finger packaging sequences for viral RNA | AG HIV-1 isolate 928 |
| 1393-3576 | Pol, inactivating point mutations in reverse transcriptase, deletion of integrase | AG HIV-1 isolate 928 |
| 3663-3877 and 6215-6305 | Tat exons #1 and #2 | AG HIV-1 isolate 928 |
| 3802-3877 and 6215-3510 | Rev exons #1 and #2 | AG HIV-1 isolate 928 |
| 3904-4149 | Vpu | AG HIV-1 isolate 928 |
| 4067-6628 | Env | AG HIV-1 isolate 928 |
| 6629-10447 | Plasmid vector | pGA1, GenBank accession # AF425297 |

FIG. 16E IC90 Mutation Chart

| Codon Change | Amino acid change | Region | Function |
|---|---|---|---|
| to AGC Position 1271-1273 | C390S | Gag | Ablation of zinc finger used in packaging |
| to AGC Position 1280-1282 | C393S | Gag | Ablation of zinc finger used in packaging |
| to AGC Position 1334-1336 | C411S | Gag | Ablation of zinc finger used in packaging |
| to AGC Position 1343-1345 | C414S | Gag | Ablation of zinc finger used in packaging |
| to ATG Position 1828-1830 | L90M | Protease | Partial inactivation of Protease |
| to AAC Position 2410-2412 | D185N | Reverse Transcriptase | Inactivation of Polymerase active site |
| to ACC Position 2653-2655 | W266T | Reverse Transcriptase | Ablation of strand transfer activity |
| to CAG Position 3289-3291 | E478Q | RNase H | Inactivation of RNase H activity |

FIG. 17A

PGA1/IN3 Sequence ggatccggcttgctgaagtgcactcggcaagaggcgaggggtggcggctggtgagtacgccaaattttatttgactagcg
gaggctagaaggagagagatgggtgcgagagcgtcaatattaagagggggaaaattagataaatgggaaaagattaggtt
aaggccagggggaaagaaacactatatgctaaaacacctagtatgggcaagcagggagctggaaagatttgcacttaacc
ctggccttttagagacatcagaaggctgtaaacaaataataaaacagctacaaccagctcttcagacaggaacagaggaa
cttaggtcattattcaatgcagtagcaactctctattgtgtacatgcagacatagaggtacgagacaccaaagaagcatt
agacaagatagaggaagaacaaaacaaaagtcagcaaaaaacgcagcaggcaaaagaggctgacaaaaaggtcgtcagtc
aaaattatcctatagtgcagaatcttcaagggcaaatggtacaccaggcactatcacctagaactttgaatgcatgggta
aaagtaatagaagaaaaagcctttagcccggaggtaatacccatgttcacagcattatcagaaggagccaccccacaaga
tttaaacaccatgttaaataccgtgggggacatcaagcagccatgcaaatgttaaaagataccatcaatgaggaggctg
cagaatgggatagattacatccagtacatgcagggcctgttgcaccaggccaaatgagagaaccaaggggaagtgacata
gcaggaactactagtaccttcaggaacaaatagcatggatgacaagtaacccacctattccagtgggagatatctataa
aagatggataattctggggttaaataaaatagtaagaatgtatagccctgtcagcattttagacataagacaagggccaa
aggaaccctttagagattatgtagaccggttctttaaaactttaagagctgaacaagcttcacaagatgtaaaaaattgg
atggcagacaccttgttggtccaaaatgcgaacccagattgtaagaccattttaagagcattaggaccaggagctacatt
agaagaaatgatgacagcatgtcaaggagtgggaggacctagccacaaagcaagagtgttggctgaggcaatgagccaaa
caggcagtaccataatgatgcagagaagcaattttaaaggctctaaaagaactgttaaatccttcaactctggcaaggaa
gggcacatagctagaaattgcagggcccctaggaaaaaggctcttggaaatctggaaaggaaggacaccaaatgaaaga
ctgtgctgagaggcaggctaattttttagggaaaatttggccttcccacaaggggaggccagggaatttccttcagaaca
ggccagagccaacagccccaccagcagagagcttcaggttcgaggagacaacccctgctccgaagcaggagctgaaagac
agggaacccttaacctccctcaaatcactctttggcagcgaccccttgtctcaataaaaataggggggccagataaaggag
gctctcttagccacaggagcagatgatacagtattagaagaaatgaatttgccaggaaaatggaaaccaaaaatgatagg
aggaattggaggttttatcaaagtaagacagtatgatcaaatacttatagaaatttgtggaaaaaaggctataggtacag
tattagtaggacccacacctgtcaacataattggaagaaatatgctgactcagattggatgcacgctaaattttccaatt
agtcccattgaaactgtaccagtaaaattaaagccaggaatggatggcccaaaggttaaacaatggccattgacagagga
gaaaataaaagcattaacagcaatttgtgatgaaatggagaaggaaggaaaaattacaaaaattgggcctgaaaatccat
ataacactccaatattcgccataaaaaagaaggacagtactaagtggagaaaattagtagatttcagagaacttaataaa
agaactcaagacttctgggaagttcaattaggaataccacacccagcagggttaaaaaagaaaaaatcagtgacagtact
agatgtgggggatgcatatttttcagttcctttagatgaaagctttaggaggtatactgcattcaccatacctagtagaa
acaatgaaacaccagggattagatatcaatataatgtgcttccacaaggatggaaaggatcaccagcaatattccagagt
agcatgacaaaaatcttagagccctttagagcacaaaatccagaaatagtcatctatcaatatatgaatgacttgtatgt
aggatctgacttagaaatagggcaacatagagcaaagatagaggaattaagagaacatctattaaggtggggatttacca
caccagacaagaaacatcagaaagaaccccccatttctttggatgggtatgaactccatcctgacaaatggacagtacag
cctatacagctgccagaaaaggagagctggactgtcaatgatatacagaagttagtgggaaaattaaacacggcaagcca
gatttacccagggattaaagtaagacaactttgtagactccttagaggggccaaagcactaacagacatagtaccactaa
ctgaagaagcagaattagaattggcagagaacagggaaattctaaaagaaccagtacatggagtatattatgacccttca
aaagacttgatagctgaaatacagaaacagggacatgaccaatggacatatcaaatttaccaagaaccattcaaaaatct
gaaaacagggaagtatgcaaaaatgaggactgcccacactaatgatgtaaaacggttaacagaggcagtgcaaaaaatag
ccttagaaagcatagtaatatggggaaagattcctaaacttaggttacccatccaaaaagaaacatgggagacatggtgg
actgactattggcaagccacctggattcctgagtgggaatttgttaatactcctcccctagtaaaattatggtaccagct
agagaaggaacccataataggagtagaaactttctatgtagatggagcagctaatagggaaaccaaaataggaaaagcag
ggtatgttactgacagaggaaggcagaaaattgtttctctaactgaaacaacaaatcagaagactcaattacaagcaatt
tatctagctttgcaagattcaggatcagaagtaaacatagtaacagactcacagtatgcattaggaattattcaagcaca
accagataagagtgaatcagggttagtcaaccaaataatagaacaattaataaaaaggaaaggtctacctgtcatggg
taccagcacataaaggtattggaggaaatgaacaagtagacaaattagtaagtagtggaatcaggagagtgctataataa
gctcgagatacttggacaggagttgaaactatcataagaatgctgcaacaactactgtttattcatttcagaattgggtg
ccagcatagcagaataggcattatgagacagagaagagcaagaaatggagccagtagatcctaacctagagccctggaac
catccaggaagtcagcctgaaactgcttgcaataactgttattgtaaacgctatagctaccattgtctagtttgctttca
gagaaaaggcttaggcatttcctatggcaggaagaagcggagacagcgacgaagcgctcctcagagcagtgaggatcatc
agaattttgtatcaaagcagtaagtatctgtaatgttagatttagattataaattagcagtaggagcatttatagtagca
ctactcatagcaatagttgtgtggaccatagtatttatagaatataggaaattgttaagacaaagaaaaatagactggtt
aattaaaagaattagggaaagagcagaagacagtggcaatgagagtgaaggggatactgaggaattatcgacaatggtgg
atatggggcatcttaggcttttggatgttaatgatttgtaatggaaacttgtgggtcacagtctattatggggtacctgt
gtggaaagaagcaaaaactactctattctgtgcatcaaatgctaaagcatatgagaaagaagtacataatgtctgggcta
cacatgcctgtgtacccacagaccccaacccacaagaaatggttttggaaaacgtaacagaaaattttaacatgtggaaa
aatgacatggtgaatcagatgcatgaggatgtaatcagcttatgggatcaaagcctaaagccatgtgtaaagttgacccc
actctgtgtcactttagaatgtagaaaggttaatgctacccataatgctaccaataatggggatgctacccataatgtta
ccaataatgggcaagaaatacaaaattgctctttcaatgcaaccacagaaataagagataggaagcagagagtgtatgca
ctttttatagacttgatatagtaccacttgataagaacaactctagtaagaacaactctagtgagtattatagattaat
aaattgtaatacctcagccataacacaagcatgtccaaaggtcagttttgatccaattcctatacactattgtgctccag
ctggttatgcgattctaaagtgtaacaataagacattcaatggacaggaccatgcaataatgtcagcacagtacaatgt
acacatggaattaagccagtggtatcaactcagctattgttaaacggtagcctagcagaaggagagataataattagatc

FIG. 17B tgaaaatctgacagacaatgtcaaaacaataatagtacatcttgatcaatctgtagaaattgtgtgtacaagacccaaca
ataatacaagaaaagtataaggatagggccaggacaaacattctatgcaacaggaggcataatagggaacatacgacaa
gcacattgtaacattagtgaagacaaatggaatgaaactttacaaagggtgggtaaaaaattagtagaacacttccctaa
taagacaataaaatttgcaccatcctcaggaggggacctagaaattacaacacatagctttaattgtagaggagaatttt
tctattgcagcacatcaagactgtttaatagtacatacatgcctaatgatacaaaaagtaagtcaaacaaaaccatcaca
atcccatgcagcataaaacaaattgtaaacatgtggcaggaggtaggacgagcaatgtatgcccctcccattgaaggaaa
cataacctgtagatcaaatatcacaggaatactattggtacgtgatggaggagtagattcagaagatccagaaaataata
agacagagacattccgacctggaggaggagatatgaggaacaattggagaagtgaattatataaatataaagcggcagaa
attaagccattgggagtagcacccactccagcaaaaaggagagtggtggagagagaaaaaagagcagtaggattaggagc
tgtgttccttggattcttgggagcagcaggaagcactatgggcgcagcgtcaataacgctgacggtacaggccagacaat
tgttgtctggtatagtgcaacagcaaagcaatttgctgagggctatcgaggcgcaacagcatctgttgcaactcacggtc
tggggcattaagcagctccagacaagagtcctggctatcgaaagatacctaaaggatcaacagctcctagggctttgggg
ctgctctggaaaactcatctgcaccactaatgtaccttggaactccagttggagtaacaaatctcaaacagatatttggg
aaaacatgacctggatgcagtgggataaagaagttagtaattacacagacacaatatacaggttgcttgaagactcgcaa
acccagcaggaaagaaatgaaaaggatttattagcattggacaattggaaaaatctgtggaattggtttagtataacaaa
ctggctgtggtatataaaaatattcataatgatagtaggaggcttgataggcttaagaataatttttgctgtgctttcta
tagtgaatagagttaggcagggatactcacctttgtcgtttcagacccttaccccaacccaaggggacccgacaggctc
ggaagaatcgaagaagaaggtggagggcaagacagagacagatcgattcgattagtgaacggattcttagcacttgcctg
ggacgacctgtggagcctgtgcctcttcagctaccaccgattgagagacttaatattggtgacagcgagagcggtggaac
ttctgggacacagcagtctcaggggactacagagggggtgggaagcccttaagtatctgggaggtattgtgcagtattgg
ggtctggaactaaaaaagagggctattagtctgcttgatactgtagcaatagcagtagctgaaggcacagataggattat
agaattcctccaaagaatttgtagagctatccgcaacatacctagaaggataagacagggctttgaagcagctttgcagt
aaaatggctagccccgggtgataaacggaccgcgcaatccctaggctgtgccttctagttgccagccatctgttgtttgc
ccctcccccgtgccttccttgaccctggaaggtgccactcccactgtcctttcctaataaaatgaggaaattgcatcgca
ttgtctgagtaggtgtcattctattctggggggtggggtggggcaggacagcaagggggaggattgggaagacaatagca
ggcatgctggggatgcggtgggctctatataaaaaacgcccggcggcaaccgagcgttctgaacgctagagtcgacaaat
tcagaagaactcgtcaagaaggcgatagaaggcgatgcgctgcgaatcgggagcggcgataccgtaaagcacgaggaagc
ggtcagcccattcgccgccaagctcttcagcaatatcacgggtagccaacgctatgtcctgatagcggtctgccacaccc
agccggccacagtcgatgaatccagaaaagcggccattttccaccatgatattcggcaagcaggcatcgccatgggtcac
gacgagatcctcgccgtcgggcatgctcgccttgagcctggcgaacagttcggctggcgcgagcccctgatgctcttcgt
ccagatcatcctgatcgacaagaccggcttccatccgagtacgtgctcgctcgatgcgatgtttcgcttggtggtcgaat
gggcaggtagccggatcaagcgtatgcagccgccgcattgcatcagccatgatggatactttctcggcaggagcaaggtg
agatgacaggagatcctgccccggcacttcgcccaatagcagccagtcccttcccgcttcagtgacaacgtcgagcacag
ctgcgcaaggaacgcccgtcgtggccagccacgatagccgcgctgcctcgtcttgcagttcattcagggcaccggacagg
tcggtcttgacaaaaagaaccgggcgcccctgcgctgacagccggaacacggcggcatcagagcagccgattgtctgttg
tgcccagtcatagccgaatagcctctccacccaagcggccggagaacctgcgtgcaatccatcttgttcaatcatgcgaa
acgatcctcatcctgtctcttgatcagatcttgatcccctgcgccatcagatccttggcggcaagaaagccatccagttt
actttgcagggcttcccaaccttaccagagggcgccccagctggcaattccggttcgcttgctgtccataaaaccgccca
gtctagctatcgccatgtaagcccactgcaagctacctgctttctctttgcgcttgcgttttcccttgtccagatagccc
agtagctgacattcatccggggtcagcaccgtttctgcggactggctttctacgtgaaaaggatctaggtgaagatcctt
tttgataatctcatgaccaaaatcccttaacgtgagttttcgttccactgagcgtcagaccccgtagaaaagatcaaagg
atcttcttgagatcctttttttctgcgcgtaatctgctgcttgcaaacaaaaaaaccaccgctaccagcggtggtttgtt
tgccggatcaagagctaccaactctttttccgaaggtaactggcttcagcagagcgcagataccaaatactgttcttcta
gtgtagccgtagttaggccaccacttcaagaactctgtagcaccgcctacatacctcgctctgctaatcctgttaccagt
ggctgctgccagtggcgataagtcgtgtcttaccgggttggactcaagacgatagttaccggataaggcgcagcggtcgg
gctgaacggggggttcgtgcacacagcccagcttggagcgaacgacctacaccgaactgagatacctacagcgtgagcta
tgagaaagcgccacgcttcccgaagggagaaaggcggacaggtatccggtaagcggcagggtcggaacaggagagcgcac
gagggagcttccagggggaaacgcctggtatctttatagtcctgtcgggtttcgccacctctgacttgagcgtcgatttt
tgtgatgctcgtcaggggggcggagcctatggaaaaacgccagcaacgcggcctttttacggttcctggccttttgctgg
ccttttgctcacatgttgtcgacaatattggctattggccattgcatacgttgtatctatatcataatatgtacatttat
attggctcatgtccaatatgaccgccatgttgacattgattattgactagttattaatagtaatcaattacggttcatt
agttcatagcccatatatggagttccgcgttacataacttacggtaaatggcccgcctggctgaccgcccaacgaccccc
gcccattgacgtcaataatgacgtatgttcccatagtaacgccaatagggactttccattgacgtcaatgggtggagtat
ttacggtaaactgcccacttggcagtacatcaagtgtatcatatgccaagtccgccccctattgacgtcaatgacggtaa
atggcccgcctggcattatgcccagtacatgaccttacgggactttcctacttggcagtacatctacggtattagtcatc
gctattaccatggtgatgcggttttggcagtacaccaatgggcgtggatagcggtttgactcacggggatttccaagtc
tccaccccattgacgtcaatgggagtttgttttggcaccaaaatcaacgggactttccaaaatgtcgtaataaccccgcc
ccgttgacgcaaatgggcggtaggcgtgtacggtgggaggtctatataagcagagctcgtttagtgaaccgtcagatcgc
ctggagacgccatccacgctgttttgacctccatagaagacaccgggaccgatccagcctccgcggccgggaacggtgca
ttggaacgcggattccccgtgccaagagtgacgtaagtaccgcctatagactctataggcacacccctttggctcttatg
catgctatactgtttttggcttggggcctatacacccccgcttccttatgctataggtgatggtatagcttagcctatag
gtgtgggttattgaccattattgaccactcccctattggtgacgatactttccattactaatccataacatggctctttg
ccacaactatctctattggctatatgccaatactctgtccttcagagactgacacggactctgtatttttacaggatggg

FIG. 17C gtcccatttattatttacaaattcacatatacaacaacgccgtcccccgtgcccgcagttttattaaacatagcgtggg
atctccacgcgaatctcgggtaccgtgttccggacatgggytcttctccggtagcggcggagcttccacatccgagccct
ggtcccatgcctccagcggctcatggtcgctcggcagctccttgctcctaacagtggaggccagacttaggcacagcaca
atgcccaccaccaccagtgtgccgcacaaggccgtggcggtagggtatgtgtctgaaaatgagctcggagattgggctcg
caccgctgacgcagatggaagacttaaggcagcggcagaagaagatgcaggcagctgagttgttgtattctgataagagt
cagaggtaactcccgttgcggtgctgttaacggtggagggcagtgtagtctgagcagtactcgttgctgccgcgcgcgcc
accagacataatagctgacagactaacagactgttcctttccatgggtcttttctgcagtcaccat FIG. 17D pGA1/IN3 Functional Regions

| **Position within sequence (starting and ending pos.)** | **Gene/ORF (indicate complete name of the gen and the expressed gene product)** | **Origin of sequence (organism)** |
|---|---|---|
| 99-1577 | Gag, inactivating point mutations in zinc finger packaging sequences for viral RNA | C HIV-1 isolate 98IN012 |
| 1382-3520 | Pol, inactivating point mutations in reverse transcriptase, deletion of integrase | C HIV-1 isolate 98IN012 |
| 3645-3859 and 6205-6295 | Tat exons #1 and #2 | C HIV-1 isolate 98IN012 |
| 3784-3859 and 6205-6452 | Rev exons #1 and #2 | C HIV-1 isolate 98IN012 |
| 3873-4121 | Vpu | C HIV-1 isolate 98IN012 |
| 4039-6642 | Env | C HIV-1 isolate 98IN012 |
| 6643-10466 | Plasmid vector | pGA1, GenBank accession # AF425297 |

FIG. 17E IN3 Mutation Chart

| Codon Change | Amino acid change | Region | Function |
|---|---|---|---|
| to TCC Position 1260-1262 | C390S | Gag | Ablation of zinc finger used in packaging |
| to TCT Position 1269-1271 | C393S | Gag | Ablation of zinc finger used in packaging |
| to TCT Position 1323-1325 | C411S | Gag | Ablation of zinc finger used in packaging |
| to TCT Position 1332-1334 | C414S | Gag | Ablation of zinc finger used in packaging |
| to GCC Position 1610-1612 | D25N | Protease | Inactivation of Protease active site |
| to AAT Position 2387-2389 | D185N | Reverse Transcriptase | Inactivation of Polymerase active site |
| to ACG Position 2630-2632 | W266T | Reverse Transcriptase | Ablation of strand transfer activity |
| to CAA Position 3266-3268 | E478Q | RNase H | Inactivation of RNase H activity |

FIG. 18A pGA1/IN2 Sequence ggatccggcttgctgaagtgcactcggcaagaggcgaggggtggcggctggtgagtacgccaaattttatttgactagcg
gaggctagaaggagagagatgggtgcgagagcgtcaatattaagaggggaaaattagataaatgggaaaagattaggtt
aaggccagggggaaagaaacactatatgctaaaacacctagtatgggcaagcagggagctggaaagatttgcacttaacc
ctggcctttagagacatcagaaggctgtaaacaaataataaaacagctacaaccagctcttcagacaggaacagaggaa
cttaggtcattattcaatgcagtagcaactctctattgtgtacatgcagacatagaggtacgagacaccaaagaagcatt
agacaagatagaggaagaacaaaacaaaagtcagcaaaaaacgcagcaggcaaaagaggctgacaaaaaggtcgtcagtc
aaaattatcctatagtgcagaatcttcaagggcaaatggtacaccaggcactatcacctagaactttgaatgcatgggta
aaagtaatagaagaaaaagcctttagcccggaggtaatacccatgttcacagcattatcagaaggagccaccccacaaga
tttaaacaccatgttaaataccgtgggggacatcaagcagccatgcaaatgttaaaagataccatcaatgaggaggctg
cagaatgggatagattacatccagtacatgcagggcctgttgcaccaggccaaatgagagaaccaaggggaagtgacata
gcaggaactactagtaccttcaggaacaaatagcatggatgacaagtaacccacctattccagtgggagatatctataa
aagatggataattctggggttaaataaaatagtaagaatgtatagccctgtcagcattttagacataagacaagggccaa
aggaaccctttagagattatgtagaccggttctttaaaactttaagagctgaacaagcttcacaagatgtaaaaaattgg
atggcagacaccttgttggtccaaaatgcgaacccagattgtaagaccattttaagagcattaggaccaggagctacatt
agaagaaatgatgacagcatgtcaaggagtgggaggacctagccacaaagcaagagtgttggctgaggcaatgagccaaa
caggcagtaccataatgatgcagagaagcaatttaaaggctctaaaagaactgttaaatgcttcaactgtggcaaggaa
gggcacatagctagaaattgcagggcccctaggaaaaaggctgttggaaatgtggaaaggaaggacaccaaatgaaaga
ctgtgctgagaggcaggctaatttttttagggaaaatttggccttcccacaaggggaggccagggaatttccttcagaaca
ggccagagccaacagccccaccagcagagagcttcaggttcgaggagacaacccctgctccgaagcaggagctgaaagac
agggaacccttaacctccctcaaatcactctttggcagcgaccccttgtctcaataaaaataggggggccagataaaggag
gctctcttagacacaggagcagatgatacagtattagaagaaatgaatttgccaggaaaatggaaaccaaaaatgatagg
aggaattggaggttttatcaaagtaagacagtatgatcaaatacttatagaaatttgtggaaaaaggctataggtacag
tattagtaggacccacacctgtcaacataattggaagaaatatgctgactcagattggatgcacgctaaattttccaatt
agtcccattgaaactgtaccagtaaaattaaagccaggaatggatggcccaaaggttaaacaatggccattgacagagga
gaaaataaaagcattaacagcaatttgtgatgaaatggagaaggaaggaaaaattacaaaaattgggcctgaaaatccat
ataacactccaatattcgccataaaaaagaaggacagtactaagtggagaaaattagtagatttcagagaacttaataaa
agaactcaagacttctgggaagttcaattaggaataccacacccagcagggttaaaaaagaaaaaatcagtgacagtact
agatgtgggggatgcatatttttcagttcctttagatgaaagctttaggaggtatactgcattcaccatacctagtagaa
acaatgaaacaccagggattagatatcaatataatgtgcttccacaaggatggaaaggatcaccagcaatattccagagt
agcatgacaaaaatcttagagccctttagagcacaaaatccagaaatagtcatctatcaatatatgaatgacttgtatgt
aggatctgacttagaaatagggcaacatagagcaaagatagaggaattaagagaacatctattaaggtggggatttacca
caccagacaagaaacatcagaaagaaccccccatttctttggatggggtatgaactccatcctgacaaatggacagtacag
cctatacagctgccagaaaaggagagctggactgtcaatgatatacagaagttagtgggaaaattaaacacggcaagcca
gatttacccagggattaaagtaagacaactttgtagactccttagaggggccaaagcactaacagacatagtaccactaa
ctgaagaagcagaattagaattggcagagaacagggaaattctaaaagaaccagtacatggagtatattatgacccttca
aaagacttgatagctgaaatacagaaacagggacatgaccaatggacatatcaaatttaccaagaaccattcaaaaatct
gaaaacagggaagtatgcaaaaatgaggactgcccacactaatgatgtaaaacggttaacagaggcagtgcaaaaaatag
ccttagaaagcatagtaatatggggaaagattcctaaacttaggttacccatccaaaaagaaacatgggagacatggtgg
actgactattggcaagccacctggattcctgagtgggaatttgttaatactcctcccctagtaaaattatggtaccagct
agagaaggaacccataataggagtagaaactttctatgtagatggagcagctaatagggaaaccaaaataggaaaagcag
ggtatgttactgacagaggaaggcagaaaattgtttctctaactgaaacaacaaatcagaagactcaattacaagcaatt
tatctagctttgcaagattcaggatcagaagtaaacatagtaacagactcacagtatgcattaggaattattcaagcaca
accagataagagtgaatcagggttagtcaaccaaataatagaacaattaataaaaaggaaagggtctacctgtcatggg
taccagcacataaaggtattggaggaaatgaacaagtagacaaattagtaagtagtggaatcaggagagtgctataataa
gctcgagatacttggacaggagttgaaactatcataagaatgctgcaacaactactgtttattcatttcagaattgggtg
ccagcatagcagaataggcattatgagacagagaagagcaagaaatggagccagtagatcctaacctagagccctggaac
catccaggaagtcagcctgaaactgcttgcaataactgttattgtaaacgctatagctaccattgtctagtttgctttca
gagaaaaggcttaggcatttcctatggcaggaagaagcggagacagcgacgaagcgctcctcagagcagtgaggatcatc
agaattttgtatcaaagcagtaagtatctgtaatgttagatttagattataaattagcagtaggagcatttatagtagca
ctactcatagcaatagttgtgtggaccatagtatttatagaatataggaaattgttaagacaaagaaaaatagactggtt
aattaaaagaattagggaaagagcagaagacagtggcaatgagagtgaaggggatactgaggaattatcgacaatggtgg
atatggggcatcttaggcttttggatgttaatgatttgtaatggaaacttgtgggtcacagtctattatggggtacctgt
gtggaaagaagcaaaaactactctattctgtgcatcaaatgctaaagcatatgagaaagaagtacataatgtctgggcta
cacatgcctgtgtacccacagaccccaacccacaagaaatggttttggaaaacgtaacagaaaattttaacatgtggaaa
aatgacatggtgaatcagatgcatgaggatgtaatcagcttatgggatcaaagcctaaagccatgtgtaaagttgacccc
actctgtgtcactttagaatgtagaaaggttaatgctacccataatgctaccaataatggggatgctacccataatgtta
ccaataatgggcaagaaatacaaaattgctctttcaatgcaaccacagaaataagagataggaagcagagagtgtatgca
ctttttatagacttgatatagtaccacttgataagaacaactctagtaagaacaactctagtgagtattatagattaat
aaattgtaatacctcagccataacacaagcatgtccaaaggtcagttttgatccaattcctatacactattgtgctccag
ctggttatgcgattctaaagtgtaacaataagacattcaatgggacaggaccatgcaataatgtcagcacagtacaatgt
acacatggaattaagccagtggtatcaactcagctattgttaaacggtagcctagcagaaggagagataataattagatc

FIG. 18B tgaaaatctgacagacaatgtcaaaacaataatagtacatcttgatcaatctgtagaaattgtgtgtacaagacccaaca
ataatacaagaaaaagtataaggatagggccaggacaaacattctatgcaacaggaggcataatagggaacatacgacaa
gcacattgtaacattagtgaagacaaatggaatgaaactttacaaagggtgggtaaaaaattagtagaacacttccctaa
taagacaataaaatttgcaccatcctcaggaggggacctagaaattacaacacatagctttaattgtagaggagaatttt
tctattgcagcacatcaagactgtttaatagtacatacatgcctaatgatacaaaaagtaagtcaaacaaaaccatcaca
atcccatgcagcataaaacaaattgtaaacatgtggcaggaggtaggacgagcaatgtatgcccctcccattgaaggaaa
cataacctgtagatcaaatatcacaggaatactattggtacgtgatggaggagtagattcagaagatccagaaaataata
agacagagacattccgacctggaggaggagatatgaggaacaattggagaagtgaattatataaatataaagcggcagaa
attaagccattgggagtagcacccactccagcaaaaggagagtggtggagagagaaaaaagagcagtaggattaggagc
tgtgttccttggattcttgggagcagcaggaagcactatgggcgcagcgtcaataacgctgacggtacaggccagacaat
tgttgtctggtatagtgcaacagcaaagcaatttgctgagggctatcgaggcgcaacagcatctgttgcaactcacggtc
tggggcattaagcagctccagacaagagtcctggctatcgaaagatacctaaaggatcaacagctcctagggctttgggg
ctgctctggaaaactcatctgcaccactaatgtaccttggaactccagttggagtaacaaatctcaaacagatatttggg
aaaacatgacctggatgcagtgggataaagaagttagtaattacacagacacaatatacaggttgcttgaagactcgcaa
acccagcaggaaagaaatgaaaaggatttattagcattggacaattggaaaaatctgtggaattggtttagtataacaaa
ctggctgtggtatataaaaatattcataatgatagtaggaggcttgataggcttaagaataatttttgctgtgctttcta
tagtgaatagagttaggcagggatactcacctttgtcgtttcagacccttaccccaaacccaaggggacccgacaggctc
ggaagaatcgaagaagaaggtggagggcaagacagagacagatcgattcgattagtgaacggattcttagcacttgcctg
ggacgacctgtggagcctgtgcctcttcagctaccaccgattgagagacttaatattggtgacagcgagagcggtggaac
ttctgggacacagcagtctcaggggactacagaggggtgggaagcccttaagtatctgggaggtattgtgcagtattgg
ggtctggaactaaaaaagagggctattagtctgcttgatactgtagcaatagcagtagctgaaggcacagataggattat
agaattcctccaaagaatttgtagagctatccgcaacatacctagaaggataagacagggctttgaagcagctttgcagt
aaaatggctagccccgggtgataaacggaccgcgcaatccctaggctgtgccttctagttgccagccatctgttgtttgc
ccctcccccgtgccttccttgaccctggaaggtgccactcccactgtcctttcctaataaaatgaggaaattgcatcgca
ttgtctgagtaggtgtcattctattctggggggtggggtggggcaggacagcaagggggaggattgggaagacaatagca
ggcatgctggggatgcggtgggctctatataaaaaacgcccggcggcaaccgagcgttctgaacgctagagtcgacaaat
tcagaagaactcgtcaagaaggcgatagaaggcgatgcgctgcgaatcgggagcggcgataccgtaaagcacgaggaagc
ggtcagcccattcgccgccaagctcttcagcaatatcacgggtagccaacgctatgtcctgatagcggtctgccacaccc
agccggccacagtcgatgaatccagaaaagcggccattttccaccatgatattcggcaagcaggcatcgccatgggtcac
gacgagatcctcgccgtcgggcatgctcgccttgagcctggcgaacagttcggctggcgcgagcccctgatgctcttcgt
ccagatcatcctgatcgacaagaccggcttccatccgagtacgtgctcgctcgatgcgatgtttcgcttggtggtcgaat
gggcaggtagccggatcaagcgtatgcagccgccgcattgcatcagccatgatggatactttctcggcaggagcaaggtg
agatgacaggagatcctgccccggcacttcgcccaatagcagccagtcccttcccgcttcagtgacaacgtcgagcacag
ctgcgcaaggaacgcccgtcgtggccagccacgatagccgcgctgcctcgtcttgcagttcattcagggcaccggacagg
tcggtcttgacaaaaagaaccgggcgcccctgcgctgacagccggaacacggcggcatcagagcagccgattgtctgttg
tgcccagtcatagccgaatagcctctccacccaagcggccggagaacctgcgtgcaatccatcttgttcaatcatgcgaa
acgatcctcatcctgtctcttgatcagatcttgatcccctgcgccatcagatccttggcggcaagaaagccatccagttt
actttgcagggcttcccaaccttaccagagggcgccccagctggcaattccggttcgcttgctgtccataaaaccgccca
gtctagctatcgccatgtaagcccactgcaagctacctgctttctctttgcgcttgcgttttcccttgtccagatagccc
agtagctgacattcatccggggtcagcaccgtttctgcggactggctttctacgtgaaaaggatctaggtgaagatcctt
tttgataatctcatgaccaaaatcccttaacgtgagttttcgttccactgagcgtcagaccccgtagaaaagatcaaagg
atcttcttgagatcctttttttctgcgcgtaatctgctgcttgcaaacaaaaaaaccaccgctaccagcggtggtttgtt
tgccggatcaagagctaccaactctttttccgaaggtaactggcttcagcagagcgcagataccaaatactgttcttcta
gtgtagccgtagttaggccaccacttcaagaactctgtagcaccgcctacatacctcgctctgctaatcctgttaccagt
ggctgctgccagtggcgataagtcgtgtcttaccgggttggactcaagacgatagttaccggataaggcgcagcggtcgg
gctgaacggggggttcgtgcacacagcccagcttggagcgaacgacctacaccgaactgagatacctacagcgtgagcta
tgagaaagcgccacgcttcccgaagggagaaaggcggacaggtatccggtaagcggcagggtcggaacaggagagcgcac
gagggagcttccagggggaaacgcctggtatctttatagtcctgtcgggtttcgccacctctgacttgagcgtcgatttt
tgtgatgctcgtcaggggggcggagcctatggaaaaacgccagcaacgcggcctttttacggttcctggccttttgctgg
ccttttgctcacatgttgtcgacaatattggctattggccattgcatacgttgtatctatatcataatatgtacatttat
attggctcatgtccaatatgaccgccatgttgacattgattattgactagttattaatagtaatcaattacggttcatt
agttcatagcccatatatggagttccgcgttacataacttacggtaaatggcccgcctggctgaccgcccaacgaccccc
gcccattgacgtcaataatgacgtatgttcccatagtaacgccaatagggactttccattgacgtcaatgggtggagtat
ttacggtaaactgcccacttggcagtacatcaagtgtatcatatgccaagtccgccccctattgacgtcaatgacggtaa
atggcccgcctggcattatgcccagtacatgaccttacgggactttcctacttggcagtacatctacggtattagtcatc
ggctattaccatggtgatgcggttttggcagtacaccaatgggcgtggatagcggtttgactcacggggatttccaagtc
tccaccccattgacgtcaatgggagtttgttttggcaccaaaatcaacgggactttccaaaatgtcgtaataaccccgcc
ccgttgacgcaaatgggcggtaggcgtgtacggtgggaggtctatataagcagagctcgtttagtgaaccgtcagatcgc
ctggagacgccatccacgctgttttgacctccatagaagacaccgggaccgatccagcctccgcggccgggaacggtgca
ttggaacgcggattccccgtgccaagagtgacgtaagtaccgcctatagactctataggcacacccctttggctcttatg
catgctatactgtttttggcttggggcctatacacccccgcttccttatgctataggtgatggtatagcttagcctatag
gtgtgggttattgaccattattgaccactcccctattggtgacgatactttccattactaatccataacatggctctttg
ccacaactatctctattggctatatgccaatactctgtccttcagagactgacacggactctgtatttttacaggatggg

FIG. 18C gtcccatttattatttacaaattcacatatacaacaacgccgtcccccgtgcccgcagttttttattaaacatagcgtggg
atctccacgcgaatctcgggtaccgtgttccggacatgggytcttctccggtagcggcggagcttccacatccgagccct
ggtcccatgcctccagcggctcatggtcgctcggcagctccttgctcctaacagtggaggccagacttaggcacagcaca
atgcccaccaccaccagtgtgccgcacaaggccgtggcggtagggtatgtgtctgaaaatgagctcggagattgggctcg
caccgctgacgcagatggaagacttaaggcagcggcagaagaagatgcaggcagctgagttgttgtattctgataagagt
cagaggtaactcccgttgcggtgctgttaacggtggagggcagtgtagtctgagcagtactcgttgctgccgcgcgcgcc
accagacataatagctgacagactaacagactgttcctttccatgggtcttttctgcagtcaccat FIG. 18D pGA1/IN2 Functional Regions

| **Position within sequence (starting and ending pos.)** | **Gene/ORF (indicate complete name of the gen and the expressed gene product)** | **Origin of sequence (organism)** |
|---|---|---|
| 99-1577 | Gag | C HIV-1 isolate 98IN012 |
| 1382-3520 | Pol, inactivating point mutaitons in reverse transcriptase, deletion of integrase | C HIV-1 isolate 98IN012 |
| 3645-3859 and 6205-6295 | Tat exons #1 and #2 | C HIV-1 isolate 98IN012 |
| 3784-3859 and 6205-6452 | Rev exons #1 and #2 | C HIV-1 isolate 98IN012 |
| 3873-4121 | Vpu | C HIV-1 isolate 98IN012 |
| 4039-6642 | Env | C HIV-1 isolate 98IN012 |
| 6643-10466 | Plasmid vector | pGA1, GenBank accession # AF425297 |

FIG. 18E IN2 Mutation Chart

| Codon Change | Amino acid change | Region | Function |
|---|---|---|---|
| to TCC Position 1260-1262 | C390S | Gag | Ablation of zinc finger used in packaging |
| to TCT Position 1269-1271 | C393S | Gag | Ablation of zinc finger used in packaging |
| to TCT Position 1323-1325 | C411S | Gag | Ablation of zinc finger used in packaging |
| to TCT Position 1332-1334 | C414S | Gag | Ablation of zinc finger used in packaging |
| to AAT Position 2387-2389 | D185N | Reverse Transcriptase | Inactivation of Polymerase active site |
| to ACG Position 2630-2632 | W266T | Reverse Transcriptase | Ablation of strand transfer activity |
| to CAA Position 3266-3268 | E478Q | RNase H | Inactivation of RNase H activity |

```
1   GAATTCGTTG GTGGTCGCCA TGGATGGTGT TATTGTATAC TGTCTAAACG CGTTAGTAAA ACATGGCGAG
    CTTAAGCAAC CACCAGCGGT ACCTACCACA ATAACATATG ACAGATTTGC GCAATCATTT TGTACCGCTC

71  GAAATAAATC ATATAAAAAA TGATTTCATG ATTAAACCAT GTTGTGAAAA AGTCAAGAAC GTTCACATTG
    CTTTATTTAG TATATTTTTT ACTAAAGTAC TAATTTGGTA CAACACTTTT TCAGTTCTTG CAAGTGTAAC

141 GCGGACAATC TAAAAACAAT ACAGTGATTG CAGATTTGCC ATATATGGAT AATGCGGTAT CCGATGTATG
    CGCCTGTTAG ATTTTTGTTA TGTCACTAAC GTCTAAACGG TATATACCTA TTACGCCATA GGCTACATAC

211 CAATTCACTG TATAAAAAGA ATGTATCAAG AATATCCAGA TTTGCTAATT TGATAAAGAT AGATGACGAT
    GTTAAGTGAC ATATTTTTCT TACATAGTTC TTATAGGTCT AAACGATTAA ACTATTTCTA TCTACTGCTA

281 GACAAGACTC CTACTGGTGT ATATAATTAT TTTAAACCTA AAGATGCCAT TCCTGTTATT ATATCCATAG
    CTGTTCTGAG GATGACCACA TATATTAATA AAATTTGGAT TTCTACGGTA AGGACAATAA TATAGGTATC

351 GAAAGGATAG AGATGTTTGT GAACTATTAA TCTCATCTGA TAAAGCGTGT GCGTGTATAG AGTTAAATTC
    CTTTCCTATC TCTACAAACA CTTGATAATT AGAGTAGACT ATTTCGCACA CGCACATATC TCAATTTAAG
```

Text File of pLW-48 and the Included Individual HIV Genes And Their Promoters

Entire pLW-48 plasmid sequences: SEQ ID NO:83

GAATTCGTTGGTGGTCGCCATGGATGGTGTTATTGTATACTGTCTAAACGCG
TTAGTAAAACATGGCGAGGAAATAAATCATATAAAAAATGATTTCATGATTAA
ACCATGTTGTGAAAAAGTCAAGAACGTTCACATTGGCGGACAATCTAAAAAC
AATACAGTGATTGCAGATTTGCCATATATGGATAATGCGGTATCCGATGTAT
GCAATTCACTGTATAAAAAGAATGTATCAAGAATATCCAGATTTGCTAATTTG
ATAAAGATAGATGACGATGACAAGACTCCTACTGGTGTATATAATTATTTTAA
ACCTAAAGATGCCATTCCTGTTATTATATCCATAGGAAAGGATAGAGATGTTT
GTGAACTATTAATCTCATCTGATAAAGCGTGTGCGTGTATAGAGTTAAATTCA
TATAAAGTAGCCATTCTTCCCATGGATGTTTCCTTTTTTACCAAAGGAAATGC
ATCATTGATTATTCTCCTGTTTGATTTCTCTATCGATGCGGCACCTCTCTTAA
GAAGTGTAACCGATAATAATGTTATTATATCTAGACACCAGCGTCTACATGA
CGAGCTTCCGAGTTCCAATTGGTTCAAGTTTTACATAAGTATAAAGTCCGAC
TATTGTTCTATATTATATATGGTTGTTGATGGATCTGTGATGCATGCAATAGC
TGATAATAGAACTTACGCAAATATTAGCAAAAATATATTAGACAATACTACAA
TTAACGATGAGTGTAGATGCTGTTATTTTGAACCACAGATTAGGATTCTTGAT
AGAGATGAGATGCTCAATGGATCATCGTGTGATATGAACAGACATTGTATTA
TGATGAATTTACCTGATGTAGGCGAATTTGGATCTAGTATGTTGGGGAAATA
TGAACCTGACATGATTAAGATTGCTCTTTCGGTGGCTGGGTACCAGGCGCG
CCTTTCATTTTGTTTTTTTCTATGCTATAAATGGTACGTCCTGTAGAAACCCC
AACCCGTGAAATCAAAAAACTCGACGGCCTGTGGGCATTCAGTCTGGATCG
CGAAAACTGTGGAATTGATCAGCGTTGGTGGGAAAGCGCGTTACAAGAAAG
CCGGGCAATTGCTGTGCCAGGCAGTTTTAACGATCAGTTCGCCGATGCAGA
TATTCGTAATTATGCGGGCAACGTCTGGTATCAGCGCGAAGTCTTTATACCG
AAAGGTTGGGCAGGCCAGCGTATCGTGCTGCGTTTCGATGCGGTCACTCAT
TACGGCAAAGTGTGGGTCAATAATCAGGAAGTGATGGAGCATCAGGGCGG
CTATACGCCATTTGAAGCCGATGTCACGCCGTATGTTATTGCCGGGAAAAG
TGTACGTATCACCGTTTGTGTGAACAACGAACTGAACTGGCAGACTATCCC
GCCGGGAATGGTGATTACCGACGAAAACGGCAAGAAAAAGCAGTCTTACTT
CCATGATTTCTTTAACTATGCCGGAATCCATCGCAGCGTAATGCTCTACACC
ACGCCGAACACCTGGGTGGACGATATCACCGTGGTGACGCATGTCGCGCA
AGACTGTAACCACGCGTCTGTTGACTGGCAGGTGGTGGCCAATGGTGATGT
CAGCGTTGAACTGCGTGATGCGGATCAACAGGTGGTTGCAACTGGACAAG
GCACTAGCGGGACTTTGCAAGTGGTGAATCCGCACCTCTGGCAACCGGGT
GAAGGTTATCTCTATGAACTGTGCGTCACAGCCAAAAGCCAGACAGAGTGT
GATATCTACCCGCTTCGCGTCGGCATCCGGTCAGTGGCAGTGAAGGGCGA
ACAGTTCCTGATTAACCACAAACCGTTCTACTTTACTGGCTTTGGTCGTCAT
GAAGATGCGGACTTGCGTGGCAAAGGATTCGATAACGTGCTGATGGTGCAC
GACCACGCATTAATGGACTGGATTGGGGCCAACTCCTACCGTACCTCGCAT
TACCCTTACGCTGAAGAGATGCTCGACTGGGCAGATGAACATGGCATCGTG

FIG. 21B

GTGATTGATGAAACTGCTGCTGTCGGCTTTAACCTCTCTTTAGGCATTGGTT
TCGAAGCGGGCAACAAGCCGAAAGAACTGTACAGCGAAGAGGCAGTCAAC
GGGGAAACTCAGCAAGCGCACTTACAGGCGATTAAAGAGCTGATAGCGCGT
GACAAAAACCACCCAAGCGTGGTGATGTGGAGTATTGCCAACGAACCGGAT
ACCCGTCCGCAAGGTGCACGGGAATATTTCGCGCCACTGGCGGAAGCAAC
GCGTAAACTCGACCCGACGCGTCCGATCACCTGCGTCAATGTAATGTTCTG
CGACGCTCACACCGATACCATCAGCGATCTCTTTGATGTGCTGTGCCTGAA
CCGTTATTACGGATGGTATGTCCAAAGCGGCGATTTGGAAACGGCAGAGAA
GGTACTGGAAAAAGAACTTCTGGCCTGGCAGGAGAAACTGCATCAGCCGAT
TATCATCACCGAATACGGCGTGGATACGTTAGCCGGGCTGCACTCAATGTA
CACCGACATGTGGAGTGAAGAGTATCAGTGTGCATGGCTGGATATGTATCA
CCGCGTCTTTGATCGCGTCAGCGCCGTCGTCGGTGAACAGGTATGGAATTT
CGCCGATTTTGCGACCTCGCAAGGCATATTGCGCGTTGGCGGTAACAAGAA
AGGGATCTTCACTCGCGACCGCAAACCGAAGTCGGCGGCTTTTCTGCTGCA
AAAACGCTGGACTGGCATGAACTTCGGTGAAAAACCGCAGCAGGGAGGCA
AACAATGAGAGCTCGGTTGTTGATGGATCTGTGATGCATGCAATAGCTGATA
ATAGAACTTACGCAAATATTAGCAAAAATATATTAGACAATACTACAATTAAC
GATGAGTGTAGATGCTGTTATTTTGAACCACAGATTAGGATTCTTGATAGAG
ATGAGATGCTCAATGGATCATCGTGTGATATGAACAGACATTGTATTATGAT
GAATTTACCTGATGTAGGCGAATTTGGATCTAGTATGTTGGGGAAATATGAA
CCTGACATGATTAAGATTGCTCTTTCGGTGGCTGGCGGCCCGCTCGAGTAA
AAAATGAAAAAATATTCTAATTTATAGGACGGTTTTGATTTTCTTTTTTTCTAT
GCTATAAATAATAAATAGCGGCCGCACCATGAAAGTGAAGGGGATCAGGAA
GAATTATCAGCACTTGTGGAAATGGGGCATCATGCTCCTTGGGATGTTGATG
ATCTGTAGTGCTGTAGAAAATTTGTGGGTCACAGTTTATTATGGGGTACCTG
TGTGGAAAGAAGCAACCACCACTCTATTTTGTGCATCAGATGCTAAAGCATA
TGATACAGAGGTACATAATGTTTGGGCCACACATGCCTGTGTACCCACAGA
CCCCAACCCACAAGAAGTAGTATTGGAAAATGTGACAGAAAATTTTAACATG
TGGAAAAATAACATGGTAGAACAGATGCATGAGGATATAATCAGTTTATGGG
ATCAAAGCCTAAAGCCATGTGTAAAATTAACCCCACTCTGTGTTACTTTAAAT
TGCACTGATTTGAGGAATGTTACTAATATCAATAATAGTAGTGAGGGAATGA
GAGGAGAAATAAAAAACTGCTCTTTCAATATCACCACAAGCATAAGAGATAA
GGTGAAGAAAGACTATGCACTTTTcTATAGACTTGATGTAGTACCAATAGATA
ATGATAATACTAGCTATAGGTTGATAAATTGTAATACCTCAACCATTACACAG
GCCTGTCCAAAGGTATCCTTTGAGCCAATTCCCATACATTATTGTACCCCGG
CTGGTTTTGCGATTCTAAAGTGTAAAGACAAGAAGTTCAATGGAACAGGGCC
ATGTAAAAATGTCAGCACAGTACAATGTACACATGGAATTAGGCCAGTAGTG
TCAACTCAACTGCTGTTAAATGGCAGTCTAGCAGAAGAAGAGGTAGTAATTA
GATCTAGTAATTTCACAGACAATGCAAAAAACATAATAGTACAGTTGAAAGAA
TCTGTAGAAATTAATTGTACAAGACCCAACAACAATACAAGGAAAAGTATAC
ATATAGGACCAGGAAGAGCATTTTATACAACAGGAGAAATAATAGGAGATAT
AAGACAAGCACATTGCAACATTAGTAGAACAAAATGGAATAACACTTTAAAT
CAAATAGCTACAAAATTAAAAGAACAATTTGGGAATAATAAAACAATAGTCTT
TAATCAATCCTCAGGAGGGGACCCAGAAATTGTAATGCACAGTTTTAATTGT
GGAGGGGAATTCTTCTACTGTAATTCAACACAACTGTTTAATAGTACTTGGA
ATTTTAATGGTACTTGGAATTTAACACAATCGAATGGTACTGAAGGAAATGA

FIG. 21C

CACTATCACACTCCCATGTAGAATAAAACAAATTATAAATATGTGGCAGGAA
GTAGGAAAAGCAATGTATGCCCCTCCCATCAGAGGACAAATTAGATGCTCAT
CAAATATTACAGGGCTAATATTAACAAGAGATGGTGGAACTAACAGTAGTGG
GTCCGAGATCTTCAGACCTGGGGGAGGAGATATGAGGGACAATTGGAGAA
GTGAATTATATAAATATAAAGTAGTAAAAATTGAACCATTAGGAGTAGCACCC
ACCAAGGCAAAAAGAAGAGTGGTGCAGAGAGAAAAAAGAGCAGTGGGAAC
GATAGGAGCTATGTTCCTTGGGTTCTTGGGAGCAGCAGGAAGCACTATGGG
CGCAGCGTCAATAACGCTGACGGTACAGGCCAGACTATTATTGTCTGGTAT
AGTGCAACAGCAGAACAATTTGCTGAGGGCTATTGAGGCGCAACAGCATCT
GTTGCAACTCACAGTCTGGGGCATCAAGCAGCTCCAGGCAAGAGTCCTGG
CTGTGGAAAGATACCTAAGGGATCAACAGCTCCTAGGGATTTGGGGTTGCT
CTGGAAAACTCATCTGCACCACTGCTGTGCCTTGGAATGCTAGTTGGAGTA
ATAAAACTCTGGATATGATTTGGGATAACATGACCTGGATGGAGTGGGAAA
GAGAAATCGAAAATTACACAGGCTTAATATACACCTTAATTGAGGAATCGCA
GAACCAACAAGAAAAGAATGAACAAGACTTATTAGCATTAGATAAGTGGGCA
AGTTTGTGGAATTGGTTTGACATATCAAATTGGCTGTGGTATGTAAAAATCTT
CATAATGATAGTAGGAGGCTTGATAGGTTTAAGAATAGTTTTTACTGTACTTT
CTATAGTAAATAGAGTTAGGCAGGGATACTCACCATTGTCATTTCAGACCCA
CCTCCCAGCCCCGAGGGGACCCGACAGGCCCGAAGGAATCGAAGAAGAAG
GTGGAGACAGAGACTAATTTTTATGCGGCCGCTGGTACCCAACCTAAAAATT
GAAAATAAATACAAAGGTTCTTGAGGGTTGTGTTAAATTGAAAGCGAGAAAT
AATCATAAATAAGCCCGGGGATCCTCTAGAGTCGACACCATGGGTGCGAGA
GCGTCAGTATTAAGCGGGGGAGAATTAGATCGATGGGAAAAAATTCGGTTA
AGGCCAGGGGGAAAGAAAAAATATAAATTAAAACATATAGTATGGGCAAGCA
GGGAGCTAGAACGATTCGCAGTTAATCCTGGCCTGTTAGAAACATCAGAAG
GCTGTAGACAAATACTGGGACAGCTACAACCATCCCTTCAGACAGGATCAG
AAGAACTTAGATCATTATATAATACAGTAGCAACCCTCTATTGTGTGCATCAA
AGGATAGAGATAAAAGACACCAAGGAAGCTTTAGACAAGATAGAGGAAGAG
CAAAACAAAAGTAAGAAAAAAGCACAGCAAGCAGCAGCTGACACAGGACAC
AGCAATCAGGTCAGCCAAAATTACCCTATAGTGCAGAACATCCAGGGGCAA
ATGGTACATCAGGCCATATCACCTAGAACTTTAAATGCATGGGTAAAAGTAG
TAGAAGAGAAGGCTTTCAGCCCAGAAGTGATACCCATGTTTTCAGCATTATC
AGAAGGAGCCACCCCACAAGATTTAAACACCATGCTAAACACAGTGGGGGG
ACATCAAGCAGCCATGCAAATGTTAAAAGAGACCATCAATGAGGAAGCTGC
AGAATGGGATAGAGTGCATCCAGTGCATGCAGGGCCTATTGCACCAGGCCA
GATGAGAGAACCAAGGGGAAGTGACATAGCAGGAACTACTAGTACCCTTCA
GGAACAAATAGGATGGATGACAAATAATCCACCTATCCCAGTAGGAGAAATT
TATAAAAGATGGATAATCCTGGGATTAAATAAAATAGTAAGAATGTATAGCCC
TACCAGCATTCTGGACATAAGACAAGGACCAAAAGAACCCTTTAGAGACTAT
GTAGACCGGTTCTATAAAACTCTAAGAGCCGAGCAAGCTTCACAGGAGGTA
AAAAATTGGATGACAGAAACCTTGTTGGTCCAAAATGCGAACCCAGATTGTA
AGACTATTTTAAAAGCATTGGGACCAGCGGCTACACTAGAAGAAATGATGAC
AGCATGTCAGGGAGTAGGAGGACCCGGCCATAAGGCAAGAGTTTTGGCTG
AAGCAATGAGCCAAGTAACAAATTCAGCTACCATAATGATGCAGAGAGGCA
ATTTTAGGAACCAAAGAAAGATTGTTAAGTGTTTCAATTGTGGCAAAGAAGG
GCACACAGCCAGAAATTGCAGGGCCCCTAGGAAAAAGGGCTGTTGGAAAT

FIG. 21D

GTGGAAAGGAAGGACACCAAATGAAAGATTGTACTGAGAGACAGGCTAATT
TTTTAGGGAAGATCTGGCCTTCCTACAAGGGAAGGCCAGGGAATTTTCTTCA
GAGCAGACCAGAGCCAACAGCCCCACCAGAAGAGAGCTTCAGGTCTGGGG
TAGAGACAACAACTCCCCCTCAGAAGCAGGAGCCGATAGACAAGGAACTGT
ATCCTTTAACTTCCCTCAGATCACTCTTTGGCAACGACCCCTCGTCACAATA
AAGATAGGGGGGCAACTAAAGGAAGCTCTATTAGATACAGGAGCAGATGAT
ACAGTATTAGAAGAAATGAGTTTGCCAGGAAGATGGAAACCAAAAATGATAG
GGGGAATTGGAGGTTTTATCAAAGTAAGACAGTATGATCAGATACTCATAGA
AATCTGTGGACATAAAGCTATAGGTACAGTATTAGTAGGACCTACACCTGTC
AACATAATTGGAAGAAATCTGTTGACTCAGATTGGTTGCACTTTAAATTTTCC
CATTAGCCCTATTGAGACTGTACCAGTAAAATTAAAGCCAGGAATGGATGGC
CCAAAAGTTAAACAATGGCCATTGACAGAAGAAAAAATAAAAGCATTAGTAG
AAATTTGTACAGAAATGGAAAAGGAAGGGAAAATTTCAAAAATTGGGCCTGA
GAATCCATACAATACTCCAGTATTTGCCATAAAGAAAAAAGACAGTACTAAAT
GGAGGAAATTAGTAGATTTCAGAGAACTTAATAAGAGAACTCAAGACTTCTG
GGAAGTTCAATTAGGAATACCACATCCCGCAGGGTTAAAAAAGAAAAAATCA
GTAACAGTACTGGATGTGGGTGATGCATATTTTTCAGTTCCCTTAGATGAAG
ACTTCAGGAAGTATACTGCATTTACCATACCTAGTATAAACAATGAGACACC
AGGGATTAGATATCAGTACAATGTGCTTCCACAGGGATGGAAAGGATCACC
AGCAATATTCCAAAGTAGCATGACAAAAATCTTAGAGCCTTTTAAAAAACAAA
ATCCAGACATAGTTATCTATCAATACATGAACGATTTGTATGTAGGATCTGAC
TTAGAAATAGGGCAGCATAGAACAAAAATAGAGGAGCTGAGACAACATCTG
TTGAGGTGGGGACTTACCACACCAGACAAAAAACATCAGAAAGAACCTCCA
TTCCTTTGGATGGGTTATGAACTCCATCCTGATAAATGGACAGTACAGCCTA
TAGTGCTGCCAGAAAAAGACAGCTGGACTGTCAATGACATACAGAAGTTAG
TGGGGAAATTGAATACCGCAAGTCAGATTTACCCAGGGATTAAAGTAAGGC
AATTATGTAAACTCCTTAGAGGAACCAAAGCACTAACAGAAGTAATACCACT
AACAGAAGAAGCAGAGCTAGAACTGGCAGAAAACAGAGAGATTCTAAAAGA
ACCAGTACATGGAGTGTATTATGACCCATCAAAAGACTTAATAGCAGAAATA
CAGAAGCAGGGGCAAGGCCAATGGACATATCAAATTTATCAAGAGCCATTT
AAAAATCTGAAAACAGGAAAATATGCAAGAATGAGGGGTGCCCACACTAAT
GATGTAAAACAATTAACAGAGGCAGTGCAAAAAATAACCACAGAAAGCATAG
TAATATGGGGAAAGACTCCTAAATTTAAACTACCCATACAAAAGGAAACATG
GGAAACATGGTGGACAGAGTATTGGCAAGCCACCTGGATTCCTGAGTGGGA
GTTTGTTAATACCCCTCCTTTAGTGAAATTATGGTACCAGTTAGAGAAAGAA
CCCATAGTAGGAGCAGAAACCTTCTATGTAGATGGGGCAGCTAACAGGGAG
ACTAAATTAGGAAAAGCAGGATATGTTACTAACAAAGGAAGACAAAAGGTTG
TCCCCCTAACTAACACAACAAATCAGAAAACTCAGTTACAAGCAATTTATCTA
GCTTTGCAGGATTCAGGATTAGAAGTAAACATAGTAACAGACTCACAATATG
CATTAGGAATCATTCAAGCACAACCAGATAAAAGTGAATCAGAGTTAGTCAA
TCAAATAATAGAGCAGTTAATAAAAAAGGAAAAGGTCTATCTGGCATGGGTA
CCAGCACACAAAGGAATTGGAGGAAATGAACAAGTAGATAAATTAGTCAGT
GCTGGAATCAGGAAAATACTATTTTTAGATGGAATAGATAAGGCCCAAGATG
AACATTAGTTTTTATGTCGACCTGCAGGGAAAGTTTTATAGGTAGTTGATAG
AACAAAATACATAATTTTGTAAAAATAAATCACTTTTTATACTAATATGACACG
ATTACCAATACTTTTGTTACTAATATCATTAGTATACGCTACACCTTTTCCTCA

FIG. 21E

GACATCTAAAAAAATAGGTGATGATGCAACTTTATCATGTAATCGAAATAATA
CAAATGACTACGTTGTTATGAGTGCTTGGTATAAGGAGCCCAATTCCATTAT
TCTTTTAGCTGCTAAAAGCGACGTCTTGTATTTTGATAATTATACCAAGGATA
AAATATCTTACGACTCTCCATACGATGATCTAGTTACAACTATCACAATTAAA
TCATTGACTGCTAGAGATGCCGGTACTTATGTATGTGCATTCTTTATGACATC
GCCTACAAATGACACTGATAAAGTAGATTATGAAGAATACTCCACAGAGTTG
ATTGTAAATACAGATAGTGAATCGACTATAGACATAATACTATCTGGATCTAC
ACATTCACCAGAAACTAGTTAAGCTTGTCTCCCTATAGTGAGTCGTATTAGA
GCTTGGCGTAATCATGGTCATAGCTGTTTCCTGTGTGAAATTGTTATCCGCT
CACAATTCCACACAACATACGAGCCGGAAGCATAAAGTGTAAAGCCTGGGG
TGCCTAATGAGTGAGCTAACTCACATTAATTGCGTTGCGCTCACTGCCCGCT
TTCGAGTCGGGAAACCTGTCGTGCCAGCTGCATTAATGAATCGGCCAACGC
GCGGGGAGAGGCGGTTTGCGTATTGGGCGCTCTTCCGCTTCCTCGCTCAC
TGACTCGCTGCGCTCGGTCGTTCGGCTGCGGCGAGCGGTATCAGCTCACT
CAAAGGCGGTAATACGGTTATCCACAGAATCAGGGGATAACGCAGGAAAGA
ACATGTGAGCAAAAGGCCAGCAAAAGGCCAGGAACCGTAAAAAGGCCGCG
TTGCTGGCGTTTTTCGATAGGCTCCGCCCCCCTGACGAGCATCACAAAAAT
CGACGCTCAAGTCAGAGGTGGCGAAACCCGACAGGACTATAAAGATACCAG
GCGTTTCCCCCTGGAAGCTCCCTCGTGCGCTCTCCTGTTCCGACCCTGCCG
CTTACCGGATACCTGTCCGCCTTTCTCCCTTCGGGAAGCGTGGCGCTTTCT
CATAGCTCACGCTGTAGGTATCTCAGTTCGGTGTAGGTCGTTCGCTCCAAG
CTGGGCTGTGTGCACGAACCCCCCGTTCAGCCCGACCGCTGCGCCTTATC
CGGTAACTATCGTCTTGAGTCCAACCCGGTAAGACACGACTTATCGCCACT
GGCAGCAGCCACTGGTAACAGGATTAGCAGAGCGAGGTATGTAGGCGGTG
CTACAGAGTTCTTGAAGTGGTGGCCTAACTACGGCTACACTAGAAGGACAG
TATTTGGTATCTGCGCTCTGCTGAAGCCAGTTACCTTCGGAAAAAGAGTTGG
TAGCTCTTGATCCGGCAAACAAACCACCGCTGGTAGCGGTGGTTTTTTTGTT
TGCAAGCAGCAGATTACGCGCAGAAAAAAAGGATCTCAAGAAGATCCTTTG
ATCTTTTCTACGGGGTCTGACGCTCAGTGGAACGAAAACTCACGTTAAGGG
ATTTTGGTCATGAGATTATCAAAAAGGATCTTCACCTAGATCCTTTTAAATTA
AAAATGAAGTTTTAAATCAATCTAAAGTATATATGAGTAAACTTGGTCTGACA
GTTACCAATGCTTAATCAGTGAGGCACCTATCTCAGCGATCTGTCTATTTCG
TTCATCCATAGTTGCCTGACTCCCCGTCGTGTAGATAACTACGATACGGGAG
GGCTTACCATCTGGCCCCAGTGCTGCAATGATACCGCGAGACCCACGCTCA
CCGGCTCCAGATTTATCAGCAATAAACCAGCCAGCCGGAAGGGCCGAGCG
CAGAAGTGGTCCTGCAACTTTATCCGCCTCCATCCAGTCTATTAATTGTTGC
CGGGAAGCTAGAGTAAGTAGTTCGCCAGTTAATAGTTTGCGCAACGTTGTT
GGCATTGCTACAGGCATCGTGGTGTCACGCTCGTCGTTTGGTATGGCTTCA
TTCAGCTCCGGTTCCCAACGATCAAGGCGAGTTACATGATCCCCCATGTTGT
GCAAAAAAGCGGTTAGCTCCTTCGGTCCTCCGATCGTTGTCAGAAGTAAGT
TGGCCGCAGTGTTATCACTCATGGTTATGGCAGCACTGCATAATTCTCTTAC
TGTCATGCCATCCGTAAGATGCTTTTCTGTGACTGGTGAGTACTCAACCAAG
TCATTCTGAGAATAGTGTATGCGGCGACCGAGTTGCTCTTGCCCGGCGTCA
ATACGGGATAATACCGCGCCACATAGCAGAACTTTAAAAGTGCTCATCATTG
GAAAACGTTCTTCGGGGCGAAAACTCTCAAGGATCTTACCGCTGTTGAGAT
CCAGTTCGATGTAACCCACTCGTGCACCCAACTGATCTTCAGCATCTTTTAC

FIG. 21F

TTTCACCAGCGTTTCTGGGTGAGCAAAAACAGGAAGGCAAAATGCCGCAAA
AAAGGGAATAAGGGCGACACGGAAATGTTGAATACTCATACTCTTCCTTTTT
CAATATTATTGAAGCATTTATCAGGGTTATTGTCTCATGAGCGGATACATATT
TGAATGTATTTAGAAAAATAAACAAATAGGGGTTCCGCGCACATTTCCCCGA
AAAGTGCCACCTGACGTCTAAGAAACCATTATTATCATGACATTAACCTATAA
AAATAGGCGTATCACGAGGCCCTTTCGTCTCGCGCGTTTCGGTGATGACGG
TGAAAACCTCTGACACATGCAGCTCCCGGAGACGGTCACAGCTTGTCTGTA
AGCGGATGCCGGGAGCAGACAAGCCCGTCAGGGCGCGTCAGCGGGTGTT
GGCGGGTGTCGGGGCTGGCTTAACTATGCGGCATCAGAGCAGATTGTACT
GAGAGTGCACCATATGCGGTGTGAAATACCGCACAGATGCGTAAGGAGAAA
ATACCGCATCAGGCGCCATTCGCCATTCAGGCTGCGCAACTGTTGGGAAGG
GCGATCGGTGCGGGCCTCTTCGCTATTACGCCAGCTGGCGAAAGGGGGAT
GTGCTGCAAGGCGATTAAGTTGGGTAACGCCAGGGTTTTCCCAGTCACGAC
GTTGTAAAACGACGGCCAGTGAATTGGATTTAGGTGACACTATA

New Psyn II Promoter which controls ADA envelope expression: SEQ ID NO:84

TAAAAAATGAAAAAATATTCTAATTTATAGGACGGTTTTGATTTTCTTTTTTTC
TATGCTATAAATAATAAATA

ADA envelope truncated: SEQ ID NO:85

ATGAAAGTGAAGGGGATCAGGAAGAATTATCAGCACTTGTGGAAATGGGGC
ATCATGCTCCTTGGGATGTTGATGATCTGTAGTGCTGTAGAAAATTTGTGGG
TCACAGTTTATTATGGGGTACCTGTGTGGAAAGAAGCAACCACCACTCTATT
TTGTGCATCAGATGCTAAAGCATATGATACAGAGGTACATAATGTTTGGGCC
ACACATGCCTGTGTACCCACAGACCCCAACCCACAAGAAGTAGTATTGGAA
AATGTGACAGAAAATTTTAACATGTGGAAAAATAACATGGTAGAACAGATGC
ATGAGGATATAATCAGTTTATGGGATCAAAGCCTAAAGCCATGTGTAAAATT
AACCCCACTCTGTGTTACTTTAAATTGCACTGATTTGAGGAATGTTACTAATA
TCAATAATAGTAGTGAGGGAATGAGAGGAGAAATAAAAAACTGCTCTTTCAA
TATCACCACAAGCATAAGAGATAAGGTGAAGAAAGACTATGCACTTTTCTAT
AGACTTGATGTAGTACCAATAGATAATGATAATACTAGCTATAGGTTGATAAA
TTGTAATACCTCAACCATTACACAGGCCTGTCCAAAGGTATCCTTTGAGCCA
ATTCCCATACATTATTGTACCCCGGCTGGTTTTGCGATTCTAAAGTGTAAAG
ACAAGAAGTTCAATGGAACAGGGCCATGTAAAAATGTCAGCACAGTACAAT
GTACACATGGAATTAGGCCAGTAGTGTCAACTCAACTGCTGTTAAATGGCAG
TCTAGCAGAAGAAGAGGTAGTAATTAGATCTAGTAATTTCACAGACAATGCA
AAAAACATAATAGTACAGTTGAAAGAATCTGTAGAAATTAATTGTACAAGACC
CAACAACAATACAAGGAAAAGTATACATATAGGACCAGGAAGAGCATTTTAT
ACAACAGGAGAAATAATAGGAGATATAAGACAAGCACATTGCAACATTAGTA
GAACAAAATGGAATAACACTTTAAATCAAATAGCTACAAAATTAAAAGAACAA
TTTGGGAATAATAAAACAATAGTCTTTAATCAATCCTCAGGAGGGGACCCAG
AAATTGTAATGCACAGTTTTAATTGTGGAGGGGAATTCTTCTACTGTAATTCA
ACACAACTGTTTAATAGTACTTGGAATTTTAATGGTACTTGGAATTTAACACA

FIG. 21G

ATCGAATGGTACTGAAGGAAATGACACTATCACACTCCCATGTAGAATAAAA
CAAATTATAAATATGTGGCAGGAAGTAGGAAAAGCAATGTATGCCCCTCCCA
TCAGAGGACAAATTAGATGCTCATCAAATATTACAGGGCTAATATTAACAAG
AGATGGTGGAACTAACAGTAGTGGGTCCGAGATCTTCAGACCTGGGGGAG
GAGATATGAGGGACAATTGGAGAAGTGAATTATATAAATATAAAGTAGTAAA
AATTGAACCATTAGGAGTAGCACCCACCAAGGCAAAAAGAAGAGTGGTGCA
GAGAGAAAAAAGAGCAGTGGGAACGATAGGAGCTATGTTCCTTGGGTTCTT
GGGAGCAGCAGGAAGCACTATGGGCGCAGCGTCAATAACGCTGACGGTAC
AGGCCAGACTATTATTGTCTGGTATAGTGCAACAGCAGAACAATTTGCTGAG
GGCTATTGAGGCGCAACAGCATCTGTTGCAACTCACAGTCTGGGGCATCAA
GCAGCTCCAGGCAAGAGTCCTGGCTGTGGAAAGATACCTAAGGGATCAACA
GCTCCTAGGGATTTGGGGTTGCTCTGGAAAACTCATCTGCACCACTGCTGT
GCCTTGGAATGCTAGTTGGAGTAATAAAACTCTGGATATGATTTGGGATAAC
ATGACCTGGATGGAGTGGGAAAGAGAAATCGAAAATTACACAGGCTTAATAT
ACACCTTAATTGAGGAATCGCAGAACCAACAAGAAAAGAATGAACAAGACTT
ATTAGCATTAGATAAGTGGGCAAGTTTGTGGAATTGGTTTGACATATCAAATT
GGCTGTGGTATGTAAAAATCTTCATAATGATAGTAGGAGGCTTGATAGGTTT
AAGAATAGTTTTTACTGTACTTTCTATAGTAAATAGAGTTAGGCAGGGATACT
CACCATTGTCATTTCAGACCCACCTCCCAGCCCCGAGGGGACCCGACAGG
CCCGAAGGAATCGAAGAAGAAGGTGGAGACAGAGAC

PmH5 promoter (which controls HXB2 gag pol expression): SEQ ID NO:86

AAAAATTGAAAATAAATACAAAGGTTCTTGAGGGTTGTGTTAAATTGAAAGC
GAGAAATAATCATAAATA

HXB2 gag pol (with safety mutations,Δintegrase): SEQ ID NO:87

ATGGGTGCGAGAGCGTCAGTATTAAGCGGGGGAGAATTAGATCGATGGGA
AAAAATTCGGTTAAGGCCAGGGGGAAAGAAAAAATATAAATTAAAACATATA
GTATGGGCAAGCAGGGAGCTAGAACGATTCGCAGTTAATCCTGGCCTGTTA
GAAACATCAGAAGGCTGTAGACAAATACTGGGACAGCTACAACCATCCCTT
CAGACAGGATCAGAAGAACTTAGATCATTATATAATACAGTAGCAACCCTCT
ATTGTGTGCATCAAAGGATAGAGATAAAAGACACCAAGGAAGCTTTAGACAA
GATAGAGGAAGAGCAAAACAAAAGTAAGAAAAAAGCACAGCAAGCAGCAGC
TGACACAGGACACAGCAATCAGGTCAGCCAAAATTACCCTATAGTGCAGAA
CATCCAGGGGCAAATGGTACATCAGGCCATATCACCTAGAACTTTAAATGCA
TGGGTAAAAGTAGTAGAAGAGAAGGCTTTCAGCCCAGAAGTGATACCCATG
TTTTCAGCATTATCAGAAGGAGCCACCCCACAAGATTTAAACACCATGCTAA
ACACAGTGGGGGGACATCAAGCAGCCATGCAAATGTTAAAAGAGACCATCA
ATGAGGAAGCTGCAGAATGGGATAGAGTGCATCCAGTGCATGCAGGGCCT
ATTGCACCAGGCCAGATGAGAGAACCAAGGGGAAGTGACATAGCAGGAAC
TACTAGTACCCTTCAGGAACAAATAGGATGGATGACAAATAATCCACCTATC
CCAGTAGGAGAAATTTATAAAAGATGGATAATCCTGGGATTAAATAAAATAG
TAAGAATGTATAGCCCTACCAGCATTCTGGACATAAGACAAGGACCAAAAGA
ACCCTTTAGAGACTATGTAGACCGGTTCTATAAAACTCTAAGAGCCGAGCAA

FIG. 21H

GCTTCACAGGAGGTAAAAAATTGGATGACAGAAACCTTGTTGGTCCAAAATG
CGAACCCAGATTGTAAGACTATTTTAAAAGCATTGGGACCAGCGGCTACACT
AGAAGAAATGATGACAGCATGTCAGGGAGTAGGAGGACCCGGCCATAAGG
CAAGAGTTTTGGCTGAAGCAATGAGCCAAGTAACAAATTCAGCTACCATAAT
GATGCAGAGAGGCAATTTTAGGAACCAAAGAAAGATTGTTAAGTGTTTCAAT
TGTGGCAAAGAAGGGCACACAGCCAGAAATTGCAGGGCCCCTAGGAAAAA
GGGCTGTTGGAAATGTGGAAAGGAAGGACACCAAATGAAAGATTGTACTGA
GAGACAGGCTAATTTTTTAGGGAAGATCTGGCCTTCCTACAAGGGAAGGCC
AGGGAATTTTCTTCAGAGCAGACCAGAGCCAACAGCCCCACCAGAAGAGAG
CTTCAGGTCTGGGGTAGAGACAACAACTCCCCCTCAGAAGCAGGAGCCGAT
AGACAAGGAACTGTATCCTTTAACTTCCCTCAGATCACTCTTTGGCAACGAC
CCCTCGTCACAATAAAGATAGGGGGGCAACTAAAGGAAGCTCTATTAGATA
CAGGAGCAGATGATACAGTATTAGAAGAAATGAGTTTGCCAGGAAGATGGA
AACCAAAAATGATAGGGGGAATTGGAGGTTTTATCAAAGTAAGACAGTATGA
TCAGATACTCATAGAAATCTGTGGACATAAAGCTATAGGTACAGTATTAGTA
GGACCTACACCTGTCAACATAATTGGAAGAAATCTGTTGACTCAGATTGGTT
GCACTTTAAATTTTCCCATTAGCCCTATTGAGACTGTACCAGTAAAATTAAAG
CCAGGAATGGATGGCCCAAAAGTTAAACAATGGCCATTGACAGAAGAAAAA
ATAAAAGCATTAGTAGAAATTTGTACAGAAATGGAAAAGGAAGGGAAAATTT
CAAAAATTGGGCCTGAGAATCCATACAATACTCCAGTATTTGCCATAAAGAA
AAAAGACAGTACTAAATGGAGGAAATTAGTAGATTTCAGAGAACTTAATAAG
AGAACTCAAGACTTCTGGGAAGTTCAATTAGGAATACCACATCCCGCAGGG
TTAAAAAAGAAAAAATCAGTAACAGTACTGGATGTGGGTGATGCATATTTTTC
AGTTCCCTTAGATGAAGACTTCAGGAAGTATACTGCATTTACCATACCTAGT
ATAAACAATGAGACACCAGGGATTAGATATCAGTACAATGTGCTTCCACAGG
GATGGAAAGGATCACCAGCAATATTCCAAAGTAGCATGACAAAAATCTTAGA
GCCTTTTAAAAAACAAAATCCAGACATAGTTATCTATCAATACATGAACGATT
TGTATGTAGGATCTGACTTAGAAATAGGGCAGCATAGAACAAAAATAGAGGA
GCTGAGACAACATCTGTTGAGGTGGGGACTTACCACACCAGACAAAAAACA
TCAGAAAGAACCTCCATTCCTTTGGATGGGTTATGAACTCCATCCTGATAAA
TGGACAGTACAGCCTATAGTGCTGCCAGAAAAAGACAGCTGGACTGTCAAT
GACATACAGAAGTTAGTGGGGAAATTGAATACCGCAAGTCAGATTTACCCA
GGGATTAAAGTAAGGCAATTATGTAAACTCCTTAGAGGAACCAAAGCACTAA
CAGAAGTAATACCACTAACAGAAGAAGCAGAGCTAGAACTGGCAGAAAACA
GAGAGATTCTAAAAGAACCAGTACATGGAGTGTATTATGACCCATCAAAAGA
CTTAATAGCAGAAATACAGAAGCAGGGGCAAGGCCAATGGACATATCAAAT
TTATCAAGAGCCATTTAAAAATCTGAAAACAGGAAAATATGCAAGAATGAGG
GGTGCCCACACTAATGATGTAAAACAATTAACAGAGGCAGTGCAAAAAATAA
CCACAGAAAGCATAGTAATATGGGGAAAGACTCCTAAATTTAAACTACCCAT
ACAAAAGGAAACATGGGAAACATGGTGGACAGAGTATTGGCAAGCCACCTG
GATTCCTGAGTGGGAGTTTGTTAATACCCCTCCTTTAGTGAAATTATGGTAC
CAGTTAGAGAAAGAACCCATAGTAGGAGCAGAAACCTTCTATGTAGATGGG
GCAGCTAACAGGGAGACTAAATTAGGAAAAGCAGGATATGTTACTAACAAA
GGAAGACAAAAGGTTGTCCCCCTAACTAACACAACAAATCAGAAAACTCAGT
TACAAGCAATTTATCTAGCTTTGCAGGATTCAGGATTAGAAGTAAACATAGTA
ACAGACTCACAATATGCATTAGGAATCATTCAAGCACAACCAGATAAAAGTG

FIG. 21I

AATCAGAGTTAGTCAATCAAATAATAGAGCAGTTAATAAAAAAGGAAAAGGT
CTATCTGGCATGGGTACCAGCACACAAAGGAATTGGAGGAAATGAACAAGT
AGATAAATTAGTCAGTGCTGGAATCAGGAAAATACTATTTTTAGATGGAATA
GATAAGGCCCAAGATGAACATTAG

FIG. 24

Sequence of new Psyn II promoter:

Early part of promoter

Critical region Early start site

TAAAAAATGAAAAAATATTCTAATTTATAGGACGGT
SEQ ID NO:88

Late part of promoter

TTGATTTTCTTTTTTTCTATGCTATAAATAATAAATA
SEQ ID NO:89

COMPOSITIONS AND METHODS FOR GENERATING AN IMMUNE RESPONSE

RELATED APPLICATIONS

This application is a continuation of U.S. patent application Ser. No. 10/336,566, which was filed on Jan. 3, 2003, which is a continuation-in-part of U.S. patent application Ser. No. 10/093,953, which was filed on Mar. 8, 2002, and which is a continuation-in-part of U.S. patent application Ser. No. 09/798,675, which was filed on Mar. 2, 2001, and which claims the benefit of the filing dates of four provisional applications (U.S. patent application No. 60/251,083, filed Dec. 1, 2000, U.S. patent application No. 60/186,364, filed Mar. 2, 2000, U.S. patent application No. 60/324,845, filed Sep. 25, 2001, and U.S. patent application No. 60/325,004, filed Sep. 26, 2001) and the benefit of the filing date of International Application No. PCT/US01/06795, which was filed on Mar. 2, 2001. The contents of which are hereby incorporated by reference in their entirety.

GOVERNMENT SUPPORT

The work described herein was supported, at least in part, by grants from the National Institutes of Health (P01 AI43045, P01 AI49364, and R21AI44325). The United States Government may therefore have certain rights in this invention.

FIELD OF THE INVENTION

The present invention is directed generally to the fields of molecular genetics and immunology. More particularly, the present invention features expression vectors and methods of administering those vectors to animals.

BACKGROUND OF THE INVENTION

Vaccines have had profound and long lasting effects on world health. Smallpox has been eradicated, polio is near elimination, and diseases such as diphtheria, measles, mumps, pertussis, and tetanus are contained. Nonetheless, current vaccines address only a handful of the infections suffered by people and domesticated animals. Common infectious diseases for which there are no vaccines cost the United States alone about $120 billion dollars per year (Robinson et al., American Academy of Microbiology, May 31-Jun. 2, 1996). In first world countries, emerging infections such as immunodeficiency viruses, as well as reemerging diseases like drug resistant forms of tuberculosis, pose new threats and challenges for vaccine development. The need for both new and improved vaccines is even more pronounced in third world countries where effective vaccines are often unavailable or cost-prohibitive.

The prevalence of HIV-1 infection has made vaccine development for this recently emergent agent a high priority for world health. Pre-clinical trials on DNA vaccines have demonstrated that DNA alone can protect against highly attenuated HIV-1 challenges in chimpanzees (Boyer et al., *Nature Med.* 3:526-532, 1997), but not against more virulent SW challenges in macaques (Lu et al., *Vaccine* 15:920-923, 1997). A combination of DNA priming plus an envelope glycoprotein boost has raised neutralizing antibody-associated protection against a homologous challenge with a non-pathogenic chimera between SIV and HIV (SHIV-IIIB) (Letvin et al., *Proc. Natl. Acad. Sci. USA* 94:9378-9383, 1997). A comparative trial testing eight different protocols for the ability to protect against a series of challenges with SHIVs (chimeras between simian and human immunodeficiency viruses) revealed the best containment of challenge infections by an immunization protocol that included priming by intradermal inoculation of DNA and boosting with recombinant fowl pox virus vectors (Robinson et al., *Nature Med.* 5:526, 1999). This containment of challenge infections was independent of the presence of neutralizing antibody to the challenge virus. Despite these and many other efforts, a vaccine for containing HIV infection is still not commercially available.

SUMMARY OF THE INVENTION

The continuing force of the AIDS epidemic illustrates the pressing need for effective vaccines against human immunodeficiency viruses (HIV), which frequently mutate and exist in several different clades (or subtypes) and recombinant forms. These subtypes and recombinant forms, which may arise either naturally or as the result of human intervention, can be distinguished by differences in the sequences of their nucleic acid. We have developed DNA and viral vectors (described at length below) that can be used, alone or in combination, as a vaccine against one HIV clade, subtype, or recombinant form of HIV or against multiple HIV clades, subtypes, or recombinant forms (unless otherwise specified, the term "clade(s)" is meant to encompass subtypes or recombinant forms of HIV). Moreover, the vectors can encode a variety of antigens, which may be obtained from one clade or from two or more different clades, and the antigens selected and/or the manner in which the vectors are formulated (e.g., mixed) can be manipulated to generate a protective immune response against a variety of clades (e.g., the clades to which a patient is most likely to be exposed).

There is also a need for an effective vaccine against poxviruses, such as the variola virus that causes smallpox; the current smallpox vaccine carries a small risk of substantial adverse side effects. Although smallpox has been eradicated, the population is still threatened by smallpox as a biological weapon. The viral vectors described herein can be used to generate an immune response against poxviruses. Thus, methods in which such vectors are administered (regardless of the precise protocol followed) can also elicit an immune response that confers protective or therapeutic effects against conditions such as smallpox (i.e., a pox viral vector can be administered before or after (e.g., 1-4 or more days after) a subject has been exposed to an agent that causes a viral disease such as smallpox). These methods can be effective regardless of whether the vectors contain vaccine inserts or what that insert encodes (e.g., proteins obtained from an HIV or proteins that elicit an immune response against one or more HIV clades).

The present invention provides plasmid vectors as well as viral vectors that can be used to deliver nucleic acids to a cell; while the invention encompasses vectors that do not contain vaccine "inserts," when immunizing or treating a patient, the vectors will include nucleic acids that encode protein antigens that induce or enhance an immune response against a pathogen (e.g., one or more HIV clades (or subtypes or recombinant forms)). The nucleic acids or polynucleotides described herein include those having linear arrays of naturally occurring and/or synthetic nucleotides (or nucleosides) derived from cDNA (or mRNA) or genomic DNA, or derivatives thereof (the pyrimidine or purine rings can be attached to a pentose sugar, such as a ribose or deoxyribose). The sequence of the nucleic acid may or may not be identical to a sequence occurring in nature (e.g., the sequence can encode a mutant form of an HIV protein that may make the vaccine safer). Specific characteristics and specific sequences of the proteins that can be expressed by way of the vectors described herein are discussed below.

Plasmid or viral vectors can include nucleic acids representing one or more genes found in one or more HIV clades or any fragments or derivatives thereof that, when expressed, elicit an immune response against the virus (or viral clade) from which the nucleic acid was derived or obtained. The nucleic acids may be purified from HIV or they may have been previously cloned, subcloned, or synthesized and, in any event, can be the same as or different from a naturally occurring nucleic acid sequence. The plasmid vectors of the present invention may be referred to herein as, inter alia, expression vectors, expression constructs, plasmid vectors or, simply, as plasmids, regardless of whether or not they include a vaccine insert (i.e., a nucleic acid sequence that encodes an antigen or immunogen). Similar variations of the term "viral vector" may appear as well (e.g., we may refer to the "viral vector" as a "poxvirus vector," a "vaccinia vector," a "modified vaccinia Ankara vector," or an "MVA vector"). The viral vector may or may not include a vaccine insert.

Accordingly, in one aspect, the invention features compositions (including pharmaceutically or physiologically acceptable compositions) that contain, but are not limited to, a vector, which may be a plasmid or viral vector, having a vaccine insert. The insert can include one or more of the sequences described herein (the features of the inserts and representative sequences are described at length below; any of these, or any combination of these, can be used as the insert). When the insert is expressed, the expressed protein(s) may generate an immune response against one or more HIV clades. One can increase the probability that the immune response will be effective against more than one clade by including sequences from more than one clade in the insert of a single vector (multi-vector vaccines are also useful and are described further below). For example, to increase the probability of generating an immune response against clade B and clade C, one can administer, to a subject, vectors that each includes an insert that encodes proteins of clade B and clade C. The subject may be a person who lives in, or travels between, parts of the world where HIV clades B and C are prevalent. Of course, expressing one or more proteins of a single clade is also beneficial and vectors that do so are within the scope of the invention (again, any inserts having the features or sequences of the exemplary inserts described herein can be used, and the inserts per se are features of the invention).

In another aspect, the invention features compositions (including pharmaceutically or physiologically acceptable compositions) that contain, but are not limited to, two vectors: a first vector that encodes one or more antigens (i.e., a vector that includes a vaccine insert) that elicit (e.g., induces or enhances) an immune response against an HIV of a first clade and a second vector that encodes one or more antigens that elicit (e.g., induces or enhances) an immune response against an HIV of a second clade. However, the compositions can contain more than first and second vectors; they can contain three, four, five, six, or more different vectors (by "different" vectors, we mean vectors that contain different regulatory elements (e.g. different promoters), or that encode different antigens or combinations of antigens, or that otherwise vary (e.g., that vary in their "backbone" sequence)). In some embodiments, the compositions can contain as many vectors as are required to elicit an immune response against two, three, four, or a majority of, if not all, HIV clades. While one vector can encode one antigen (e.g., Gag-Pol), one or more of the vectors (i.e., the first vector, the second vector, or both; the first, second, third, or all three vectors; etc.) can include nucleic acids encoding at least three antigens (e.g. Gag-Pol and Env), each of which can elicit an immune response directed primarily against the same HIV clade (i.e., the first vector can express three antigens, each of which generates a response against, primarily, clade A and a second vector can express three antigens, each of which generates a response against, primarily, clade B). In other embodiments, one or more of the vectors can elicit an immune response against more than one HIV clade (i.e., the first vector can express a first antigen (e.g., Gag-Pol) that generates a response against clade A and a second antigen (e.g., Env) that generates a response against clade B). Thus, one or more of the vectors can elicit an immune response against more than one HIV clade. Any of the types of vectors described herein, whether they are plasmid or viral vectors, or whether they individually encode antigens that elicit immune responses against primarily one, or more than one, HIV clade, can be used alone or in combination with one another, depending on the particular HIV clades to which one wishes to generate immunity.

The vaccine inserts per se (i.e., the sequences encoding HIV proteins that serve as antigens or immunogens) are also within the scope of the invention. While these inserts are described at length below, we note here that the invention features a variety of isolated nucleic acids that represent modified HIV genomes (e.g., fragments or recombinant forms of a genome or one or more HIV genes that are recombined or mutated in some way). For example, one or more nucleic acids can be deleted from one or more genes or replaced with other nucleic acids (i.e., the sequences can be fragments of a gene or genes and can contain point mutations). More specifically, the invention features isolated nucleic acids that represent HIV genomes having safety mutations (e.g., deletion of the LTRs and of sequences encoding integrase (IN), Vif, Vpr and Nef). The nucleic acids can encode Gag, PR, RT, Env, Tat, Rev, and Vpu proteins, one or more of which may contain safety mutations (particular mutations are described at length below). Moreover, the isolated nucleic acids can be of any HIV clade and nucleic acids from different clades can be used in combination (as described further below). In the work described herein, clade B inserts are designated JS (e.g., JS2, JS7, and JS7.1), clade AG inserts are designated IC (e.g., IC2, IC25, IC48, and IC90), and clade C inserts are designated IN (e.g., IN2 and IN3). These inserts are within the scope of the present invention, as are vectors (whether plasmid or viral) containing them (particular vector/insert combinations are referred to below as, for example, pGA1/JS2, pGA2/JS2 etc.

Expression vectors that carry DNA are necessarily limited in that they can only be used to immunize patients with products (i.e., proteins) encoded by DNA, and it is possible that bacterial and parasitic proteins may be atypically processed by eukaryotic cells. Another problem with existing DNA vaccines is that some vaccine insert sequences are unstable during the growth and amplification of DNA vaccine plasmids in bacteria. Instability can arise during plasmid growth where the secondary structure of the vaccine insert or of the plasmid vector (the "backbone") can be altered by bacterial endonucleases. The expression vectors of the present invention can include a termination sequence that improves stability. The termination sequence and other regulatory components (e.g., promoters and polyadenylation sequences) are discussed at length below.

The compositions of the invention can be administered to humans, including children. Accordingly, the invention features methods of immunizing a patient (or of eliciting an immune response in a patient, which may include multi-epitope $CD8^+$ T cell responses) by administering one or more types of vectors (e.g., one or more plasmids, which may or may not have identical sequences, components, or inserts (i.e., sequences that can encode antigens) and/or one or more viral vectors, which may or may not be identical or express identical antigens). As noted above, the vectors, whether plasmid or viral vectors, can include one or more nucleic acids obtained from or derived from (e.g., a mutant sequence is a derivative sequence) one or more HIV clades. When these sequences are expressed, they produce an antigen or antigens that elicit an immune response to one or more HIV clades. In particular embodiments, patients receive a first vector and a second vector. The first vector can encode one or more antigens of a first HIV clade (these antigens can elicit (e.g., induce or enhance) an immune response against that HIV clade) and the second vector can encode one or more antigens of a second HIV clade (here again, these antigens can elicit (e.g., induce or enhance) an immune response against the second HIV clade). In alternative embodiments, the subject can receive a third, fourth, fifth, etc. vector encoding one or more antigens from a third, fourth, fifth, etc. HIV clade (or mutants thereof). Moreover, and as in other embodiments, the antigen(s) can be from any clade (e.g., from one or more of clades A-L) or any HIV isolate.

Where the compositions contain vectors that differ either in their backbone, regulatory elements, or insert(s), the ratio of the vectors in the compositions, and the routes by which they are administered, can vary. The ratio of one type of vector to another can be equal or roughly equal (e.g., roughly 1:1 or 1:1:1, etc.). Alternatively, the ratio can be in any desired proportion (e.g., 1:2, 1:3, 1:4 . . . 1:10; 1:2:1, 1:3:1, 1:4:1 . . . 1:10:1; etc.). Thus, the invention features compositions containing a variety of vectors, the relative amounts of antigen-expressing vectors being roughly equal or in a desired proportion. While preformed mixtures may be made (and may be more convenient), one can, of course, achieve the same objective by administering two or more vector-containing compositions (on, for example, the same occasion (e.g., within minutes of one another) or nearly the same occasion (e.g., on consecutive days)).

Plasmid vectors can be administered alone (i.e., a plasmid can be administered on one or several occasions with or without an alternative type of vaccine formulation (e.g., with or without administration of protein or another type of vector, such as a viral vector)) and, optionally, with an adjuvant or in conjunction with (e.g., prior to) an alternative booster immunization (e.g., a live-vectored vaccine such as a recombinant modified vaccinia Ankara vector (MVA)) comprising an insert that may be distinct from that of the “prime” portion of the immunization or may be a related vaccine insert(s). For example, the viral vector can contain at least some of the sequence contained with the plasmid administered as the “prime” portion of the inoculation protocol (e.g., sequences encoding one or more, and possibly all, of the same antigens). The adjuvant can be a “genetic adjuvant” (i.e., a protein delivered by way of a DNA sequence). Similarly, as described further below, one can immunize a patient (or elicit an immune response, which can include multi-epitope $CD8^+$ T cell responses) by administering a live-vectored vaccine (e.g., an MVA vector) without administering a plasmid-based (or “DNA”) vaccine. Thus, in alternative embodiments, the invention features compositions having only viral vectors (with, optionally, one or more of any of the inserts described here, or inserts having their features) and methods of administering them. The viral-based regimens (e.g., “MVA only” or “MVA-MVA” vaccine regimens) are the same as those described herein for “DNA-MVA” regimens, and the MVAs in any vaccine can be in any proportion desired. For example, in any case (whether the immunization protocol employs only plasmid-based immunogens, only viral-carried immunogens, or a combination of both), one can include an adjuvant and administer a variety of antigens, including those obtained from any HIV clade, by way of the plurality of vectors administered.

As implied by the term “immunization” (and variants thereof), the compositions of the invention can be administered to a subject who has not yet become infected with a pathogen (thus, the terms “subject” or “patient,” as used herein encompasses apparently healthy or non-HIV-infected individuals), but the invention is not so limited; the compositions described herein can also be administered to treat a subject or patient who has already been exposed to, or who is known to be infected with, a pathogen (e.g., an HIV of any clade, including those presently known as clades A-L or mutant or recombinant forms thereof).

An advantage of DNA and rMVA immunizations is that the immunogen may be presented by both MHC class I and class II molecules. Endogenously synthesized proteins readily enter processing pathways that load peptide epitopes onto MHC I as well as MHC II molecules. MHC I-presented epitopes raise CD8 cytotoxic T cell (Tc) responses, whereas MHC II-presented epitopes raise CD4 helper T cells (Th). By contrast, immunogens that are not synthesized in cells are largely restricted to the loading of MHC II epitopes and therefore raise CD4 Th but not CD8 Tc. In addition, DNA plasmids express only the immunizing antigens in transfected cells and can be used to focus the immune response on only those antigens desired for immunization. In contrast, live virus vectors express many antigens (e.g., those of the vector as well as the immunizing antigens) and prime immune responses against both the vector and the immunogen. Thus, we believed these vectors could be highly effective at boosting a DNA-primed response by virtue of the large amounts of antigen that can be expressed by a live vector preferentially boosting the highly targeted DNA-primed immune response. The live virus vectors also stimulate the production of pro-inflammatory cytokines that augment immune responses. Thus, administering one or more of the DNA vectors described herein (as a “prime”) and subsequently administering one or more of the viral vectors (as a “boost”), could be more effective than DNA-alone or live vectors-alone at raising both cellular and humoral immunity. Insofar as these vaccines may be administered by DNA expression vectors and/or recombinant viruses, there is a need for plasmids that are stable in bacterial hosts and safe in animals. Plasmid-based vaccines that may have this added stability are disclosed herein, together with methods for administering them to animals, including humans.

The antigens encoded by DNA or rMVA are necessarily proteinaceous. The terms “protein,” “polypeptide,” and “peptide” are generally interchangeable, although the term “peptide” is commonly used to refer to a short sequence of amino acid residues or a fragment of a larger protein. In any event, serial arrays of amino acid residues, linked through peptide bonds, can be obtained by using recombinant techniques to express DNA (e.g., as was done for the vaccine inserts described and exemplified herein), purified from a natural source, or synthesized.

Other advantages of DNA-based vaccines (and of viral vectors, such as pox virus-based vectors) are described below. The details of one or more embodiments of the invention are set forth in the accompanying drawings and the description below. Other features, objects, and advantages of the invention will be apparent from the description and drawings, and from the claims.

BRIEF DESCRIPTION OF THE DRAWINGS

FIG. 2A and FIG. 2B relate to pGA1. FIG. 2A is an illustration of the nucleotide sequence of pGA1 (SEQ ID NO:1), and FIG. 2B is a table listing the functional regions of pGA1, their positions within the SEQ ID NO:1, and the origins of the sequences.

FIG. 3A and FIG. 3B relate to pGA1.1. FIG. 3A is an illustration of pGA1.1 (SEQ ID NO:2), and FIG. 3B is a table listing the functional regions of pGA1.1, their positions within SEQ ID NO:2, and the origins of the sequences. pGA1.1 differs from pGA1 in that it includes an EcoR I restriction site in its multiple cloning site.

FIG. 4A and 4B relate to pGA1.2. FIG. 4A is an illustration of pGA1.2 (SEQ ID NO:3) and FIG. 4B is a table listing the functional regions of pGA1.2, their positions within SEQ ID NO:3, and the origins of the sequences. pGA1.2 differs from pGA1.1 in that it includes a BamH I site in its multiple cloning site.

FIG. 6A and FIG. 6B relate to pGA2. FIG. 6A is an illustration of the nucleotide sequence of pGA2 (SEQ ID NO:4), and FIG. 6B is a table listing the functional regions of pGA2, their positions within SEQ ID NO:4, and the origins of the sequences.

FIG. 7A and FIG. 7B relate to pGA2.1. FIG. 7A is an illustration of pGA2.1 (SEQ ID NO:5) and FIG. 7B is a table listing the functional regions of pGA2.1, the positions within SEQ ID NO:5, and the origins of the sequences. pGA2.1 differs from pGA2 in having an EcoR I site in its multiple cloning site.

FIG. 8A and FIG. 8B relate to pGA2.2. FIG. 8A is an illustration of pGA2.2 (SEQ ID NO:6), and FIG. 8B is a table listing the functional regions of pGA2.2, their positions with SEQ ID NO:6, and the origins of the sequences. pGA2.2 differs from pGA2.1 in having a BamH I site in its multiple cloning site.

FIG. 10A to FIG. 10D relate to pGA2/JS2. FIG. 10A to FIG. 10B illustrate the sequence of the pGA2/JS2 clade B vaccine vector (SEQ ID NO:7), and FIG. 10C is a table listing the positions of seven functional regions of pGA2/JS2, the gene sequences within those regions (describing mutations, where present), and the origins of their sequences. FIG. 10D is a table listing codons that were changed, the resulting amino acid change (e.g., C392S indicates a substitution of serine for cysteine at amino acid residue 392), the region of the genome where the mutation resides, and the mutation's function.

FIG. 11A-FIG. 11D relate to pGA2/JS7. FIG. 11A to FIG. 11B illustrate the sequence of the pGA2/JS7 clade B vaccine vector (SEQ ID NO:8), and FIG. 11C is a table listing the positions of seven functional regions of pGA2/JS7, the gene sequences within those regions (describing mutations, where present), and the origins of their sequences. FIG. 11D is a table listing codons that were changed, the resulting amino acid change (e.g., C395S indicates a substitution of serine for cysteine at amino acid residue 395), the region of the genome where the mutation resides, and the mutation's function.

FIG. 12A-12E relate to pGA2/JS7.1. FIG. 12A to FIG. 12C illustrate the sequence of the pGA2/JS7.1 clade B vaccine vector (SEQ ID NO:9), and FIG. 12D is a table listing the positions of functional regions of pGA2/JS7.1, the gene sequences within those regions (describing mutations, where present), and the origins of their sequences. FIG. 12E is a table listing codons that were changed, the resulting amino acid change, the region of the genome where the mutation resides, and the mutation's function.

FIG. 13A-FIG. 13C relate to pGA1/IC25. FIG. 13A to FIG. 13C illustrate the sequence of the pGA1/IC25 clade AG vaccine vector (SEQ ID NO:10), and FIG. 13D is a table listing the positions of functional regions within pGA1/IC25, the gene sequences within those regions (describing mutations, where present), and the origins of their sequences. FIG. 13E is a table listing codons that were changed, the resulting amino acid change, the region of the genome where the mutation resides, and the mutation's function.

FIG. 14A to FIG. 14E relate to pGA1/IC2. FIG. 14C to FIG. 14C illustrate the sequence of the pGA1/IC2 clade AG vaccine vector (SEQ ID NO:11), and FIG. 14D is a table listing the positions of functional regions within pGA1/IC2, the gene sequences within those regions (describing mutations, where present), and the origins of their sequences. FIG. 14E is a table listing codons that were changed, the resulting amino acid change, the region of the genome where the mutation resides, and the mutation's function.

FIG. 15A to FIG. 15E relate to pGA1/IC48. FIG. 15A to FIG. 15C illustrate the sequence of the pGA1/IC48 clade AG vaccine vector (SEQ ID NO:12), and FIG. 15D is a table listing the positions of functional regions within pGA1/IC48, the gene sequences within those regions (describing mutations, where present), and the origins of their sequences. FIG. 15E is a table listing codons that were changed, the resulting amino acid change, the region of the genome where the mutation resides, and the mutation's function.

FIG. 16A-FIG. 16E relate to pGA1/IC90. FIG. 16A to FIG. 16C illustrate the sequence of the pGA1/IC90 clade AG vaccine vector (SEQ ID NO:13), and FIG. 16D is a table listing the positions of functional regions within pGA1/IC90, the gene sequences within those regions (describing mutations, where present), and the origins of their sequences. FIG. 16E is a table listing codons that were changed, the resulting amino acid change, the region of the genome where the mutation resides, and the mutation's function.

FIG. 17A to FIG. 17E relate to pGA1/IN3. FIG. 17A to FIG. 17C illustrate the sequence of the pGA1/IN3 clade C vaccine vector (SEQ ID NO:14), and FIG. 17D is a table listing the positions of functional regions within pGA1/IN3, the gene sequences within those regions (describing mutations, where present), and the origins of their sequences. FIG. 17E is a table listing codons that were changed, the resulting amino acid change, the region of the genome where the mutation resides, and the mutation's function.

FIG. 18A to FIG. 18E relate to pGA1/IN2. FIG. 18A to FIG. 18C illustrate the sequence of the pGA1/IN2 clade C vaccine vector (SEQ ID NO:15), and FIG. 18D is a table listing the positions of functional regions within pGA1/IN2, the gene sequences within those regions (describing mutations, where present), and the origins of their sequences. FIG. 18E is a table listing codons that were changed, the resulting amino acid change, the region of the genome where the mutation resides, and the mutation's function.

FIG. 20A to FIG. 20B relate to the plasmid transfer vector pLW-48. FIG. 20A is a map of pLW-48 and FIG. 20B is a representation of its sequence.

FIG. 21A to FIG. 21I represent the sequences of the plasmid transfer vector pLW-48, (FIG. 21A to FIG. 21F), the Psy II promoter (which controls ADA envelope expression) (FIG. 21F), the ADA envelope (truncated), (FIG. 21F to FIG. 21G), the PmH5 promoter (which controls HXB2 gag and pol expression), (FIG. 21G), and HXB2 gag-pol (with safety mutations, inactivating point mutations in RT and the deletion of integrase) (FIG. 21G to FIG. 21I).

FIG. 24 is a representation of a Psyn II promoter.

DETAILED DESCRIPTION

Figure 1:
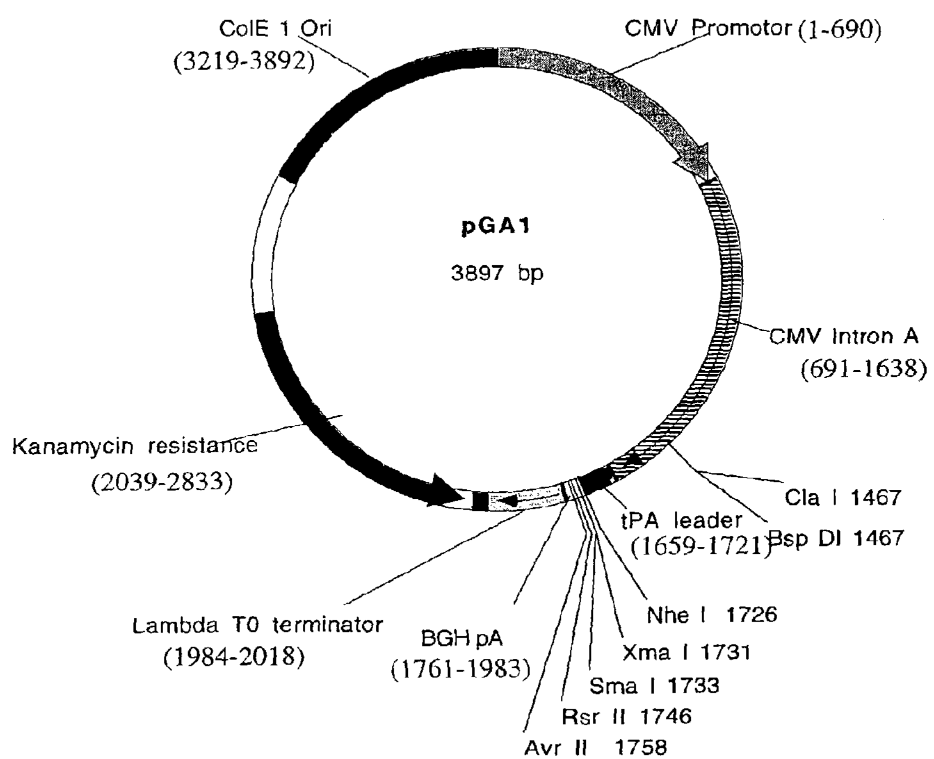
FIG. 1 is a schematic illustration of the plasmid construct pGA1. The identities and positions of elements present in the vector (e.g., the promoter (here, a CMV promoter including intron A), the multiple-cloning site, a terminator sequence (here, the lambda T0 terminator), and a selection gene (here, the kanamycin resistance gene) are shown. Unique restriction endonuclease sites, which are useful for cloning vaccine inserts into the plasmid, are also shown.

This invention encompasses a wide variety of vectors and types of vectors (e.g., plasmid and viral vectors), each of which can, but do not necessarily, include one or more nucleic acid sequences that encode one or more antigens that elicit (e.g., that induce or enhance) an immune response against the pathogen from which the antigen was obtained or derived (the sequences encoding proteins that elicit an immune response may be referred to herein as "vaccine inserts" or, simply, "inserts"; when a mutation is introduced into a naturally occurring sequence, the resulting mutant is "derived" from the naturally occurring sequence). We point out that the vectors do not necessarily encode antigens to make it clear that vectors without "inserts" are within the scope of the invention and that the inserts per se are also compositions of the invention.

Accordingly, the invention features the nucleic acid sequences disclosed herein, analogs thereof, and compositions containing those nucleic acids (whether vector plus insert or insert only; e.g., physiologically acceptable solutions, which may include carriers such as liposomes, calcium, particles (e.g., gold beads) or other reagents used to deliver DNA to cells). The analogs can be sequences that are not identical to those disclosed herein, but that include the same or similar mutations (e.g., the same point mutation or a similar point mutation) at positions analogous to those included in the present sequences (e.g., any of the JS, IC, or IN sequences disclosed herein). A given residue or domain can be identified in various HIV clades even though it does not appear at precisely the same numerical position. The analogs can also be sequences that include mutations that, while distinct from those described herein, similarly inactivate an HIV gene product. For example, a gene that is truncated to a greater or lesser extent than one of the genes described here, but that is similarly inactivated (e.g., that loses a particular enzymatic activity) is within the scope of the present invention.

The pathogens and antigens, which are described in more detail below, include human immunodeficiency viruses of any clade (e.g. from any known clade or from any isolate (e.g., clade A, AG, B, C, D, E, F, G, H, I, J, K, or L)). When the vectors include sequences from a pathogen, they can be administered to a patient to elicit an immune response. Thus, methods of administering antigen-encoding vectors, alone or in combination with one another, are also described herein. These methods can be carried out to either immunize patients (thereby reducing the patient's risk of becoming infected) or to treat patients who have already become infected; when expressed, the antigens may elicit both cell-mediated and humoral immune responses that may substantially prevent the infection (e.g., immunization can protect against subsequent challenge by the pathogen) or limit the extent of its impact on the patient's health. While in many instances the patient will be a human patient, the invention is not so limited. Other animals, including non-human primates, domesticated animals and livestock can also be treated.

The compositions described herein, regardless of the pathogen or pathogenic subtype (e.g., the HIV clade(s)) they are directed against, can include a nucleic acid vector (e.g., a plasmid). As noted herein, vectors having one or more of the features or characteristics (particularly the oriented termination sequence and a strong promoter) of the plasmids designated pGA1, pGA2 (including, of course, those vectors per se), can be used as the basis for a vaccine or therapy. Such vectors can be engineered using standard recombinant techniques (several of which are illustrated in the examples, below) to include sequences that encode antigens that, when administered to, and subsequently expressed in, a patient will elicit (e.g., induce or enhance) an immune response that provides the patient with some form of protection against the pathogen from which the antigens were obtained or derived (e.g., protection against infection, protection against disease, or amelioration of one or more of the signs or symptoms of a disease). The encoded antigens can be of any HIV clade or subtype or any recombinant form thereof. With respect to inserts from immunodeficiency viruses, different isolates exhibit clustal diversity, with each isolate having overall similar diversity from the consensus sequence for the clade (see, e.g., Subbarao et al., AIDS 10(Suppl A):S13-23, 1996). Thus, any isolate can be used as a reasonable representative of sequences for other isolates of the same clade. Accordingly, the compositions of the invention can be made with, and the methods described herein can be practiced with, natural variants of genes or nucleic acid molecules that result from recombination events, alternative splicing, or mutations (these variants may be referred to herein simply as "recombinant forms" of HIV).

Moreover, one or more of the inserts within any construct can be mutated to decrease their natural biological activity (and thereby increase their safety) in humans (these human-made variants may also be referred to herein as "recombinant forms" of HIV (there are naturally occurring recombinant forms as well)). As noted above in the description of JS2, JS7 and JS7.1 and as described below (see, e.g., Examples 7-10), mutations can be introduced into sequences that participate in encapsidation. For example, one can mutate (by, for example, deletion of all or a part of) a cis-acting RNA encapsidation sequence in the non-coding regulatory sequence of an HIV (e.g., HIV-1). Alternatively, or in addition, one can mutate sequences that encode any antigenic proteins (e.g., any HIV antigen, including those listed above (e.g., the viral RT or protease).

For example, the compositions of the invention include those having two vectors: (a) a first vector comprising a vaccine insert encoding one or more antigens that elicit an immune response against a human immunodeficiency virus (HIV) of a first subtype or recombinant form and (b) a second vector comprising a vaccine insert encoding one or more antigens that elicit an immune response against an HIV of a second subtype or recombinant form. The compositions can be pharmaceutically acceptable and may include a carrier or adjuvant (discussed further below). Moreover, the insert of the first vector or the insert of the second vector can include the sequences of two or more of: (a) a gag, pol, env, tat, rev, nef, vif, vpr, or vpu gene or (b) mutants thereof and, optionally, (c) non-coding regulatory sequences (including the sequences of single promoters) of the HIV genome. At least one of the two or more sequences can be mutant or mutated so as to limit the encapsidation of viral RNA (preferably, the mutation(s) limit encapsidation appreciably).

One can introduce mutations and determine their effect (on, for example, expression or immunogenicity) using techniques known in the art; antigens that remain well expressed (e.g., antigens that are expressed about as well as or better than their wild type counterparts), but are less biologically active than their wild type counterparts, are within the scope of the invention. Techniques are also available for assessing the immune response. One can, for example, detect anti-viral antibodies or virus-specific T cells.

The mutant constructs (e.g., a vaccine insert) can include sequences encoding one or more of the substitution mutants described herein (see, e.g. the Examples) or an analogous mutation in another HIV clade. In addition to, or alternatively, HIV antigens can be rendered less active by deleting part of the gene sequences that encode them. Thus, the compositions of the invention can include constructs that encode antigens that, while capable of eliciting an immune response, are mutant (whether encoding a protein of a different length or content than a corresponding wild type sequence) and thereby less able to carry out their normal biological function when expressed in a patient. As noted above, expression, immunogenicity, and activity can be assessed using standard techniques for molecular biology and immunology.

Several plasmids have been constructed and used to express antigens (e.g., the pGA2/JS2 construct has gone through immunogenicity studies in macaques). The plasmids made and used include pGA1 and its derivatives pGA1.1 and pGA1.2; and pGA2, and its derivatives pGA2.1 and pGA2.2 (see Examples 1-8). The vaccine constructs we made are typically referred to with the "backbone" vector and the "insert" being separated by a backslash. These constructs express HIV-1 antigens, and those constructs can be administered to patients as described herein. While antigens (wild type and those containing mutations that render them safer for administration) are discussed at length below, we note here that, based upon our present evidence, plasmids containing JS7-like inserts appear to exhibit better immunogenicity and are more efficient in priming an immune response (as evidenced by anti-Env antibodies) than are plasmids containing JS2-like inserts. pGA2/JS7 and pGA2/JS7.1 differ from pGA2/JS2 in several ways, one of which is the source of their respective antigens. In pGA2/JS7 and pGA2/JS7.1, the Gag and Pol genes were obtained from HIV-1 HXB2, whereas in pGA2/JS2 those genes were obtained from a closely related isolate of HIV-1, HIV-1 BH10. Accordingly, the invention features inserts (as well as vectors and compositions containing them) that include Gag and Pol genes obtained from HIV-1 HXB2. Moreover, these inserts can contain mutations that inhibit one or more of the biological activities carried out by Gag-Pol. The vaccine inserts designated JS7 and JS2 also differ in that JS7 has an inactivating point mutation in its protease gene. This mutation facilitates the formation of viral like particles (VLPs) by, we believe, precluding premature intracellular cleavage of the pr55 Gag protein. pGA2/JS7 and pGA2/JS7.1 both contain this protease mutation and both constructs produce VLPs in abundance. Accordingly, the invention features inserts that include mutant gag and/or pol sequences (e.g., mutations (e.g., one or more deletions or point mutations) that inhibit the protease gene). Additional point mutations in the vpu gene in pGA2/JS7.1 resulted in a loss of Vpu expression and an increase in Env expression (in pGA2/JS7.1, the start site of Vpu is mutated along with a downstream ATG to eliminate translation of Vpu). The increase in Env expression does not compromise Gag expression.

Identical or analogous changes can be made in any vaccine insert that includes gag, pol; any vaccine insert that encodes a viral protease; or any vaccine insert that includes a vpu gene (regardless of the clade or isolate from which it was obtained). Moreover, these changes can be made in vaccine inserts that are placed in any of the plasmid or live-vectored vaccines (e.g., MVA) described herein (i.e., in any plasmid having one or more of the features or characteristics of the pGA vectors, the pGA vectors themselves, or the vaccinia vectors that may be used alone or in conjunction with (e.g., to boost) a DNA-primed patient).

Any plasmid within the scope of the invention can be tested for expression by transfecting cells, such as 293T cells (a human embryonic kidney cell line) and assessing the level of antigen expression (by, for example, an antigen-capture ELISA or a Western blot). Plasmids that express immunogens at a level comparable to, or higher than, the plasmids tested herein are strong therapeutic candidates and are within the scope of the invention (of course, any construct that elicits an effective immune response (e.g., any desirable degree of protection from infection or other therapeutic benefit) is within the scope of the invention, regardless of the level of antigen expression it generates). One can similarly assess the ability of candidate vectors to produce VLPs; the more the vectors' products resemble VLPs, the more likely they are to elicit a strong antibody response (while this is a desirable feature, vectors that fail to form VLPs are nevertheless useful and are within the scope of the present invention). In addition to assessing expression and VLP formation in cell culture, one can assess candidate vectors in vivo. For example, one can assess immunogenicity in animal models (and, eventually, in human patients). Plasmids that have substantially the same sequence as the pGA vectors described herein and that express one or more of the antigens described herein are within the scope of the invention so long as they are immunogenic enough to induce or enhance a therapeutically beneficial response in a patient (a plasmid can have substantially the same sequence as a pGA vector even if one or more of the component parts of the plasmid, such as the marker gene or antibiotic-resistance gene, has been deleted). In tests in animals for immunogenicity, one can perform an intracellular cytokine assay or an ELISPOT assay for IFN-γ production in response to stimulation with an antigenic peptide to evaluate the frequency of responding T cells to that peptide. Proliferation assays can also be carried out. Antigens produced by transient transfection can be used for stimulation, and supernatants from mock-transfected cultures can serve as controls. If desired, the data can be presented as a stimulation index (the growth of cultures in the presence of pathogenic (e.g., viral) antigens divided by the growth of cultures in the presence of mock antigen).

Figure 19:
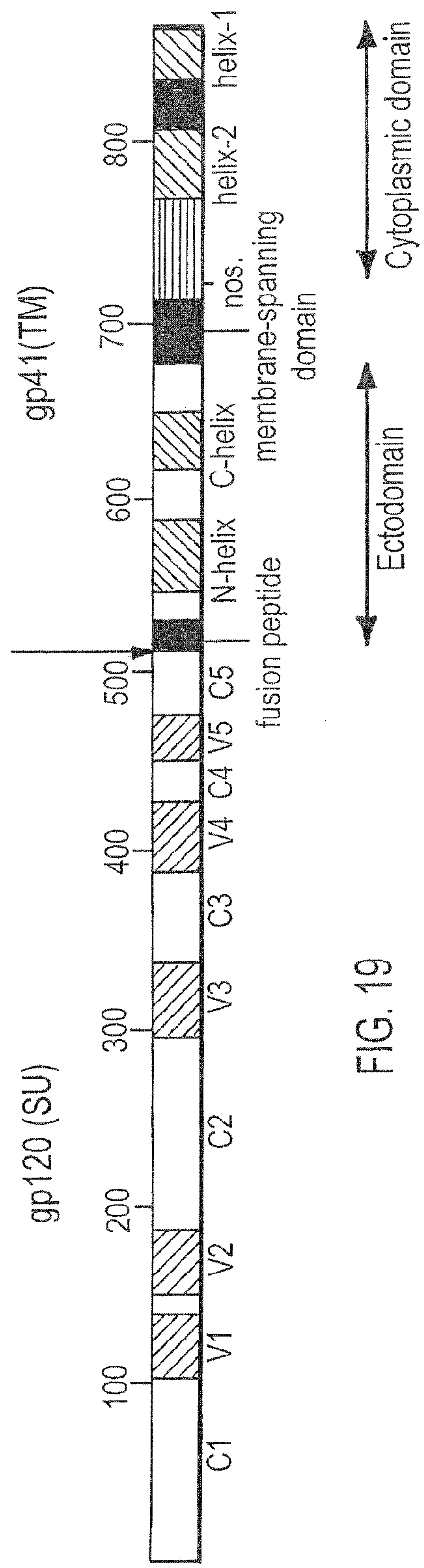
FIG. 19 is a schematic representation of an HIV-1 Env glycoprotein. The arrow indicates the site of gp160 cleavage to gp120 and gp41. In gp120, cross-hatched areas represent variable domains ($V_1$ to $V_2$) and open boxes depict conserved sequences ($C_1$ to $C_5$). In the gp41 ectodomain, several domains are indicated: the N-terminal fusion peptide and the two ectodomain helices (N- and C-helices). The membrane-spanning domain is represented by a black box. In the gp41 cytoplasmic domain, the Tyr-X-X-Leu (YXXL) endocytosis motif and two predicted helical domains (helix-1 and helix-2) are shown. Amino acid residues are numbered at intervals of 100.

The nucleic acid vectors of the invention, including pGA1 and pGA2 and their derivatives can encode at least one antigen (which may also be referred to as an immunogen) obtained from, or derived from, any HIV clade or isolate (i.e., any subtype or recombinant form of HIV). The antigen (or immunogen) may be: a structural component of an HIV virus; glycosylated, myristoylated, or phosphorylated; one that is expressed intracellularly, on the cell surface, or secreted (antigens that are not normally secreted may be linked to a signal sequence that directs secretion). More specifically, the antigen can be all, or an antigenic portion of, Gag, gp120, Pol, Env (e.g., a CCR5-using Env; see, for example, FIG. 19), Tat, Rev, Vpu, Nef, Vif, Vpr, or a VLP (e.g., a polypeptide derived from a VLP that is capable of forming a VLP, including an Env-defective HIV VLP).

Particular inserts and insert-bearing compositions include the following. Where the composition includes either a vector with an insert or an insert alone, and that insert encodes a single antigen, the antigen can be a wild type or mutant gag sequence (e.g., a gag sequence having a mutation in one or more of the sequences encoding a zinc finger (e.g., a mutation at a nucleotide at any of positions 1279-1281, 1288-1290, 1342-1344, or 1351-1353 of SEQ ID NOs:7 or 8 or at an analogous position in an HIV gag sequence of another clade). As the mutation is intended to alter the encoded protein, it will not be a silent mutation (e.g., one at the third-base wobble position of a codon (this is true in the context of gag or any other HIV sequence included in an insert of the invention). A mutation at one or more of the positions just listed would change one or more of the cysteine residues at positions 392, 395, 413, or 416 to another residue (e.g., serine). Alternatively, the mutation can be at any of positions 1271-1273, 1280-1282, 1334-1336, or 1343-1345 of any of SEQ ID NOs: 10-13) or at an analogous position in an HIV gag sequence of another clade. Such a mutation would change one or more of the cysteine residues at positions 390, 393, 411, or 414 to another residue (e.g., serine). Alternatively, the mutation can be at any of positions 1260-1262, 1269-1271, 1323-1325, or 1332-1334 of SEQ ID NOs:14 or 15 or at an analogous position in an HIV gag sequence of another clade. Such a mutation would change one or more of the cysteine residues at positions 390, 393, 411, or 414 to another residue (e.g., serine).

Where the composition includes either a vector with an insert or an insert alone, and that insert encodes multiple protein antigens, one of the antigens can be a wild type or mutant gag sequence, including those described above. Similarly, where a composition includes more than one type of vector or more than one type of insert, at least one of the vectors or inserts (whether encoding a single antigen or multiple antigens) can include a wild type or mutant gag sequence, including those described above or analogous sequences from other HIV clades. For example, where the composition includes first and second vectors, the vaccine insert in either or both vectors (whether the insert encodes single or multiple antigens) can encode Gag; where both vectors encode Gag, the Gag sequence in the first vector can be from one HIV clade (e.g., clade B) and that in the second vector can be from another HIV clade (e.g., clade C).

Where the composition includes either a vector with an insert or an insert alone, and that insert encodes a single antigen, the antigen can be wild type or mutant Pol. The sequence can be mutated by deleting or replacing one or more nucleic acids, and those deletions or substitutions can result in a Pol gene product that has less enzymatic activity than its wild type counterpart (e.g., less integrase activity, less reverse transcriptase (RT) activity, or less protease activity). For example, one can inhibit RT by introducing a mutation at one or more of positions 2454-2456 or 2697-2699 of SEQ ID NO:7 or at an analogous position in a sequence of another subtype or recombinant form. While the invention is not limited to mutations that have any particular effect on enzyme activity, we believe the mutation at position 2454-2456 inhibits RT by inactivating the polymerase's active site and that the mutation at position 2697-2699 inhibits RT by ablating strand transfer activity. Accordingly, these mutations and others that have similar effects on the activity of the gene product are within the scope of the invention. More specifically, the mutation can change the amino acid encoded by the nucleotides at 2454-2456 of SEQ ID NO:7 (aspartic acid (D)) to any another amino acid (e.g., asparagine (N)). Alternatively, or in addition, one can inhibit the polymerase's RNase H activity by, for example, introducing a mutation at nucleotides 3333-3335 of SEQ ID NO:7 (e.g., a mutation that changes the glutamic acid residue (E) to tryptophan (W)). Alternatively, the mutation can be at any of positions 2418-2420, 2661-2663, or 3297-3299 of SEQ ID NOs:8 or 9 (other clade B inserts). Alternatively, the mutation can be at any of positions 2410-2412, 2653-2655, or 3289-3291 of any of SEQ ID NOs: 10-13 (for example, the aspartic acid (D), tryptophan (W) and glutamic acid (E) residues at those positions can be changed to asparagine (N), threonine (T), and/or glutamine (Q), respectively). Alternatively, the mutation can be at any of positions 2387-2389, 2630-2632, or 3266-3268 of SEQ ID NOs:14 or 15. Nucleic acids encoding analogous residues in other clades can be identified by one of ordinary skill in the art, even if those residues are not found at precisely the same position as they were in the clades tested here.

Where the composition includes either a vector with an insert or an insert alone, and that insert encodes multiple protein antigens, one of the antigens can be a wild type or mutant pol sequence, including those described above (these multi-protein-encoding inserts can also encode the wild type or mutant gag sequences described above). Similarly, where a composition includes more than one type of vector or more than one type of insert, at least one of the vectors or inserts (whether encoding a single antigen or multiple antigens) can include a wild type or mutant pol sequence, including those described above (and, optionally, a wild type or mutant gag sequence, including those described above (i.e., the inserts can encode Gag-Pol)). For example, where the composition includes first and second vectors, the vaccine insert in either or both vectors (whether the insert encodes single or multiple antigens) can encode Pol; where both vectors encode Pol, the Pol sequence in the first vector can be from one HIV clade (e.g., clade B) and that in the second vector can be from another HIV clade (e.g., clade AG).

Where an insert includes some or all of the pol sequence, another portion of the pol sequence that can be altered is the sequence encoding the protease activity (regardless of whether or not sequences affecting other enzymatic activities of Pol have been altered). For example, one can introduce a mutation at position 1641-1643 of SEQ ID NO:8 (e.g., a mutation that changes the glutamic acid residue normally encoded by this codon to another amino acid residue, such as alanine (A)). As with the other mutants (e.g., gag mutants) described herein, analogous mutations can be made in sequences obtained from other HIV clades. For example, one can introduce a mutation at position 1633-1635 of SEQ ID NO:10 (changing arginine (R) to another amino acid, such as asparagine (N)), at position 1703-1705 of SEQ ID NO:12 (changing glycine (G) to another residue, such as valine (V)), or at position 1828-1830 of SEQ ID NO:13 (changing leucine (L) to another residue, such as methionine (M) (SEQ ID NOs:10, 12, and 13 all represent clade AG sequences). In an insert from clade C, one can introduce a mutation at position 1610-1612 of SEQ ID NO:14 (changing aspartic acid (D) to another amino acid residue, such as asparagine (N)).

Where the composition includes either a vector with an insert or an insert alone, and that insert encodes a single antigen, the antigen can be a wild type or mutant Env, Tat, Rev, Nef, Vif, Vpr, or Vpu. Where the composition includes either a vector with an insert or an insert alone, and that insert encodes multiple protein antigens, one of the antigens can be a wild type or mutant Env. For example, multi-protein expressing inserts can encode wild type or mutant Gag-Pol and Env; they can also encode wild type or mutant Gag-Pol and Env and one or more of Tat, Rev, Nef, Vif, Vpr, or Vpu (each of which can be wild type or mutant). As with other antigens, Env, Tat, Rev, Nef, Vif, Vpr, or Vpu can be mutant by virtue of a deletion, addition, or substitution of one or more amino acid residues (e.g., any of these antigens can include a point mutation). With respect to Env, one or more mutations can be in any of the domains shown in FIG. 19. For example, one or more amino acids can be deleted from the gp120 surface and/or gp41 transmembrane cleavage products. With respect to Gag, one or more amino acids can be deleted from one or more of: the matrix protein (p17), the capsid protein (p24), the nucleocapsid protein (p7) and the C-terminal peptide (p6). For example, amino acids in one or more of these regions can be deleted (this may be especially desired where the vector is a viral vector, such as MVA). With respect to Pol, one or more amino acids can be deleted from the protease protein (p10), the reverse transcriptase protein (p66/p51), or the integrase protein (p32).

More specifically, the compositions of the invention can include a vector (e.g., a plasmid or viral vector) that encodes: (a) a Gag protein in which one or more of the zinc fingers has been inactivated to limit the packaging of viral RNA; (b) a Pol protein in which (i) the integrase activity has been inhibited by deletion of some or all of the pol sequence and (ii) the polymerase, strand transfer and/or RNase H activity of reverse transcriptase has been inhibited by one or more point mutations within the pol sequence; and (c) Env, Tat, Rev, and Vpu, with or without mutations. In this embodiment, as in others, the encoded proteins can be obtained or derived from a subtype A, B or C HIV (e.g., HIV-1) or recombinant forms thereof. Where the compositions include non-identical vectors, the sequence in each type of vector can be from a different HIV clade (or subtype or recombinant form thereof). For example, the invention features compositions that include plasmid vectors encoding the antigens just described (Gag-Pol, Env etc.), where some of the plasmids include antigens that are obtained from, or derived from, one dale and other plasmids include antigens that are obtained (or derived) from another clade. Mixtures representing two, three, four, five, six, or more clades (including all clades) are within the scope of the invention.

Where first and second vectors are included in a composition, either vector can be pGA1/JS2, pGA1/JS7, pGA1/JS7.1, pGA2/JS2, pGA2/JS7, pGA2/JS7.1 (pGA1.1 or pGA1.2 can be used in place of pGA1 and pGA2.1 or pGA2.2 can by used in place of pGA2). Similarly, either vector can be pGA1/IC25, pGA1/IC2, pGA1/IC48, pGA1/IC90, pGA2/IC25, pGA2/IC2, pGA2/IC48, or pGA2/IC90 (here again, pGA1.1 or pGA1.2 can be used in place of pGA1 and pGA2.1 or pGA2.2 can be used in place of pGA2). In alternative embodiments, the encoded proteins can be those of, or those derived from, a subtype C HIV (e.g., HIV-1) or a recombinant form thereof. For example, the vector can be pGA1/IN2, pGA1.1/IN2, pGA1.2/IN2, pGA1/IN3, pGA1.1/IN3, pGA1.2/IN3, pGA2/IN2, pGA2.1/IN2, pGA2.2/IN2, pGA2/IN3, pGA2.1/IN3, or pGA2.2/IN3.

The encoded proteins can also be those of, or those derived from, any of HIV clades (or subtypes) E, F, G, H, I, J, K or L or recombinant forms thereof. An HIV-1 classification system has been published by Los Alamos National Laboratory (HIV Sequence Compendium-2001, Kuiken et al, published by Theoretical Biology and Biophysics Group T-10, Los Alamos, N. Mex., (2001); http://hiv-web.lanl.gov).

The compositions of the invention can also include a vector (e.g., a plasmid vector) encoding: (a) a Gag protein in which one or both zinc fingers have been inactivated; (b) a Pol protein in which (i) the integrase activity has been inhibited by deletion of some or all of the pol sequence, (ii) the polymerase, strand transfer and/or RNase H activity of reverse transcriptase has been inhibited by one or more point mutations within the pol sequence and (iii) the proteolytic activity of the protease has been inhibited by one or more point mutations; and (c) Env, Tat, Rev, and Vpu, with or without mutations. As noted above, proteolytic activity can be inhibited by introducing a mutation at positions 1641-1643 of SEQ ID NO:8 or at an analogous position in the sequence of another HIV clade. For example, the plasmids can contain the inserts described herein as JS7, IC25, and IN3. As is true for plasmids encoding other antigens, plasmids encoding the antigens just described can be combined with (e.g., mixed with) other plasmids that encode antigens obtained from, or derived from, a different HIV clade (or subtype or recombinant form thereof). The inserts per se (sans vector) are also within the scope of the invention.

Other vectors of the invention include plasmids encoding a Gag protein (e.g., a Gag protein in which one or both of the zinc fingers have been inactivated); a Pol protein (e.g., a Pol protein in which integrase, RT, and/or protease activities have been inhibited; a Vpu protein (which may be encoded by a sequence having a mutant start codon); and Env, Tat, and/or Rev proteins (in a wild type or mutant form). As is true for plasmids encoding other antigens, plasmids encoding the antigens just described can be combined with (e.g., mixed with) other plasmids that encode antigens obtained from, or derived from, a different HIV clade (or subtype or recombinant form thereof). The inserts per se (sans vector) are also within the scope of the invention.

The plasmids described above, including those that express the JS2 or JS7 series of clade B HIV-1 sequences, can be administered to any subject, but may be most beneficially administered to subjects who have been, or who are likely to be, exposed to an HIV of clade B (the same is true for vectors other than plasmid vectors). Similarly, plasmids or other vectors that express an IN series of clade C HIV-1 sequences can be administered to a subject who has been, or who may be, exposed to an HIV of clade C. As vectors expressing antigens of various clades can be combined to elicit an immune response against more than one clade (this can be achieved whether one vector expresses multiple antigens from different clades or multiple vectors express single antigens from different clades), one can tailor the vaccine formulation to best protect a given subject. For example, if a subject is likely to be exposed to regions of the world where clades other than clade B predominate, one can formulate and administer a vector or vectors that express an antigen (or antigens) that will optimize the elicitation of an immune response to the predominant clade or clades.

The antigens they express are not the only parts of the plasmid vectors that can vary. Useful plasmids may or may not contain a terminator sequence that substantially inhibits transcription (the process by which RNA molecules are formed upon DNA templates by complementary base pairing). Useful terminator sequences include the lambda T0 terminator and functional fragments or variants thereof. The terminator sequence is positioned within the vector in the same orientation and at the C terminus of any open reading frame that is expressed in prokaryotes (i.e., the terminator sequence and the open reading frame are operably linked). By preventing read through from the selectable marker into the vaccine insert as the plasmid replicates in prokaryotic cells, the terminator stabilizes the insert as the bacteria grow and the plasmid replicates.

Selectable marker genes are known in the art and include, for example, genes encoding proteins that confer antibiotic resistance on a cell in which the marker is expressed (e.g., resistance to kanamycin, ampicillin, or penicillin). The selectable marker is so-named because it allows one to select cells by virtue of their survival under conditions that, absent the marker, would destroy them. The selectable marker, the terminator sequence, or both (or parts of each or both) can be, but need not be, excised from the plasmid before it is administered to a patient. Similarly, plasmid vectors can be administered in a circular form, after being linearized by digestion with a restriction endonuclease, or after some of the vector "backbone" has been altered or deleted.

The nucleic acid vectors can also include an origin of replication (e.g., a prokaryotic ori) and a transcription cassette that, in addition to containing one or more restriction endonuclease sites, into which an antigen-encoding insert can be cloned, optionally includes a promoter sequence and a polyadenylation signal. Promoters known as strong promoters can be used and may be preferred. One such promoter is the cytomegalovirus (CMV) intermediate early promoter, although other (including weaker) promoters may be used without departing from the scope of the present invention. Similarly, strong polyadenylation signals may be selected (e.g., the signal derived from a bovine growth hormone (BCH) encoding gene, or a rabbit β globin polyadenylation signal (Bohm et al., *J. Immunol. Methods* 193:29-40, 1996; Chapman et al., *Nucl. Acids Res.* 19:3979-3986, 1991; Hartikka et al., *Hum. Gene Therapy* 7:1205-1217, 1996; Manthorpe et al., *Hum. Gene Therapy* 4:419-431, 1993; Montgomery et al., *DNA Cell Biol.* 12:777-783, 1993)).

The vectors can further include a leader sequence (a leader sequence that is a synthetic homolog of the tissue plasminogen activator gene leader sequence (tPA) is optional in the transcription cassette) and/or an intron sequence such as a cytomegalovirus (CMV) intron A or an SV40 intron. The presence of intron A increases the expression of many antigens from RNA viruses, bacteria, and parasites, presumably by providing the expressed RNA with sequences that support processing and function as a eukaryotic mRNA. Expression can also be enhanced by other methods known in the art including, but not limited to, optimizing the codon usage of prokaryotic mRNAs for eukaryotic cells (Andre et al., *J. Virol.* 72:1497-1503, 1998; Uchijima et al., *J. Immunol.* 161: 5594-5599, 1998). Multi-cistronic vectors may be used to express more than one immunogen or an immunogen and an immunostimulatory protein (Iwasaki et al., *J. Immunol.* 158: 4591-4601, 1997a; Wild et al., *Vaccine* 16:353-360, 1998). Thus (and as is true with other optional components of the vector constructs), vectors encoding one or more antigens from one or more HIV clades or isolates may, but do not necessarily, include a leader sequence and an intron (e.g., the CMV intron A).

The vectors of the present invention differ in the sites that can be used for accepting antigen-encoding sequences and in whether the transcription cassette includes intron A sequences in the CMVIE promoter. Accordingly, one of ordinary skill in the art may modify the insertion site(s) or cloning site(s) within the plasmid without departing from the scope of the invention. Both intron A and the tPA leader sequence have been shown in certain instances to enhance antigen expression (Chapman et al., *Nucleic Acids Research* 19:3979-3986, 1991).

As described further below, the vectors of the present invention can be administered with an adjuvant, including a genetic adjuvant. Accordingly, the nucleic acid vectors, regardless of the antigen they express, can optionally include such genetic adjuvants as GM-CSF, IL-2, interferon response factors, secreted forms of flt-3, and mutated caspase genes. Genetic adjuvants can also be supplied in the form of fusion proteins, for example by fusing one or more C3d gene sequences (e.g., 1-3 (or more) C3d gene sequences) to an expressed antigen.

Figure 5:
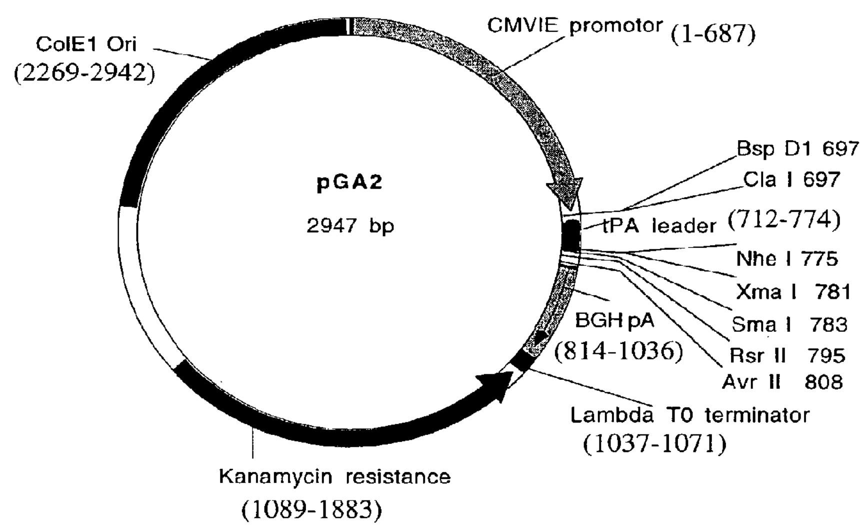
FIG. 5 is a schematic illustration of the plasmid construct pGA2. The identities and positions of elements present in the vector (e.g., a promoter (here the CMV promoter without intron A), the multi-cloning site, a terminator sequence (here, the lambda T0 terminator), and a selection gene (here, the kanamycin resistance gene) are shown. Unique restriction endonuclease sites, which are useful for cloning vaccine inserts into the plasmid, are also shown.

In the event the vector administered is a pGA vector, it can comprise the sequence of, for example, pGA1 (SEQ ID NO:1) or derivatives thereof (e.g., SEQ ID NOs:2 and 3) or pGA2 (SEQ ID NO:4) or derivatives thereof (e.g., SEQ ID NOs:5 and 6). The pGA vectors are described in more detail here (see also Examples 1-8). pGA1 is a 3897 bp plasmid that includes a promoter (bp 1-690), the CMV-intron A (bp 691-1638), a synthetic mimic of the tPA leader sequence (bp 1659-1721), the bovine growth hormone polyadenylation sequence (bp1761-1983), the lambda T0 terminator (bp 1984-2018), the kanamycin resistance gene (bp 2037-2830) and the ColEI replicator (bp 2831-3890). The DNA sequence of the pGA1 construct (SEQ ID NO:1) is shown in FIG. 2. In FIG. 1, the indicated restriction sites are useful for cloning antigen-encoding sequences. The Cla I or BspD I sites are used when the 5' end of a vaccine insert is cloned upstream of the tPA leader. The Nhe I site is used for cloning a sequence in frame with the tPA leader sequence. The sites listed between Sma I and Bln I are used for cloning the 3' terminus of an antigen-encoding sequence.

pGA2 is a 2947 bp plasmid lacking the 947 bp of intron A sequences found in pGA1. pGA2 is the same as pGA1, except for the deletion of intron A sequences. pGA2 is valuable for cloning sequences which do not require an upstream intron for efficient expression, or for cloning sequences in which an upstream intron might interfere with the pattern of splicing needed for good expression. FIG. 5 presents a schematic map of pGA2 with useful restriction sites for cloning vaccine inserts. FIG. 6*a* shows the DNA sequence of pGA2 (SEQ ID NO:2). The use of restriction sites for cloning vaccine inserts into pGA2 is the same as that used for cloning fragments into pGA1. pGA2.1 and pGA2.2 are multiple cloning site derivatives of pGA2. FIGS. 7*a* and 8*a* show the DNA sequence of pGA2.1 (SEQ ID NO:5) and pGA2.2 (SEQ ID NO:6) respectively.

pGA plasmids having "backbone" sequences that differ from those disclosed herein are also within the scope of the invention so long as the plasmids retain substantially all of the characteristics necessary to be therapeutically effective (e.g., one can substitute nucleotides, add nucleotides, or delete nucleotides so long as the plasmid, when administered to a patient, induces or enhances an immune response against a given or desired pathogen). For example, 1-10, 11-20, 21-30, 31-40, 41-50, 51-60, 61-70, 71-80, 81-90, 91-100, or more than 100 nucleotides can be deleted or replaced.

In one embodiment, the methods of the invention (e.g., methods of eliciting an immune response in a patient) can be carried out by administering to the patient a therapeutically effective amount of a physiologically acceptable composition that includes a vector, which can contain a vaccine insert that encodes one or more antigens that elicit an immune response against an HIV. The vector can be a plasmid vector having one or more of the characteristics of the pGA constructs described above (e.g., a selectable marker gene, a prokaryotic origin of replication, a termination sequence (e.g., the lambda T0 terminator) and operably linked to the selectable gene marker, and a eukaryotic transcription cassette comprising a promoter sequence, a nucleic acid insert encoding at least one antigen derived from an immunodeficiency virus, and a polyadenylation signal sequence). Of course, the vaccine inserts of the invention may be delivered by plasmid vectors that do not have the characteristics of the pGA constructs (e.g., vectors other than pGA1 or pGA2). Alternatively, the composition can include any viral or bacterial vector that includes an insert described herein. The invention, therefore, encompasses administration of a single type of vector (i.e., plasmid or viral vectors that contain the same vaccine insert (i.e., an insert encoding the same antigens)). As is made clear elsewhere, the patient may receive two types of vectors, and each of those vectors can elicit an immune response against an HIV of a different clade. For example, the invention features methods in which a patient receives a composition that includes (a) a first vector comprising a vaccine insert encoding one or more antigens that elicit an immune response against a human immunodeficiency virus (HIV) of a first subtype or recombinant form and (b) a second vector comprising a vaccine insert encoding one or more antigens that elicit an immune response against an HIV of a second subtype or recombinant form. The first and second vectors can be any of those described herein. Similarly, the inserts in the first and second vectors can be any of those described herein.

A therapeutically effective amount of a vector (whether considered the first, second, third, etc. vector) can be administered by an intramuscular or an intradermal route, together with a physiologically acceptable carrier, diluent, or excipient, and, optionally, an adjuvant. A therapeutically effective amount of the same or a different vector can subsequently be administered by an intramuscular or an intradermal route, together with a physiologically acceptable carrier, diluent, or excipient, and, optionally, an adjuvant to boost an immune response. Such components can be readily selected by one of ordinary skill in the art, regardless of the precise nature of the antigens incorporated in the vaccine or the vector by which they are delivered.

The methods of eliciting an immune response can be carried out by administering only the plasmid vectors of the invention, by administering only the viral vectors of the invention, or by administering both (e.g., one can administer a plasmid vector (or a mixture or combination of plasmid vectors)) to "prime" the immune response and a viral vector (or a mixture or combination of viral vectors)) to "boost" the immune response. Where plasmid and viral vectors are administered, their inserts may be "matched." To be "matched," one or more of the sequences of the inserts (e.g., the sequences encoding Gag, or the sequences encoding Env, etc.) within the plasmid and viral vectors may be identical, but the term is not so limited. "Matched" sequences can also differ from one another. For example, inserts expressed by viral vectors are "matched" to those expressed by DNA vectors when the sequences used in the DNA vector are mutated or further mutated to allow (or optimize) replication of a viral vector that encodes those sequences and expression of the encoded antigens (e.g., Gag, Gag-Pol, or Env) in cells infected with the viral vector.

At least some of the immunodeficiency virus vaccine inserts of the present invention were designed to generate non-infectious VLPs (a term that can encompass true VLPs as well as aggregates of viral proteins) from a single DNA. This was achieved using the subgenomic splicing elements normally used by immunodeficiency viruses to express multiple gene products from a single viral RNA. The subgenomic splicing patterns are influenced by (i) splice sites and acceptors present in full length viral RNA, (ii) the Rev responsive element (RRE) and (iii) the Rev protein. The splice sites in retroviral RNAs use the canonical sequences for splice sites in eukaryotic RNAs. The RRE is an approximately 200 bp RNA structure that interacts with the Rev protein to allow transport of viral RNAs from the nucleus to the cytoplasm. In the absence of Rev, the approximately 10 kb RNA of immunodeficiency virus mostly undergoes splicing to the mRNAs for the regulatory genes Tat, Rev, and Nef. These genes are encoded by exons present between RT and Env and at the 3' end of the genome. In the presence of Rev, the singly spliced mRNA for Env and the unspliced mRNA for Gag and Pol are expressed in addition to the multiply spliced mRNAs for Tat, Rev, and Nef.

The expression of non-infectious VLPs from a single DNA affords a number of advantages to an immunodeficiency virus vaccine. The expression of a number of proteins from a single DNA affords the vaccinated host the opportunity to respond to the breadth of T- and B-cell epitopes encompassed in these proteins. The expression of proteins containing multiple epitopes allows epitope presentation by diverse histocompatibility types. By using whole proteins, one offers hosts of different histocompatibility types the opportunity to raise broad-based T cell responses. This may be essential for the effective containment of immunodeficiency virus infections, whose high mutation rate supports ready escape from immune responses (Evans et al., *Nat. Med.* 5:1270-1276, 1999; Poignard et al., *Immunity* 10:431-438, 1999, Evans et al., 1995). In the context of the present vaccination scheme, just as in drug therapy, multi-epitope T cell responses that require multiple mutations for escape will provide better protection than single epitope T cell responses (which require only a single mutation for escape).

Immunogens can also be engineered to be more or less effective for raising antibody or Tc by targeting the expressed antigen to specific cellular compartments. For example, antibody responses are raised more effectively by antigens that are displayed on the plasma membrane of cells, or secreted therefrom, than by antigens that are localized to the interior of cells (Boyle et al., *Int. Immunol.* 9:1897-1906, 1997; Inchauspe et al., *DNA Cell. Biol.* 16:185-195, 1997). Tc responses may be enhanced by using N-terminal ubiquitination signals which target the DNA-encoded protein to the proteosome causing rapid cytoplasmic degradation and more efficient peptide loading into the MHC I pathway (Rodriguez et al., *J. Virol.* 71:8497-8503, 1997; Tobery et al., *J. Exp. Med.* 185:909-920, 1997; Wu et al., *J. Immunol.* 159:6037-6043, 1997). For a review on the mechanistic basis for DNA-raised immune responses, refer to Robinson and Pertmer, *Advances in Virus Research*, vol. 53, Academic Press (2000).

Another approach to manipulating immune responses is to fuse immunogens to immunotargeting or immunostimulatory molecules. To date, the most successful of these fusions have targeted secreted immunogens to antigen presenting cells (APCs) or lymph nodes (Boyle et al., *Nature* 392:408-411, 1998). Accordingly, the invention features the HIV antigens described herein fused to immunotargeting or immunostimulatory molecules such as CTLA-4, L-selectin, or a cytokine (e.g., an interleukin such as IL-1, IL-2, IL-4, IL-7, IL-10, IL-15, or IL-21). Nucleic acids encoding such fusions and compositions containing them (e.g., vectors and physiologically acceptable preparations) are also within the scope of the present invention.

DNA can be delivered in a variety of ways, any of which can be used to deliver the plasmids of the present invention to a subject. For example, DNA can be injected in, for example, saline (e.g., using a hypodermic needle) or delivered biolistically (by, for example, a gene gun that accelerates DNA-coated beads). Saline injections deliver DNA into extracellular spaces, whereas gene gun deliveries bombard DNA directly into cells. The saline injections require much larger amounts of DNA (typically 100-1000 times more) than the gene gun (Fynan et al., *Proc. Natl. Acad. Sci. USA* 90:11478-11482, 1993). These two types of delivery also differ in that saline injections bias responses towards type 1 T-cell help, whereas gene gun deliveries bias responses towards type 2 T-cell help (Feltquate et al., *J. Immunol.* 158:2278-2284, 1997; Pertmer et al., *J. Virol.* 70:6119-6125, 1996). DNAs injected in saline rapidly spread throughout the body. DNAs delivered by the gun are more localized at the target site. Following either method of inoculation, extracellular plasmid DNA has a short half life of about 10 minutes (Kawabata et al., *Pharm. Res.* 12:825-830, 1995; Lew et al., *Hum. Gene Ther.* 6:553, 1995). Vaccination by saline injections can be intramuscular (i.m.) or intradermal (i.d.); gene gun deliveries can be administered to the skin or to surgically exposed tissue such as muscle.

While other routes of delivery are generally less favored, they can nevertheless be used to administer the compositions of the invention. For example, the DNA can be applied to the mucosa or by a parenteral route of inoculation. Intranasal administration of DNA in saline has met with both good (Asakura et al., *Scand. J. Immunol.* 46:326-330, 1997; Sasaki et al., *Infect. Immun.* 66:823-826, 1998b) and limited (Fynan et al., *Proc. Natl. Acad. Sci. USA* 90:11478-82, 1993) success. The gene gun has successfully raised IgG following the delivery of DNA to the vaginal mucosa (Livingston et al., *Ann. New York Acad. Sci.* 772:265-267, 1995). Some success at delivering DNA to mucosal surfaces has also been achieved using liposomes (McCluskie et al., *Antisense Nucleic Acid Drug Dev.* 8:401-414, 1998), microspheres (Chen et al., *J. Virol.* 72:5757-5761, 1998a; Jones et al., *Vaccine* 15:814-817, 1997) and recombinant *Shigella* vectors (Sizemore et al., *Science* 270:299-302, 1995; Sizemore et al., *Vaccine* 15:804-807, 1997). Agents such as these (liposomes, microspheres and recombinant *Shigella* vectors) can be used to deliver the nucleic acids of the present invention.

The dose of DNA needed to raise a response depends upon the method of delivery, the host, the vector, and the encoded antigen. The method of delivery may be the most influential parameter. From 10 μg to 5 mg of DNA is generally used for saline injections of DNA, whereas from 0.2 μg to 20 μg of DNA is used more typically for gene gun deliveries of DNA. In general, lower doses of DNA are used in mice (10-100 μg for saline injections and 0.2 μg to 2 μg for gene gun deliveries), and higher doses in primates (100 μg to 1 mg for saline injections and 2 μg to 20 μg for gene gun deliveries). The much lower amount of DNA required for gene gun deliveries reflect the gold beads directly delivering DNA into cells.

In addition to the DNA vectors described above, a number of different poxviruses can be used either alone (i.e., without a nucleic acid or DNA prime) or as the boost component of a vaccine regimen. MVA has been particularly effective in mouse models (Schneider et al., *Nat. Med.* 4:397-402, 1998). MVA is a highly attenuated strain of vaccinia virus that was developed toward the end of the campaign for the eradication of smallpox, and it has been safety tested in more than 100,000 people (Mahnel et al., *Berl. Munch Tierarztl Wochenschr* 107:253-256, 1994; Mayr et al. *Zentralbl. Bakteriol.* 167:375-390, 1978). During over 500 passages in chicken cells, MVA lost about 10% of its genome and the ability to replicate efficiently in primate cells. Despite its limited replication, MVA has proved to be a highly effective expression vector (Sutter et al., *Proc. Natl. Acad. Sci. USA* 89:10847-10851, 1992), raising protective immune responses in primates for parainfluenza virus (Durbin et al. *J. Infect. Dis.* 179:1345-1351, 1999), measles (Stittelaar et al. *J. Virol.* 74:4236-4243, 2000), and immunodeficiency viruses (Barouch et al., *J. Virol.* 75:5151-5158, 2001; Ourmanov et al., *J. Virol.* 74:2740-2751, 2000; Amara et al., *J. Virol.* 76:7625-7631, 2002). The relatively high immunogenicity of MVA has been attributed in part to the loss of several viral anti-immune defense genes (Blanchard et al., *J. Gen. Virol.* 79:1159-1167, 1998).

Vaccinia viruses have been used to engineer viral vectors for recombinant gene expression and as recombinant live vaccines (Mackett et al., *Proc. Natl. Acad. Sci. USA* 79:7415-7419; Smith et al., *Biotech. Genet. Engin. Rev.* 2:383-407, 1984). DNA sequences, which may encode any of the HIV antigens described herein, can be introduced into the genomes of vaccinia viruses. If the gene is integrated at a site in the viral DNA that is non-essential for the life cycle of the virus, it is possible for the newly produced recombinant vaccinia virus to be infectious (i.e., able to infect foreign cells) and to express the integrated DNA sequences. Preferably, the viral vectors featured in the compositions and methods of the present invention are highly attenuated. Several attenuated strains of vaccinia virus were developed to avoid undesired side effects of smallpox vaccination. The modified vaccinia Ankara (MVA) virus was generated by long-term serial passages of the Ankara strain of vaccinia virus on chicken embryo fibroblasts (CVA; see Mayr et al., *Infection* 3:6-14, 1975). The MVA virus is publicly available from the American Type Culture Collection (ATCC; No. VR-1508; Manassas, Va.). The desirable properties of the MVA strain have been demonstrated in clinical trials (Mayr et al., *Zentralbl. Bakteriol.* 167:375-390, 1978; Stickl et al., *Dtsch. Med. Wschr.* 99:2386-2392, 1974; see also, Sutter and Moss, *Proc. Natl. Acad. Sci. USA* 89:10847-10851, 1992). During these studies in over 120,000 humans, including high-risk patients, no side effects were associated with the use of MVA vaccine.

The MVA vectors can be prepared as follows. A DNA construct that contains a DNA sequence that encodes a foreign polypeptide (e.g., any of the HIV antigens described herein) and that is flanked by MVA DNA sequences adjacent to a naturally occurring deletion with the MVA genome (e.g., deletion III or other non-essential site(s); six major deletions of genomic DNA (designated deletions I, II, III, IV, V, and VI)

totaling 31,000 base pairs have been identified (Meyer et al., *J. Gen. Virol.* 72:1031-1038, 1991)) is introduced into cells infected with MVA under conditions that permit homologous recombination to occur. Once the DNA construct has been introduced into the eukaryotic cell and the foreign DNA has recombined with the viral DNA, the recombinant vaccinia virus can be isolated by methods known in the art (isolation can be facilitated by use of a detectable marker). The DNA constructed to be inserted can be linear or circular (e.g., a plasmid, linearized plasmid, gene, gene fragment, or modified HIV genome). The foreign DNA sequence is inserted between the sequences flanking the naturally occurring deletion. For better expression of a DNA sequence, the sequence can include regulatory sequences (e.g., a promoter, such as the promoter of the vaccinia 11 kDa gene or the 7.5 kDa gene). The DNA construct can be introduced into MVA-infected cells by a variety of methods, including calcium phosphate-assisted transfection (Graham et al., *Virol.* 52:456-467, 1973 and Wigler et al., *Cell* 16:777-785, 1979), electroporation (Neumann et al., *EMBO J.* 1:841-845, 1982) microinjection (Graessmann et al., *Meth. Enzymol.* 101:482-492, 1983), by means of liposomes (Straubinger et al., *Meth. Enzymol.* 101:512-527, 1983), by means of spheroplasts (Schaffner, *Proc. Natl. Acad. Sci. USA* 77:2163-2167, 1980), or by other methods known in the art.

One can arrive at an appropriate dosage when delivering DNA by way of a viral vector, just as one can when a plasmid vector is used. For example, one can deliver $1\times10^8$ pfu of an MVA-based vaccine, and administration can be carried out intramuscularly, intradermally, intravenously, or mucosally.

Accordingly, the invention features a composition comprising: (a) a first viral vector comprising a vaccine insert encoding one or more antigens that elicit an immune response against a human immunodeficiency virus (HIV) of a first subtype or recombinant form and (b) a second viral vector comprising a vaccine insert encoding one or more antigens that elicit an immune response against an HIV of a second subtype or recombinant form. The viral vector can be a recombinant poxvirus or a modified vaccinia Ankara (MVA) virus, and the insert can be any of the HIV antigens described herein from any clade (e.g., one can administer a prophylactically or therapeutically effective amount of an MVA that encodes a clade A, B, or C HIV (e.g., HIV-1 antigen). Moreover, when administered in conjunction with a plasmid vector (e.g., when administered subsequent to a "DNA prime"), the MVA-borne sequence can be "matched" to the plasmid-borne sequence. For example, a vaccinia virus (e.g., MVA) that expresses a recombinant clade B sequence can be matched to the JS series of plasmid inserts. Similarly, a vaccinia virus (e.g., MVA) that expresses a recombinant clade A sequence can be matched to the IC series of plasmid inserts; a vaccinia virus (e.g., MVA) that expresses a recombinant clade C sequence can be matched to the IN series of plasmid inserts. While particular clades are exemplified below, the invention is not so limited. The compositions that contain a viral vector, can include viral vectors that express an HIV antigen from any known clade (including clades A, B, C, D, E, F, G, H, I, J, K or L). Methods of eliciting an immune response can, of course, be carried out with compositions expressing antigens from any of these clades as well.

Either the plasmid or viral vectors described here can be administered with an adjuvant (i.e., any substance that is added to a vaccine to increase the vaccine's immunogenicity) and they can be administered by any conventional route of administration (e.g., intramuscular, intradermal, intravenous or mucosally; see below). The adjuvant used in connection with the vectors described here (whether DNA or viral-based) can be one that slowly releases antigen (e.g., the adjuvant can be a liposome), or it can be an adjuvant that is strongly immunogenic in its own right (these adjuvants are believed to function synergistically). Accordingly, the vaccine compositions described here can include known adjuvants or other substances that promote DNA uptake, recruit immune system cells to the site of the inoculation, or facilitate the immune activation of responding lymphoid cells. These adjuvants or substances include oil and water emulsions, *Corynebacterium parvum, Bacillus* Calmette Guerin, aluminum hydroxide, glucan, dextran sulfate, iron oxide, sodium alginate, Bacto-Adjuvant, certain synthetic polymers such as poly amino acids and co-polymers of amino acids, saponin, REGRESSIN (Vetrepharm, Athens, Ga.), AVRIDINE (N,N-dioctadecyl-N',N'-bis(2-hydroxyethyl)-propanediamine), paraffin oil, and muramyl dipeptide. Genetic adjuvants, which encode immunomodulatory molecules on the same or a co-inoculated vector, can also be used. For example, GM-CSF, IL-15, IL-2, interferon response factors, and mutated caspase genes can be included on a vector that encodes a pathogenic immunogen (such as an HIV antigen) or on a separate vector that is administered at or around the same time as the immunogen is administered. Expressed antigens can also be fused to an adjuvant sequence such as one, two, three or more copies of C3d.

The compositions described herein can be administered in a variety of ways including through any parenteral or topical route. For example, an individual can be inoculated by intravenous, intraperitoneal, intradermal, subcutaneous or intramuscular methods. Inoculation can be, for example, with a hypodermic needle, needleless delivery devices such as those that propel a stream of liquid into the target site, or with the use of a gene gun that bombards DNA on gold heads into the target site. The vector comprising the pathogen vaccine insert can be administered to a mucosal surface by a variety of methods including intranasal administration, i.e., nose drops or inhalants, or intrarectal or intravaginal administration by solutions, gels, foams, or suppositories. Alternatively, the vector comprising the vaccine insert can be orally administered in the form of a tablet, capsule, chewable tablet, syrup, emulsion, or the like. In an alternate embodiment, vectors can be administered transdermally, by passive skin patches, iontophoretic means, and the like.

Any physiologically acceptable medium can be used to introduce a vector (whether nucleic acid-based or live-vectored) comprising a vaccine insert into a patient. For example, suitable pharmaceutically acceptable carriers known in the art include, but are not limited to, sterile water, saline, glucose, dextrose, or buffered solutions. The media may include auxiliary agents such as diluents, stabilizers (i.e., sugars (glucose and dextrose were noted previously) and amino acids), preservatives, wetting agents, emulsifying agents, pH buffering agents, additives that enhance viscosity or syringability, colors, and the like. Preferably, the medium or carrier will not produce adverse effects, or will only produce adverse effects that are far outweighed by the benefit conveyed.

The present invention is further illustrated by the following examples, which are provided by way of illustration and should not be construed as limiting. The contents of all references, published patent applications and patents cited throughout the present application are hereby incorporated by reference in their entirety. A number of embodiments of the invention have been described. Nevertheless, it will be understood that various modifications may be made without departing from the spirit and scope of the invention.

Example 1 pGA1 pGA1 (see FIGS. 1 and 2) contains (1) the ColE1 origin of replication (a 672 bp sequence that contains the origin of replication (ori) and encodes an RNA primer and two negative regulators of replication initiation) (2) the kanamycin resistance gene (an antibiotic resistance gene for plasmid selection in bacteria), (3) the lambda T0 terminator, and (4) a eukaryotic expression cassette that includes an upstream intron (here, CMV Intron A), the CMV immediate early (CMVIE) promoter, and termination sequences from the bovine growth hormone polyadenylation sequence (BGHpA). A synthetic mimic of the leader sequence for tissue plasminogen activator (tPA) can also be included within the expression cassette. The expression cassette can include multiple restriction sites, and those sites can be included or excluded as desired to facilitate inclusion of expression cassettes that encode antigens from any HIV clade. The cloning sites in pGA1 include a Cla I site upstream of the tPA leader, a Nhe I site for cloning in frame with the tPA leader, and Xmn I, Sma I, Rsr II, and Avr II sites for cloning prior to the BGHpA. The originally constructed plasmid containing the ColE1 replicator was pBR322 (Bolivar et al., *Gene* 2:95-113, 1977; Sutcliffe et al., *Cold Spring Harbor Quant. Biol.* 43:77-90, 1978).

The lambda T0 terminator (Scholtissek et al., *Nucleic Acids Res.* 15:3185, 1987) prevents read through from the kanamycin resistance gene into the eukaryotic expression cassette (in this case the vaccine transcription cassette) during prokaryotic growth of the plasmid. By preventing read through into the vaccine expression cassette, the terminator helps stabilize plasmid inserts during growth in bacteria.

The ColE1 replicator, the kanamycin resistance gene, and the transcriptional control elements for eukaryotic cells were combined in one plasmid using PCR fragments from the commercial vector pZErO-2.1 (Invitrogen, Carlsbad, Calif.) and a eukaryotic expression vector pJW4303 (Lu et al., *Vaccine* 15:920-923, 1997).

An 1859 bp fragment from pZErO-2.1 (nucleotides 1319 to 3178) included the ColE1 origin of replication and the kanamycin resistance gene. A 2040 bp fragment from pJW4303 (nucleotides 376 to 2416) included the CMVIE promoter with intron A, a synthetic homolog of the tissue plasminogen activator leader (tPA), and the bovine growth hormone polyadenylation site (BGHpA). Fragments were amplified by polymerase chain reaction (PCR) with oligonucleotide primers containing Sal I sites. A ligation product with the transcription cassettes for kanamycin resistance from pZErO2 and the eukaryotic transcription cassette form pJW4303 in opposite transcriptional orientations, was identified for further development. Nucleotide numbering for this parent of the pGA vectors was started from the first by of the 5' end of the CMV promoter.

The T0 terminator was introduced into this parent for the pGA vectors by PCR amplification of a 391 bp fragment with a BamH I restriction endonuclease site at its 5' end and an Xba I restriction endonuclease site at its 3' end. The initial 355 bp of the fragment were sequences in the BGHpA sequence derived from the pJW4303 transcription cassette, the next 36 bases in a synthetic oligonucleotide introduced the T0 sequence and the Xba I site. The introduced T0 terminator sequences comprised the sequence: 5'-ATAAAAAACGCCCGGCGGCAACCGAGCGTTCTGAA-3' (SEQ ID NO: 16).

The T0 terminator containing the BamH I-Xba I fragment was substituted for the homologous fragment without the T0 terminator in the plasmid created from pZErO-2 and pJW4303. The product was sequenced to verify the T0 orientation (FIG. 1).

A region in the eukaryotic transcription cassette between nucleotides 1755-1845 contained the last 30 bp of the reading frame for SIV nef. This region was removed from pGA by mutating the sequence at nt 1858 and generating an Avr II restriction endonuclease site. A naturally occurring Avr II site is located at nt 1755. Digestion with Avr II enzyme and then religation with T4 DNA ligase allowed for removal of the SIV segment of DNA between nucleotides 1755-1845. To facilitate cloning of HIV-1 sequences into pGA vectors, a Cla I site was introduced at bp1648 and an Rsr II site at by 1747 using standard techniques for site directed mutagenesis. Constructions were verified by sequence analyses.

Example 2 pGA1.1 pGA1.1 (SEQ ID NO: 2) is identical to pGA1 except that the multiple cloning site has been altered to include an EcoRI site. This was accomplished by site directed mutagenesis using the following primers: 5'-GCTGCTGCTGTGTGGAGAATTCTTCGTTTCGGC-3'(forward) and 5'-GCCGAAACGAAGAATTCTCCACACAGCAGCAGC-3' (reverse) (SEQ ID NOs:17 and 18 respectively). Accordingly, the pGA1.1 vector is an embodiment of the invention; as are other vectors having one or more of the features or characteristics of a pGA plasmid (see the detailed description), but different restriction endonuclease sites in the multi-cloning site (e.g., the invention encompasses plasmids that are otherwise substantially similar to pGA1 but that have more, less, or different restriction endonuclease sites in their multi-cloning site).

Example 3 pGA1.2 pGA1.2 (SEQ ID NO: 3) is identical to pGA1.1 except that the multiple cloning site has been altered to include BamHI and XhoI sites 5' to the EcoRI site. This was accomplished by site directed mutagenesis using the primer 5'-CTGCAGTCACCATGGATCCTTGCACT-CGAGGATGCAATGAAGAG-3' (SEQ ID NO:19) and the reverse primer 5'-CTCTTCATTGCATCCTCGAGTGCAAGGATCCATGGTGACTGCAG-3' (SEQ ID NO:20).

Example 4 pGA2 pGA2 is schematically illustrated in FIG. 5, and its nucleotide sequence is shown in FIG. 6 (SEQ ID NO: 4). pGA2 is identical to pGA1 except that the intron A sequence has been deleted from the CMV promoter of pGA2. pGA2 was created from pGA1 by introducing a Cla I site 8 bp downstream from the mRNA cap site in the CMV promoter; the Cla I site was introduced using oligonucleotide-directed mutagenesis using complimentary primers having the SEQuences: 5'-CCGTCAGATCGCATCGATACGCCATCCACG-3' (SEQ ID NO: 19) and 5'-CGTGGATGGCGTATCGATGCGATCTGACGG-3' (SEQ ID NO: 20). After insertion of the new Cla I site, pGA1 was digested with Cla I to remove the 946 bp Cla I fragment from pGA1, and then religated to yield pGA2.

Example 5 pGA2.1

PGA2.1 (SEQ ID NO:5) is identical to pGA2 except that the multiple cloning site has been altered to include an EcoRI sites. This was accomplished by site directed mutagenesis using the following primers: forward 5'-GCTGCTGCTGTGTGGAGAATTCTTCGTTTCGGC-3' (SEQ ID NO:17) and reverse 5'-GCCGAAACGAAGAATTCTCCACACAGCAGCAGC-3' (SEQ ID NO:18). Accordingly, the pGA2.1 vector is an embodiment of the invention; as are other vectors having one or more of the features or characteristics of a pGA plasmid (see the detailed description), but different restriction endonuclease sites in the multi-cloning site (e.g., the invention encompasses plasmids that are otherwise substantially similar to pGA1 but that have more, less, or different restriction endonuclease sites in their multi-cloning site).

Example 6 pGA2.2

PGA2.2 (SEQ ID NO: 6) is identical to pGA1.1 except that the multiple cloning site has been altered to include a BamHI and a XhoI site 5' to the EcoRI site. This was accomplished by site directed mutagenesis using the forward primer 5'-GAACTCATTCTATGGATCCTTGC-TCGAGTGGATGCAATGAAGAG-3' and the reverse primer 5'-CTCTTCATTGCATC-CACTCGAGCAAGGATCCATAGAATGAGTTC-3' (SEQ ID NOs:23 and 24 respectively)

Example 7

Immunodeficiency Virus Vaccine Inserts

Figure 9:
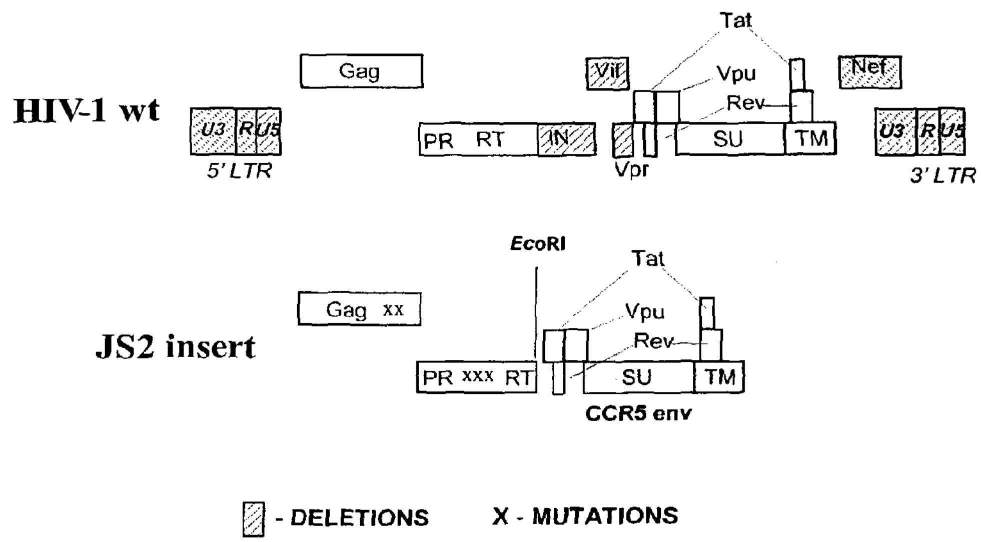
FIG. 9 is a schematic representation of the proviral (integrated DNA) form of the HIV genome (HIV-1 wt) and a representative vaccine insert. This representative insert has safety mutations that include deletion of the LTRs, deletion of sequences encoding integrase (IN), Vif, Vpr and Nef. The insert encodes Gag, PR, RT, Env, Tat, Rev, and Vpu proteins. Clade B inserts are designated JS (clade B), IC (clade AG) and IN (clade C) with arabic numerals designating the specific vaccine constructs (e.g., JS2, JS7 and JS7.1 are examples of specific clade B vaccine constructs; IC2, IC25, IC48 and IC90, examples of specific AG vaccine constructs; and IN2 and IN3 are examples of specific clade C vaccine constructs). When inserted into the pGA1 vector, the insert-bearing plasmids are referred to as pGA1/JS2 etc; when inserted into the pGA2 vector, plasmids are referred to as pGA2/JS2 etc.

HIV-1 vaccine inserts for the pGA1 and pGA2 series of vectors were constructed to express multiple HIV-1 proteins from a single RNA transcript using the same subgenomic splicing mechanisms used by immunodeficiency viruses. To ensure that these multiprotein-expressing vectors did not form infectious virus, deletions and point mutations were introduced to cripple essential steps in the retrovirus life cycle. FIG. 9 presents schematics of the normal retroviral genome and a representative vaccine insert. Regions that have been deleted in the insert are stippled. X's indicate point mutations. The deletions included both of the long terminal repeat (LTR) sequences that encode cis-acting elements for reverse transcription, integration, and expression of proviral DNA. 5' sequences adjacent to the 5'LTR that promote encapsidation of viral RNA have been deleted. Coding sequences for the region of pol encoding integrase as well as the auxiliary genes vif and vpr have been deleted. And finally, nef, a gene encoding the Nef regulatory protein has been deleted. The seven point mutations that are common to all inserts described in the examples below are included in the schematic. These include four mutations in the zinc fingers in the nucleocapsid protein to limit zinc-finger-mediated packaging of viral RNA and three mutations in reverse transcriptase to prevent reverse transcription of viral RNA. Analogous changes can be made in any vaccine insert that includes gag and/or pol. Moreover, these changes (or analogous changes) can be made in vaccine inserts that are placed in any of the plasmid or live-vectored vaccines described herein (i.e., in any plasmid having one or more of the features or characteristics of the pGA vectors, the pGA vectors themselves, or the vaccinia vectors that may be used alone or in conjunction with (e.g., to boost) a DNA-primed patient).

The HIV-1 vaccine inserts described below can be expressed in any of the pGA vectors or further derivatives of these vectors. The examples for inserts that are given below are given with the example of the pGA vector that is planned for future use of that insert. However, any of these inserts can be used in any of the pGA vectors as well as other eukaryotic expression vectors.

Example 8 pGA2/JS2, Multiprotein Clade B HIV-1 Insert

The sequence of pGA2/JS2 is shown in FIG. 7*a* (SEQ ID NO:7), its functional regions and the origins of these regions in FIG. 7*b* and the positions of its point mutations in FIG. 7*c*. The JS2 insert described here was designed with clade B HIV-1 sequences so that it would elicit an immune response against HIV-1 sequences that are endemic in the United States, Europe, and Japan. As noted above, any clade B isolate can be used as a reasonable representative for other clade B isolates. Since HIV-1 isolates use different chemokine receptors as co-receptors, and the vast majority of viruses that are undergoing transmission use the CCR-5 co-receptor (Berger, *AIDS* 11(*Suppl A*):S3-16, 1997), the vaccine insert we designed had a CCR-5-using Env. Of course, Envs that function through any other co-receptor or that have been constructed from naturally occurring or synthetic sequences so as to increase immunogenicity can be made and used as well.

To achieve a multiprotein-expressing clade B vaccine insert with high expression, candidate vaccines were constructed from seven different HIV-1 sequences, as shown in Table 1.

TABLE 1

Comparison of candidate vaccine inserts

| Plasmid designation | SEQuences tested | Ability to grow plasmid | Expression of Gag | Expression of Env | Comment |
|---|---|---|---|---|---|
| BH10-VLP | BH10 | Good | Good | Good | X4 Env |
| 6A-VLP | 6A env in BH10-VLP | Poor | Not tested | not tested | |
| BAL-VLP | BAL env in BH10-VLP | Good | Poor | Poor | |
| ADA-VLP | ADA env in BH10-VLP | Good | Good | Good | chosen for vaccine, renamed pGA1/JS1 |
| CDC-A-VLP | CDC-A env in BH10-VLP | Good | Good | Poor | |

TABLE 1-continued

| Comparison of candidate vaccine inserts | | | | | |
|---|---|---|---|---|---|
| Plasmid designation | SEQuences tested | Ability to grow plasmid | Expression of Gag | Expression of Env | Comment |
| CDC-B-VLP | CDC-B-env in BH10-VLP | Good | Good | Good | not as favorable expression as ADA |
| CDC-C-VLP | CDC-C env in BH10-VLP | Good | Good | Good | not as favorable expression as ADA |

An initial construct, pBH10-VLP, was prepared from IIIB sequences that are stable in bacteria and have high expression in eukaryotic cells. The HIV-1-BH10 sequences were obtained from the NIH-sponsored AIDS Repository (catalog #90). The parental pHIV-1-BH10 was used as the template for PCR reactions to construct pBH10-VLP.

Primers were designed to yield a Gag-Rt PCR product (5' PCR product) encompassing (from 5' to 3') 105 bp of the 5' untranslated leader sequence and sequences from the start codon for Gag to the end of the RT coding sequence. The oligonucleotide primers introduced a Cla I site at the 5' end of the PCR product and EcoR I and Nhe I sites at the 3' end of the PCR product. Sense primer (5'-GAGCTCTATCGATGCAG-GACTCGGCTTGC-3' (SEQ ID NO:25 and antisense primer (5'-GGCAGGTTTTAATCGCTAGCCTATGCTCTCC-3' (SEQ ID NO:26) were used to amplify the 5' PCR product.

The PCR product for the env region of HIV-1 (3' PCR product) encompassed the vpu, tat, rev, and env sequences and the splice acceptor sites necessary for proper processing and expression of their respective mRNAs. An EcoR I site was introduced at the 5' end of this product and Nhe I and Rsr II sites were introduced into the 3' end. Sense primer (5'-GGGCAGGAGTGCTAGCC-3' (SEQ ID NO:27) and anti-sense primer 5'-CCACACTACTTTCGGACCGCTAGC-CACCC-3' (SEQ ID NO: 28)) were used to amplify the 3' PCR product. The 5' PCR product was cloned into pGA1 at the Cla I and Nhe I sites of pGA1 and the identity of the construct confirmed by sequencing. The 3' PCR product was then inserted into the 5' clone at the EcoR I and Nhe I sites to yield pBH10. The construction of this plasmid resulted in proviral sequences that lacked LTRs, integrase, vif, vpr and nef sequences (see FIG. 9).

Because pBH10-VLP encoded a CXCR-4 using Env, rather than a CCR-5 using Env, sequences encoding six different R5 Envs were substituted for env sequence in the pBH10 intermediate (Table 1). EcoR I to BamH I fragments encompassing tat, rev, vpu and env coding sequences from different viral genomes were substituted into pBH10. The resulting env and rev sequences were chimeras for the substituted sequences and HIV-1-BH10 sequences (see FIG. 9). In the case of the HIV-1-ADA envelope, a BamH I site was introduced into the HIV-1-ADA sequence to facilitate substituting an EcoR I to BamH I fragment for the EcoR I to BamH I region of pBH10. The results of these constructions are summarized in Table 1. Of the six sequences tested, one, the 6A-VLP gave poor plasmid growth in transformed bacteria. The plasmid 6A-VLP was not developed further. Among the other constructs, the pBH10/ADA chimera produced the best expression of viral Gag and Env proteins (Table 1). In transient transfections in 293T cells, the expression from the pBH10/ADA chimera was higher than that of wt proviruses for HIV-1-ADA or HIV-1-IIIB Expression was also higher than for a previous multiprotein-expressing HIV-1 vaccine (dpol) (Richmond et al., *J. Virol.* 72:9092-9100, 1998) that had successfully primed cytotoxic T cell responses in rhesus macaques (Kent et al., *J. Virol.* 72:10180-10188, 1998). The pBH10/ADA chimera was now designated JS1. It should be recognized that plasmids having any given or desired HIV-1 inserts can be similarly assessed.

Next, inactivating point mutations were introduced into JS1 to further increase the safety of this construct for use in humans as a non-infectious vaccine agent (of course, mutations can be made preemptively, before any testing at all) (see FIG. 10*c*). Four codon mutations were introduced into the Zinc fingers in nucleocapsid to limit the encapsidation of viral RNA and three codon mutations were introduced into the reverse transcriptase region of pol to inactivate the viral reverse transcriptase. The JS1 insert with these mutations was designated JS2.

The mutations were made using a site directed mutagenesis kit (Stratagene) following the manufacturer's protocol. All mutations were confirmed by sequencing. Primer pairs used for the mutagenesis were:

```
(A)
                        (C392S, C395S; SEQ ID NO: 29)
5'-GGTTAAGAGCTTCAATAGCGGCAAAGAAGGGC-3'
and
                        (C392S, C395S; SEQ ID NO: 30)
5'-GCCCTTCTTTGCCGCTATTGAAGCTCTTAACC-3';

(B)
                        (C413S, C416S; SEQ ID NO: 31)
5'-GGGCAGCTGGAAAAGCGGAAAGGAAGG-3'
and
                        (C413S, C416S; SEQ ID NO: 32)
5'-CCTTCCTTTCCGCTTTTCCAGCTGCCC-3';

(C)
                               (D185N; SEQ ID NO: 33)
5'-CCAGACATAGTTATCTATCAATACATGAACGATTTGTATGTAGG-3'
and
                               (D185N; SEQ ID NO: 34)
5'-CCTACATACAAATCGTTCATGTATTGATAGATAACTATGTCTGG-3';

(D)
                               (W266T; SEQ ID NO: 35)
5'-GGGGAAATTGAATACCGCAAGTCAGATTTACCC-3';
and
                               (W266T; SEQ ID NO: 36)
5'-GGGTAAATCTGACTTGCGGTATTCAATTTCCCC-3';

(E)
                               (E478Q; SEQ ID NO: 37)
5'-CCCTAACTAACACAACAAATCAGAAAACTCAGTTACAAGC-3'
and
                               (E478Q; SEQ ID NO: 38)
5'-GCTTGTAACTGAGTTTTCTGATTTGTTGTGTTAGTTAGGG-3'.
```

Example 9 pGA2/JS7 Vaccine Plasmid

The sequence of pGA2/JS7 is shown in FIG. 11*a* (SEQ ID NO:8), its functional regions and the origins of these regions in FIG. 11C and the positions of its codon mutations in FIG. 11D. In the JS7 insert, Gag sequences of HIV-1-HXB-2 are substituted for the Gag sequences of BH10. This was accomplished by PCR amplification of the HXB-2 sequence (p5' plasmid, NIH AIDS Research and Reference Program, catalog #3119) using the following primers: forward 5'-GAGCTCTATCGATGCAGGACTCGGCTTGC-3' (SEQ ID NO:39) and reverse 5'-CTCCAATTACTGTGAGAAT-TCTAATGTTCATCTTGGG-3' (SEQ ID NO:40). The forward primer introduced a Cla I site at the same position as that found in the JS2 insert and the reverse primer introduced a unique EcoR I site analogous to the same site in the JS2 insert. This PCR fragment was then inserted into pGA1.1 for mutagenesis. The safety mutations in the zinc finger regions and the RT mutations were then introduced as previously described for the JS2 insert. JS7 also differs from JS2 in having an inactivating codon mutation at the active site of protease. This mutation was introduced using the primers: 5'-GGCAACTAAAGGAAGCTCTATTAGCCA-CAGGAGC-3' (D25A Prt1; forward; SEQ ID NO:41) and 5'-GCTCCTGTGGCTAATAGAGCTTCCTT-TAGTTGCC-3' (D25A Prt2; reverse; SEQ ID NO:42). Once the mutations were confirmed by sequencing, the HXB-2 Gag-Pol insert was introduced into pGA2/JS2 via the Cla I and EcoR I sites. In contrast to the JS2 insert that expresses aggregates of HIV-1 proteins due to premature cleavage of the pr55Gag polyprotein by the viral protease, the JS7 insert forms immature virus like particles (VLPs) that bud from the plasma membrane of DNA-expressing cells.

Example 10 pGA2/JS7.1 Vaccine Plasmid

The sequence of pGA2/JS7.1 is shown in FIG. 12*a* (SEQ ID NO:9), its functional regions and the origins of these regions in FIG. 12D and the positions of its codon mutations in FIG. 12E. pGA2/JS7.1 is a derivative of pGA2/JS7 in which the start codon as well as an immediately upstream ATG have been mutated in vpu. These mutations were introduced to increase the level of the expression of Env. The mutations in the start codon for Vpu were accomplished using a site directed mutagenesis kit (Stratagene) and the oligonucleotides: forward 5'-GCAGTAAGTAGTAAATCTAATC-CAACCTTTAC-3' (SEQ ID NO:43) and reverse 5'-GTAAAGGTTGGATTAGATTTACTACTTACTGC-3' (SEQ ID NO:44).

Example 11 pGA1/IC25 Vaccine Plasmid

The sequence of pGA1/IC25 is shown in FIG. 13*a* (SEQ ID NO:10), its functional regions and the origins of these regions in FIG. 13D and the positions of its point mutations in FIG. 13E. The IC25 insert described here was designed with a circulating recombinant form of clades A and G (designated AG) so that it would elicit an immune response against HIV-1 sequences that predominate in West Africa. As noted above, any clade AG isolate from West Africa could be used as a reasonable representative for other clade AG isolates. Since HIV-1 isolates use different chemokine receptors as co-receptors, and the vast majority of viruses that are undergoing transmission use the CCR-5 co-receptor (Berger, *AIDS* 11(Suppl A):S3-16, 1997), the AG vaccine insert we designed had a CCR-5-using Env. Of course, Envs that function through any other co-receptor or that have been constructed from naturally occurring or synthetic AG sequences so as to increase immunogenicity can be made and used as well.

To achieve a multiprotein-expressing clade AG vaccine insert with high expression, candidate vaccines were constructed from four different AG HIV-1 isolates, as shown in Table 2.

TABLE 2

Comparison of candidate AG vaccine inserts

| Plasmid designation | SEQuences tested | Ability to grow plasmid | Expression of Gag | Expression of Env | Comment |
|---|---|---|---|---|---|
| 418/928 | 418 gag in 928-VLP | Poor | Poor | not tested | |
| 421/928 | 421 gag in 928-VLP | Good | Good | Poor | |
| 896/928 | 896 gag in 928-VLP | Good | Good | Poor | |
| 928/928 | 928 | Good | Good | Good | chosen for vaccine, renamed pGA1/IC1 |

For each isolate, the forward primer 5'-AAGATCTATC-GATGCAAGGACTCGGCTTGC-3' (SEQ ID NO:45) and the reverse primer 5'-TTCCAATTGCTGTGAGAAT-TCTCA-TGCTCTTCTTGGG-3' (SEQ ID NO:46) were used to amplify the 5' Gag-RT PCR product. The 3' PCR product for the Env region encompassed the vpu, tat, rev, and env sequences and the splice acceptor sites necessary for proper processing and expression of their respective mRNAs. An EcoR I site was introduced at the 5' end of this product and Nhe I and Rsr II sites were introduced into the 3' end. A forward primer 5'-AAGGGGTTAAAGCTATAATAAG-AATTCTGCA-3' (SEQ ID NO:47) and a reverse primer 5'-CCTTTGCTGCCCTATCTGA-TTCTTCTAGG-3' (SEQ ID NO:48) were used to amplify the 3' PCR product. Of these, those from patient 928 proved particularly favorable for further development (Table 2. The 928 sequences with deletions but not codon mutations were designated IC1.

The strategy used to construct IC25, a more disabled virus than IC1, was similar to that used to construct JS7 from JS1. Specifically four codon mutations were introduced into gag sequences to inactivate the zinc fingers that are involved in RNA packaging, three codon mutations were introduced into pol sequences to inactivate transcription, strand transfer and RNaseH activities of reverse transcriptase and the codon at the active site of the protease was mutated to limit proteolytic cleavage of viral Gag proteins and the maturation of viral particles. The protease mutations also limited premature cleavage of the Gag polyprotein and allowed budding of immature VLPs.

The inactivating codon mutations were made using a site directed mutagenesis kit (Stratagene) following the manufacturer's protocol. All mutations were confirmed by sequencing. Primer pairs used for the mutagenesis were:

```
(A)
                              (C390S, C393S; SEQ ID NO: 49)
5'-GCCAGAGAATAATAAAGAGCTTCAACAGCGGCAAAGAAGG-3'
and
                              (C390S, C393S; SEQ ID NO: 50)
5'-CCTTCTTTGCCGCTGTTGAAGCTCTTTATTATTCTCTGGC-3';

(B)
                              (C411S, C414S; SEQ ID NO: 51)
5'-CCTAGAAAGAGAGGCAGCTGGAAAAGCGGAAAGGAAGG-3'
and
                             (C414S 928 ZN4; SEQ ID NO: 52)
5'-CCTTCCTTTCCGCTTTTCCAGCTGCCTCTCTTTCTAGG-3';

(C)
                                   (D185N; SEQ ID NO: 53)
5'-CCAATATATGAACGATTTATATGTAGGATCTGAC-3'
and
                                   (D185N; SEQ ID NO: 54)
5'-GTCAGATCCTACATATAAATCGTTCATATATTGG-3';

(D)
                                   (W266T; SEQ ID NO: 55)
5'-GGGAAAACTAAATACCGCAAGTCAGATTTATGCAGG-3'
and
                                   (W266T; SEQ ID NO: 56)
5'-CCTGCATAAATCTGACTTGCGGTATTTAGTTTTCCC-3';
and

(E)
                                   (E478Q; SEQ ID NO: 57)
5'-CCCTAATTGAGACAACAAATCAAAAGACTCAGTTACATGC-3'
and
                                   (E478Q; SEQ ID NO: 58)
5'-GCATGTAACTGAGTCTTTTGATTTGTTGTCTCAATTAGGG-3'.

(F)
                                    (D25A; SEQ ID NO: 59)
5'-GCCAATAGAAGCCCTATTAAACACAGGAGC-3'
and
                                    (D25A; SEQ ID NO: 60)
5'-GCTCCTGTGTTTAATAGGGCTTCTATTGGC-3'.
```

Example 12

PGA1/IC2

The sequence of pGA1/IC2 is shown in FIG. 14*a* (SEQ ID NO:11), its functional regions and the origins of these regions in FIG. 14D and the positions of its point mutations in FIG. 14E. pGA1/IC2 is identical to pGA1/IC25 except for not containing the inactivating point mutation in protease.

Example 13

PGA1/IC48

The sequence of pGA1/IC48 is shown in FIG. 15*a* (SEQ ID NO:12), its functional regions and the origins of these regions in FIG. 15D and the positions of its point mutations in FIG. 15E. pGA1/IC48 is identical to pGA1/IC25 except that the codon mutation in protease is one that occurred in a drug resistant mutant (Jacobsen et al., *Virology* 206:527-534, 1995). This mutation only partially inactivates the protease function. Mutagenesis was carried out using Stratagene kits and the following oligonucleotides: 5'-CCAAAAATGATAGtGGGAATTGGAGG-3' (G48V 928; SEQ ID NO:61) and 5'-CCTCCAATTCCCaCTATCATTTTTGG-3' (G48V 928; SEQ ID NO:62). This mutation only partially inactivates the protease function.

Example 14

PGA1/IC90

The sequence of pGA1/IC90 is shown in FIG. 16*a* (SEQ ID NO:13), its functional regions and the origins of these regions in FIG. 16D and the positions of its point mutations in FIG. 16E. pGA1/IC90 is identical to pGA1/IC25 except that the codon mutation in protease is one that occurred in a drug resistant mutant (Jacobsen et al., *Virology* 206:527-534, 1995). This mutation only partially inactivates the protease function. Mutagenesis was carried out using Stratagene kits and the following oligonucleotides: 5'-GGACGAAATATGaTGACTCAGATTGGT-3' (M90L; SEQ ID NO:63) and 5'-ACCAATCTGAGTCAtCATATTTCGTCC-3' (M90L; SEQ ID NO:64).

Example 15 pGA1/IN3

The sequence of pGA1/IN3 is shown in FIG. 17*a* (SEQ ID NO:14), its functional regions and the origins of these regions in FIG. 17D and the positions of its point mutations in FIG. 17E. The IN3 insert described here was constructed from a clade C sequence recovered from a virus in India. As noted above, any clade C isolate could be used as a reasonable representative for other clade C isolates. Since HIV-1 isolates use different chemokine receptors as co-receptors, and the vast majority of viruses that are undergoing transmission use the CCR-5 co-receptor (Berger, *AIDS* 11(Suppl A):S3-16, 1997), the C vaccine insert we chose to construct had a CCR-5-using Env. Of course, Envs that function through any other co-receptor or that have been constructed from naturally occurring or synthetic C sequences so as to increase immunogenicity can be made and used as well.

To achieve a multiprotein-expressing clade C vaccine insert with high expression, candidate vaccines were constructed from four different clade C HIV-1 sequences that were obtained from the US NIAID AIDS repository, as shown in Table 3. Of these, those from the Indian clone proved particularly favorable for further development.

TABLE 3

Comparison of clade C candidate vaccine inserts

| Isolate and Genbank Accession # | Ability to grow plasmid | Expression of Gag | Expression of Env | Comment |
|---|---|---|---|---|
| South Africa AF286227 | Good | Good | Good | |
| Israel AF286233 | Good | Good | Good | |
| Tanzania AF286235 | Good | Good | Good | |

TABLE 3-continued

| Comparison of clade C candidate vaccine inserts | | | | |
|---|---|---|---|---|
| Isolate and Genbank Accession # | Ability to grow plasmid | Expression of Gag | Expression of Env | Comment |
| India AF286231 | Good | Good | Very good | Chosen for vaccine, renamed pGA1/IN1 |

5' and 3' sequences from the Indian clone were cloned into pGA1.2 using oligonucleotides and PCR to generate 5' and 3' fragments. The 5' fragment encoding Gag and RT was generated using the forward primer 5'-CGCAGGATCCGGCTTGCTGAAG-3' (SEQ ID NO:65), which incorporated a BamH I site at the 5' end of the fragment, and the reverse primer 5'-TCTACTCGAGCTTATTATAGCACTCTCCTG-3' (SEQ ID NO:66), which incorporated an Xho I site as well as two stop codons at the 3' end of the fragment. The 3' fragment encoding Tat, Rev, Vpu, and Env was generated using the forward primer 5'-CCTCTCGAGATACTTGGACAGGAG-3' (SEQ ID NO:67) and the reverse primer 5'-CACTTGCTAGCCATTTTACTGCAAAGC-3' (SEQ ID NO:68). These were designed such that Xho 1 and Nhe 1 restriction sites were incorporated at the 5' and 3' ends, respectively of the 3' fragment. These fragments were introduced into pGA1.2 using directed cloning to create pGA1.2/IN1.

The strategy used to construct IN3, a more disabled virus than IN1, was similar to that used to construct JS7 from JS1. Specifically four codon mutations were introduced into gag sequences to inactivate the zinc fingers that are involved in RNA packaging, three codon mutations were introduced into pol sequences to inactivate transcription, strand transfer and RNaseII activities of reverse transcriptase and the codon at the active site of the protease was mutated to limit proteolytic cleavage of viral Gag proteins and the maturation of viral particles. The protease mutations also limited premature cleavage of the Gag polyprotein and allowed budding of immature VLPs.

The inactivating codon mutations were made using a site directed mutagenesis kit (Stratagene) following the manufacturer's protocol. All mutations were confirmed by sequencing. Primer pairs used for the mutagenesis were:

```
(A)
                          (C390S, C393S; SEQ ID NO: 70)
5'-CTAAAAGAACTGTTAAATCCTTCAACTCTGGCAAGGAAGGGCAC-3'
and
                          (C390S, C393S; SEQ ID NO: 71)
5'-GTGCCCTTCCTTGCCAGAGTTGAAGGATTTAACAGTTCTTTTAG-3';

(B)
                          (C411S, C414S; SEQ ID NO: 72)
5'-CTAGGAAAAAAGGCTCTTGGAAATCTGGAAAGGAAGGACAC
and
                      (C411S and C414S; SEQ ID NO: 73)
5'-GTGTCCTTCCTTTCCAGATTTCCAAGAGCCTTTTTTCCTAG-3':

(C)
                                 (D185N, SEQ ID NO: 74)
5'-GTCATCTATCAATATATGAATGACTTGTATGTAG-3'
and
                                 (D185N, SEQ ID NO: 75)
5'-CTACATACAAGTCATTCATATATTGATAGATGAC-3';
```

-continued

```
(D)
                                 (W266T, SEQ ID NO: 76)
5'-GTGGGAAAATTAAACACGGCAAGCCAGATTTAC-3'
and
                                 (W266T, SEQ ID NO: 77)
5'-GTAAATCTGGCTTGCCGTGTTTAATTTTCCCAC-3';

(E)
                                 (E478Q, SEQ ID NO: 78)
5'-CAAATCAGAAGACTCAATTACAAGCAATTTATC-3'
and
                                 (E478Q, SEQ ID NO: 79)
5'-GATAAATTGCTTGTAATTGAGTCTTCTGATTTG-3'
and

(F)
                                  (D25N, SEQ ID NO: 80)
5'-GGAGGCTCTCTTAGcCACAGGAGCAGATG-3'
and
                                   (D25N, SEQ ID NO 81)
5'-CATCTGCTCCTGTGgCTAAGAGAGCCTCC-3'.
```

Example 16 pGA1/IN2

The sequence of pGA1/IN2 is shown in FIG. 18*a* (SEQ ID NO: 5), its functional regions and the origins of these regions in FIG. 18D and the positions of its point mutations in FIG. 18E. pGA1IN2 differs from pGA1/IN3 in not having the D25N Inactivating point mutation in protease.

Example 17

Sequences Provided for Matched rMVAs

Sequences for the JS, IC, and IN inserts were used to prepare matched recombinant modified vaccinia Ankara (rMVA) vectors. These matched vectors can be used as booster inoculations for the various DNAs. They can also be used for both priming and boosting an anti-HIV immune response. The sequences provided to generate the viral vector included the three inactivating point mutations in reverse transcriptase. A representative study, in which a recombinant MVA vector was constructed and characterized, follows.

Figure 20A:
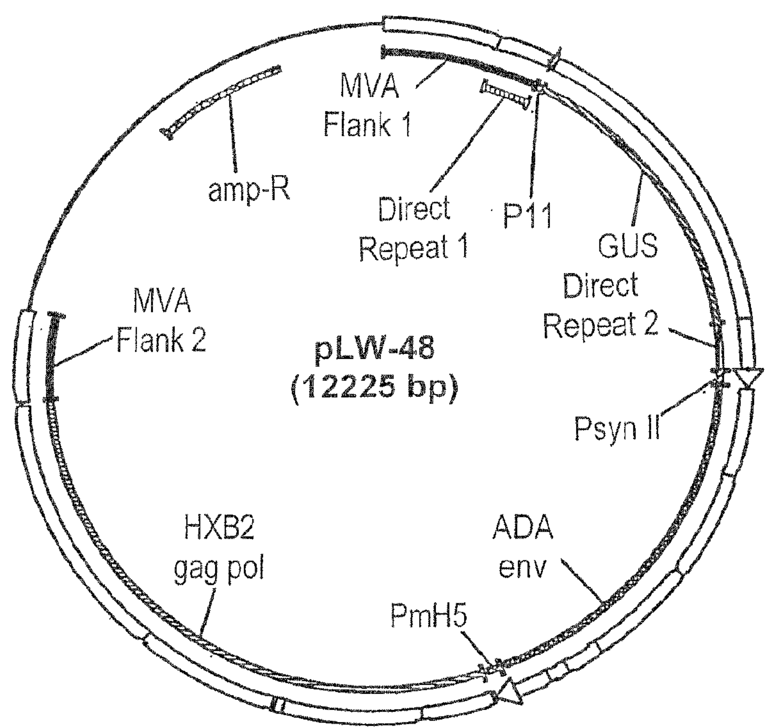
Figure 22:
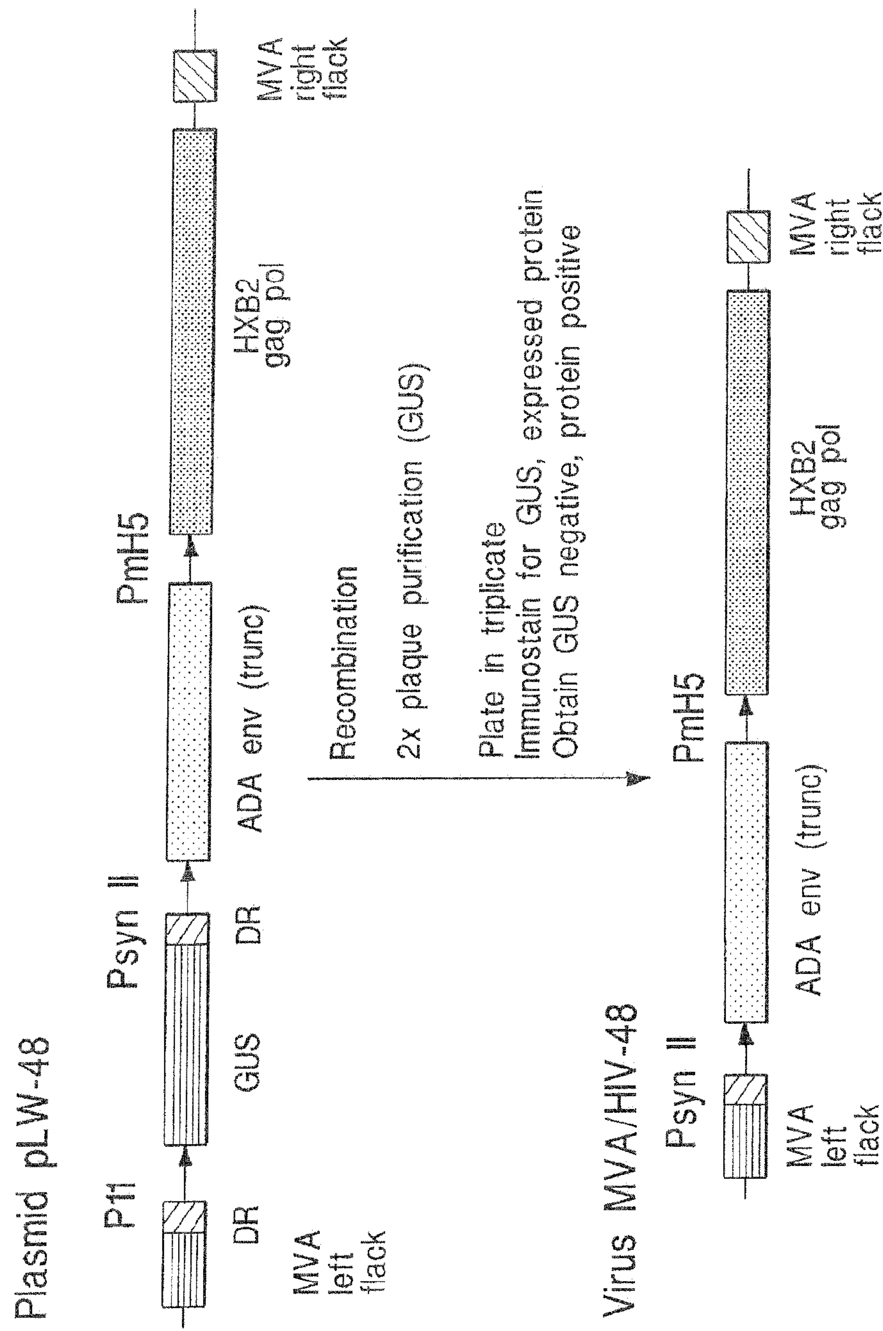
FIG. 22 is a representation of the plasmid transfer vector pLW-48 and a scheme for making an MVA recombinant virus (MVA/HIV 48).
Figure 23:
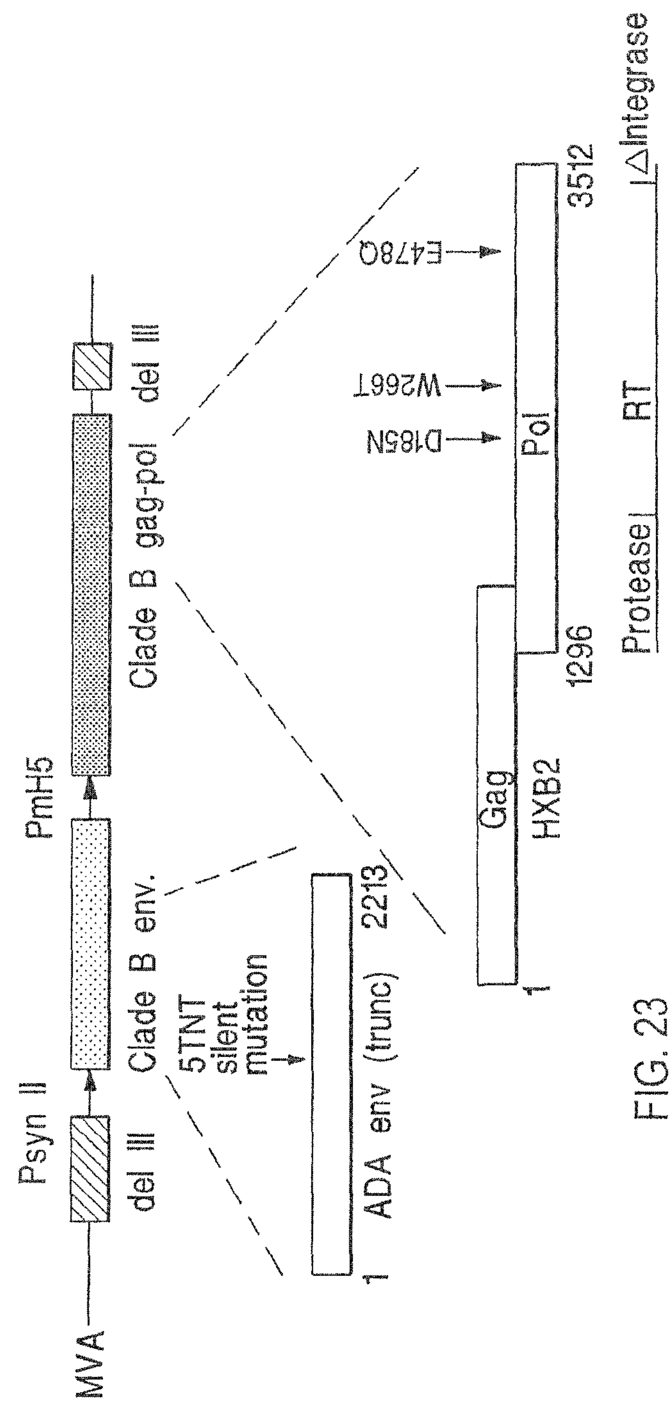
FIG. 23 is a representation of a clade B gag pot.

MVA virus (which may be obtained from the American Type Culture Collection) was plaque purified three times by terminal dilutions in chicken embryo fibroblasts (CEF), which were made from 9-day old SPF Premium SPAFAS fertile chicken eggs, distributed by B and E eggs (Stevens, Pa.). Secondary CEF cells were infected at an MOI of 0.05 of MVA and transfected with 2 pLW-48 (as described above; see FIGS. 20A and 20B). Following a two-day incubation at 37° C., the virus was harvested, frozen and thawed three times. It was then plated on CEF plates. At "four days," those foci of infection that stained blue after addition of X-gluc substrate, indicating that recombination had occurred between the plasmid and the infecting virus, were picked and inoculated on CEF plates. Again, those foci that stained blue were picked. These GUS-containing foci were plated out in triplicate and analyzed for GUS staining (which we wanted to now delete) and ADA envelope expression. Individual foci were picked from the third replicate plates of those samples that had about equal numbers of mixed populations of GUS staining and non-staining foci as well as mostly envelope staining foci. These foci were again plated out in triplicate and analyzed the same way. After five passages, a virus was derived that expressed the envelope protein but which had deleted the GUS gene because of the double repeat. By immunostaining, this virus also expressed the Gag-Pol protein.

Aliquots of MVA/HIV48 infected cell lysates were analyzed by radio-immunoprecipitation and immunostaining with monoclonal antibodies for expression of both the Env and Gag-Pol protein. In both of these tests, each of these proteins was detected. The recombinant virus was shown to produce gag particles in the supernatant of infected cells by pelleting the $^{35}$S-labeled particles on a 20% sucrose cushion. By electron microscopy, gag particles were visualized both outside and budding from cells as well as within vacuoles of cells. The gag particles had envelope protein on their surface.

Thus, we made a recombinant MVA virus that expressed the ADA truncated envelope and the HXB2 Gag-Pol protein. The MVA recombinant virus is made using a transiently expressed GUS marker that is deleted in the final virus. High expression of the ADA envelope is possible because of a new hybrid early/late promoter (Psyn II; see, e.g., FIGS. 21A-I, 22, and 24). In addition, the envelope has been truncated, as this may enhance the amount of protein on the surface of the infected cells and hence enhance immunogenicity. Stability of the recombinant may also be enhanced.

What is claimed is:

1. A vector comprising a insert encoding one or more antigens that elicit an immune response against an HIV of a subtype or recombinant form, said insert encoding for (a) a HIV-1 Gag protein in which both zinc fingers have been inactivated by amino acid changes corresponding to HIV Clade B HXB2 C392S, C395S, C413S and C416S; (b) a HIV-1 Pol protein in which (i) the integrase activity is inhibited by the deletion of integrase, (ii) the reverse transcriptase activity is inhibited by amino acid changes corresponding to HIV *Clade* B HXB2 D185N, W266T and E478Q, and (iii) the protease activity is inhibited by amino acid change corresponding to HIV Clade B HXB2D25A.

2. A vector comprising a insert encoding one or more antigens that elicit an immune response against an HIV of a subtype or recombinant form, said insert encoding for (a) a HIV Gag protein in which both zinc fingers have been inactivated by amino acid changes corresponding to HIV Clade B HXB2 C392S, C395S, C413S, and C416S; (b) a HIV-1 Pol protein in which (i) the integrase activity is inhibited by the deletion of integrase, (ii) the reverse transcriptase activity is inhibited by amino acid changes corresponding to HIV Clade B HXB2 D185N, W266T and E478Q, and (iii) the protease activity is inhibited by amino acid change corresponding to HIV Clade B HXB2 D25A; (c) a HIV-1 ADA Vpu protein comprising a mutant start codon by having a nucleic acid change G2C in the encoding sequence start site and having the nucleic acid sequence ATC at positions −5 to −3 upstream of the encoding start site.

3. The vector of claim 1, said insert having nucleic acid residues 106-6626 of SEQ ID NO:8.

4. The vector of claim 2, said insert having nucleic acid residues 106-6626 of SEQ ID NO: 9.

5. The vector of claim 1, said vector having nucleic acid residues 6627-9506 of SEQ ID NO:8.

6. The vector of claim 1 having the nucleotide sequence of SEQ ID NO:8.

7. The vector of claim 1 having the nucleotide sequence of SEQ ID NO:9.

8. A composition comprising a therapeutically effective amount of the vector of claim 1 and a pharmaceutically acceptable carrier.

9. The composition of claim 8 comprising an adjuvant selected from GM-CSF, IL-15 or IL-2.

10. The composition of claim 8, further comprising a second vector comprising a vaccine insert encoding one or more antigens that elicit an immune response against an HIV of a second subtype or recombinant form.

11. A method of eliciting a cellular and humoral immune response to an HIV antigen in a subject, the method comprising: administering to the subject a therapeutically effective amount of a composition comprising the vector of claim 1.

12. The method of claim 11 wherein administration of the composition produces virus-like particles (VLPs) when administered to the subject.

13. The method of claim 11 wherein the composition comprises a second vector comprising an insert encoding one or more antigens that elicit an immune response against an HIV of a second subtype or recombinant form.

14. The method of claim 13 wherein the composition comprises a third vector comprising an insert encoding one or more antigens that elicit an immune response against an HIV of a third subtype or recombinant form.

15. The method of claim 13, wherein administering the composition comprises administering a plasmid vector on more than one occasion for the purposes of priming or boosting a protective immune response.

16. The method of claim 12, wherein administering the composition comprises administering a plasmid vector on one or more than one occasion for the purpose of priming or boosting an immune response and administering a modified vaccinia Ankara on one or more than one subsequent occasion for the purpose of boosting or priming the immune response.

17. The method of claim 15, wherein the second vector insert is selected from the insert designated JS2, JS7, or JS7.1, and/or the insert designated IC2, IC25, IC48, or IC90, and/or the insert designated IN2 or IN3 and wherein the boosting comprises administering modified vaccinia Ankara vectors containing HIV sequences matched to the plasmids used for priming.

18. The method of claim 15, wherein the plasmid vector comprises an insert obtained from an HIV clade A and/or clade B, and/or clade C, and/or clade D, and/or clade E and/or clade F, and/or clade G and/or clade H and/or clade J, and/or clade K, and/or clade L and/or a recombinant subtype thereof and wherein the boosting comprises administering modified vaccinia Ankara vectors containing HIV sequences matched to the plasmids used for priming.

19. The method of claim 12, wherein administering the composition comprises administering modified vaccinia Ankara vectors on more than one occasion for the purposes of priming and boosting a protective immune response.

20. The method of claim 15, wherein the priming comprises administering clade B recombinant MVA and/or clade A recombinant MVA and/or clade C recombinant MVA and or any recombinant subtype thereof wherein the boosting comprises administering the same modified vaccinia Ankara vectors used for priming.

21. The method of claim 15, wherein the priming comprises administering clade A and/or clade B, and/or clade C, and/or clade D, and or/clade E and/or clade F, and/or clade G and/or clade H and/or clade J, and/or clade K, and/or clade L and/or any recombinant subtype thereof in a modified vaccinia Ankara vector and wherein the boosting comprises administering the same modified vaccinia Ankara vectors used for priming.

22. The method of claim 15, wherein the composition is administered by intradermal or intramuscular injection.

* * * * *

SEQUENCE LISTING

```
<160> NUMBER OF SEQ ID NOS: 89

<210> SEQ ID NO 1
<211> LENGTH: 3897
<212> TYPE: DNA
<213> ORGANISM: Artificial Sequence
<220> FEATURE:
<223> OTHER INFORMATION: Synthetically generated vector sequence-pGA-1

<400> SEQUENCE: 1

cgacaatatt ggctattggc cattgcatac gttgtatcta tatcataata tgtacattta     60

tattggctca tgtccaatat gaccgccatg ttgacattga ttattgacta gttattaata    120

gtaatcaatt acgggttcat tagttcatag cccatatatg gagttccgcg ttacataact    180

tacggtaaat ggcccgcctg gctgaccgcc caacgacccc cgcccattga cgtcaataat    240

gacgtatgtt cccatagtaa cgccaatagg gactttccat tgacgtcaat gggtggagta    300

tttacggtaa actgcccact tggcagtaca tcaagtgtat catatgccaa gtccgccccc    360

tattgacgtc aatgacggta aatggcccgc ctggcattat gcccagtaca tgaccttacg    420

ggactttcct acttggcagt acatctacgg tattagtcat cggctattac catggtgatg    480

cggttttggc agtacaccaa tgggcgtgga tagcggtttg actcacgggg atttccaagt    540

ctccacccca ttgacgtcaa tgggagtttg ttttggcacc aaaatcaacg ggactttcca    600

aaatgtcgta ataaccccgc cccgttgacg caaatgggcg gtaggcgtgt acggtgggag    660

gtctatataa gcagagctcg tttagtgaac cgtcagatcg cctggagacg ccatccacgc    720

tgttttgacc tccatagaag acaccgggac cgatccagcc tccgcggccg ggaacggtgc    780

attggaacgc ggattccccg tgccaagagt gacgtaagta ccgcctatag actctatagg    840

cacacccctt tggctcttat gcatgctata ctgtttttgg cttggggcct atacaccccc    900

gcttccttat gctataggtg atggtatagc ttagcctata ggtgtgggtt attgaccatt    960

attgaccact cccctattgg tgacgatact ttccattact aatccataac atggctcttt   1020

gccacaacta tctctattgg ctatatgcca atactctgtc cttcagagac tgacacggac   1080

tctgtatttt tacaggatgg ggtcccattt attatttaca aattcacata tacaacaacg   1140

ccgtcccccg tgcccgcagt ttttattaaa catagcgtgg gatctccacg cgaatctcgg   1200

gtaccgtgtt ccggacatgg gytcttctcc ggtagcggcg gagcttccac atccgagccc   1260

tggtcccatg cctccagcgg ctcatggtcg ctcggcagct ccttgctcct aacagtggag   1320

gccagactta ggcacagcac aatgcccacc accaccagtg tgccgcacaa ggccgtggcg   1380

gtagggtatg tgtctgaaaa tgagctcgga gattgggctc gcaccgctga cgcagatgga   1440

agacttaagg cagcggcaga agaagatgca ggcagctgag ttgttgtatt ctgataagag   1500

tcagaggtaa ctcccgttgc ggtgctgtta acggtggagg gcagtgtagt ctgagcagta   1560

ctcgttgctg ccgcgcgcgc caccagacat aatagctgac agactaacag actgttcctt   1620
```

```
tccatgggtc ttttctgcag tcaccatcga tgcttgcaat catggatgca atgaagagag   1680
ggctctgctg tgtgctgctg ctgtgtggag cagtcttcgt ttcggctagc cccgggtgat   1740
aaacggaccg cgcaatccct aggctgtgcc ttctagttgc cagccatctg ttgtttgccc   1800
ctcccccgtg ccttccttga ccctggaagg tgccactccc actgtccttt cctaataaaa   1860
tgaggaaatt gcatcgcatt gtctgagtag gtgtcattct attctggggg gtggggtggg   1920
gcaggacagc aagggggagg attgggaaga caatagcagg catgctgggg atgcggtggg   1980
ctctatataa aaaacgcccg gcggcaaccg agcgttctga acgctagagt cgacaaattc   2040
agaagaactc gtcaagaagg cgatagaagg cgatgcgctg cgaatcggga gcggcgatac   2100
cgtaaagcac gaggaagcgg tcagcccatt cgccgccaag ctcttcagca atatcacggg   2160
tagccaacgc tatgtcctga tagcggtctg ccacacccag ccggccacag tcgatgaatc   2220
cagaaaagcg gccattttcc accatgatat tcggcaagca ggcatcgcca tgggtcacga   2280
cgagatcctc gccgtcgggc atgctcgcct tgagcctggc gaacagttcg gctggcgcga   2340
gcccctgatg ctcttcgtcc agatcatcct gatcgacaag accggcttcc atccgagtac   2400
gtgctcgctc gatgcgatgt ttcgcttggt ggtcgaatgg gcaggtagcc ggatcaagcg   2460
tatgcagccg ccgcattgca tcagccatga tggatacttt ctcggcagga gcaaggtgag   2520
atgacaggag atcctgcccc ggcacttcgc ccaatagcag ccagtccctt cccgcttcag   2580
tgacaacgtc gagcacagct gcgcaaggaa cgcccgtcgt ggccagccac gatagccgcg   2640
ctgcctcgtc ttgcagttca ttcagggcac cggacaggtc ggtcttgaca aaaagaaccg   2700
ggcgcccctg cgctgacagc cggaacacgg cggcatcaga gcagccgatt gtctgttgtg   2760
cccagtcata gccgaatagc ctctccaccc aagcggccgg agaacctgcg tgcaatccat   2820
cttgttcaat catgcgaaac gatcctcatc ctgtctcttg atcagatctt gatcccctgc   2880
gccatcagat ccttggcggc aagaaagcca tccagtttac tttgcagggc ttcccaacct   2940
taccagaggg cgccccagct ggcaattccg gttcgcttgc tgtccataaa accgcccagt   3000
ctagctatcg ccatgtaagc ccactgcaag ctacctgctt tctctttgcg cttgcgtttt   3060
cccttgtcca gatagcccag tagctgacat tcatccgggg tcagcaccgt ttctgcggac   3120
tggctttcta cgtgaaaagg atctaggtga agatcctttt tgataatctc atgaccaaaa   3180
tcccttaacg tgagttttcg ttccactgag cgtcagaccc cgtagaaaag atcaaaggat   3240
cttcttgaga tccttttttt ctgcgcgtaa tctgctgctt gcaaacaaaa aaaccaccgc   3300
taccagcggt ggtttgtttg ccggatcaag agctaccaac tctttttccg aaggtaactg   3360
gcttcagcag agcgcagata ccaaatactg ttcttctagt gtagccgtag ttaggccacc   3420
acttcaagaa ctctgtagca ccgcctacat acctcgctct gctaatcctg ttaccagtgg   3480
ctgctgccag tggcgataag tcgtgtctta ccgggttgga ctcaagacga tagttaccgg   3540
ataaggcgca gcggtcgggc tgaacggggg gttcgtgcac acagcccagc ttggagcgaa   3600
cgacctacac cgaactgaga tacctacagc gtgagctatg agaaagcgcc acgcttcccg   3660
aagggagaaa ggcggacagg tatccggtaa gcggcagggt cggaacagga gagcgcacga   3720
gggagcttcc agggggaaac gcctggtatc tttatagtcc tgtcgggttt cgccacctct   3780
gacttgagcg tcgatttttg tgatgctcgt caggggggcg gagcctatgg aaaaacgcca   3840
gcaacgcggc ctttttacgg ttcctggcct tttgctggcc ttttgctcac atgttgt      3897
```

<210> SEQ ID NO 2
<211> LENGTH: 3925

<212> TYPE: DNA
<213> ORGANISM: Artificial Sequence
<220> FEATURE:
<223> OTHER INFORMATION: Synthetically generated vector sequence-pGA 1.1

<400> SEQUENCE: 2

```
cgacaatatt ggctattggc cattgcatac gttgtatcta tatcataata tgtacattta     60

tattggctca tgtccaatat gaccgccatg ttgacattga ttattgacta gttattaata    120

gtaatcaatt acgggttcat tagttcatag cccatatatg gagttccgcg ttacataact    180

tacggtaaat ggcccgcctg gctgaccgcc caacgacccc cgcccattga cgtcaataat    240

gacgtatgtt cccatagtaa cgccaatagg gactttccat tgacgtcaat gggtggagta    300

tttacggtaa actgcccact tggcagtaca tcaagtgtat catatgccaa gtccgccccc    360

tattgacgtc aatgacggta aatggcccgc ctggcattat gcccagtaca tgaccttacg    420

ggactttcct acttggcagt acatctacgg tattagtcat cggctattac catggtgatg    480

cggttttggc agtacaccaa tgggcgtgga tagcggtttg actcacgggg atttccaagt    540

ctccacccca ttgacgtcaa tgggagtttg ttttggcacc aaaatcaacg ggactttcca    600

aaatgtcgta ataaccccgc cccgttgacg caaatgggcg gtaggcgtgt acggtgggag    660

gtctatataa gcagagctcg tttagtgaac cgtcagatcg cctggagacg ccatccacgc    720

tgttttgacc tccatagaag acaccgggac cgatccagcc tccgcggccg ggaacggtgc    780

attggaacgc ggattccccg tgccaagagt gacgtaagta ccgcctatag actctatagg    840

cacacccctt tggctcttat gcatgctata ctgtttttgg cttggggcct atacaccccc    900

gcttccttat gctataggtg atggtatagc ttagcctata ggtgtgggtt attgaccatt    960

attgaccact cccctattgg tgacgatact ttccattact aatccataac atggctcttt   1020

gccacaacta tctctattgg ctatatgcca atactctgtc cttcagagac tgacacggac   1080

tctgtatttt tacaggatgg ggtcccattt attatttaca aattcacata tacaacaacg   1140

ccgtcccccg tgcccgcagt ttttattaaa catagcgtgg gatctccacg cgaatctcgg   1200

gtaccgtgtt ccggacatgg gytcttctcc ggtagcggcg gagcttccac atccgagccc   1260

tggtcccatg cctccagcgg ctcatggtcg ctcggcagct ccttgctcct aacagtggag   1320

gccagactta ggcacagcac aatgcccacc accaccagtg tgccgcacaa ggccgtggcg   1380

gtagggtatg tgtctgaaaa tgagctcgga gattgggctc gcaccgctga cgcagatgga   1440

agacttaagg cagcggcaga agaagatgca ggcagctgag ttgttgtatt ctgataagag   1500

tcagaggtaa ctcccgttgc ggtgctgtta acggtggagg gcagtgtagt ctgagcagta   1560

ctcgttgctg ccgcgcgcgc caccagacat aatagctgac agactaacag actgttcctt   1620

tccatgggtc ttttctgcag tcaccatcga tgcttgcaat catggatgca atgaagagag   1680

ggctctgctg tgtgctgctg ctgtgtggag aattcttcgt ttctgctgct gtgtggagaa   1740

ttcttcgttt cggctagccc cgggtgataa acggaccgcg caatccctag gctgtgcctt   1800

ctagttgcca gccatctgtt gtttgcccct cccccgtgcc ttccttgacc ctggaaggtg   1860

ccactcccac tgtcctttcc taataaaatg aggaaattgc atcgcattgt ctgagtaggt   1920

gtcattctat tctggggggt ggggtggggc aggacagcaa gggggaggat tgggaagaca   1980

atagcaggca tgctggggat gcggtgggct ctatataaaa aacgcccggc ggcaaccgag   2040

cgttctgaac gctagagtcg acaaattcag aagaactcgt caagaaggcg atagaaggcg   2100

atgcgctgcg aatcgggagc ggcgataccg taaagcacga ggaagcggtc agcccattcg   2160
```

```
ccgccaagct cttcagcaat atcacgggta gccaacgcta tgtcctgata gcggtctgcc   2220

acacccagcc ggccacagtc gatgaatcca gaaaagcggc cattttccac catgatattc   2280

ggcaagcagg catcgccatg ggtcacgacg agatcctcgc cgtcgggcat gctcgccttg   2340

agcctggcga acagttcggc tggcgcgagc ccctgatgct cttcgtccag atcatcctga   2400

tcgacaagac cggcttccat ccgagtacgt gctcgctcga tgcgatgttt cgcttggtgg   2460

tcgaatgggc aggtagccgg atcaagcgta tgcagccgcc gcattgcatc agccatgatg   2520

gatactttct cggcaggagc aaggtgagat gacaggagat cctgccccgg cacttcgccc   2580

aatagcagcc agtcccttcc cgcttcagtg acaacgtcga gcacagctgc gcaaggaacg   2640

cccgtcgtgg ccagccacga tagccgcgct gcctcgtctt gcagttcatt cagggcaccg   2700

gacaggtcgg tcttgacaaa aagaaccggg cgcccctgcg ctgacagccg gaacacggcg   2760

gcatcagagc agccgattgt ctgttgtgcc cagtcatagc cgaatagcct ctccacccaa   2820

gcggccggag aacctgcgtg caatccatct tgttcaatca tgcgaaacga tcctcatcct   2880

gtctcttgat cagatcttga tcccctgcgc catcagatcc ttggcggcaa gaaagccatc   2940

cagtttactt tgcagggctt cccaacctta ccagagggcg ccccagctgg caattccggt   3000

tcgcttgctg tccataaaac cgcccagtct agctatcgcc atgtaagccc actgcaagct   3060

acctgctttc tctttgcgct tgcgttttcc cttgtccaga tagcccagta gctgacattc   3120

atccggggtc agcaccgttt ctgcggactg gctttctacg tgaaaaggat ctaggtgaag   3180

atcctttttg ataatctcat gaccaaaatc ccttaacgtg agttttcgtt ccactgagcg   3240

tcagaccccg tagaaaagat caaaggatct tcttgagatc cttttttct gcgcgtaatc   3300

tgctgcttgc aaacaaaaaa accaccgcta ccagcggtgg tttgtttgcc ggatcaagag   3360

ctaccaactc tttttccgaa ggtaactggc ttcagcagag cgcagatacc aaatactgtt   3420

cttctagtgt agccgtagtt aggccaccac ttcaagaact ctgtagcacc gcctacatac   3480

ctcgctctgc taatcctgtt accagtggct gctgccagtg gcgataagtc gtgtcttacc   3540

gggttggact caagacgata gttaccggat aaggcgcagc ggtcgggctg aacggggggt   3600

tcgtgcacac agcccagctt ggagcgaacg acctacaccg aactgagata cctacagcgt   3660

gagctatgag aaagcgccac gcttcccgaa gggagaaagg cggacaggta tccggtaagc   3720

ggcagggtcg gaacaggaga gcgcacgagg gagcttccag ggggaaacgc ctggtatctt   3780

tatagtcctg tcgggtttcg ccacctctga cttgagcgtc gatttttgtg atgctcgtca   3840

gggggcgga gcctatggaa aaacgccagc aacgcggccc ttttacggtt cctggccttt   3900

tgctggcctt ttgctcacat gttgt                                          3925
```

<210> SEQ ID NO 3
<211> LENGTH: 3925
<212> TYPE: DNA
<213> ORGANISM: Artificial Sequence
<220> FEATURE:
<223> OTHER INFORMATION: Synthetically generated vector sequence-pGA 1.2

<400> SEQUENCE: 3

```
cgacaatatt ggctattggc cattgcatac gttgtatcta tatcataata tgtacattta     60

tattggctca tgtccaatat gaccgccatg ttgacattga ttattgacta gttattaata    120

gtaatcaatt acgggttcat tagttcatag cccatatatg gagttccgcg ttacataact    180

tacggtaaat ggcccgcctg gctgaccgcc caacgacccc cgcccattga cgtcaataat    240

gacgtatgtt cccatagtaa cgccaatagg gactttccat tgacgtcaat gggtggagta    300
```

```
tttacggtaa actgcccact tggcagtaca tcaagtgtat catatgccaa gtccgccccc    360
tattgacgtc aatgacggta aatggcccgc ctggcattat gcccagtaca tgaccttacg    420
ggactttcct acttggcagt acatctacgg tattagtcat cggctattac catggtgatg    480
cggttttggc agtacaccaa tgggcgtgga tagcggtttg actcacgggg atttccaagt    540
ctccacccca ttgacgtcaa tgggagtttg ttttggcacc aaaatcaacg ggactttcca    600
aaatgtcgta ataaccccgc cccgttgacg caaatgggcg gtaggcgtgt acggtgggag    660
gtctatataa gcagagctcg tttagtgaac cgtcagatcg cctggagacg ccatccacgc    720
tgttttgacc tccatagaag acaccgggac cgatccagcc tccgcggccg ggaacggtgc    780
attggaacgc ggattccccg tgccaagagt gacgtaagta ccgcctatag actctatagg    840
cacacccctt tggctcttat gcatgctata ctgtttttgg cttggggcct atacaccccc    900
gcttccttat gctataggtg atggtatagc ttagcctata ggtgtgggtt attgaccatt    960
attgaccact cccctattgg tgacgatact ttccattact aatccataac atggctcttt   1020
gccacaacta tctctattgg ctatatgcca atactctgtc cttcagagac tgacacggac   1080
tctgtatttt tacaggatgg ggtcccattt attatttaca aattcacata tacaacaacg   1140
ccgtcccccg tgcccgcagt ttttattaaa catagcgtgg gatctccacg cgaatctcgg   1200
gtaccgtgtt ccggacatgg gytcttctcc ggtagcggcg gagcttccac atccgagccc   1260
tggtcccatg cctccagcgg ctcatggtcg ctcggcagct ccttgctcct aacagtggag   1320
gccagactta ggcacagcac aatgcccacc accaccagtg tgccgcacaa ggccgtggcg   1380
gtagggtatg tgtctgaaaa tgagctcgga gattgggctc gcaccgctga cgcagatgga   1440
agacttaagg cagcggcaga agaagatgca ggcagctgag ttgttgtatt ctgataagag   1500
tcagaggtaa ctcccgttgc ggtgctgtta acggtggagg gcagtgtagt ctgagcagta   1560
ctcgttgctg ccgcgcgcgc caccagacat aatagctgac agactaacag actgttcctt   1620
tccatgggtc ttttctgcag tcaccatgga tccttgcact cgaggatgca atgaagagag   1680
ggctctgctg tgtgctgctg ctgtgtggag aattcttcgt ttctgctgct gtgtggagaa   1740
ttcttcgttt cggctagccc cgggtgataa acggaccgcg caatccctag gctgtgcctt   1800
ctagttgcca gccatctgtt gtttgcccct cccccgtgcc ttccttgacc ctggaaggtg   1860
ccactcccac tgtcctttcc taataaaatg aggaaattgc atcgcattgt ctgagtaggt   1920
gtcattctat tctggggggt ggggtggggc aggacagcaa gggggaggat tgggaagaca   1980
atagcaggca tgctggggat gcggtgggct ctatataaaa aacgcccggc ggcaaccgag   2040
cgttctgaac gctagagtcg acaaattcag aagaactcgt caagaaggcg atagaaggcg   2100
atgcgctgcg aatcgggagc ggcgataccg taaagcacga ggaagcggtc agcccattcg   2160
ccgccaagct cttcagcaat atcacgggta gccaacgcta tgtcctgata gcggtctgcc   2220
acacccagcc ggccacagtc gatgaatcca gaaaagcggc cattttccac catgatattc   2280
ggcaagcagg catcgccatg ggtcacgacg agatcctcgc cgtcgggcat gctcgccttg   2340
agcctggcga acagttcggc tggcgcgagc ccctgatgct cttcgtccag atcatcctga   2400
tcgacaagac cggcttccat ccgagtacgt gctcgctcga tgcgatgttt cgcttggtgg   2460
tcgaatgggc aggtagccgg atcaagcgta tgcagccgcc gcattgcatc agccatgatg   2520
gatactttct cggcaggagc aaggtgagat gacaggagat cctgccccgg cacttcgccc   2580
aatagcagcc agtcccttcc cgcttcagtg acaacgtcga gcacagctgc gcaaggaacg   2640
```

```
cccgtcgtgg ccagccacga tagccgcgct gcctcgtctt gcagttcatt cagggcaccg   2700

gacaggtcgg tcttgacaaa aagaaccggg cgcccctgcg ctgacagccg gaacacggcg   2760

gcatcagagc agccgattgt ctgttgtgcc cagtcatagc cgaatagcct ctccacccaa   2820

gcggccggag aacctgcgtg caatccatct tgttcaatca tgcgaaacga tcctcatcct   2880

gtctcttgat cagatcttga tcccctgcgc catcagatcc ttggcggcaa gaaagccatc   2940

cagtttactt tgcagggctt cccaacctta ccagagggcg ccccagctgg caattccggt   3000

tcgcttgctg tccataaaac cgcccagtct agctatcgcc atgtaagccc actgcaagct   3060

acctgctttc tctttgcgct tgcgttttcc cttgtccaga tagcccagta gctgacattc   3120

atccggggtc agcaccgttt ctgcggactg gctttctacg tgaaaaggat ctaggtgaag   3180

atcctttttg ataatctcat gaccaaaatc ccttaacgtg agttttcgtt ccactgagcg   3240

tcagaccccg tagaaaagat caaaggatct tcttgagatc ctttttttct gcgcgtaatc   3300

tgctgcttgc aaacaaaaaa accaccgcta ccagcggtgg tttgtttgcc ggatcaagag   3360

ctaccaactc tttttccgaa ggtaactggc ttcagcagag cgcagatacc aaatactgtt   3420

cttctagtgt agccgtagtt aggccaccac ttcaagaact ctgtagcacc gcctacatac   3480

ctcgctctgc taatcctgtt accagtggct gctgccagtg gcgataagtc gtgtcttacc   3540

gggttggact caagacgata gttaccggat aaggcgcagc ggtcgggctg aacggggggt   3600

tcgtgcacac agcccagctt ggagcgaacg acctacaccg aactgagata cctacagcgt   3660

gagctatgag aaagcgccac gcttcccgaa gggagaaagg cggacaggta tccggtaagc   3720

ggcagggtcg gaacaggaga gcgcacgagg gagcttccag ggggaaacgc ctggtatctt   3780

tatagtcctg tcgggtttcg ccacctctga cttgagcgtc gatttttgtg atgctcgtca   3840

gggggcgga gcctatggaa aaacgccagc aacgcggccc ttttacggtt cctggccttt   3900

tgctggcctt ttgctcacat gttgt                                         3925
```

```
<210> SEQ ID NO 4
<211> LENGTH: 2947
<212> TYPE: DNA
<213> ORGANISM: Artificial Sequence
<220> FEATURE:
<223> OTHER INFORMATION: Synthetically generated vector sequence-pGA 2

<400> SEQUENCE: 4
```

```
cgacaatatt ggctattggc cattgcatac gttgtatcta tatcataata tgtacattta     60

tattggctca tgtccaatat gaccgccatg ttgacattga ttattgacta gttattaata    120

gtaatcaatt acggggtcat tagttcatag cccatatatg gagttccgcg ttacataact    180

tacggtaaat ggcccgcctg gctgaccgcc caacgacccc cgcccattga cgtcaataat    240

gacgtatgtt cccatagtaa cgccaatagg gactttccat tgacgtcaat gggtggagta    300

tttacggtaa actgcccact tggcagtaca tcaagtgtat catatgccaa gtccgccccc    360

tattgacgtc aatgacggta aatggcccgc ctggcattat gcccagtaca tgaccttacg    420

ggactttcct acttggcagt acatctacgt attagtcatc gctattacca tggtgatgcg    480

gttttggcag tacaccaatg ggcgtggata gcggtttgac tcacggggat ttccaagtct    540

ccaccccatt gacgtcaatg ggagtttgtt ttggcaccaa aatcaacggg actttccaaa    600

atgtcgtaat aaccccgccc cgttgacgca aatgggcggt aggcgtgtac ggtgggaggt    660

ctatataagc agagctcgtt tagtgaactc attctatcga tgcttgcaat catggatgca    720

atgaagagag ggctctgctg tgtgctgctg ctgtgtggag cagtcttcgt ttcggctagc    780
```

```
cccgggtgat aaacggaccg cgcaatccct aggctgtgcc ttctagttgc cagccatctg     840

ttgtttgccc ctcccccgtg ccttccttga ccctggaagg tgccactccc actgtccttt     900

cctaataaaa tgaggaaatt gcatcgcatt gtctgagtag gtgtcattct attctggggg     960

gtggggtggg gcaggacagc aagggggagg attgggaaga caatagcagg catgctgggg    1020

atgcggtggg ctctatataa aaaacgcccg gcggcaaccg agcgttctga acgctagagt    1080

cgacaaattc agaagaactc gtcaagaagg cgatagaagg cgatgcgctg cgaatcggga    1140

gcggcgatac cgtaaagcac gaggaagcgg tcagcccatt cgccgccaag ctcttcagca    1200

atatcacggg tagccaacgc tatgtcctga tagcggtctg ccacacccag ccggccacag    1260

tcgatgaatc cagaaaagcg gccattttcc accatgatat tcggcaagca ggcatcgcca    1320

tgggtcacga cgagatcctc gccgtcgggc atgctcgcct tgagcctggc gaacagttcg    1380

gctggcgcga gcccctgatg ctcttcgtcc agatcatcct gatcgacaag accggcttcc    1440

atccgagtac gtgctcgctc gatgcgatgt ttcgcttggt ggtcgaatgg gcaggtagcc    1500

ggatcaagcg tatgcagccg ccgcattgca tcagccatga tggatacttt ctcggcagga    1560

gcaaggtgag atgacaggag atcctgcccc ggcacttcgc ccaatagcag ccagtccctt    1620

cccgcttcag tgacaacgtc gagcacagct gcgcaaggaa cgcccgtcgt ggccagccac    1680

gatagccgcg ctgcctcgtc ttgcagttca ttcagggcac cggacaggtc ggtcttgaca    1740

aaaagaaccg ggcgcccctg cgctgacagc cggaacacgg cggcatcaga gcagccgatt    1800

gtctgttgtg cccagtcata gccgaatagc ctctccaccc aagcggccgg agaacctgcg    1860

tgcaatccat cttgttcaat catgcgaaac gatcctcatc ctgtctcttg atcagatctt    1920

gatcccctgc gccatcagat ccttggcggc aagaaagcca tccagtttac tttgcagggc    1980

ttcccaacct taccagaggg cgccccagct ggcaattccg gttcgcttgc tgtccataaa    2040

accgcccagt ctagctatcg ccatgtaagc ccactgcaag ctacctgctt tctctttgcg    2100

cttgcgtttt cccttgtcca gatagcccag tagctgacat tcatccgggg tcagcaccgt    2160

ttctgcggac tggctttcta cgtgaaaagg atctaggtga agatcctttt tgataatctc    2220

atgaccaaaa tcccttaacg tgagttttcg ttccactgag cgtcagaccc cgtagaaaag    2280

atcaaaggat cttcttgaga tccttttttt ctgcgcgtaa tctgctgctt gcaaacaaaa    2340

aaaccaccgc taccagcggt ggtttgtttg ccggatcaag agctaccaac tctttttccg    2400

aaggtaactg gcttcagcag agcgcagata ccaaatactg ttcttctagt gtagccgtag    2460

ttaggccacc acttcaagaa ctctgtagca ccgcctacat acctcgctct gctaatcctg    2520

ttaccagtgg ctgctgccag tggcgataag tcgtgtctta ccgggttgga ctcaagacga    2580

tagttaccgg ataaggcgca gcggtcgggc tgaacggggg gttcgtgcac acagcccagc    2640

ttggagcgaa cgacctacac cgaactgaga tacctacagc gtgagctatg agaaagcgcc    2700

acgcttcccg aagggagaaa ggcggacagg tatccggtaa gcggcagggt cggaacagga    2760

gagcgcacga gggagcttcc agggggaaac gcctggtatc tttatagtcc tgtcgggttt    2820

cgccacctct gacttgagcg tcgatttttg tgatgctcgt caggggggcg gagcctatgg    2880

aaaaacgcca gcaacgcggc cttttacgg ttcctggcct tttgctggcc ttttgctcac     2940

atgttgt                                                              2947
```

<210> SEQ ID NO 5
<211> LENGTH: 2978
<212> TYPE: DNA

<213> ORGANISM: Artificial Sequence
<220> FEATURE:
<223> OTHER INFORMATION: Synthetically generated vector sequence-pGA 2.1

<400> SEQUENCE: 5

```
cgacaatatt ggctattggc cattgcatac gttgtatcta tatcataata tgtacattta     60
tattggctca tgtccaatat gaccgccatg ttgacattga ttattgacta gttattaata    120
gtaatcaatt acggggtcat tagttcatag cccatatatg gagttccgcg ttacataact    180
tacggtaaat ggcccgcctg gctgaccgcc caacgacccc cgcccattga cgtcaataat    240
gacgtatgtt cccatagtaa cgccaatagg gactttccat tgacgtcaat gggtggagta    300
tttacggtaa actgcccact tggcagtaca tcaagtgtat catatgccaa gtccgccccc    360
tattgacgtc aatgacggta aatggcccgc ctggcattat gcccagtaca tgaccttacg    420
ggactttcct acttggcagt acatctacgt attagtcatc gctattacca tggtgatgcg    480
gttttggcag tacaccaatg ggcgtggata gcggtttgac tcacggggat ttccaagtct    540
ccaccccatt gacgtcaatg ggagtttgtt ttggcaccaa aatcaacggg actttccaaa    600
atgtcgtaat aaccccgccc cgttgacgca aatgggcggt aggcgtgtac ggtgggaggt    660
ctatataagc agagctcgtt tagtgaactc attctatcga tgcttgcaat catggatgca    720
atgaagagag ggctctgctg tgtgctgctg ctgtgtggag aattcttcgt ttcggctgct    780
gctgtgtgga gaattcttcg tttcggctag ccccgggtga taaacggacc gcgcaatccc    840
taggctgtgc cttctagttg ccagccatct gttgtttgcc cctcccccgt gccttccttg    900
accctggaag gtgccactcc cactgtcctt tcctaataaa atgaggaaat tgcatcgcat    960
tgtctgagta ggtgtcattc tattctgggg ggtggggtgg ggcaggacag caagggggag   1020
gattgggaag acaatagcag gcatgctggg gatgcggtgg gctctatata aaaaacgccc   1080
ggcggcaacc gagcgttctg aacgctagag tcgacaaatt cagaagaact cgtcaagaag   1140
gcgatagaag gcgatgcgct gcgaatcggg agcggcgata ccgtaaagca cgaggaagcg   1200
gtcagcccat tcgccgccaa gctcttcagc aatatcacgg gtagccaacg ctatgtcctg   1260
atagcggtct gccacaccca gccggccaca gtcgatgaat ccagaaaagc ggccattttc   1320
caccatgata ttcggcaagc aggcatcgcc atgggtcacg acgagatcct cgccgtcggg   1380
catgctcgcc ttgagcctgg cgaacagttc ggctggcgcg agcccctgat gctcttcgtc   1440
cagatcatcc tgatcgacaa gaccggcttc catccgagta cgtgctcgct cgatgcgatg   1500
tttcgcttgg tggtcgaatg ggcaggtagc cggatcaagc gtatgcagcc gccgcattgc   1560
atcagccatg atggatactt tctcggcagg agcaaggtga gatgacagga gatcctgccc   1620
cggcacttcg cccaatagca gccagtccct tcccgcttca gtgacaacgt cgagcacagc   1680
tgcgcaagga acgcccgtcg tggccagcca cgatagccgc gctgcctcgt cttgcagttc   1740
attcagggca ccggacaggt cggtcttgac aaaaagaacc gggcgcccct gcgctgacag   1800
ccggaacacg gcggcatcag agcagccgat tgtctgttgt gcccagtcat agccgaatag   1860
cctctccacc caagcggccg gagaacctgc gtgcaatcca tcttgttcaa tcatgcgaaa   1920
cgatcctcat cctgtctctt gatcagatct tgatcccctg cgccatcaga tccttggcgg   1980
caagaaagcc atccagttta ctttgcaggg cttcccaacc ttaccagagg gcgccccagc   2040
tggcaattcc ggttcgcttg ctgtccataa aaccgcccag tctagctatc gccatgtaag   2100
cccactgcaa gctacctgct ttctctttgc gcttgcgttt tcccttgtcc agatagccca   2160
gtagctgaca ttcatccggg gtcagcaccg tttctgcgga ctggctttct acgtgaaaag   2220
```

```
gatctaggtg aagatccttt ttgataatct catgaccaaa atcccttaac gtgagttttc   2280

gttccactga gcgtcagacc ccgtagaaaa gatcaaagga tcttcttgag atcctttttt   2340

tctgcgcgta atctgctgct tgcaaacaaa aaaaccaccg ctaccagcgg tggtttgttt   2400

gccggatcaa gagctaccaa ctctttttcc gaaggtaact ggcttcagca gagcgcagat   2460

accaaatact gttcttctag tgtagccgta gttaggccac cacttcaaga actctgtagc   2520

accgcctaca tacctcgctc tgctaatcct gttaccagtg gctgctgcca gtggcgataa   2580

gtcgtgtctt accgggttgg actcaagacg atagttaccg gataaggcgc agcggtcggg   2640

ctgaacgggg ggttcgtgca cacagcccag cttggagcga acgacctaca ccgaactgag   2700

atacctacag cgtgagctat gagaaagcgc cacgcttccc gaagggagaa aggcggacag   2760

gtatccggta agcggcaggg tcggaacagg agagcgcacg agggagcttc caggggggaaa   2820

cgcctggtat ctttatagtc ctgtcgggtt tcgccacctc tgacttgagc gtcgattttt   2880

gtgatgctcg tcaggggggc ggagcctatg gaaaaacgcc agcaacgcgg cctttttacg   2940

gttcctggcc ttttgctggc cttttgctca catgttgt                           2978


<210> SEQ ID NO 6
<211> LENGTH: 2978
<212> TYPE: DNA
<213> ORGANISM: Artificial Sequence
<220> FEATURE:
<223> OTHER INFORMATION: Synthetically generated vector sequence-pGA 2.2

<400> SEQUENCE: 6

cgacaatatt ggctattggc cattgcatac gttgtatcta tatcataata tgtacattta     60

tattggctca tgtccaatat gaccgccatg ttgacattga ttattgacta gttattaata    120

gtaatcaatt acggggtcat tagttcatag cccatatatg gagttccgcg ttacataact    180

tacggtaaat ggcccgcctg gctgaccgcc caacgacccc cgcccattga cgtcaataat    240

gacgtatgtt cccatagtaa cgccaatagg gactttccat tgacgtcaat gggtggagta    300

tttacggtaa actgcccact tggcagtaca tcaagtgtat catatgccaa gtccgccccc    360

tattgacgtc aatgacggta aatggcccgc ctggcattat gcccagtaca tgaccttacg    420

ggactttcct acttggcagt acatctacgt attagtcatc gctattacca tggtgatgcg    480

gttttggcag tacaccaatg ggcgtggata gcggtttgac tcacggggat ttccaagtct    540

ccaccccatt gacgtcaatg ggagtttgtt ttggcaccaa aatcaacggg actttccaaa    600

atgtcgtaat aaccccgccc cgttgacgca aatgggcggt aggcgtgtac ggtgggaggt    660

ctatataagc agagctcgtt tagtgaactc attctatgga tccttgctcg agtggatgca    720

atgaagagag ggctctgctg tgtgctgctg ctgtgtggag aattcttcgt ttcggctgct    780

gctgtgtgga gaattcttcg tttcggctag ccccgggtga taaacggacc gcgcaatccc    840

taggctgtgc cttctagttg ccagccatct gttgtttgcc cctcccccgt gccttccttg    900

accctggaag gtgccactcc cactgtcctt tcctaataaa atgaggaaat tgcatcgcat    960

tgtctgagta ggtgtcattc tattctgggg ggtggggtgg ggcaggacag caagggggag   1020

gattgggaag acaatagcag gcatgctggg gatgcggtgg gctctatata aaaaacgccc   1080

ggcggcaacc gagcgttctg aacgctagag tcgacaaatt cagaagaact cgtcaagaag   1140

gcgatagaag gcgatgcgct gcgaatcggg agcggcgata ccgtaaagca cgaggaagcg   1200

gtcagcccat tcgccgccaa gctcttcagc aatatcacgg gtagccaacg ctatgtcctg   1260
```

```
atagcggtct gccacaccca gccggccaca gtcgatgaat ccagaaaagc ggccattttc   1320

caccatgata ttcggcaagc aggcatcgcc atgggtcacg acgagatcct cgccgtcggg   1380

catgctcgcc ttgagcctgg cgaacagttc ggctggcgcg agcccctgat gctcttcgtc   1440

cagatcatcc tgatcgacaa gaccggcttc catccgagta cgtgctcgct cgatgcgatg   1500

tttcgcttgg tggtcgaatg ggcaggtagc cggatcaagc gtatgcagcc gccgcattgc   1560

atcagccatg atggatactt tctcggcagg agcaaggtga gatgacagga gatcctgccc   1620

cggcacttcg cccaatagca gccagtccct tcccgcttca gtgacaacgt cgagcacagc   1680

tgcgcaagga acgcccgtcg tggccagcca cgatagccgc gctgcctcgt cttgcagttc   1740

attcagggca ccggacaggt cggtcttgac aaaaagaacc gggcgcccct gcgctgacag   1800

ccggaacacg gcggcatcag agcagccgat tgtctgttgt gcccagtcat agccgaatag   1860

cctctccacc caagcggccg gagaacctgc gtgcaatcca tcttgttcaa tcatgcgaaa   1920

cgatcctcat cctgtctctt gatcagatct tgatcccctg cgccatcaga tccttggcgg   1980

caagaaagcc atccagttta ctttgcaggg cttcccaacc ttaccagagg gcgccccagc   2040

tggcaattcc ggttcgcttg ctgtccataa aaccgcccag tctagctatc gccatgtaag   2100

cccactgcaa gctacctgct ttctctttgc gcttgcgttt tcccttgtcc agatagccca   2160

gtagctgaca ttcatccggg gtcagcaccg tttctgcgga ctggctttct acgtgaaaag   2220

gatctaggtg aagatccttt ttgataatct catgaccaaa atcccttaac gtgagttttc   2280

gttccactga gcgtcagacc ccgtagaaaa gatcaaagga tcttcttgag atcctttttt   2340

tctgcgcgta atctgctgct tgcaaacaaa aaaaccaccg ctaccagcgg tggtttgttt   2400

gccggatcaa gagctaccaa ctctttttcc gaaggtaact ggcttcagca gagcgcagat   2460

accaaatact gttcttctag tgtagccgta gttaggccac cacttcaaga actctgtagc   2520

accgcctaca tacctcgctc tgctaatcct gttaccagtg gctgctgcca gtggcgataa   2580

gtcgtgtctt accgggttgg actcaagacg atagttaccg gataaggcgc agcggtcggg   2640

ctgaacgggg ggttcgtgca cacagcccag cttggagcga acgacctaca ccgaactgag   2700

atacctacag cgtgagctat gagaaagcgc cacgcttccc gaagggagaa aggcggacag   2760

gtatccggta agcggcaggg tcggaacagg agagcgcacg agggagcttc caggggggaaa   2820

cgcctggtat ctttatagtc ctgtcgggtt tcgccacctc tgacttgagc gtcgattttt   2880

gtgatgctcg tcaggggggc ggagcctatg gaaaaacgcc agcaacgcgg ccctttttacg   2940

gttcctggcc ttttgctggc cttttgctca catgttgt                           2978
```

```
<210> SEQ ID NO 7
<211> LENGTH: 9544
<212> TYPE: DNA
<213> ORGANISM: Artificial Sequence
<220> FEATURE:
<223> OTHER INFORMATION: Synthetically generated vector sequence-pGA
      2/JS2

<400> SEQUENCE: 7

atcgatgcag gactcggctt gctgaagcgc gcacggcaag aggcgagggg cggcgactgg     60

tgggtacgcc aaaaattttg actagcggag gctagaagga gagagatggg tgcgagagcg    120

tcagtattaa gcgggggaga attagatcga tgggaaaaaa ttcggttaag gccaggggga    180

aagaaaaaat ataaattaaa acatatagta tgggcaagca gggagctaga acgattcgca    240

gttaatcctg gcctgttaga aacatcagaa ggctgtagac aaatactggg acagctacaa    300
```

```
ccatcccttc agacaggatc agaagaactt agatcattat ataatacagt agcaaccctc    360
tattgtgtgc atcaaaggat agagataaaa gacaccaagg aagctttaga caagatagag    420
gaagagcaaa acaaaagtaa gaaaaaagca cagcaagcag cagctgacac aggacacagc    480
agtcaggtca gccaaaatta ccctatagtg cagaacatcc aggggcaaat ggtacatcag    540
gccatatcac ctagaacttt aaatgcatgg gtaaaagtag tagaagagaa ggctttcagc    600
ccagaagtaa tacccatgtt ttcagcatta tcagaaggag ccaccccaca agatttaaac    660
accatgctaa acacagtggg gggacatcaa gcagccatgc aaatgttaaa agagaccatc    720
aatgaggaag ctgcagaatg ggatagagta catccagtgc atgcagggcc tattgcacca    780
ggccagatga gagaaccaag gggaagtgac atagcaggaa ctactagtac ccttcaggaa    840
caaataggat ggatgacaaa taatccacct atcccagtag gagaaattta taaaagatgg    900
ataatcctgg gattaaataa aatagtaaga atgtatagcc ctaccagcat tctggacata    960
agacaaggac caaaagaacc ttttagagac tatgtagacc ggttctataa aactctaaga   1020
gccgagcaag cttcacagga ggtaaaaaat tggatgacag aaaccttgtt ggtccaaaat   1080
gcgaacccag attgtaagac tattttaaaa gcattgggac cagcggctac actagaagaa   1140
atgatgacag catgtcaggg agtaggagga cccggccata aggcaagagt tttggctgaa   1200
gcaatgagcc aagtaacaaa tacagctacc ataatgatgc agagaggcaa ttttaggaac   1260
caaagaaaga tggttaagag cttcaatagc ggcaaagaag ggcacacagc cagaaattgc   1320
agggccccta ggaaaaaggg cagctggaaa agcggaaagg aaggacacca aatgaaagat   1380
tgtactgaga gacaggctaa tttttaggg aagatctggc cttcctacaa gggaaggcca   1440
gggaattttc ttcagagcag accagagcca acagccccac catttcttca gagcagacca   1500
gagccaacag ccccaccaga agagagcttc aggtctgggg tagagacaac aactccccct   1560
cagaagcagg agccgataga caaggaactg tatcctttaa cttccctcag atcactcttt   1620
ggcaacgacc cctcgtcaca ataaagatag gggggcaact aaaggaagct ctattagata   1680
caggagcaga tgatacagta ttagaagaaa tgagtttgcc aggaagatgg aaaccaaaaa   1740
tgataggggg aattggaggt tttatcaaag taagacagta tgatcagata ctcatagaaa   1800
tctgtggaca taaagctata ggtacagtat tagtaggacc tacacctgtc aacataattg   1860
gaagaaatct gttgactcag attggttgca ctttaaattt tcccattagc cctattgaga   1920
ctgtaccagt aaaattaaag ccaggaatgg atggcccaaa agttaaacaa tggccattga   1980
cagaagaaaa aataaaagca ttagtagaaa tttgtacaga aatggaaaag gaagggaaaa   2040
tttcaaaaat tgggcctgag aatccataca atactccagt atttgccata aagaaaaaag   2100
acagtactaa atggagaaaa ttagtagatt tcagagaact taataagaga actcaagact   2160
tctgggaagt tcaattagga ataccacatc ccgcagggtt aaaaaagaaa aaatcagtaa   2220
cagtactgga tgtgggtgat gcatattttt cagttccctt agatgaagac ttcaggaagt   2280
atactgcatt taccatacct agtataaaca atgagacacc agggattaga tatcagtaca   2340
atgtgcttcc acagggatgg aaaggatcac cagcaatatt ccaaagtagc atgacaaaaa   2400
tcttagagcc ttttaaaaaa caaaatccag acatagttat ctatcaatac atgaacgatt   2460
tgtatgtagg atctgactta gaaatagggc agcatagaac aaaaatagag gagctgagac   2520
aacatctgtt gaggtgggga cttaccacac cagacaaaaa acatcagaaa gaacctccat   2580
tcctttggat gggttatgaa ctccatcctg ataaatggac agtacagcct atagtgctgc   2640
cagaaaaaga cagctggact gtcaatgaca tacagaagtt agtggggaaa ttgaataccg   2700
```

```
caagtcagat ttacccaggg attaaagtaa ggcaattatg taaactcctt agaggaacca   2760
aagcactaac agaagtaata ccactaacag aagaagcaga gctagaactg gcagaaaaca   2820
gagagattct aaaagaacca gtacatggag tgtattatga cccatcaaaa gacttaatag   2880
cagaaataca gaagcagggg caaggccaat ggacatatca aatttatcaa gagccattta   2940
aaaatctgaa aacaggaaaa tatgcaagaa tgaggggtgc ccacactaat gatgtaaaac   3000
aattaacaga ggcagtgcaa aaaataacca cagaaagcat agtaatatgg ggaaagactc   3060
ctaaatttaa actacccata caaaaggaaa catgggaaac atggtggaca gagtattggc   3120
aagccacctg gattcctgag tgggagtttg ttaatacccc tcctttagtg aaattatggt   3180
accagttaga gaaagaaccc atagtaggag cagaaacctt ctatgtagat ggggcagcta   3240
acagggagac taaattagga aaagcaggat atgttactaa caaaggaaga caaaaggttg   3300
tccccctaac taacacaaca aatcagaaaa ctcagttaca agcaatttat ctagctttgc   3360
aggattcagg attagaagta aacatagtaa cagactcaca atatgcatta ggaatcattc   3420
aagcacaacc agataaaagt gaatcagagt tagtcaatca aataatagag cagttaataa   3480
aaaaggaaaa ggtctatctg gcatgggtac cagcacacaa aggaattgga ggaaatgaac   3540
aagtagataa attagtcagt gctggaatca ggaaaatact atttttagat ggaatagata   3600
aggcccaaga tgaacattag aattctgcaa caactgctgt ttatccattt tcagaattgg   3660
gtgtcgacat agcagaatag gcgttactcg acagaggaga gcaagaaatg gagccagtag   3720
atcctagact agagccctgg aagcatccag gaagtcagcc taaaactgct tgtaccaatt   3780
gctattgtaa aaagtgttgc tttcattgcc aagtttgttt cataacaaaa gccttaggca   3840
tctcctatgg caggaagaag cggagacagc gacgaagacc tcctcaagac agtcagactc   3900
atcaagtttc tctatcaaag cagtaagtag taaatgtaat gcaaccttta caaatattag   3960
caatagtagc attagtagta gcagcaataa tagcaatagt tgtgtggacc atagtattca   4020
tagaatatag gaaaatatta agacaaagaa aaatagacag gttaattgat aggataacag   4080
aaagagcaga agacagtggc aatgaaagtg aaggggatca ggaagaatta tcagcacttg   4140
tggaaatggg gcatcatgct ccttgggatg ttgatgatct gtagtgctgt agaaaatttg   4200
tgggtcacag tttattatgg ggtacctgtg tggaaagaag caaccaccac tctattttgt   4260
gcatcagatg ctaaagcata tgatacagag gtacataatg tttgggccac acatgcctgt   4320
gtacccacag accccaaccc acaagaagta gtattggaaa atgtgacaga aaattttaac   4380
atgtggaaaa ataacatggt agaacagatg catgaggata taatcagttt atgggatcaa   4440
agcctaaagc catgtgtaaa attaacccca ctctgtgtta ctttaaattg cactgatttg   4500
aggaatgtta ctaatatcaa taatagtagt gagggaatga gaggagaaat aaaaaactgc   4560
tctttcaata tcaccacaag cataagagat aaggtgaaga aagactatgc actttttat    4620
agacttgatg tagtaccaat agataatgat aatactagct ataggttgat aaattgtaat   4680
acctcaacca ttacacaggc ctgtccaaag gtatcctttg agccaattcc catacattat   4740
tgtaccccgg ctggttttgc gattctaaag tgtaaagaca agaagttcaa tggaacaggg   4800
ccatgtaaaa atgtcagcac agtacaatgt acacatggaa ttaggccagt agtgtcaact   4860
caactgctgt taaatggcag tctagcagaa gaagaggtag taattagatc tagtaatttc   4920
acagacaatg caaaaaacat aatagtacag ttgaaagaat ctgtagaaat taattgtaca   4980
agacccaaca acaatacaag gaaaagtata catataggac caggaagagc atttatacaa   5040
```

```
acaggagaaa taataggaga tataagacaa gcacattgca acattagtag aacaaaatgg   5100
aataacactt taaatcaaat agctacaaaa ttaaaagaac aatttgggaa taataaaaca   5160
atagtcttta atcaatcctc aggaggggac ccagaaattg taatgcacag ttttaattgt   5220
ggaggggaat ttttctactg taattcaaca caactgttta atagtacttg gaattttaat   5280
ggtacttgga atttaacaca atcgaatggt actgaaggaa atgacactat cacactccca   5340
tgtagaataa aacaaattat aaatatgtgg caggaagtag gaaaagcaat gtatgcccct   5400
cccatcagag gacaaattag atgctcatca aatattacag ggctaatatt aacaagagat   5460
ggtggaacta acagtagtgg gtccgagatc ttcagacctg gggggaggaga tatgagggac   5520
aattggagaa gtgaattata taaatataaa gtagtaaaaa ttgaaccatt aggagtagca   5580
cccaccaagg caaaaagaag agtggtgcag agagaaaaaa gagcagtggg aacgatagga   5640
gctatgttcc ttgggttctt gggagcagca ggaagcacta tgggcgcagc gtcaataacg   5700
ctgacggtac aggccagact attattgtct ggtatagtgc aacagcagaa caatttgctg   5760
agggctattg aggcgcaaca gcatctgttg caactcacag tctggggcat caagcagctc   5820
caggcaagag tcctggctct ggaaagatac ctaagggatc aacagctcct agggatttgg   5880
ggttgctctg gaaaactcat ctgcaccact gctgtgcctt ggaatgctag ttggagtaat   5940
aaaactctgg atatgatttg ggataacatg acctggatgg agtgggaaag agaaatcgaa   6000
aattacacag gcttaatata caccttaatt gaagaatcgc agaaccaaca agaaaagaat   6060
gaacaagact tattagcatt agataagtgg gcaagtttgt ggaattggtt tgacatatca   6120
aattggctgt ggtgtataaa aatcttcata atgatagtag gaggcttgat aggtttaaga   6180
atagtttttta ctgtactttc tatagtaaat agagttaggc agggatactc accattgtca   6240
tttcagaccc acctcccagc cccgagggga cccgacaggc ccgaaggaat cgaagaagaa   6300
ggtggagaca gagacagaga cagatccgtg cgattagtgg atggatcctt agcacttatc   6360
tgggacgatc tgcggagcct gtgcctcttc agctaccacc gcttgagaga cttactcttg   6420
attgtaacga ggattgtgga acttctggga cgcagggggt gggaagccct caaatattgg   6480
tggaatctcc tacagtattg gagtcaggag ctaaagaata gtgctgttag cttgctcaat   6540
gccacagcta tagcagtagc tgaggggaca gatagggtta tagaagtagt acaaggagct   6600
tatagagcta ttcgccacat acctagaaga ataagacagg gcttggaaag gattttgcta   6660
taagatgggt ggctagcccc gggtgataaa cggaccgcgc aatccctagg ctgtgccttc   6720
tagttgccag ccatctgttg tttgcccctc ccccgtgcct tccttgaccc tggaaggtgc   6780
cactcccact gtcctttcct aataaaatga ggaaattgca tcgcattgtc tgagtaggtg   6840
tcattctatt ctggggggtg gggtggggca ggacagcaag ggggaggatt gggaagacaa   6900
tagcaggcat gctggggatg cggtgggctc tatataaaaa acgcccggcg gcaaccgagc   6960
gttctgaacg ctagagtcga caaattcaga agaactcgtc aagaaggcga tagaaggcga   7020
tgcgctgcga atcgggagcg gcgataccgt aaagcacgag gaagcggtca gcccattcgc   7080
cgccaagctc ttcagcaata tcacgggtag ccaacgctat gtcctgatag cggtctgcca   7140
cacccagccg gccacagtcg atgaatccag aaaagcggcc attttccacc atgatattcg   7200
gcaagcaggc atcgccatgg gtcacgacga gatcctcgcc gtcgggcatg ctcgccttga   7260
gcctggcgaa cagttcggct ggcgcgagcc cctgatgctc ttcgtccaga tcatcctgat   7320
cgacaagacc ggcttccatc cgagtacgtg ctcgctcgat gcgatgtttc gcttggtggt   7380
cgaatgggca ggtagccgga tcaagcgtat gcagccgccg cattgcatca gccatgatgg   7440
```

```
atactttctc ggcaggagca aggtgagatg acaggagatc ctgccccggc acttcgccca   7500

atagcagcca gtcccttccc gcttcagtga caacgtcgag cacagctgcg caaggaacgc   7560

ccgtcgtggc cagccacgat agccgcgctg cctcgtcttg cagttcattc agggcaccgg   7620

acaggtcggt cttgacaaaa agaaccgggc gcccctgcgc tgacagccgg aacacggcgg   7680

catcagagca gccgattgtc tgttgtgccc agtcatagcc gaatagcctc tccacccaag   7740

cggccggaga acctgcgtgc aatccatctt gttcaatcat gcgaaacgat cctcatcctg   7800

tctcttgatc agatcttgat cccctgcgcc atcagatcct tggcggcgag aaagccatcc   7860

agtttacttt gcagggcttc ccaaccttac cagagggcgc cccagctggc aattccggtt   7920

cgcttgctgt ccataaaacc gcccagtcta gctatcgcca tgtaagccca ctgcaagcta   7980

cctgctttct ctttgcgctt gcgttttccc ttgtccagat agcccagtag ctgacattca   8040

tccggggtca gcaccgtttc tgcggactgg ctttctacgt gaaaaggatc taggtgaaga   8100

tcctttttga taatctcatg accaaaatcc cttaacgtga gttttcgttc cactgagcgt   8160

cagaccccgt agaaaagatc aaaggatctt cttgagatcc tttttttctg cgcgtaatct   8220

gctgcttgca aacaaaaaaa ccaccgctac cagcggtggt ttgtttgccg gatcaagagc   8280

taccaactct ttttccgaag gtaactggct tcagcagagc gcagatacca aatactgtcc   8340

ttctagtgta gccgtagtta ggccaccact tcaagaactc tgtagcaccg cctacatacc   8400

tcgctctgct aatcctgtta ccagtggctg ctgccagtgg cgataagtcg tgtcttaccg   8460

ggttggactc aagacgatag ttaccggata aggcgcagcg gtcgggctga acggggggtt   8520

cgtgcacaca gcccagcttg gagcgaacga cctacaccga actgagatac ctacagcgtg   8580

agctatgaga aagcgccacg cttcccgaag ggagaaaggc ggacaggtat ccggtaagcg   8640

gcagggtcgg aacaggagag cgcacgaggg agcttccagg gggaaacgcc tggtatcttt   8700

atagtcctgt cgggtttcgc cacctctgac ttgagcgtcg atttttgtga tgctcgtcag   8760

gggggcggag cctatggaaa acgccagcaa cgcggccttt ttacggttcc tggccttttg   8820

ctggcctttt gctcacatgt tgtcgaccga caatattggc tattggccat tgcatacgtt   8880

gtatctatat cataatatgt acatttatat tggctcatgt ccaatatgac cgccatgttg   8940

acattgatta ttgactagtt attaatagta atcaattacg gggtcattag ttcatagccc   9000

atatatggag ttccgcgtta cataacttac ggtaaatggc ccgcctcgtg accgcccaac   9060

gacccccgcc cattgacgtc aataatgacg tatgttccca tagtaacgcc aatagggact   9120

ttccattgac gtcaatgggt ggagtattta cggtaaactg cccacttggc agtacatcaa   9180

gtgtatcata tgccaagtcc gcccctattg acgtcaatga cggtaaatgg cccgcctggc   9240

attatgccca gtacatgacc ttacgggact ttcctacttg gcagtacatc tacgtattag   9300

tcatcgctat taccatggtg atgcggtttt ggcagtacac caatgggcgt ggatagcggt   9360

ttgactcacg gggatttcca agtctccacc ccattgacgt caatgggagt ttgttttggc   9420

accaaaatca acgggacttt ccaaaatgtc gtaataaccc cgccccgttg acgcaaatgg   9480

gcggtaggcg tgtacggtgg gaggtctata taagcagagc tcgtttagtg aaccgtcaga   9540

tcgc                                                                9544
```

<210> SEQ ID NO 8
<211> LENGTH: 9506
<212> TYPE: DNA
<213> ORGANISM: Artificial Sequence
<220> FEATURE:

<223> OTHER INFORMATION: Synthetically generated vector sequence-pGA 2/JS7

<400> SEQUENCE: 8

```
atcgatgcag gactcggctt gctgaagcgc gcacggcaag aggcgagggg cggcgactgg     60
tgagtacgcc aaaaattttg actagcggag gctagaagga gagagatggg tgcgagagcg    120
tcagtattaa gcgggggaga attagatcga tgggaaaaaa ttcggttaag gccaggggga    180
aagaaaaaat ataaattaaa acatatagta tgggcaagca gggagctaga acgattcgca    240
gttaatcctg gcctgttaga aacatcagaa ggctgtagac aaatactggg acagctacaa    300
ccatcccttc agacaggatc agaagaactt agatcattat ataatacagt agcaaccctc    360
tattgtgtgc atcaaaggat agagataaaa gacaccaagg aagctttaga caagatagag    420
gaagagcaaa acaaaagtaa gaaaaaagca cagcaagcag cagctgacac aggacacagc    480
aatcaggtca gccaaaatta ccctatagtg cagaacatcc aggggcaaat ggtacatcag    540
gccatatcac ctagaacttt aaatgcatgg gtaaaagtag tagaagagaa ggctttcagc    600
ccagaagtga tacccatgtt ttcagcatta tcagaaggag ccaccccaca agatttaaac    660
accatgctaa acacagtggg gggacatcaa gcagccatgc aaatgttaaa agagaccatc    720
aatgaggaag ctgcagaatg ggatagagtg catccagtgc atgcagggcc tattgcacca    780
ggccagatga gagaaccaag gggaagtgac atagcaggaa ctactagtac ccttcaggaa    840
caaataggat ggatgacaaa taatccacct atcccagtag gagaaattta taaaagatgg    900
ataatcctgg gattaaataa aatagtaaga atgtatagcc ctaccagcat tctggacata    960
agacaaggac caaaagaacc ctttagagac tatgtagacc ggttctataa aactctaaga   1020
gccgagcaag cttcacagga ggtaaaaaat tggatgacag aaaccttgtt ggtccaaaat   1080
gcgaacccag attgtaagac tattttaaaa gcattgggac cagcggctac actagaagaa   1140
atgatgacag catgtcaggg agtaggagga cccggccata aggcaagagt tttggctgaa   1200
gcaatgagcc aagtaacaaa ttcagctacc ataatgatgc agagaggcaa ttttaggaac   1260
caaagaaaga ttgttaagag cttcaatagc ggcaaagaag ggcacacagc cagaaattgc   1320
agggccccta ggaaaaaggg cagctggaaa agcggaaagg aaggacacca aatgaaagat   1380
tgtactgaga gacaggctaa tttttaggg aagatctggc cttcctacaa gggaaggcca   1440
gggaattttc ttcagagcag accagagcca acagccccac cagaagagag cttcaggtct   1500
ggggtagaga caacaactcc ccctcagaag caggagccga tagacaagga actgtatcct   1560
ttaacttccc tcagatcact ctttggcaac gacccctcgt cacaataaag ataggggggc   1620
aactaaagga agctctatta gccacaggag cagatgatac agtattagaa gaaatgagtt   1680
tgccaggaag atggaaacca aaaatgatag gggggaattgg aggttttatc aaagtaagac   1740
agtatgatca gatactcata gaaatctgtg gacataaagc tataggtaca gtattagtag   1800
gacctacacc tgtcaacata attggaagaa atctgttgac tcagattggt tgcactttaa   1860
attttcccat tagccctatt gagactgtac cagtaaaatt aaagccagga atggatggcc   1920
caaaagttaa acaatggcca ttgacagaag aaaagataaa agcattagta gaaatttgta   1980
cagagatgga aaaggaaggg aaaatttcaa aaattgggcc tgaaaatcca tacaatactc   2040
cagtatttgc cataaagaaa aaagacagta ctaaatggag aaaattagta gatttcagag   2100
aacttaataa gagaactcaa gacttctggg aagttcaatt aggaatacca catcccgcag   2160
ggttaaaaaa gaaaaaatca gtaacagtac tggatgtggg tgatgcatat tttcagttc    2220
```

```
ccttagatga agacttcagg aaatatactg catttaccat acctagtata aacaatgaga   2280

caccagggat tagatatcag tacaatgtgc ttccacaggg atggaaagga tcaccagcaa   2340

tattccaaag tagcatgaca aaaatcttag agccttttag aaaacaaaat ccagacatag   2400

ttatctatca atacatgaac gatttgtatg taggatctga cttagaaata gggcagcata   2460

gaacaaaaat agaggagctg agacaacatc tgttgaggtg gggacttacc acaccagaca   2520

aaaaacatca gaaagaacct ccattccttt ggatgggtta tgaactccat cctgataaat   2580

ggacagtaca gcctatagtg ctgccagaaa aagacagctg gactgtcaat gacatacaga   2640

agttagtggg gaaattgaat accgcaagtc agatttaccc agggattaaa gtaaggcaat   2700

tatgtaaact ccttagagga accaaagcac taacagaagt aataccacta acagaagaag   2760

cagagctaga actggcagaa aacagagaga ttctaaaaga accagtacat ggagtgtatt   2820

atgacccatc aaaagactta atagcagaaa tacagaagca ggggcaaggc caatggacat   2880

atcaaattta tcaagagcca tttaaaaatc tgaaaacagg aaaatatgca agaatgaggg   2940

gtgcccacac taatgatgta aaacaattaa cagaggcagt gcaaaaaata accacagaaa   3000

gcatagtaat atggggaaag actcctaaat ttaaactgcc catacaaaag gaaacatggg   3060

aaacatggtg gacagagtat tggcaagcca cctggattcc tgagtgggag tttgttaata   3120

cccctccttt agtgaaatta tggtaccagt tagagaaaga acccatagta ggagcagaaa   3180

ccttctatgt agatggggca gctaacaggg agactaaatt aggaaaagca ggatatgtta   3240

ctaatagagg aagacaaaaa gttgtcaccc taactaacac aacaaatcag aaaactcagt   3300

tacaagcaat ttatctagct ttgcaggatt cgggattaga agtaaacata gtaacagact   3360

cacaatatgc attaggaatc attcaagcac aaccagatca aagtgaatca gagttagtca   3420

atcaaataat agagcagtta ataaaaaagg aaaaggtcta tctggcatgg gtaccagcac   3480

acaaaggaat tggaggaaat gaacaagtag ataaattagt cagtgctgga atcaggaaag   3540

tactattttt agatggaata gataaggccc aagatgaaca ttagaattct gcaacaactg   3600

ctgtttatcc atttcagaat tgggtgtcga catagcagaa taggcgttac tcgacagagg   3660

agagcaagaa atggagccag tagatcctag actagagccc tggaagcatc caggaagtca   3720

gcctaaaact gcttgtacca attgctattg taaaaagtgt tgctttcatt gccaagtttg   3780

tttcataaca aaagccttag gcatctccta tggcaggaag aagcggagac agcgacgaag   3840

agctcctcaa gacagtcaga ctcatcaagt ttctctatca aagcagtaag tagtaaatgt   3900

aatgcaacct ttacaaatat tagcaatagt agcattagta gtagcagcaa taatagcaat   3960

agttgtgtgg accatagtat tcatagaata taggaaaata ttaagacaaa gaaaaataga   4020

caggttaatt gataggataa cagaaagagc agaagacagt ggcaatgaaa gtgaaggggga   4080

tcaggaagaa ttatcagcac ttgtggaaat ggggcatcat gctccttggg atgttgatga   4140

tctgtagtgc tgtagaaaat ttgtgggtca cagtttatta tggggtacct gtgtggaaag   4200

aagcaaccac cactctattt tgtgcatcag atgctaaagc atatgataca gaggtacata   4260

atgtttgggc cacacatgcc tgtgtaccca cagaccccaa cccacaagaa gtagtattgg   4320

aaaatgtgac agaaaatttt aacatgtgga aaaataacat ggtagaacag atgcatgagg   4380

atataatcag tttatgggat caaagcctaa agccatgtgt aaaattaacc ccactctgtg   4440

ttactttaaa ttgcactgat ttgaggaatg ttactaatat caataatagt agtgagggaa   4500

tgagaggaga aataaaaaac tgctctttca atatcaccac aagcataaga gataaggtga   4560

agaaagacta tgcacttttt tatagacttg atgtagtacc aatagataat gataatacta   4620
```

```
gctataggtt gataaattgt aatacctcaa ccattacaca ggcctgtcca aaggtatcct   4680
ttgagccaat tcccatacat tattgtaccc cggctggttt tgcgattcta aagtgtaaag   4740
acaagaagtt caatggaaca gggccatgta aaaatgtcag cacagtacaa tgtacacatg   4800
gaattaggcc agtagtgtca actcaactgc tgttaaatgg cagtctagca gaagaagagg   4860
tagtaattag atctagtaat ttcacagaca atgcaaaaaa cataatagta cagttgaaag   4920
aatctgtaga aattaattgt acaagaccca acaacaatac aaggaaaagt atacatatag   4980
gaccaggaag agcattttat acaacaggag aaataatagg agatataaga caagcacatt   5040
gcaacattag tagaacaaaa tggaataaca ctttaaatca aatagctaca aaattaaaag   5100
aacaatttgg gaataataaa acaatagtct ttaatcaatc ctcaggaggg gacccagaaa   5160
ttgtaatgca cagttttaat tgtggagggg aatttttcta ctgtaattca acacaactgt   5220
ttaatagtac ttggaatttt aatggtactt ggaatttaac acaatcgaat ggtactgaag   5280
gaaatgacac tatcacactc ccatgtagaa taaaacaaat tataaatatg tggcaggaag   5340
taggaaaagc aatgtatgcc cctcccatca gaggacaaat tagatgctca tcaaatatta   5400
cagggctaat attaacaaga gatggtggaa ctaacagtag tgggtccgag atcttcagac   5460
ctgggggagg agatatgagg gacaattgga gaagtgaatt atataaatat aaagtagtaa   5520
aaattgaacc attaggagta gcacccacca aggcaaaaag aagagtggtg cagagagaaa   5580
aaagagcagt gggaacgata ggagctatgt tccttgggtt cttgggagca gcaggaagca   5640
ctatgggcgc agcgtcaata acgctgacgg tacaggccag actattattg tctggtatag   5700
tgcaacagca gaacaatttg ctgagggcta ttgaggcgca acagcatctg ttgcaactca   5760
cagtctgggg catcaagcag ctccaggcaa gagtcctggc tgtggaaaga tacctaaggg   5820
atcaacagct cctagggatt tggggttgct ctggaaaact catctgcacc actgctgtgc   5880
cttggaatgc tagttggagt aataaaactc tggatatgat ttgggataac atgacctgga   5940
tggagtggga aagagaaatc gaaaattaca caggcttaat atacacctta attgaagaat   6000
cgcagaacca acaagaaaag aatgaacaag acttattagc attagataag tgggcaagtt   6060
tgtggaattg gtttgacata tcaaattggc tgtggtatgt aaaaatcttc ataatgatag   6120
taggaggctt gataggttta agaatagttt ttactgtact ttctatagta aatagagtta   6180
ggcagggata ctcaccattg tcatttcaga cccacctccc agccccgagg ggacccgaca   6240
ggcccgaagg aatcgaagaa gaaggtggag acagagacag agacagatcc gtgcgattag   6300
tggatggatc cttagcactt atctgggacg atctgcggag cctgtgcctc ttcagctacc   6360
accgcttgag agacttactc ttgattgtaa cgaggattgt ggaacttctg ggacgcaggg   6420
ggtgggaagc cctcaaatat tggtggaatc tcctacagta ttggagtcag gagctaaaga   6480
atagtgctgt tagcttgctc aatgccacag ctatagcagt agctgagggg acagataggg   6540
ttatagaagt agtacaagga gcttatagag ctattcgcca catacctaga agaataagac   6600
agggcttgga aaggattttg ctataagatg ggtggctagc cccgggtgat aaacggaccg   6660
cgcaatccct aggctgtgcc ttctagttgc cagccatctg ttgtttgccc ctcccccgtg   6720
ccttccttga ccctggaagg tgccactccc actgtccttt cctaataaaa tgaggaaatt   6780
gcatcgcatt gtctgagtag gtgtcattct attctggggg gtggggtggg gcaggacagc   6840
aagggggagg attgggaaga caatagcagg catgctgggg atgcggtggg ctctatataa   6900
aaaacgcccg gcggcaaccg agcgttctga acgctagagt cgacaaattc agaagaactc   6960
```

-continued

```
ggcaagaagg cgatagaagg cgatgcgctg cgaatcggga gcggcgatac cgtaaagcac   7020

gaggaagcgg tcagcccatt cgccgccaag ctcttcagca atatcacggg tagccaacgc   7080

tatgtcctga tagcggtctg ccacacccag ccggccacag tcgatgaatc cagaaaagcg   7140

gccattttcc accatgatat tcggcaagca ggcatcgcca tgggtcacga cgagatcctc   7200

gccgtcgggc atgctcgcct tgagcctggc gaacagttcg gctggcgcga gcccctgatg   7260

ctcttcgtcc agatcatcct gatcgacaag accggcttcc atccgagtac gtgctcgctc   7320

gatgcgatgt ttcgcttggt ggtcgaatgg gcaggtagcc ggatcaagcg tatgcagccg   7380

ccgcattgca tcagccatga tggatacttt ctcggcagga gcaaggtgag atgacaggag   7440

atcctgcccc ggcacttcgc ccaatagcag ccagtccctt cccgcttcag tgacaacgtc   7500

gagcacagct gcgcaaggaa cgcccgtcgt ggccagccac gatagccgcg ctgcctcgtc   7560

ttgcagttca ttcagggcac cggacaggtc ggtcttgaca aaaagaaccg ggcgcccctg   7620

cgctgacagc cggaacacgg cggcatcaga gcagccgatt gtctgttgtg cccagtcata   7680

gccgaatagc ctctccaccc aagcggccgg agaacctgcg tgcaatccat cttgttcaat   7740

catgcgaaac gatcctcatc ctgtctcttg atcagatctt gatcccctgc gccatcagat   7800

ccttggcggc aagaaagcca tccagtttac tttgcagggc ttcccaacct taccagaggg   7860

cgccccagct ggcaattccg gttcgcttgc tgtccataaa accgcccagt ctagctatcg   7920

ccatgtaagc ccactgcaag ctacctgctt tctctttgcg cttgcgtttt cccttgtcca   7980

gatagcccag tagctgacat tcatccgggg tcagcaccgt ttctgcggac tggctttcta   8040

cgtgaaaagg atctaggtga agatcctttt tgataatctc atgaccaaaa tcccttaacg   8100

tgagttttcg ttccactgag cgtcagaccc cgtagaaaag atcaaaggat cttcttgaga   8160

tccttttttt ctgcgcgtaa tctgctgctt gcaaacaaaa aaaccaccgc taccagcggt   8220

ggtttgtttg ccggatcaag agctaccaac tctttttccg aaggtaactg gcttcagcag   8280

agcgcagata ccaaatactg ttcttctagt gtagccgtag ttaggccacc acttcaagaa   8340

ctctgtagca ccgcctacat acctcgctct gctaatcctg ttaccagtgg ctgctgccag   8400

tggcgataag tcgtgtctta ccgggttgga ctcaagacga tagttaccgg ataaggcgca   8460

gcggtcgggc tgaacggggg gttcgtgcac acagcccagc ttggagcgaa cgacctacac   8520

cgaactgaga tacctacagc gtgagctatg agaaagcgcc acgcttcccg aagggagaaa   8580

ggcggacagg tatccggtaa gcggcagggt cggaacagga gagcgcacga gggagcttcc   8640

agggggaaac gcctggtatc tttatagtcc tgtcgggttt cgccacctct gacttgagcg   8700

tcgatttttg tgatgctcgt caggggggcg gagcctatgg aaaaacgcca gcaacgcggc   8760

ctttttacgg ttcctggcct tttgctggcc ttttgctcac atgttgtcga caatattggc   8820

tattggccat tgcatacgtt gtatctatat cataatatgt acatttatat tggctcatgt   8880

ccaatatgac cgccatgttg acattgatta ttgactagtt attaatagta atcaattacg   8940

ggttcattag ttcatagccc atatatggag ttccgcgtta cataacttac ggtaaatggc   9000

ccgcctggct gaccgcccaa cgacccccgc ccattgacgt caataatgac gtatgttccc   9060

atagtaacgc caatagggac tttccattga cgtcaatggg tggagtattt acggtaaact   9120

gcccacttgg cagtacatca agtgtatcat atgccaagtc cgccccctat tgacgtcaat   9180

gacggtaaat ggcccgcctg gcattatgcc cagtacatga ccttacggga ctttcctact   9240

tggcagtaca tctacgtatt agtcatcgct attaccatgg tgatgcggtt ttggcagtac   9300

accaatgggc gtggatagcg gtttgactca cggggatttc caagtctcca ccccattgac   9360
```

```
gtcaatggga gtttgttttg gcaccaaaat caacgggact ttccaaaatg tcgtaataac   9420

cccgccccgt tgacgcaaat gggcggtagg cgtgtacggt gggaggtcta tataagcaga   9480

gctcgtttag tgaaccgtca gatcgc                                         9506


<210> SEQ ID NO 9
<211> LENGTH: 9505
<212> TYPE: DNA
<213> ORGANISM: Artificial Sequence
<220> FEATURE:
<223> OTHER INFORMATION: Synthetically generated vector
      sequence-pGA2/JS7.1

<400> SEQUENCE: 9

atcgatgcag gactcggctt gctgaagcgc gcacggcaag aggcgagggg cggcgactgg     60

tgagtacgcc aaaaattttg actagcggag gctagaagga gagagatggg tgcgagagcg    120

tcagtattaa gcgggggaga attagatcga tgggaaaaaa ttcggttaag gccaggggga    180

aagaaaaaat ataaattaaa acatatagta tgggcaagca gggagctaga acgattcgca    240

gttaatcctg gcctgttaga aacatcagaa ggctgtagac aaatactggg acagctacaa    300

ccatcccttc agacaggatc agaagaactt agatcattat ataatacagt agcaaccctc    360

tattgtgtgc atcaaaggat agagataaaa gacaccaagg aagctttaga caagatagag    420

gaagagcaaa acaaaagtaa gaaaaaagca cagcaagcag cagctgacac aggacacagc    480

aatcaggtca gccaaaatta ccctatagtg cagaacatcc aggggcaaat ggtacatcag    540

gccatatcac ctagaacttt aaatgcatgg gtaaaagtag tagaagagaa ggctttcagc    600

ccagaagtga tacccatgtt ttcagcatta tcagaaggag ccaccccaca agatttaaac    660

accatgctaa acacagtggg gggacatcaa gcagccatgc aaatgttaaa agagaccatc    720

aatgaggaag ctgcagaatg ggatagagtg catccagtgc atgcagggcc tattgcacca    780

ggccagatga gagaaccaag gggaagtgac atagcaggaa ctactagtac ccttcaggaa    840

caaataggat ggatgacaaa taatccacct atcccagtag gagaaattta taaaagatgg    900

ataatcctgg gattaaataa aatagtaaga atgtatagcc ctaccagcat tctggacata    960

agacaaggac caaaagaacc ctttagagac tatgtagacc ggttctataa aactctaaga   1020

gccgagcaag cttcacagga ggtaaaaaat tggatgacag aaaccttgtt ggtccaaaat   1080

gcgaacccag attgtaagac tattttaaaa gcattgggac cagcggctac actagaagaa   1140

atgatgacag catgtcaggg agtaggagga cccggccata aggcaagagt tttggctgaa   1200

gcaatgagcc aagtaacaaa ttcagctacc ataatgatgc agagaggcaa ttttaggaac   1260

caaagaaaga ttgttaagag cttcaatagc ggcaaagaag ggcacacagc cagaaattgc   1320

agggccccta ggaaaaaggg cagctggaaa agcggaaagg aaggacacca aatgaaagat   1380

tgtactgaga gacaggctaa tttttttaggg aagatctggc cttcctacaa gggaaggcca   1440

gggaatttc ttcagagcag accagagcca acagccccac cagaagagag cttcaggtct   1500

ggggtagaga caacaactcc ccctcagaag caggagccga tagacaagga actgtatcct   1560

ttaacttccc tcagatcact ctttggcaac gacccctcgt cacaataaag atagggggc   1620

aactaaagga agctctatta gccacaggag cagatgatac agtattagaa gaaatgagtt   1680

tgccaggaag atggaaacca aaaatgatag ggggaattgg aggttttatc aaagtaagac   1740

agtatgatca gatactcata gaaatctgtg gacataaagc tataggtaca gtattagtag   1800

gacctacacc tgtcaacata attggaagaa atctgttgac tcagattggt tgcactttaa   1860
```

```
attttcccat tagccctatt gagactgtac cagtaaaatt aaagccagga atggatggcc   1920
caaaagttaa acaatggcca ttgacagaag aaaagataaa agcattagta gaaatttgta   1980
cagagatgga aaaggaaggg aaaatttcaa aaattgggcc tgaaaatcca tacaatactc   2040
cagtatttgc cataaagaaa aaagacagta ctaaatggag aaaattagta gatttcagag   2100
aacttaataa gagaactcaa gacttctggg aagttcaatt aggaatacca catcccgcag   2160
ggttaaaaaa gaaaaaatca gtaacagtac tggatgtggg tgatgcatat ttttcagttc   2220
ccttagatga agacttcagg aaatatactg catttaccat acctagtata aacaatgaga   2280
caccagggat tagatatcag tacaatgtgc ttccacaggg atggaaagga tcaccagcaa   2340
tattccaaag tagcatgaca aaaatcttag agccttttag aaaacaaaat ccagacatag   2400
ttatctatca atacatgaac gatttgtatg taggatctga cttagaaata gggcagcata   2460
gaacaaaaat agaggagctg agacaacatc tgttgaggtg gggacttacc acaccagaca   2520
aaaaacatca gaaagaacct ccattccttt ggatgggtta tgaactccat cctgataaat   2580
ggacagtaca gcctatagtg ctgccagaaa aagacagctg gactgtcaat gacatacaga   2640
agttagtggg gaaattgaat accgcaagtc agatttaccc agggattaaa gtaaggcaat   2700
tatgtaaact ccttagagga accaaagcac taacagaagt aataccacta acagaagaag   2760
cagagctaga actggcagaa aacagagaga ttctaaaaga accagtacat ggagtgtatt   2820
atgacccatc aaaagactta atagcagaaa tacagaagca ggggcaaggc caatggacat   2880
atcaaattta tcaagagcca tttaaaaatc tgaaaacagg aaaatatgca agaatgaggg   2940
gtgcccacac taatgatgta aaacaattaa cagaggcagt gcaaaaaata accacagaaa   3000
gcatagtaat atggggaaag actcctaaat ttaaactgcc catacaaaag gaaacatggg   3060
aaacatggtg gacagagtat tggcaagcca cctggattcc tgagtgggag tttgttaata   3120
cccctccttt agtgaaatta tggtaccagt tagagaaaga acccatagta ggagcagaaa   3180
ccttctatgt agatggggca gctaacaggg agactaaatt aggaaaagca ggatatgtta   3240
ctaatagagg aagacaaaaa gttgtcaccc taactaacac aacaaatcag aaaactcagt   3300
tacaagcaat ttatctagct ttgcaggatt cgggattaga agtaaacata gtaacagact   3360
cacaatatgc attaggaatc attcaagcac aaccagatca aagtgaatca gagttagtca   3420
atcaaataat agagcagtta ataaaaaagg aaaaggtcta tctggcatgg gtaccagcac   3480
acaaaggaat tggaggaaat gaacaagtag ataaattagt cagtgctgga atcaggaaag   3540
tactattttt agatggaata gataaggccc aagatgaaca ttagaattct gcaacaactg   3600
ctgtttatcc atttcagaat tgggtgtcga catagcagaa taggcgttac tcgacagagg   3660
agagcaagaa atggagccag tagatcctag actagagccc tggaagcatc caggaagtca   3720
gcctaaaact gcttgtacca attgctattg taaaaagtgt tgctttcatt gccaagtttg   3780
tttcataaca aaagccttag gcatctccta tggcaggaag aagcggagac agcgacgaag   3840
agctcctcaa gacagtcaga ctcatcaagt ttctctatca aagcagtaag tagtaaatct   3900
aatccaacct ttacaaatat tagcaatagt agcattagta gtagcagcaa taatagcaat   3960
agttgtgtgg accatagtat tcatagaata taggaaaata ttaagacaaa gaaaaataga   4020
caggttaatt gataggataa cagaaagagc agaagacagt ggcaatgaaa gtgaagggga   4080
tcaggaagaa ttatcagcac ttgtggaaat ggggcatcat gctccttggg atgttgatga   4140
tctgtagtgc tgtagaaaat ttgtgggtca cagtttatta tggggtacct gtgtggaaag   4200
```

```
aagcaaccac cactctattt tgtgcatcag atgctaaagc atatgataca gaggtacata   4260
atgtttgggc cacacatgcc tgtgtaccca cagaccccaa cccacaagaa gtagtattgg   4320
aaaatgtgac agaaaatttt aacatgtgga aaaataacat ggtagaacag atgcatgagg   4380
atataatcag tttatgggat caaagcctaa agccatgtgt aaaattaacc ccactctgtg   4440
ttactttaaa ttgcactgat ttgaggaatg ttactaatat caataatagt agtgagggaa   4500
tgagaggaga aataaaaaac tgctctttca atatcaccac aagcataaga gataaggtga   4560
agaaagacta tgcacttttt tatagacttg atgtagtacc aatagataat gataatacta   4620
gctataggtt gataaattgt aatacctcaa ccattacaca ggcctgtcca aaggtatcct   4680
ttgagccaat tcccatacat tattgtaccc cggctggttt tgcgattcta aagtgtaaag   4740
acaagaagtt caatggaaca gggccatgta aaaatgtcag cacagtacaa tgtacacatg   4800
gaattaggcc agtagtgtca actcaactgc tgttaaatgg cagtctagca gaagaagagg   4860
tagtaattag atctagtaat ttcacagaca atgcaaaaaa cataatagta cagttgaaag   4920
aatctgtaga aattaattgt acaagaccca acaacaatac aaggaaaagt atacatatag   4980
gaccaggaag agcattttat acaacaggag aaataatagg agatataaga caagcacatt   5040
gcaacattag tagaacaaaa tggaataaca ctttaaatca aatagctaca aaattaaaag   5100
aacaatttgg gaataataaa acaatagtct ttaatcaatc ctcaggaggg gacccagaaa   5160
ttgtaatgca cagttttaat tgtggagggg aatttttcta ctgtaattca acacaactgt   5220
ttaatagtac ttggaatttt aatggtactt ggaatttaac acaatcgaat ggtactgaag   5280
gaaatgacac tatcacactc ccatgtagaa taaaacaaat tataaatatg tggcaggaag   5340
taggaaaagc aatgtatgcc cctcccatca gaggacaaat tagatgctca tcaaatatta   5400
cagggctaat attaacaaga gatggtggaa ctaacagtag tgggtccgag atcttcagac   5460
ctgggggagg agatatgagg gacaattgga gaagtgaatt atataaatat aaagtagtaa   5520
aaattgaacc attaggagta gcacccacca aggcaaaaag aagagtggtg cagagagaaa   5580
aaagagcagt gggaacgata ggagctatgt tccttgggtt cttgggagca gcaggaagca   5640
ctatgggcgc agcgtcaata acgctgacgg tacaggccag actattattg tctggtatag   5700
tgcaacagca gaacaatttg ctgagggcta ttgaggcgca acagcatctg ttgcaactca   5760
cagtctgggg catcaagcag ctccaggcaa gagtcctggc tgtggaaaga tacctaaggg   5820
atcaacagct cctagggatt tggggttgct ctggaaaact catctgcacc actgctgtgc   5880
cttggaatgc tagttggagt aataaaaactc tggatatgat ttgggataac atgacctgga   5940
tggagtggga aagagaaatc gaaaattaca caggcttaat atacacctta attgaagaat   6000
cgcagaacca acaagaaaag aatgaacaag acttattagc attagataag tgggcaagtt   6060
tgtggaattg gtttgacata tcaaattggc tgtggtatgt aaaaatcttc ataatgatag   6120
taggaggctt gataggttta agaatagttt ttactgtact ttctatagta aatagagtta   6180
ggcagggata ctcaccattg tcatttcaga cccacctccc agccccgagg ggacccgaca   6240
ggcccgaagg aatcgaagaa gaaggtggag acagagacag agacagatcc gtgcgattag   6300
tggatggatc cttagcactt atctgggacg atctgcggag cctgtgcctc ttcagctacc   6360
accgcttgag agacttactc ttgattgtaa cgaggattgt ggaacttctg ggacgcaggg   6420
ggtgggaagc cctcaaatat tggtggaatc tcctacagta ttggagtcag gagctaaaga   6480
atagtgctgt tagcttgctc aatgccacag ctatagcagt agctgagggg acagataggg   6540
ttatagaagt agtacaagga gcttatagag ctattcgcca catacctaga agaataagac   6600
```

```
agggcttgga aaggattttg ctataagatg ggtggctagc cccgggtgat aaacggaccg   6660
cgcaatccct aggctgtgcc ttctagttgc cagccatctg ttgtttgccc ctcccccgtg   6720
ccttccttga ccctggaagg tgccactccc actgtccttt cctaataaaa tgaggaaatt   6780
gcatcgcatt gtctgagtag gtgtcattct attctggggg gtggggtggg gcaggacagc   6840
aagggggagg attgggaaga caatagcagg catgctgggg atgcggtggg ctctatataa   6900
aaaacgcccg gcggcaaccg agcgttctga acgctagagt cgacaaattc agaagaactc   6960
gtcaagaagg cgatagaagg cgatgcgctg cgaatcggga gcggcgatac cgtaaagcac   7020
gaggaagcgg tcagcccatt cgccgccaag ctcttcagca atatcacggg tagccaacgc   7080
tatgtcctga tagcggtctg ccacacccag ccggccacag tcgatgaatc cagaaaagcg   7140
gccattttcc accatgatat tcggcaagca ggcatcgcca tgggtcacga cgagatcctc   7200
gccgtcgggc atgctcgcct tgagcctggc gaacagttcg gctggcgcga gcccctgatg   7260
ctcttcgtcc agatcatcct gatcgacaag accggcttcc atccgagtac gtgctcgctc   7320
gatgcgatgt ttcgcttggt ggtcgaatgg gcaggtagcc ggatcaagcg tatgcagccg   7380
ccgcattgca tcagccatga tggatacttt ctcggcagga gcaaggtgag atgacaggag   7440
atcctgcccc ggcacttcgc ccaatagcag ccagtccctt cccgcttcag tgacaacgtc   7500
gagcacagct gcgcaaggaa cgcccgtcgt ggccagccac gatagccgcg ctgcctcgtc   7560
ttgcagttca ttcagggcac cggacaggtc ggtcttgaca aaaagaaccg ggcgcccctg   7620
cgctgacagc cggaacacgg cggcatcaga gcagccgatt gtctgttgtg cccagtcata   7680
gccgaatagc ctctccaccc aagcggccgg agaacctgcg tgcaatccat cttgttcaat   7740
catgcgaaac gatcctcatc ctgtctcttg atcagatctt gatcccctgc gccatcagat   7800
ccttggcggc ragaaagcca tccagtttac tttgcagggc ttcccaacct taccagaggg   7860
cgccccagct ggcaattccg gttcgcttgc tgtccataaa accgcccagt ctagctatcg   7920
ccatgtaagc ccactgcaag ctacctgctt tctctttgcg cttgcgtttt cccttgtcca   7980
gatagcccag tagctgacat tcatccgggg tcagcaccgt ttctgcggac tggctttcta   8040
cgtgaaaagg atctaggtga agatcctttt tgataatctc atgaccaaaa tcccttaacg   8100
tgagttttcg ttccactgag cgtcagaccc cgtagaaaag atcaaaggat cttcttgaga   8160
tccttttttt ctgcgcgtaa tctgctgctt gcaaacaaaa aaaccaccgc taccagcggt   8220
ggtttgtttg ccggatcaag agctaccaac tctttttccg aaggtaactg gcttcagcag   8280
agcgcagata ccaaatactg ttcttctagt gtagccgtag ttaggccacc acttcaagaa   8340
ctctgtagca ccgcctacat acctcgctct gctaatcctg ttaccagtgg ctgctgccag   8400
tggcgataag tcgtgtctta ccgggttgga ctcaagacga tagttaccgg ataaggcgca   8460
gcggtcgggc tgaacggggg gttcgtgcac acagcccagc ttggagcgaa cgacctacac   8520
cgaactgaga tacctacagc gtgagctatg agaaagcgcc acgcttcccg aagggagaaa   8580
ggcggacagg tatccggtaa gcggcagggt cggaacagga gagcgcacga gggagcttcc   8640
agggggaaac gcctggtatc tttatagtcc tgtcgggttt cgccacctct gacttgagcg   8700
tcgatttttg tgatgctcgt caggggggcg gagcctatgg aaaaacgcca gcaacgcggc   8760
ctttttacgg ttcctggcct tttgctggcc ttttgctcac atgttgtcga caatattggc   8820
tattggccat tgcatacgtt gtatctatat cataatatgt acatttatat tggctcatgt   8880
ccaatatgac cgccatgttg acattgatta ttgactagtt attaatagta atcaattacg   8940
```

```
ggktcattag ttcatagccc atatatggag ttccgcgtta cataacttac ggtaaatggc   9000

ccgcctggct gaccgcccaa cgacccccgc ccattgacgt caataatgac gtatgttccc   9060

atagtaacgc caatagggac tttccattga cgtcaatggg tggagtattt acggtaaact   9120

gcccacttgg cagtacatca agtgtatcat atgccaagtc cgcccctatt gacgtcaatg   9180

acggtaaatg gcccgcctgg cattatgccc agtacatgac cttacgggac tttcctactt   9240

ggcagtacat ctacgtatta gtcatcgcta ttaccatggt gatgcggttt tggcagtaca   9300

ccaatgggcg tggatagcgg tttgactcac ggggatttcc aagtctccac cccattgacg   9360

tcaatgggag tttgtttkgs caccaaaatc aacgggactt tccaaaatgt cgtaataacc   9420

ccgccccgtt gacgcaaatg ggcggtaggc gtgtacggtg ggaggtctat ataagcagag   9480

ctcgtttagt gaaccgtcag atcgc                                         9505
```

<210> SEQ ID NO 10
<211> LENGTH: 10447
<212> TYPE: DNA
<213> ORGANISM: Artificial Sequence
<220> FEATURE:
<223> OTHER INFORMATION: Synthetically generated vector sequence-pGA1/IC25

<400> SEQUENCE: 10

```
atcgatgcaa ggactcggct tgctgaggtg cacacagcaa gaggcgagag cgacgactgg     60

tgagtacgcc aatttttgac tagcggaggc tagaaggaga gagatgggtg cgagagcgtc    120

agtgttaacg gggggaaaat tagattcatg ggagaaaatt aggttaaggc caggggggaaa    180

gaaaagatat agactaaaac acctagtatg ggcaagcagg gagctggaga gattcgcact    240

taaccctggc ctattagaaa cagcagaagg atgtcaacaa ctaatgggac agttacaacc    300

agctctcagg acaggatcag aagagtttaa atcattatat aatatagtag caaccctttg    360

gtgcgtacat caaagaatag acataaaaga cacccaggag gccttagata aagtagagga    420

aaaacaaaat aagagcaagc aaaaggcaca gcaggcagca gctgcaacag ccgccacagg    480

aagcagcagc caaaattacc ctatagtgca aaatgcacaa gggcaaatgg tacatcagtc    540

catgtcacct aggactttaa atgcatgggt gaaggtaata gaagaaaagg cttttagccc    600

agaggtaata cccatgtttt cagcattatc agagggagcc accccacaag atttaaatat    660

gatgctaaac atagtggggg gacaccaggc agcaatgcag atgttaaaag ataccatcaa    720

tgatgaagct gcagaatggg acagagtaca tccagtacat gcagggccta ttccaccagg    780

ccaaatgagg gaaccaaggg gaagtgacat agcaggaact actagtaccc ttcaagaaca    840

aataggatgg atgacaagta atccacctat cccagtggga gaaatctata aaagatggat    900

agtcctggga ttaaataaaa tagtaagaat gtatagccct accagcattt tggacataag    960

acaagggcca aaagaaccct ttagagatta tgtagacagg ttctttaaaa ctttgagagc   1020

tgaacaagct acgcaggagg taaaaaactg gatgacagaa accttgttgg tccaaaatgc   1080

gaatccagac tgcaagtcca ttttaagagc attaggacca ggggctacat tagaagaaat   1140

gatgacatca tgtcagggag tgggaggacc tggccataaa gcaagggttt tggctgaggc   1200

aatgagtcaa gtacaacaga ccaatgtaat gatgcagaga ggcaatttta gaggccagag   1260

aataataaag agcttcaaca gcggcaaaga aggacaccta gccagaaatt gcaaggctcc   1320

tagaaagaga ggcagctgga aaagcggaaa ggaaggacac caaatgaaag actgtactga   1380

aagacaggct aattttttag ggaaaatttg gccttcccac aaggggaggc caggaaattt   1440
```

```
tcctcagagc agaccagaac caacagcccc gccagcagag agctttggag tgggggaaga   1500
gataccctcc tctccgaagc aggagccgag ggacaaggga ctatatcctc ccttaacttc   1560
cctcaaatca ctctttggca acgaccagta gtcacagtaa gaatagggg acagccaata   1620
gaagccctat taaacacagg agcagatgat acagtattag aagaaataag tttaccagga   1680
aaatggaaac caaaaatgat agggggaatt ggaggtttta tcaaagtaag acagtatgat   1740
cagatatcta tagaaatttg tggaaaaagg gccataggta cagtattagt aggacctaca   1800
cctgtcaaca taattggacg aaatatgttg actcagattg gttgtacttt aaattttcca   1860
attagtccta ttgaaactgt gccagtaaaa ttaaagtcag gaatggatgg cccaaaggtt   1920
aaacaatggc cattgacaga agaaaaaata aaagcattaa aagaaatttg tgcagagatg   1980
gaaaaggaag gaaaaatttc aaaaattggg cctgaaaacc catacaatac tccaatattt   2040
gccataaaga aaaaagatag tactaaatgg agaaaattag tagatttcag agaactcaat   2100
aagagaactc aagacttctg ggaggtccaa ttaggaatac ctcatcctgc gggattaaaa   2160
aagaaaaaat cagtaacagt actagatgtg ggggatgcat atttttcagt tcccttagat   2220
gaagacttta gaaaatatac tgcattcacc atacctagtt taaataatga gacaccaggg   2280
attagatatc agtacaatgt actcccacag ggatggaaag gatcaccagc aatatttcag   2340
gcaagcatga caaaaatctt agagcccttt agagcaaaaa atccagagat agtgatctac   2400
caatatatga acgatttata tgtaggatct gacttagaaa tagggcagca tagagcaaaa   2460
atagaggagt tgagagaaca tctattgaaa tggggattta ccacaccaga caaaaaacat   2520
cagaaagaac ctccatttct ttggatggga tatgaactcc atcctgacaa atggacagtc   2580
cagcctatac agctgccaga aaaagacagc tggactgtca atgatataca aaaattagtg   2640
ggaaaactaa ataccgcaag tcagatttat gcaggaatta aagtaaagca attgtgtaga   2700
ctcctcaggg gagccaaagc gctaacagat gtagtaacac tgactgagga agcagaatta   2760
gaattggcag agaacaggga aattctaaaa gaacctgtac atggagtata ttatgaccca   2820
acaaaagact tagtggcaga aatacagaaa caagggcaag atcaatggac atatcaaatt   2880
tatcaagagc catttaaaaa tctaaagaca ggaaaaatatg caaaaaagag gtcggcccac   2940
actaatgatg taaaacaatt aacagaggta gtgcagaaaa tagccataga aagcatagta   3000
atatggggaa agacccctaa atttagacta cccatacaaa gagaaacatg ggaagcatgg   3060
tggatggagt attggcaggc tacctggatt cctgaatggg agtttgtcaa tacccctcct   3120
ctagtaaaat tatggtacca gttagagaag gaccccataa tgggagcaga aactttctat   3180
gtagatgggg cagctaatag ggagactaag ctaggaaaag cagggtatgt cactgacaga   3240
ggaagacaaa aggttgtttc cctaattcag acaacaaatc aaaagactca gttacatgca   3300
attcatctag ccttgcagga ttcaggatca gaagtaaata tagtaacaga ctcacagtat   3360
gcattaggaa tcattcaggc acaaccagac aggagtgaat cagagttagt caatcaaata   3420
atagagaaac taatagaaaa ggacaaagtc tacctgtcat gggtaccagc acacaaaggg   3480
attggaggaa atgaacaagt agataaatta gtcagtagtg gaatcagaaa ggtactattt   3540
ttagatggaa tagataaagc ccaagatgaa cattagaatt ctgcaacagc tactgtttgt   3600
tcatttcaga attgggtgtc aacatagcag aataggcatt attccaggga gaagaggcag   3660
gaatggagct ggtagatcct agcctagagc cctggaacca cccgggaagt cagcctacaa   3720
ctgcttgtag caagtgttac tgtaaaaaat gctgctggca ttgccaattg tgctttctga   3780
acaagggctt aggcatctcc tatggcagga agaagcggag acgccgacga ggaactcctc   3840
```

```
aggaccgtca ggttcatcaa aatcctgtac caaaacagta agtagtagta attagtatat   3900
gtgatgcaat ctttacaaat agctgcaata gtaggactag tagtagcatc catagtagcc   3960
atagttgtgt ggtccatagt atttatagaa tatagaaaaa taaggaaaca gaagaaaata   4020
gacaggttac ttgagagaat aagagaaaga gcagaagata gtggcaatga gagtgatggg   4080
gatacagaag aattatccac tcttatggag agggggtatg acaatatttt ggttaatgat   4140
gatttgtaat gctgaaaagt tgtgggtcac agtctactat ggggtacctg tgtggagaga   4200
cgcagagacc accctattct gtgcatcaga tgctaaagca tatgacaaag aagcacacaa   4260
tgtctgggct acgcatgcct gcgtacccac agaccctgac ccacaagaat tacctttggt   4320
aaatgtaaca gaagagttta acatgtggaa aaataatatg gtagaacaga tgcatgaaga   4380
tataattagt ctatgggacc aaagcttaaa gccatgtgta cagctaaccc ctctctgcgt   4440
tactttaggg tgtgctgacg ctcaaaacgt caccgacacc aacaccacca tatctaatga   4500
aatgcaaggg gaaataaaaa actgctcttt caatatgacc acagaattaa gagataagaa   4560
gcagaaagtg tatgcacttt tttatagacc tgatgtaata gaaattaata aaactaagat   4620
taacaatagt aatagtagtc agtatatgtt aataaattgt aatacctcaa ccattacaca   4680
gacttgtcca aaggtatcct ttgagccaat tcccatacat tattgtgccc cagctggttt   4740
tgcaattcta aagtgtaatg atacggagtt cagtggaaaa gggacatgca agagtgtcag   4800
cacagtacaa tgcacacatg gaatcaagcc agtagtatca actcaactgc tgttaaatgg   4860
cagtctagca gaaggaaaga tagcgattag atctgagaat atctcaaaca atgccaaaac   4920
tataatagta caattgactg agcctgtaga aattaattgt atcagacctg gcaacaatac   4980
aagaaaaagt gtacgcatag gaccaggaca aacattctat gcaacaggtg acataatagg   5040
agatataaga caagcacact gtaatgttag taaaatagca tgggaagaaa ctttacaaaa   5100
ggtagctgca caattaagga agcactttca gaatgccaca ataaaattta ctaaacactc   5160
aggaggggat ttagaaatta caacaaatag ttttaattgt ggaggagaat tttctattg    5220
caatacaaca aagctgttta atagcacttg gaataatgat aactcaaacc tcacagagga   5280
aaagagaaag gaaaacataa ctctccactg cagaataaag caaattgtaa atatgtggcc   5340
aagagtagga caagcaatat atgcccctcc catcccagga aacataactt gtggatcaaa   5400
cattactggg ctactattaa caagagatgg agggaataat ggtacaaatg atactgagac   5460
cttcaggcct ggaggaggag atatgaggga caattggaga agtgaattat ataaatataa   5520
agtagtaaaa attgaaccac taggtgtagc accaacccct gcaaaaagaa gagtggtgga   5580
aagagaaaaa agagcagttg gaatgggagc tttgatcttt gagttcttag gagcagcagg   5640
aagcactatg ggcgcggcgt caatggcgct gacggtacag gccagacaat tattgtctgg   5700
tatagtgcaa cagcagagca atctgctgaa ggctatagag gctcaacaac atctgttgag   5760
actcacggtc tggggcatta aacagctcca ggcaagagtc ctggctctgg aaagatacct   5820
aaaggatcaa cagctcctag gaatttgggg ctgctctgga aaactcattt gcaccactgc   5880
tgtaccttgg aactctagct ggagtaataa aagttataat gacatatggg ataacatgac   5940
ctggctgcaa tgggataaag aaattaacaa ttacacatac ataatatata atctacttga   6000
aaaatcgcag aaccagcagg aaattaatga acaagactta ttggcattag acaagtgggc   6060
aagtctgtgg aattggtttg acataacaag ctggctatgg tatataagat taggtataat   6120
gatagtagga ggcgtaatag gcttaagaat aatttttgct gtgcttacta tagtgaatag   6180
```

```
agttaggcag ggatactcac ctttgtcatt ccagaccctt gcccaccacc agagggaacc   6240
cgacaggccc gaaagaatcg aagaaggagg tggcgagcaa gacagagaga gatccgtgcg   6300
cttagtgagc ggattcttag cacttgcctg ggaagatctg cggagcctgt gcctcttcag   6360
ctaccgccga ttgagagact tagtcttgat tgcagcaagg actgtggaac tcctgggaca   6420
cagcagtctc aagggactga gactggggtg ggaagccctc aaatatctgt ggaaccttct   6480
atcatactgg ggtcaggaac taaagaatag tgctattaat ttgcttgata caatagcaat   6540
agcagtagct aactggacag atagagttat aaaaatagta caaagaactg gtagagctat   6600
tcttaacata cctagaagga tcagataggg ctagccccgg gtgataaacg gaccgcgcaa   6660
tccctaggct gtgccttcta gttgccagcc atctgttgtt tgcccctccc ccgtgccttc   6720
cttgaccctg gaaggtgcca ctcccactgt cctttcctaa taaaatgagg aaattgcatc   6780
gcattgtctg agtaggtgtc attctattct ggggggtggg gtggggcagg acagcaaggg   6840
ggaggattgg gaagacaata gcaggcatgc tggggatgcg gtgggctcta tataaaaaac   6900
gcccggcggc aaccgagcgt tctgaacgct agagtcgaca aattcagaag aactcgtcaa   6960
gaaggcgata gaaggcgatg cgctgcgaat cgggagcggc gataccgtaa agcacgagga   7020
agcggtcagc ccattcgccg ccaagctctt cagcaatatc acgggtagcc aacgctatgt   7080
cctgatagcg gtctgccaca cccagccggc cacagtcgat gaatccagaa aagcggccat   7140
tttccaccat gatattcggc aagcaggcat cgccatgggt cacgacgaga tcctcgccgt   7200
cgggcatgct cgccttgagc ctggcgaaca gttcggctgg cgcgagcccc tgatgctctt   7260
cgtccagatc atcctgatcg acaagaccgg cttccatccg agtacgtgct cgctcgatgc   7320
gatgtttcgc ttggtggtcg aatgggcagg tagccggatc aagcgtatgc agccgccgca   7380
ttgcatcagc catgatggat actttctcgg caggagcaag gtgagatgac aggagatcct   7440
gccccggcac ttcgcccaat agcagccagt cccttcccgc ttcagtgaca acgtcgagca   7500
cagctgcgca aggaacgccc gtcgtggcca gccacgatag ccgcgctgcc tcgtcttgca   7560
gttcattcag ggcaccggac aggtcggtct tgacaaaaag aaccgggcgc ccctgcgctg   7620
acagccggaa cacggcggca tcagagcagc cgattgtctg ttgtgcccag tcatagccga   7680
atagcctctc cacccaagcg gccggagaac ctgcgtgcaa tccatcttgt tcaatcatgc   7740
gaaacgatcc tcatcctgtc tcttgatcag atcttgatcc cctgcgccat cagatccttg   7800
gcggcaagaa agccatccag tttactttgc agggcttccc aaccttacca gagggcgccc   7860
cagctggcaa ttccggttcg cttgctgtcc ataaaaccgc ccagtctagc tatcgccatg   7920
taagcccact gcaagctacc tgctttctct ttgcgcttgc gttttccctt gtccagatag   7980
cccagtagct gacattcatc cggggtcagc accgtttctg cggactggct ttctacgtga   8040
aaaggatcta ggtgaagatc ctttttgata atctcatgac caaaatccct taacgtgagt   8100
tttcgttcca ctgagcgtca gaccccgtag aaaagatcaa aggatcttct tgagatcctt   8160
tttttctgcg cgtaatctgc tgcttgcaaa caaaaaaacc accgctacca gcggtggttt   8220
gtttgccgga tcaagagcta ccaactcttt ttccgaaggt aactggcttc agcagagcgc   8280
agataccaaa tactgttctt ctagtgtagc cgtagttagg ccaccacttc aagaactctg   8340
tagcaccgcc tacatacctc gctctgctaa tcctgttacc agtggctgct gccagtggcg   8400
ataagtcgtg tcttaccggg ttggactcaa gacgatagtt accggataag gcgcagcggt   8460
cgggctgaac ggggggttcg tgcacacagc ccagcttgga gcgaacgacc tacaccgaac   8520
tgagatacct acagcgtgag ctatgagaaa gcgccacgct tcccgaaggg agaaaggcgg   8580
```

```
acaggtatcc ggtaagcggc agggtcggaa caggagagcg cacgagggag cttccagggg   8640

gaaacgcctg gtatctttat agtcctgtcg ggtttcgcca cctctgactt gagcgtcgat   8700

ttttgtgatg ctcgtcaggg gggcggagcc tatggaaaaa cgccagcaac gcggcccttt   8760

tacggttcct ggccttttgc tggccttttg ctcacatgtt gtcgacaata ttggctattg   8820

gccattgcat acgttgtatc tatatcataa tatgtacatt tatattggct catgtccaat   8880

atgaccgcca tgttgacatt gattattgac tagttattaa tagtaatcaa ttacgggttc   8940

attagttcat agcccatata tggagttccg cgttacataa cttacggtaa atggcccgcc   9000

tggctgaccg cccaacgacc cccgcccatt gacgtcaata atgacgtatg ttcccatagt   9060

aacgccaata gggactttcc attgacgtca atgggtggag tatttacggt aaactgccca   9120

cttggcagta catcaagtgt atcatatgcc aagtccgccc cctattgacg tcaatgacgg   9180

taaatggccc gcctggcatt atgcccagta catgacctta cgggactttc ctacttggca   9240

gtacatctac ggtattagtc atcggctatt accatggtga tgcggttttg gcagtacacc   9300

aatgggcgtg gatagcggtt tgactcacgg ggatttccaa gtctccaccc cattgacgtc   9360

aatgggagtt tgttttggca ccaaaatcaa cgggactttc caaaatgtcg taataacccc   9420

gccccgttga cgcaaatggg cggtaggcgt gtacggtggg aggtctatat aagcagagct   9480

cgtttagtga accgtcagat cgcctggaga cgccatccac gctgttttga cctccataga   9540

agacaccggg accgatccag cctccgcggc cgggaacggt gcattggaac gcggattccc   9600

cgtgccaaga gtgacgtaag taccgcctat agactctata ggcacacccc tttggctctt   9660

atgcatgcta tactgttttt ggcttggggc ctatacaccc ccgcttcctt atgctatagg   9720

tgatggtata gcttagccta taggtgtggg ttattgacca ttattgacca ctcccctatt   9780

ggtgacgata ctttccatta ctaatccata acatggctct ttgccacaac tatctctatt   9840

ggctatatgc caatactctg tccttcagag actgacacgg actctgtatt tttacaggat   9900

ggggtcccat ttattattta caaattcaca tatacaacaa cgccgtcccc cgtgcccgca   9960

gtttttatta aacatagcgt gggatctcca cgcgaatctc gggtaccgtg ttccggacat  10020

gggytcttct ccggtagcgg cggagcttcc acatccgagc cctggtccca tgcctccagc  10080

ggctcatggt cgctcggcag ctccttgctc ctaacagtgg aggccagact taggcacagc  10140

acaatgccca ccaccaccag tgtgccgcac aaggccgtgg cggtagggta tgtgtctgaa  10200

aatgagctcg gagattgggc tcgcaccgct gacgcagatg gaagacttaa ggcagcggca  10260

gaagaagatg caggcagctg agttgttgta ttctgataag agtcagaggt aactcccgtt  10320

gcggtgctgt taacggtgga gggcagtgta gtctgagcag tactcgttgc tgccgcgcgc  10380

gccaccagac ataatagctg acagactaac agactgttcc tttccatggg tcttttctgc  10440

agtcacc                                                            10447
```

<210> SEQ ID NO 11
<211> LENGTH: 10447
<212> TYPE: DNA
<213> ORGANISM: Artificial Sequence
<220> FEATURE:
<223> OTHER INFORMATION: Synthetically generated vector sequence-pGA1/IC2

<400> SEQUENCE: 11

```
atcgatgcaa ggactcggct tgctgaggtg cacacagcaa gaggcgagag cgacgactgg     60

tgagtacgcc aatttttgac tagcggaggc tagaaggaga gagatgggtg cgagagcgtc    120
```

```
agtgttaacg gggggaaaat tagattcatg ggagaaaatt aggttaaggc cagggggaaa    180
gaaaagatat agactaaaac acctagtatg ggcaagcagg gagctggaga gattcgcact    240
taaccctggc ctattagaaa cagcagaagg atgtcaacaa ctaatgggac agttacaacc    300
agctctcagg acaggatcag aagagtttaa atcattatat aatatagtag caaccctttg    360
gtgcgtacat caaagaatag acataaaaga cacccaggag gccttagata aagtagagga    420
aaaacaaaat aagagcaagc aaaaggcaca gcaggcagca gctgcaacag ccgccacagg    480
aagcagcagc caaaattacc ctatagtgca aaatgcacaa gggcaaatgg tacatcagtc    540
catgtcacct aggactttaa atgcatgggt gaaggtaata gaagaaaagg cttttagccc    600
agaggtaata cccatgtttt cagcattatc agagggagcc accccacaag atttaaatat    660
gatgctaaac atagtggggg gacaccaggc agcaatgcag atgttaaaag ataccatcaa    720
tgatgaagct gcagaatggg acagagtaca tccagtacat gcagggccta ttccaccagg    780
ccaaatgagg gaaccaaggg gaagtgacat agcaggaact actagtaccc ttcaagaaca    840
aataggatgg atgacaagta atccacctat cccagtggga gaaatctata aaagatggat    900
agtcctggga ttaaataaaa tagtaagaat gtatagccct accagcattt tggacataag    960
acaagggcca aaagaaccct ttagagatta tgtagacagg ttctttaaaa ctttgagagc   1020
tgaacaagct acgcaggagg taaaaaactg gatgacagaa accttgttgg tccaaaatgc   1080
gaatccagac tgcaagtcca ttttaagagc attaggacca ggggctacat tagaagaaat   1140
gatgacatca tgtcagggag tgggaggacc tggccataaa gcaagggttt tggctgaggc   1200
aatgagtcaa gtacaacaga ccaatgtaat gatgcagaga ggcaatttta gaggccagag   1260
aataataaag agcttcaaca gcggcaaaga aggacaccta gccagaaatt gcaaggctcc   1320
tagaaagaga ggcagctgga aaagcggaaa ggaaggacac caaatgaaag actgtactga   1380
aagacaggct aattttttag ggaaaatttg gccttcccac aaggggaggc caggaaattt   1440
tcctcagagc agaccagaac caacagcccc gccagcagag agctttggag tgggggaaga   1500
gataccctcc tctccgaagc aggagccgag ggacaaggga ctatatcctc ccttaacttc   1560
cctcaaatca ctctttggca acgaccagta gtcacagtaa gaataggggg acagccaata   1620
gaagccctat tagacacagg agcagatgat acagtattag aagaaataag tttaccagga   1680
aaatggaaac caaaaatgat agggggaatt ggaggtttta tcaaagtaag acagtatgat   1740
cagatatcta tagaaatttg tggaaaaagg gccataggta cagtattagt aggacctaca   1800
cctgtcaaca taattggacg aaatatgttg actcagattg gttgtacttt aaattttcca   1860
attagtccta ttgaaactgt gccagtaaaa ttaaagtcag gaatggatgg cccaaaggtt   1920
aaacaatggc cattgacaga agaaaaaata aaagcattaa aagaaatttg tgcagagatg   1980
gaaaaggaag gaaaaatttc aaaaattggg cctgaaaacc catacaatac tccaatattt   2040
gccataaaga aaaaagatag tactaaatgg agaaaattag tagatttcag agaactcaat   2100
aagagaactc aagacttctg ggaggtccaa ttaggaatac ctcatcctgc gggattaaaa   2160
aagaaaaaat cagtaacagt actagatgtg ggggatgcat atttttcagt tcccttagat   2220
gaagacttta gaaaatatac tgcattcacc atacctagtt taaataatga gacaccaggg   2280
attagatatc agtacaatgt actcccacag ggatggaaag gatcaccagc aatatttcag   2340
gcaagcatga caaaaatctt agagcccttt agagcaaaaa atccagagat agtgatctac   2400
caatatatga acgatttata tgtaggatct gacttagaaa tagggcagca tagagcaaaa   2460
```

-continued

```
atagaggagt tgagagaaca tctattgaaa tggggattta ccacaccaga caaaaaacat   2520
cagaaagaac ctccatttct ttggatggga tatgaactcc atcctgacaa atggacagtc   2580
cagcctatac agctgccaga aaaagacagc tggactgtca atgatataca aaaattagtg   2640
ggaaaactaa ataccgcaag tcagatttat gcaggaatta aagtaaagca attgtgtaga   2700
ctcctcaggg gagccaaagc gctaacagat gtagtaacac tgactgagga agcagaatta   2760
gaattggcag agaacaggga aattctaaaa gaacctgtac atggagtata ttatgaccca   2820
acaaaagact tagtggcaga aatacagaaa caagggcaag atcaatggac atatcaaatt   2880
tatcaagagc catttaaaaa tctaaagaca ggaaaatatg caaaaaagag gtcggcccac   2940
actaatgatg taaaacaatt aacagaggta gtgcagaaaa tagccataga aagcatagta   3000
atatggggaa agacccctaa atttagacta cccatacaaa gagaaacatg ggaagcatgg   3060
tggatggagt attggcaggc tacctggatt cctgaatggg agtttgtcaa tacccctcct   3120
ctagtaaaat tatggtacca gttagagaag gaccccataa tgggagcaga aactttctat   3180
gtagatgggg cagctaatag ggagactaag ctaggaaaag cagggtatgt cactgacaga   3240
ggaagacaaa aggttgtttc cctaattcag acaacaaatc aaaagactca gttacatgca   3300
attcatctag ccttgcagga ttcaggatca gaagtaaata tagtaacaga ctcacagtat   3360
gcattaggaa tcattcaggc acaaccagac aggagtgaat cagagttagt caatcaaata   3420
atagagaaac taatagaaaa ggacaaagtc tacctgtcat gggtaccagc acacaaaggg   3480
attggaggaa atgaacaagt agataaatta gtcagtagtg gaatcagaaa ggtactattt   3540
ttagatggaa tagataaagc ccaagatgaa cattagaatt ctgcaacagc tactgtttgt   3600
tcatttcaga attgggtgtc aacatagcag aataggcatt attccaggga gaagaggcag   3660
gaatggagct ggtagatcct agcctagagc cctggaacca cccgggaagt cagcctacaa   3720
ctgcttgtag caagtgttac tgtaaaaaat gctgctggca ttgccaattg tgctttctga   3780
acaagggctt aggcatctcc tatggcagga agaagcggag acgccgacga ggaactcctc   3840
aggaccgtca ggttcatcaa aatcctgtac caaaacagta agtagtagta attagtatat   3900
gtgatgcaat ctttacaaat agctgcaata gtaggactag tagtagcatc catagtagcc   3960
atagttgtgt ggtccatagt atttatagaa tatagaaaaa taaggaaaca gaagaaaata   4020
gacaggttac ttgagagaat aagagaaaga gcagaagata gtggcaatga gagtgatggg   4080
gatacagaag aattatccac tcttatggag agggggtatg acaatatttt ggttaatgat   4140
gatttgtaat gctgaaaagt tgtgggtcac agtctactat ggggtacctg tgtggagaga   4200
cgcagagacc accctattct gtgcatcaga tgctaaagca tatgacaaag aagcacacaa   4260
tgtctgggct acgcatgcct gcgtacccac agaccctgac ccacaagaat tacctttggt   4320
aaatgtaaca gaagagttta acatgtggaa aaataatatg gtagaacaga tgcatgaaga   4380
tataattagt ctatgggacc aaagcttaaa gccatgtgta cagctaaccc ctctctgcgt   4440
tactttaggg tgtgctgacg ctcaaaacgt caccgacacc aacaccacca tatctaatga   4500
aatgcaaggg gaaataaaaa actgctcttt caatatgacc acagaattaa gagataagaa   4560
gcagaaagtg tatgcacttt tttatagacc tgatgtaata gaaattaata aaactaagat   4620
taacaatagt aatagtagtc agtatatgtt aataaattgt aatacctcaa ccattacaca   4680
gacttgtcca aaggtatcct ttgagccaat tcccatacat tattgtgccc cagctggttt   4740
tgcaattcta aagtgtaatg atacggagtt cagtggaaaa gggacatgca agagtgtcag   4800
cacagtacaa tgcacacatg gaatcaagcc agtagtatca actcaactgc tgttaaatgg   4860
```

```
cagtctagca gaaggaaaga tagcgattag atctgagaat atctcaaaca atgccaaaac   4920
tataatagta caattgactg agcctgtaga aattaattgt atcagacctg gcaacaatac   4980
aagaaaaagt gtacgcatag gaccaggaca aacattctat gcaacaggtg acataatagg   5040
agatataaga caagcacact gtaatgttag taaaatagca tgggaagaaa ctttacaaaa   5100
ggtagctgca caattaagga agcactttca gaatgccaca ataaaattta ctaaacactc   5160
aggaggggat ttagaaatta caacaaatag ttttaattgt ggaggagaat ttttctattg   5220
caatacaaca aagctgttta atagcacttg gaataatgat aactcaaacc tcacagagga   5280
aaagagaaag gaaaacataa ctctccactg cagaataaag caaattgtaa atatgtggcc   5340
aagagtagga caagcaatat atgcccctcc catcccagga aacataactt gtggatcaaa   5400
cattactggg ctactattaa caagagatgg agggaataat ggtacaaatg atactgagac   5460
cttcaggcct ggaggaggag atatgaggga caattggaga agtgaattat ataaatataa   5520
agtagtaaaa attgaaccac taggtgtagc accaacccct gcaaaaagaa gagtggtgga   5580
aagagaaaaa agagcagttg gaatgggagc tttgatcttt gagttcttag gagcagcagg   5640
aagcactatg ggcgcggcgt caatggcgct gacggtacag gccagacaat tattgtctgg   5700
tatagtgcaa cagcagagca atctgctgaa ggctatagag gctcaacaac atctgttgag   5760
actcacggtc tggggcatta aacagctcca ggcaagagtc ctggctctgg aaagatacct   5820
aaaggatcaa cagctcctag gaatttgggg ctgctctgga aaactcattt gcaccactgc   5880
tgtaccttgg aactctagct ggagtaataa aagttataat gacatatggg ataacatgac   5940
ctggctgcaa tgggataaag aaattaacaa ttacacatac ataatatata atctacttga   6000
aaaatcgcag aaccagcagg aaattaatga acaagactta ttggcattag acaagtgggc   6060
aagtctgtgg aattggtttg acataacaag ctggctatgg tatataagat taggtataat   6120
gatagtagga ggcgtaatag gcttaagaat aatttttgct gtgcttacta tagtgaatag   6180
agttaggcag ggatactcac ctttgtcatt ccagaccctt gcccaccacc agagggaacc   6240
cgacaggccc gaaagaatcg aagaaggagg tggcgagcaa gacagagaga gatccgtgcg   6300
cttagtgagc ggattcttag cacttgcctg ggaagatctg cggagcctgt gcctcttcag   6360
ctaccgccga ttgagagact tagtcttgat tgcagcaagg actgtggaac tcctgggaca   6420
cagcagtctc aagggactga gactggggtg ggaagccctc aaatatctgt ggaaccttct   6480
atcatactgg ggtcaggaac taaagaatag tgctattaat ttgcttgata caatagcaat   6540
agcagtagct aactggacag atagagttat aaaaatagta caaagaactg gtagagctat   6600
tcttaacata cctagaagga tcagataggg ctagccccgg gtgataaacg gaccgcgcaa   6660
tccctaggct gtgccttcta gttgccagcc atctgttgtt tgcccctccc ccgtgccttc   6720
cttgaccctg gaaggtgcca ctcccactgt cctttcctaa taaaatgagg aaattgcatc   6780
gcattgtctg agtaggtgtc attctattct ggggggtggg gtggggcagg acagcaaggg   6840
ggaggattgg gaagacaata gcaggcatgc tggggatgcg gtgggctcta tataaaaaac   6900
gcccggcggc aaccgagcgt tctgaacgct agagtcgaca aattcagaag aactcgtcaa   6960
gaaggcgata gaaggcgatg cgctgcgaat cgggagcggc gataccgtaa agcacgagga   7020
agcggtcagc ccattcgccg ccaagctctt cagcaatatc acgggtagcc aacgctatgt   7080
cctgatagcg gtctgccaca cccagccggc cacagtcgat gaatccagaa aagcggccat   7140
tttccaccat gatattcggc aagcaggcat cgccatgggt cacgacgaga tcctcgccgt   7200
```

-continued cgggcatgct cgccttgagc ctggcgaaca gttcggctgg cgcgagcccc tgatgctctt 7260
cgtccagatc atcctgatcg acaagaccgg cttccatccg agtacgtgct cgctcgatgc 7320
gatgtttcgc ttggtggtcg aatgggcagg tagccggatc aagcgtatgc agccgccgca 7380
ttgcatcagc catgatggat actttctcgg caggagcaag gtgagatgac aggagatcct 7440
gccccggcac ttcgcccaat agcagccagt cccttcccgc ttcagtgaca acgtcgagca 7500
cagctgcgca aggaacgccc gtcgtggcca gccacgatag ccgcgctgcc tcgtcttgca 7560
gttcattcag ggcaccggac aggtcggtct tgacaaaaag aaccgggcgc ccctgcgctg 7620
acagccggaa cacggcggca tcagagcagc cgattgtctg ttgtgcccag tcatagccga 7680
atagcctctc cacccaagcg gccggagaac ctgcgtgcaa tccatcttgt tcaatcatgc 7740
gaaacgatcc tcatcctgtc tcttgatcag atcttgatcc cctgcgccat cagatccttg 7800
gcggcaagaa agccatccag tttactttgc agggcttccc aaccttacca gagggcgccc 7860
cagctggcaa ttccggttcg cttgctgtcc ataaaaccgc ccagtctagc tatcgccatg 7920
taagcccact gcaagctacc tgctttctct ttgcgcttgc gttttccctt gtccagatag 7980
cccagtagct gacattcatc cggggtcagc accgtttctg cggactggct ttctacgtga 8040
aaaggatcta ggtgaagatc ctttttgata atctcatgac caaaatccct taacgtgagt 8100
tttcgttcca ctgagcgtca gaccccgtag aaaagatcaa aggatcttct tgagatcctt 8160
tttttctgcg cgtaatctgc tgcttgcaaa caaaaaaacc accgctacca gcggtggttt 8220
gtttgccgga tcaagagcta ccaactcttt ttccgaaggt aactggcttc agcagagcgc 8280
agataccaaa tactgttctt ctagtgtagc cgtagttagg ccaccacttc aagaactctg 8340
tagcaccgcc tacatacctc gctctgctaa tcctgttacc agtggctgct gccagtggcg 8400
ataagtcgtg tcttaccggg ttggactcaa gacgatagtt accggataag gcgcagcggt 8460
cgggctgaac ggggggttcg tgcacacagc ccagcttgga gcgaacgacc tacaccgaac 8520
tgagatacct acagcgtgag ctatgagaaa gcgccacgct tcccgaaggg agaaaggcgg 8580
acaggtatcc ggtaagcggc agggtcggaa caggagagcg cacgagggag cttccagggg 8640
gaaacgcctg gtatctttat agtcctgtcg ggtttcgcca cctctgactt gagcgtcgat 8700
ttttgtgatg ctcgtcaggg gggcggagcc tatggaaaaa cgccagcaac gcggcccttt 8760
tacggttcct ggccttttgc tggccttttg ctcacatgtt gtcgacaata ttggctattg 8820
gccattgcat acgttgtatc tatatcataa tatgtacatt tatattggct catgtccaat 8880
atgaccgcca tgttgacatt gattattgac tagttattaa tagtaatcaa ttacgggttc 8940
attagttcat agcccatata tggagttccg cgttacataa cttacggtaa atggcccgcc 9000
tggctgaccg cccaacgacc cccgcccatt gacgtcaata atgacgtatg ttcccatagt 9060
aacgccaata gggactttcc attgacgtca atgggtggag tatttacggt aaactgccca 9120
cttggcagta catcaagtgt atcatatgcc aagtccgccc cctattgacg tcaatgacgg 9180
taaatggccc gcctggcatt atgcccagta catgacctta cgggactttc ctacttggca 9240
gtacatctac ggtattagtc atcggctatt accatggtga tgcggttttg gcagtacacc 9300
aatgggcgtg gatagcggtt tgactcacgg ggatttccaa gtctccaccc cattgacgtc 9360
aatgggagtt tgttttggca ccaaaatcaa cgggactttc caaaatgtcg taataacccc 9420
gccccgttga cgcaaatggg cggtaggcgt gtacggtggg aggtctatat aagcagagct 9480
cgtttagtga accgtcagat cgcctggaga cgccatccac gctgttttga cctccataga 9540
agacaccggg accgatccag cctccgcggc cgggaacggt gcattggaac gcggattccc 9600

```
cgtgccaaga gtgacgtaag taccgcctat agactctata ggcacacccc tttggctctt   9660
atgcatgcta tactgttttt ggcttggggc ctatacaccc ccgcttcctt atgctatagg   9720
tgatggtata gcttagccta taggtgtggg ttattgacca ttattgacca ctcccctatt   9780
ggtgacgata ctttccatta ctaatccata acatggctct ttgccacaac tatctctatt   9840
ggctatatgc caatactctg tccttcagag actgacacgg actctgtatt tttacaggat   9900
ggggtcccat ttattattta caaattcaca tatacaacaa cgccgtcccc cgtgcccgca   9960
gtttttatta aacatagcgt gggatctcca cgcgaatctc gggtaccgtg ttccggacat  10020
gggytcttct ccggtagcgg cggagcttcc acatccgagc cctggtccca tgcctccagc  10080
ggctcatggt cgctcggcag ctccttgctc ctaacagtgg aggccagact taggcacagc  10140
acaatgccca ccaccaccag tgtgccgcac aaggccgtgg cggtagggta tgtgtctgaa  10200
aatgagctcg gagattgggc tcgcaccgct gacgcagatg gaagacttaa ggcagcggca  10260
gaagaagatg caggcagctg agttgttgta ttctgataag agtcagaggt aactcccgtt  10320
gcggtgctgt taacggtgga gggcagtgta gtctgagcag tactcgttgc tgccgcgcgc  10380
gccaccagac ataatagctg acagactaac agactgttcc tttccatggg tcttttctgc  10440
agtcacc                                                            10447
```

<210> SEQ ID NO 12
<211> LENGTH: 10447
<212> TYPE: DNA
<213> ORGANISM: Artificial Sequence
<220> FEATURE:
<223> OTHER INFORMATION: Synthetically generated vector sequence-pGA1/IC48

<400> SEQUENCE: 12

```
atcgatgcaa ggactcggct tgctgaggtg cacacagcaa gaggcgagag cgacgactgg     60
tgagtacgcc aatttttgac tagcggaggc tagaaggaga gagatgggtg cgagagcgtc    120
agtgttaacg ggggaaaat tagattcatg ggagaaaatt aggttaaggc caggggggaaa    180
gaaaagatat agactaaaac acctagtatg ggcaagcagg gagctggaga gattcgcact    240
taaccctggc ctattagaaa cagcagaagg atgtcaacaa ctaatgggac agttacaacc    300
agctctcagg acaggatcag aagagtttaa atcattatat aatatagtag caaccctttg    360
gtgcgtacat caaagaatag acataaaaga cacccaggag gccttagata aagtagagga    420
aaaacaaaat aagagcaagc aaaaggcaca gcaggcagca gctgcaacag ccgccacagg    480
aagcagcagc caaaattacc ctatagtgca aaatgcacaa gggcaaatgg tacatcagtc    540
catgtcacct aggactttaa atgcatgggt gaaggtaata gaagaaaagg cttttagccc    600
agaggtaata cccatgtttt cagcattatc agagggagcc accccacaag atttaaatat    660
gatgctaaac atagtggggg gacaccaggc agcaatgcag atgttaaaag ataccatcaa    720
tgatgaagct gcagaatggg acagagtaca tccagtacat gcagggccta ttccaccagg    780
ccaaatgagg gaaccaaggg gaagtgacat agcaggaact actagtaccc ttcaagaaca    840
aataggatgg atgacaagta atccacctat cccagtggga gaaatctata aaagatggat    900
agtcctggga ttaaataaaa tagtaagaat gtatagccct accagcattt tggacataag    960
acaagggcca aaagaaccct ttagagatta tgtagacagg ttctttaaaa ctttgagagc   1020
tgaacaagct acgcaggagg taaaaaactg gatgacagaa accttgttgg tccaaaatgc   1080
gaatccagac tgcaagtcca ttttaagagc attaggacca ggggctacat tagaagaaat   1140
```

```
gatgacatca tgtcagggag tgggaggacc tggccataaa gcaagggttt tggctgaggc   1200
aatgagtcaa gtacaacaga ccaatgtaat gatgcagaga ggcaatttta gaggccagag   1260
aataataaag agcttcaaca gcggcaaaga aggacaccta gccagaaatt gcaaggctcc   1320
tagaaagaga ggcagctgga aaagcggaaa ggaaggacac caaatgaaag actgtactga   1380
aagacaggct aattttttag ggaaaatttg gccttcccac aaggggaggc caggaaattt   1440
tcctcagagc agaccagaac caacagcccc gccagcagag agctttggag tgggggaaga   1500
gataccctcc tctccgaagc aggagccgag ggacaaggga ctatatcctc ccttaacttc   1560
cctcaaatca ctctttggca acgaccagta gtcacagtaa gaatagggggg acagccaata   1620
gaagccctat tagacacagg agcagatgat acagtattag aagaaataag tttaccagga   1680
aaatggaaac caaaaatgat aggtggaatt ggaggtttta tcaaagtaag acagtatgat   1740
cagatatcta tagaaatttg tggaaaaagg gccataggta cagtattagt aggacctaca   1800
cctgtcaaca taattggacg aaatatgttg actcagattg gttgtacttt aaattttcca   1860
attagtccta ttgaaactgt gccagtaaaa ttaaagtcag gaatggatgg cccaaaggtt   1920
aaacaatggc cattgacaga agaaaaaata aaagcattaa aagaaatttg tgcagagatg   1980
gaaaaggaag gaaaaatttc aaaaattggg cctgaaaacc catacaatac tccaatattt   2040
gccataaaga aaaaagatag tactaaatgg agaaaattag tagatttcag agaactcaat   2100
aagagaactc aagacttctg ggaggtccaa ttaggaatac ctcatcctgc gggattaaaa   2160
aagaaaaaat cagtaacagt actagatgtg ggggatgcat atttttcagt tcccttagat   2220
gaagacttta gaaaatatac tgcattcacc atacctagtt taaataatga gacaccaggg   2280
attagatatc agtacaatgt actcccacag ggatggaaag gatcaccagc aatatttcag   2340
gcaagcatga caaaaatctt agagcccttt agagcaaaaa atccagagat agtgatctac   2400
caatatatga acgatttata tgtaggatct gacttagaaa tagggcagca tagagcaaaa   2460
atagaggagt tgagagaaca tctattgaaa tggggattta ccacaccaga caaaaaacat   2520
cagaaagaac ctccatttct ttggatggga tatgaactcc atcctgacaa atggacagtc   2580
cagcctatac agctgccaga aaaagacagc tggactgtca atgatataca aaaattagtg   2640
ggaaaactaa ataccgcaag tcagatttat gcaggaatta aagtaaagca attgtgtaga   2700
ctcctcaggg gagccaaagc gctaacagat gtagtaacac tgactgagga agcagaatta   2760
gaattggcag agaacaggga aattctaaaa gaacctgtac atggagtata ttatgaccca   2820
acaaaagact tagtggcaga aatacagaaa caagggcaag atcaatggac atatcaaatt   2880
tatcaagagc catttaaaaa tctaaagaca ggaaaatatg caaaaaagag gtcggcccac   2940
actaatgatg taaaacaatt aacagaggta gtgcagaaaa tagccataga aagcatagta   3000
atatggggaa agacccctaa atttagacta cccatacaaa gagaaacatg ggaagcatgg   3060
tggatggagt attggcaggc tacctggatt cctgaatggg agtttgtcaa taccccctcct   3120
ctagtaaaat tatggtacca gttagagaag gaccccataa tgggagcaga aactttctat   3180
gtagatgggg cagctaatag ggagactaag ctaggaaaag cagggtatgt cactgacaga   3240
ggaagacaaa aggttgtttc cctaattcag acaacaaatc aaaagactca gttacatgca   3300
attcatctag ccttgcagga ttcaggatca gaagtaaata tagtaacaga ctcacagtat   3360
gcattaggaa tcattcaggc acaaccagac aggagtgaat cagagttagt caatcaaata   3420
atagagaaac taatagaaaa ggacaaagtc tacctgtcat gggtaccagc acacaaaggg   3480
```

```
attggaggaa atgaacaagt agataaatta gtcagtagtg gaatcagaaa ggtactattt   3540
ttagatggaa tagataaagc ccaagatgaa cattagaatt ctgcaacagc tactgtttgt   3600
tcatttcaga attgggtgtc aacatagcag aataggcatt attccaggga gaagaggcag   3660
gaatggagct ggtagatcct agcctagagc cctggaacca cccgggaagt cagcctacaa   3720
ctgcttgtag caagtgttac tgtaaaaaat gctgctggca ttgccaattg tgctttctga   3780
acaagggctt aggcatctcc tatggcagga agaagcggag acgccgacga ggaactcctc   3840
aggaccgtca ggttcatcaa aatcctgtac caaaacagta agtagtagta attagtatat   3900
gtgatgcaat ctttacaaat agctgcaata gtaggactag tagtagcatc catagtagcc   3960
atagttgtgt ggtccatagt atttatagaa tatagaaaaa taaggaaaca gaagaaaata   4020
gacaggttac ttgagagaat aagagaaaga gcagaagata gtggcaatga gagtgatggg   4080
gatacagaag aattatccac tcttatggag agggggtatg acaatatttt ggttaatgat   4140
gatttgtaat gctgaaaagt tgtgggtcac agtctactat ggggtacctg tgtggagaga   4200
cgcagagacc accctattct gtgcatcaga tgctaaagca tatgacaaag aagcacacaa   4260
tgtctgggct acgcatgcct gcgtacccac agaccctgac ccacaagaat tacctttggt   4320
aaatgtaaca gaagagttta acatgtggaa aaataatatg gtagaacaga tgcatgaaga   4380
tataattagt ctatgggacc aaagcttaaa gccatgtgta cagctaaccc ctctctgcgt   4440
tactttaggg tgtgctgacg ctcaaaacgt caccgacacc aacaccacca tatctaatga   4500
aatgcaaggg gaaataaaaa actgctcttt caatatgacc acagaattaa gagataagaa   4560
gcagaaagtg tatgcacttt tttatagacc tgatgtaata gaaattaata aaactaagat   4620
taacaatagt aatagtagtc agtatatgtt aataaattgt aatacctcaa ccattacaca   4680
gacttgtcca aaggtatcct ttgagccaat tcccatacat tattgtgccc cagctggttt   4740
tgcaattcta aagtgtaatg atacggagtt cagtggaaaa gggacatgca agagtgtcag   4800
cacagtacaa tgcacacatg gaatcaagcc agtagtatca actcaactgc tgttaaatgg   4860
cagtctagca gaaggaaaga tagcgattag atctgagaat atctcaaaca atgccaaaac   4920
tataatagta caattgactg agcctgtaga aattaattgt atcagacctg gcaacaatac   4980
aagaaaaagt gtacgcatag gaccaggaca aacattctat gcaacaggtg acataatagg   5040
agatataaga caagcacact gtaatgttag taaaatagca tggaagaaaa ctttacaaaa   5100
ggtagctgca caattaagga agcactttca gaatgccaca ataaaattta ctaaacactc   5160
aggaggggat ttagaaatta caacaaatag ttttaattgt ggaggagaat tttctattg    5220
caatacaaca aagctgttta atagcacttg gaataatgat aactcaaacc tcacagagga   5280
aaagagaaag gaaaacataa ctctccactg cagaataaag caaattgtaa atatgtggcc   5340
aagagtagga caagcaatat atgcccctcc catcccagga aacataactt gtggatcaaa   5400
cattactggg ctactattaa caagagatgg agggaataat ggtacaaatg atactgagac   5460
cttcaggcct ggaggaggag atatgaggga caattggaga agtgaattat ataaatataa   5520
agtagtaaaa attgaaccac taggtgtagc accaacccct gcaaaaagaa gagtggtgga   5580
aagagaaaaa agagcagttg gaatgggagc tttgatcttt gagttcttag gagcagcagg   5640
aagcactatg ggcgcggcgt caatggcgct gacggtacag gccagacaat tattgtctgg   5700
tatagtgcaa cagcagagca atctgctgaa ggctatagag gctcaacaac atctgttgag   5760
actcacggtc tggggcatta aacagctcca ggcaagagtc ctggctctgg aaagatacct   5820
aaaggatcaa cagctcctag gaatttgggg ctgctctgga aaactcattt gcaccactgc   5880
```

```
tgtaccttgg aactctagct ggagtaataa aagttataat gacatatggg ataacatgac   5940
ctggctgcaa tgggataaag aaattaacaa ttacacatac ataatatata atctacttga   6000
aaaatcgcag aaccagcagg aaattaatga acaagactta ttggcattag acaagtgggc   6060
aagtctgtgg aattggtttg acataacaag ctggctatgg tatataagat taggtataat   6120
gatagtagga ggcgtaatag gcttaagaat aatttttgct gtgcttacta tagtgaatag   6180
agttaggcag ggatactcac ctttgtcatt ccagaccctt gcccaccacc agagggaacc   6240
cgacaggccc gaaagaatcg aagaaggagg tggcgagcaa gacagagaga gatccgtgcg   6300
cttagtgagc ggattcttag cacttgcctg ggaagatctg cggagcctgt gcctcttcag   6360
ctaccgccga ttgagagact tagtcttgat tgcagcaagg actgtggaac tcctgggaca   6420
cagcagtctc aagggactga gactggggtg ggaagccctc aaatatctgt ggaaccttct   6480
atcatactgg ggtcaggaac taaagaatag tgctattaat ttgcttgata caatagcaat   6540
agcagtagct aactggacag atagagttat aaaaatagta caaagaactg gtagagctat   6600
tcttaacata cctagaagga tcagataggg ctagccccgg gtgataaacg gaccgcgcaa   6660
tccctaggct gtgccttcta gttgccagcc atctgttgtt tgcccctccc ccgtgccttc   6720
cttgaccctg gaaggtgcca ctcccactgt cctttcctaa taaaatgagg aaattgcatc   6780
gcattgtctg agtaggtgtc attctattct ggggggtggg gtggggcagg acagcaaggg   6840
ggaggattgg gaagacaata gcaggcatgc tggggatgcg gtgggctcta tataaaaaac   6900
gcccggcggc aaccgagcgt tctgaacgct agagtcgaca aattcagaag aactcgtcaa   6960
gaaggcgata gaaggcgatg cgctgcgaat cgggagcggc gataccgtaa agcacgagga   7020
agcggtcagc ccattcgccg ccaagctctt cagcaatatc acgggtagcc aacgctatgt   7080
cctgatagcg gtctgccaca cccagccggc cacagtcgat gaatccagaa aagcggccat   7140
tttccaccat gatattcggc aagcaggcat cgccatgggt cacgacgaga tcctcgccgt   7200
cgggcatgct cgccttgagc ctggcgaaca gttcggctgg cgcgagcccc tgatgctctt   7260
cgtccagatc atcctgatcg acaagaccgg cttccatccg agtacgtgct cgctcgatgc   7320
gatgtttcgc ttggtggtcg aatgggcagg tagccggatc aagcgtatgc agccgccgca   7380
ttgcatcagc catgatggat actttctcgg caggagcaag gtgagatgac aggagatcct   7440
gccccggcac ttcgcccaat agcagccagt cccttcccgc ttcagtgaca acgtcgagca   7500
cagctgcgca aggaacgccc gtcgtggcca gccacgatag ccgcgctgcc tcgtcttgca   7560
gttcattcag ggcaccggac aggtcggtct tgacaaaaag aaccgggcgc ccctgcgctg   7620
acagccggaa cacggcggca tcagagcagc cgattgtctg ttgtgcccag tcatagccga   7680
atagcctctc cacccaagcg gccggagaac ctgcgtgcaa tccatcttgt tcaatcatgc   7740
gaaacgatcc tcatcctgtc tcttgatcag atcttgatcc cctgcgccat cagatccttg   7800
gcggcaagaa agccatccag tttactttgc agggcttccc aaccttacca gagggcgccc   7860
cagctggcaa ttccggttcg cttgctgtcc ataaaaccgc ccagtctagc tatcgccatg   7920
taagcccact gcaagctacc tgctttctct ttgcgcttgc gttttccctt gtccagatag   7980
cccagtagct gacattcatc cggggtcagc accgtttctg cggactggct ttctacgtga   8040
aaaggatcta ggtgaagatc ctttttgata atctcatgac caaaatccct taacgtgagt   8100
tttcgttcca ctgagcgtca gaccccgtag aaaagatcaa aggatcttct tgagatcctt   8160
tttttctgcg cgtaatctgc tgcttgcaaa caaaaaaacc accgctacca gcggtggttt   8220
```

```
gtttgccgga tcaagagcta ccaactcttt ttccgaaggt aactggcttc agcagagcgc   8280
agataccaaa tactgttctt ctagtgtagc cgtagttagg ccaccacttc aagaactctg   8340
tagcaccgcc tacatacctc gctctgctaa tcctgttacc agtggctgct gccagtggcg   8400
ataagtcgtg tcttaccggg ttggactcaa gacgatagtt accggataag gcgcagcggt   8460
cgggctgaac ggggggttcg tgcacacagc ccagcttgga gcgaacgacc tacaccgaac   8520
tgagatacct acagcgtgag ctatgagaaa gcgccacgct tcccgaaggg agaaaggcgg   8580
acaggtatcc ggtaagcggc agggtcggaa caggagagcg cacgagggag cttccagggg   8640
gaaacgcctg gtatctttat agtcctgtcg ggtttcgcca cctctgactt gagcgtcgat   8700
ttttgtgatg ctcgtcaggg gggcggagcc tatggaaaaa cgccagcaac gcggcccttt   8760
tacggttcct ggccttttgc tggccttttg ctcacatgtt gtcgacaata ttggctattg   8820
gccattgcat acgttgtatc tatatcataa tatgtacatt tatattggct catgtccaat   8880
atgaccgcca tgttgacatt gattattgac tagttattaa tagtaatcaa ttacgggttc   8940
attagttcat agcccatata tggagttccg cgttacataa cttacggtaa atggcccgcc   9000
tggctgaccg cccaacgacc cccgcccatt gacgtcaata atgacgtatg ttcccatagt   9060
aacgccaata gggactttcc attgacgtca atgggtggag tatttacggt aaactgccca   9120
cttggcagta catcaagtgt atcatatgcc aagtccgccc cctattgacg tcaatgacgg   9180
taaatggccc gcctggcatt atgcccagta catgacctta cgggactttc ctacttggca   9240
gtacatctac ggtattagtc atcggctatt accatggtga tgcggttttg gcagtacacc   9300
aatgggcgtg gatagcggtt tgactcacgg ggatttccaa gtctccaccc cattgacgtc   9360
aatgggagtt tgttttggca ccaaaatcaa cgggactttc caaaatgtcg taataacccc   9420
gccccgttga cgcaaatggg cggtaggcgt gtacggtggg aggtctatat aagcagagct   9480
cgtttagtga accgtcagat cgcctggaga cgccatccac gctgttttga cctccataga   9540
agacaccggg accgatccag cctccgcggc cgggaacggt gcattggaac gcggattccc   9600
cgtgccaaga gtgacgtaag taccgcctat agactctata ggcacacccc tttggctctt   9660
atgcatgcta tactgttttt ggcttggggc ctatacaccc ccgcttcctt atgctatagg   9720
tgatggtata gcttagccta taggtgtggg ttattgacca ttattgacca ctcccctatt   9780
ggtgacgata ctttccatta ctaatccata acatggctct ttgccacaac tatctctatt   9840
ggctatatgc caatactctg tccttcagag actgacacgg actctgtatt tttacaggat   9900
ggggtcccat ttattattta caaattcaca tatacaacaa cgccgtcccc cgtgcccgca   9960
gtttttatta aacatagcgt gggatctcca cgcgaatctc gggtaccgtg ttccggacat  10020
gggytcttct ccggtagcgg cggagcttcc acatccgagc cctggtccca tgcctccagc  10080
ggctcatggt cgctcggcag ctccttgctc ctaacagtgg aggccagact taggcacagc  10140
acaatgccca ccaccaccag tgtgccgcac aaggccgtgg cggtagggta tgtgtctgaa  10200
aatgagctcg gagattgggc tcgcaccgct gacgcagatg gaagacttaa ggcagcggca  10260
gaagaagatg caggcagctg agttgttgta ttctgataag agtcagaggt aactcccgtt  10320
gcggtgctgt taacggtgga gggcagtgta gtctgagcag tactcgttgc tgccgcgcgc  10380
gccaccagac ataatagctg acagactaac agactgttcc tttccatggg tcttttctgc  10440
agtcacc                                                            10447
```

<210> SEQ ID NO 13
<211> LENGTH: 10447

<212> TYPE: DNA
<213> ORGANISM: Artificial Sequence
<220> FEATURE:
<223> OTHER INFORMATION: Synthetically generated vector sequence-pGA1/IC90

<400> SEQUENCE: 13

```
atcgatgcaa ggactcggct tgctgaggtg cacacagcaa gaggcgagag cgacgactgg     60

tgagtacgcc aatttttgac tagcggaggc tagaaggaga gagatgggtg cgagagcgtc    120

agtgttaacg gggggaaaat tagattcatg ggagaaaatt aggttaaggc caggggggaaa    180

gaaaagatat agactaaaac acctagtatg ggcaagcagg gagctggaga gattcgcact    240

taaccctggc ctattagaaa cagcagaagg atgtcaacaa ctaatgggac agttacaacc    300

agctctcagg acaggatcag aagagtttaa atcattatat aatatagtag caaccctttg    360

gtgcgtacat caaagaatag acataaaaga cacccaggag gccttagata aagtagagga    420

aaaacaaaat aagagcaagc aaaaggcaca gcaggcagca gctgcaacag ccgccacagg    480

aagcagcagc caaaattacc ctatagtgca aaatgcacaa gggcaaatgg tacatcagtc    540

catgtcacct aggactttaa atgcatgggt gaaggtaata gaagaaaagg cttttagccc    600

agaggtaata cccatgtttt cagcattatc agagggagcc accccacaag atttaaatat    660

gatgctaaac atagtggggg gacaccaggc agcaatgcag atgttaaaag ataccatcaa    720

tgatgaagct gcagaatggg acagagtaca tccagtacat gcagggccta ttccaccagg    780

ccaaatgagg gaaccaaggg gaagtgacat agcaggaact actagtaccc ttcaagaaca    840

aataggatgg atgacaagta atccacctat cccagtggga gaaatctata aaagatggat    900

agtcctggga ttaaataaaa tagtaagaat gtatagccct accagcattt tggacataag    960

acaagggcca aaagaaccct ttagagatta tgtagacagg ttctttaaaa ctttgagagc   1020

tgaacaagct acgcaggagg taaaaaactg gatgacagaa accttgttgg tccaaaatgc   1080

gaatccagac tgcaagtcca ttttaagagc attaggacca ggggctacat tagaagaaat   1140

gatgacatca tgtcagggag tgggaggacc tggccataaa gcaagggttt tggctgaggc   1200

aatgagtcaa gtacaacaga ccaatgtaat gatgcagaga ggcaatttta gaggccagag   1260

aataataaag agcttcaaca gcggcaaaga aggacaccta gccagaaatt gcaaggctcc   1320

tagaaagaga ggcagctgga aagcggaaaa ggaaggacac caaatgaaag actgtactga   1380

aagacaggct aatttttag ggaaaatttg gccttcccac aaggggaggc caggaaattt   1440

tcctcagagc agaccagaac caacagcccc gccagcagag agctttggag tgggggaaga   1500

gataccctcc tctccgaagc aggagccgag ggacaaggga ctatatcctc ccttaacttc   1560

cctcaaatca ctctttggca acgaccagta gtcacagtaa gaatagggg acagccaata   1620

gaagccctat tagacacagg agcagatgat acagtattag aagaaataag tttaccagga   1680

aaatggaaac caaaaatgat agggggaatt ggaggtttta tcaaagtaag acagtatgat   1740

cagatatcta tagaaatttg tggaaaaagg gccataggta cagtattagt aggacctaca   1800

cctgtcaaca taattggacg aaatatgatg actcagattg gttgtacttt aaattttcca   1860

attagtccta ttgaaactgt gccagtaaaa ttaaagtcag gaatggatgg cccaaaggtt   1920

aaacaatggc cattgacaga agaaaaaata aaagcattaa aagaaatttg tgcagagatg   1980

gaaaaggaag gaaaaatttc aaaaattggg cctgaaaacc catacaatac tccaatattt   2040

gccataaaga aaaaagatag tactaaatgg agaaaattag tagatttcag agaactcaat   2100

aagagaactc aagacttctg ggaggtccaa ttaggaatac ctcatcctgc gggattaaaa   2160
```

```
aagaaaaaat cagtaacagt actagatgtg gggatgcat atttttcagt tcccttagat   2220
gaagacttta gaaaatatac tgcattcacc atacctagtt taaataatga gacaccaggg   2280
attagatatc agtacaatgt actcccacag ggatggaaag gatcaccagc aatatttcag   2340
gcaagcatga caaaaatctt agagcccttt agagcaaaaa atccagagat agtgatctac   2400
caatatatga acgatttata tgtaggatct gacttagaaa tagggcagca tagagcaaaa   2460
atagaggagt tgagagaaca tctattgaaa tggggattta ccacaccaga caaaaaacat   2520
cagaaagaac ctccatttct ttggatggga tatgaactcc atcctgacaa atggacagtc   2580
cagcctatac agctgccaga aaaagacagc tggactgtca atgatataca aaaattagtg   2640
ggaaaactaa ataccgcaag tcagatttat gcaggaatta aagtaaagca attgtgtaga   2700
ctcctcaggg gagccaaagc gctaacagat gtagtaacac tgactgagga agcagaatta   2760
gaattggcag agaacaggga aattctaaaa gaacctgtac atggagtata ttatgaccca   2820
acaaaagact tagtggcaga aatacagaaa caagggcaag atcaatggac atatcaaatt   2880
tatcaagagc catttaaaaa tctaaagaca ggaaaatatg caaaaaagag gtcggcccac   2940
actaatgatg taaaacaatt aacagaggta gtgcagaaaa tagccataga aagcatagta   3000
atatggggaa agacccctaa atttagacta cccatacaaa gagaaacatg ggaagcatgg   3060
tggatggagt attggcaggc tacctggatt cctgaatggg agtttgtcaa tacccctcct   3120
ctagtaaaat tatggtacca gttagagaag gaccccataa tgggagcaga aactttctat   3180
gtagatgggg cagctaatag ggagactaag ctaggaaaag cagggtatgt cactgacaga   3240
ggaagacaaa aggttgtttc cctaattcag acaacaaatc aaaagactca gttacatgca   3300
attcatctag ccttgcagga ttcaggatca gaagtaaata tagtaacaga ctcacagtat   3360
gcattaggaa tcattcaggc acaaccagac aggagtgaat cagagttagt caatcaaata   3420
atagagaaac taatagaaaa ggacaaagtc tacctgtcat gggtaccagc acacaaaggg   3480
attggaggaa atgaacaagt agataaatta gtcagtagtg gaatcagaaa ggtactattt   3540
ttagatggaa tagataaagc ccaagatgaa cattagaatt ctgcaacagc tactgtttgt   3600
tcatttcaga attgggtgtc aacatagcag aataggcatt attccaggga gaagaggcag   3660
gaatggagct ggtagatcct agcctagagc cctggaacca cccgggaagt cagcctacaa   3720
ctgcttgtag caagtgttac tgtaaaaaat gctgctggca ttgccaattg tgctttctga   3780
acaagggctt aggcatctcc tatggcagga agaagcggag acgccgacga ggaactcctc   3840
aggaccgtca ggttcatcaa aatcctgtac caaaacagta agtagtagta attagtatat   3900
gtgatgcaat ctttacaaat agctgcaata gtaggactag tagtagcatc catagtagcc   3960
atagttgtgt ggtccatagt atttatagaa tatagaaaaa taaggaaaca gaagaaaata   4020
gacaggttac ttgagagaat aagagaaaga gcagaagata gtggcaatga gagtgatggg   4080
gatacagaag aattatccac tcttatggag agggggtatg acaatatttt ggttaatgat   4140
gatttgtaat gctgaaaagt tgtgggtcac agtctactat ggggtacctg tgtggagaga   4200
cgcagagacc accctattct gtgcatcaga tgctaaagca tatgacaaag aagcacacaa   4260
tgtctgggct acgcatgcct gcgtacccac agaccctgac ccacaagaat tacctttggt   4320
aaatgtaaca gaagagttta acatgtggaa aaataatatg gtagaacaga tgcatgaaga   4380
tataattagt ctatgggacc aaagcttaaa gccatgtgta cagctaaccc ctctctgcgt   4440
tactttaggg tgtgctgacg ctcaaaacgt caccgacacc aacaccacca tatctaatga   4500
```

```
aatgcaaggg gaaataaaaa actgctcttt caatatgacc acagaattaa gagataagaa   4560
gcagaaagtg tatgcacttt tttatagacc tgatgtaata gaaattaata aaactaagat   4620
taacaatagt aatagtagtc agtatatgtt aataaattgt aatacctcaa ccattacaca   4680
gacttgtcca aaggtatcct ttgagccaat tcccatacat tattgtgccc cagctggttt   4740
tgcaattcta aagtgtaatg atacggagtt cagtggaaaa gggacatgca agagtgtcag   4800
cacagtacaa tgcacacatg gaatcaagcc agtagtatca actcaactgc tgttaaatgg   4860
cagtctagca gaaggaaaga tagcgattag atctgagaat atctcaaaca atgccaaaac   4920
tataatagta caattgactg agcctgtaga aattaattgt atcagacctg gcaacaatac   4980
aagaaaaagt gtacgcatag gaccaggaca aacattctat gcaacaggtg acataatagg   5040
agatataaga caagcacact gtaatgttag taaaatagca tgggaagaaa ctttacaaaa   5100
ggtagctgca caattaagga agcactttca gaatgccaca ataaaattta ctaaacactc   5160
aggaggggat ttagaaatta caacaaatag ttttaattgt ggaggagaat tttctattg   5220
caatacaaca aagctgttta atagcacttg gaataatgat aactcaaacc tcacagagga   5280
aaagagaaag gaaaacataa ctctccactg cagaataaag caaattgtaa atatgtggcc   5340
aagagtagga caagcaatat atgcccctcc catcccagga aacataactt gtggatcaaa   5400
cattactggg ctactattaa caagagatgg agggaataat ggtacaaatg atactgagac   5460
cttcaggcct ggaggaggag atatgaggga caattggaga agtgaattat ataaatataa   5520
agtagtaaaa attgaaccac taggtgtagc accaacccct gcaaaaagaa gagtggtgga   5580
aagagaaaaa agagcagttg gaatgggagc tttgatcttt gagttcttag gagcagcagg   5640
aagcactatg ggcgcggcgt caatggcgct gacggtacag gccagacaat tattgtctgg   5700
tatagtgcaa cagcagagca atctgctgaa ggctatagag gctcaacaac atctgttgag   5760
actcacggtc tggggcatta aacagctcca ggcaagagtc ctggctctgg aaagatacct   5820
aaaggatcaa cagctcctag gaatttgggg ctgctctgga aaactcattt gcaccactgc   5880
tgtaccttgg aactctagct ggagtaataa aagttataat gacatatggg ataacatgac   5940
ctggctgcaa tgggataaag aaattaacaa ttacacatac ataatatata atctacttga   6000
aaaatcgcag aaccagcagg aaattaatga acaagactta ttggcattag acaagtgggc   6060
aagtctgtgg aattggtttg acataacaag ctggctatgg tatataagat taggtataat   6120
gatagtagga ggcgtaatag gcttaagaat aatttttgct gtgcttacta tagtgaatag   6180
agttaggcag ggatactcac ctttgtcatt ccagaccctt gcccaccacc agagggaacc   6240
cgacaggccc gaaagaatcg aagaaggagg tggcgagcaa gacagagaga gatccgtgcg   6300
cttagtgagc ggattcttag cacttgcctg ggaagatctg cggagcctgt gcctcttcag   6360
ctaccgccga ttgagagact tagtcttgat tgcagcaagg actgtggaac tcctgggaca   6420
cagcagtctc aagggactga gactggggtg ggaagccctc aaatatctgt ggaaccttct   6480
atcatactgg ggtcaggaac taaagaatag tgctattaat ttgcttgata caatagcaat   6540
agcagtagct aactggacag atagagttat aaaaatagta caaagaactg gtagagctat   6600
tcttaacata cctagaagga tcagataggg ctagccccgg gtgataaacg gaccgcgcaa   6660
tccctaggct gtgccttcta gttgccagcc atctgttgtt tgcccctccc ccgtgccttc   6720
cttgaccctg gaaggtgcca ctcccactgt cctttcctaa taaaatgagg aaattgcatc   6780
gcattgtctg agtaggtgtc attctattct ggggggtggg gtggggcagg acagcaaggg   6840
ggaggattgg gaagacaata gcaggcatgc tggggatgcg gtgggctcta tataaaaaac   6900
```

```
gcccggcggc aaccgagcgt tctgaacgct agagtcgaca aattcagaag aactcgtcaa   6960
gaaggcgata gaaggcgatg cgctgcgaat cgggagcggc gataccgtaa agcacgagga   7020
agcggtcagc ccattcgccg ccaagctctt cagcaatatc acgggtagcc aacgctatgt   7080
cctgatagcg gtctgccaca cccagccggc cacagtcgat gaatccagaa aagcggccat   7140
tttccaccat gatattcggc aagcaggcat cgccatgggt cacgacgaga tcctcgccgt   7200
cgggcatgct cgccttgagc ctggcgaaca gttcggctgg cgcgagcccc tgatgctctt   7260
cgtccagatc atcctgatcg acaagaccgg cttccatccg agtacgtgct cgctcgatgc   7320
gatgtttcgc ttggtggtcg aatgggcagg tagccggatc aagcgtatgc agccgccgca   7380
ttgcatcagc catgatggat actttctcgg caggagcaag gtgagatgac aggagatcct   7440
gccccggcac ttcgcccaat agcagccagt cccttcccgc ttcagtgaca acgtcgagca   7500
cagctgcgca aggaacgccc gtcgtggcca gccacgatag ccgcgctgcc tcgtcttgca   7560
gttcattcag ggcaccggac aggtcggtct tgacaaaaag aaccgggcgc ccctgcgctg   7620
acagccggaa cacggcggca tcagagcagc cgattgtctg ttgtgcccag tcatagccga   7680
atagcctctc cacccaagcg gccggagaac ctgcgtgcaa tccatcttgt tcaatcatgc   7740
gaaacgatcc tcatcctgtc tcttgatcag atcttgatcc cctgcgccat cagatccttg   7800
gcggcaagaa agccatccag tttactttgc agggcttccc aaccttacca gagggcgccc   7860
cagctggcaa ttccggttcg cttgctgtcc ataaaaccgc ccagtctagc tatcgccatg   7920
taagcccact gcaagctacc tgctttctct ttgcgcttgc gttttccctt gtccagatag   7980
cccagtagct gacattcatc cggggtcagc accgtttctg cggactggct ttctacgtga   8040
aaaggatcta ggtgaagatc ctttttgata atctcatgac caaaatccct taacgtgagt   8100
tttcgttcca ctgagcgtca gaccccgtag aaaagatcaa aggatcttct tgagatcctt   8160
tttttctgcg cgtaatctgc tgcttgcaaa caaaaaaacc accgctacca gcggtggttt   8220
gtttgccgga tcaagagcta ccaactcttt ttccgaaggt aactggcttc agcagagcgc   8280
agataccaaa tactgttctt ctagtgtagc cgtagttagg ccaccacttc aagaactctg   8340
tagcaccgcc tacatacctc gctctgctaa tcctgttacc agtggctgct gccagtggcg   8400
ataagtcgtg tcttaccggg ttggactcaa gacgatagtt accggataag gcgcagcggt   8460
cgggctgaac ggggggttcg tgcacacagc ccagcttgga gcgaacgacc tacaccgaac   8520
tgagatacct acagcgtgag ctatgagaaa gcgccacgct tcccgaaggg agaaaggcgg   8580
acaggtatcc ggtaagcggc agggtcggaa caggagagcg cacgagggag cttccagggg   8640
gaaacgcctg gtatctttat agtcctgtcg ggtttcgcca cctctgactt gagcgtcgat   8700
ttttgtgatg ctcgtcaggg gggcggagcc tatggaaaaa cgccagcaac gcggcccttt   8760
tacggttcct ggccttttgc tggccttttg ctcacatgtt gtcgacaata ttggctattg   8820
gccattgcat acgttgtatc tatatcataa tatgtacatt tatattggct catgtccaat   8880
atgaccgcca tgttgacatt gattattgac tagttattaa tagtaatcaa ttacgggttc   8940
attagttcat agcccatata tggagttccg cgttacataa cttacggtaa atggcccgcc   9000
tggctgaccg cccaacgacc cccgcccatt gacgtcaata atgacgtatg ttcccatagt   9060
aacgccaata gggactttcc attgacgtca atgggtggag tatttacggt aaactgccca   9120
cttggcagta catcaagtgt atcatatgcc aagtccgccc cctattgacg tcaatgacgg   9180
taaatggccc gcctggcatt atgcccagta catgacctta cgggactttc ctacttggca   9240
```

```
gtacatctac ggtattagtc atcggctatt accatggtga tgcggttttg gcagtacacc   9300

aatgggcgtg gatagcggtt tgactcacgg ggatttccaa gtctccaccc cattgacgtc   9360

aatgggagtt tgttttggca ccaaaatcaa cgggactttc caaaatgtcg taataacccc   9420

gccccgttga cgcaaatggg cggtaggcgt gtacggtggg aggtctatat aagcagagct   9480

cgtttagtga accgtcagat cgcctggaga cgccatccac gctgttttga cctccataga   9540

agacaccggg accgatccag cctccgcggc cgggaacggt gcattggaac gcggattccc   9600

cgtgccaaga gtgacgtaag taccgcctat agactctata ggcacacccc tttggctctt   9660

atgcatgcta tactgttttt ggcttggggc ctatacaccc ccgcttcctt atgctatagg   9720

tgatggtata gcttagccta taggtgtggg ttattgacca ttattgacca ctcccctatt   9780

ggtgacgata ctttccatta ctaatccata acatggctct ttgccacaac tatctctatt   9840

ggctatatgc caatactctg tccttcagag actgacacgg actctgtatt tttacaggat   9900

ggggtcccat ttattattta caaattcaca tatacaacaa cgccgtcccc cgtgcccgca   9960

gtttttatta aacatagcgt gggatctcca cgcgaatctc gggtaccgtg ttccggacat  10020

gggytcttct ccggtagcgg cggagcttcc acatccgagc cctggtccca tgcctccagc  10080

ggctcatggt cgctcggcag ctccttgctc ctaacagtgg aggccagact taggcacagc  10140

acaatgccca ccaccaccag tgtgccgcac aaggccgtgg cggtagggta tgtgtctgaa  10200

aatgagctcg gagattgggc tcgcaccgct gacgcagatg gaagacttaa ggcagcggca  10260

gaagaagatg caggcagctg agttgttgta ttctgataag agtcagaggt aactcccgtt  10320

gcggtgctgt taacggtgga gggcagtgta gtctgagcag tactcgttgc tgccgcgcgc  10380

gccaccagac ataatagctg acagactaac agactgttcc tttccatggg tcttttctgc  10440

agtcacc                                                            10447
```

```
<210> SEQ ID NO 14
<211> LENGTH: 10466
<212> TYPE: DNA
<213> ORGANISM: Artificial Sequence
<220> FEATURE:
<223> OTHER INFORMATION: Synthetically generated vector
      sequence-pGA1/IN3

<400> SEQUENCE: 14
```

```
ggatccggct tgctgaagtg cactcggcaa gaggcgaggg gtggcggctg gtgagtacgc     60

caaattttat ttgactagcg gaggctagaa ggagagagat gggtgcgaga gcgtcaatat    120

taagaggggg aaaattagat aaatgggaaa agattaggtt aaggccaggg ggaaagaaac    180

actatatgct aaaacaccta gtatgggcaa gcagggagct ggaaagattt gcacttaacc    240

ctggcctttt agagacatca gaaggctgta aacaaataat aaaacagcta caaccagctc    300

ttcagacagg aacagaggaa cttaggtcat tattcaatgc agtagcaact ctctattgtg    360

tacatgcaga catagaggta cgagacacca aagaagcatt agacaagata gaggaagaac    420

aaaacaaaag tcagcaaaaa acgcagcagg caaaagaggc tgacaaaaag gtcgtcagtc    480

aaaattatcc tatagtgcag aatcttcaag ggcaaatggt acaccaggca ctatcaccta    540

gaactttgaa tgcatgggta aaagtaatag aagaaaaagc ctttagcccg gaggtaatac    600

ccatgttcac agcattatca gaaggagcca ccccacaaga tttaaacacc atgttaaata    660

ccgtgggggg acatcaagca gccatgcaaa tgttaaaaga taccatcaat gaggaggctg    720

cagaatggga tagattacat ccagtacatg cagggcctgt tgcaccaggc caaatgagag    780
```

```
aaccaagggg aagtgacata gcaggaacta ctagtaacct tcaggaacaa atagcatgga    840

tgacaagtaa cccacctatt ccagtgggag atatctataa aagatggata attctggggt    900

taaataaaat agtaagaatg tatagccctg tcagcatttt agacataaga caagggccaa    960

aggaaccctt tagagattat gtagaccggt tctttaaaac tttaagagct gaacaagctt   1020

cacaagatgt aaaaaattgg atggcagaca ccttgttggt ccaaaatgcg aacccagatt   1080

gtaagaccat tttaagagca ttaggaccag gagctacatt agaagaaatg atgacagcat   1140

gtcaaggagt gggaggacct agccacaaag caagagtgtt ggctgaggca atgagccaaa   1200

caggcagtac cataatgatg cagagaagca attttaaagg ctctaaaaga actgttaaat   1260

ccttcaactc tggcaaggaa gggcacatag ctagaaattg cagggcccct aggaaaaaag   1320

gctcttggaa atctggaaag gaaggacacc aaatgaaaga ctgtgctgag aggcaggcta   1380

atttttttagg gaaaatttgg ccttcccaca aggggaggcc agggaatttc cttcagaaca   1440

ggccagagcc aacagcccca ccagcagaga gcttcaggtt cgaggagaca acccctgctc   1500

cgaagcagga gctgaaagac agggaaccct taacctccct caaatcactc tttggcagcg   1560

acccccttgtc tcaataaaaa tagggggcca gataaaggag gctctcttag ccacaggagc   1620

agatgataca gtattagaag aaatgaattt gccaggaaaa tggaaaccaa aaatgatagg   1680

aggaattgga ggttttatca aagtaagaca gtatgatcaa atacttatag aaatttgtgg   1740

aaaaaaggct ataggtacag tattagtagg acccacacct gtcaacataa ttggaagaaa   1800

tatgctgact cagattggat gcacgctaaa ttttccaatt agtcccattg aaactgtacc   1860

agtaaaatta aagccaggaa tggatggccc aaaggttaaa caatggccat tgacagagga   1920

gaaaataaaa gcattaacag caatttgtga tgaaatggag aaggaaggaa aaattacaaa   1980

aattgggcct gaaaatccat ataacactcc aatattcgcc ataaaaaaga aggacagtac   2040

taagtggaga aaattagtag atttcagaga acttaataaa agaactcaag acttctggga   2100

agttcaatta ggaataccac acccagcagg gttaaaaaag aaaaaatcag tgacagtact   2160

agatgtgggg gatgcatatt tttcagttcc tttagatgaa agctttagga ggtatactgc   2220

attcaccata cctagtagaa acaatgaaac accagggatt agatatcaat ataatgtgct   2280

tccacaagga tggaaaggat caccagcaat attccagagt agcatgacaa aaatcttaga   2340

gccctttaga gcacaaaatc cagaaatagt catctatcaa tatatgaatg acttgtatgt   2400

aggatctgac ttagaaatag ggcaacatag agcaaagata gaggaattaa gagaacatct   2460

attaaggtgg ggatttacca caccagacaa gaaacatcag aaagaacccc catttctttg   2520

gatggggtat gaactccatc ctgacaaatg gacagtacag cctatacagc tgccagaaaa   2580

ggagagctgg actgtcaatg atatacagaa gttagtggga aaattaaaca cggcaagcca   2640

gatttaccca gggattaaag taagacaact ttgtagactc cttagagggg ccaaagcact   2700

aacagacata gtaccactaa ctgaagaagc agaattagaa ttggcagaga acagggaaat   2760

tctaaaagaa ccagtacatg gagtatatta tgacccttca aaagacttga tagctgaaat   2820

acagaaacag ggacatgacc aatggacata tcaaatttac caagaaccat tcaaaaatct   2880

gaaaacaggg aagtatgcaa aaatgaggac tgcccacact aatgatgtaa aacggttaac   2940

agaggcagtg caaaaaatag ccttagaaag catagtaata tggggaaaga ttcctaaact   3000

taggttaccc atccaaaaag aaacatggga gacatggtgg actgactatt ggcaagccac   3060

ctggattcct gagtgggaat ttgttaatac tcctccccta gtaaaattat ggtaccagct   3120

agagaaggaa cccataatag gagtagaaac tttctatgta gatggagcag ctaataggga   3180
```

```
aaccaaaata ggaaaagcag ggtatgttac tgacagagga aggcagaaaa ttgtttctct   3240
aactgaaaca acaaatcaga agactcaatt acaagcaatt tatctagctt tgcaagattc   3300
aggatcagaa gtaaacatag taacagactc acagtatgca ttaggaatta ttcaagcaca   3360
accagataag agtgaatcag ggttagtcaa ccaaataata gaacaattaa taaaaaagga   3420
aagggtctac ctgtcatggg taccagcaca taaaggtatt ggaggaaatg aacaagtaga   3480
caaattagta agtagtggaa tcaggagagt gctataataa gctcgagata cttggacagg   3540
agttgaaact atcataagaa tgctgcaaca actactgttt attcatttca gaattgggtg   3600
ccagcatagc agaataggca ttatgagaca gagaagagca agaaatggag ccagtagatc   3660
ctaacctaga gccctggaac catccaggaa gtcagcctga aactgcttgc aataactgtt   3720
attgtaaacg ctatagctac cattgtctag tttgctttca gagaaaaggc ttaggcattt   3780
cctatggcag gaagaagcgg agacagcgac gaagcgctcc tcagagcagt gaggatcatc   3840
agaattttgt atcaaagcag taagtatctg taatgttaga tttagattat aaattagcag   3900
taggagcatt tatagtagca ctactcatag caatagttgt gtggaccata gtatttatag   3960
aatataggaa attgttaaga caaagaaaaa tagactggtt aattaaaaga attagggaaa   4020
gagcagaaga cagtggcaat gagagtgaag ggatactga ggaattatcg acaatggtgg   4080
atatggggca tcttaggctt ttggatgtta atgatttgta atggaaactt gtgggtcaca   4140
gtctattatg ggtacctgt gtggaaagaa gcaaaaacta ctctattctg tgcatcaaat   4200
gctaaagcat atgagaaaga agtacataat gtctgggcta cacatgcctg tgtacccaca   4260
gaccccaacc cacaagaaat ggttttggaa aacgtaacag aaaattttaa catgtggaaa   4320
aatgacatgg tgaatcagat gcatgaggat gtaatcagct tatgggatca aagcctaaag   4380
ccatgtgtaa agttgacccc actctgtgtc actttagaat gtagaaaggt taatgctacc   4440
cataatgcta ccaataatgg ggatgctacc cataatgtta ccaataatgg gcaagaaata   4500
caaaattgct ctttcaatgc aaccacagaa ataagagata ggaagcagag agtgtatgca   4560
ctttttata gacttgatat agtaccactt gataagaaca actctagtaa gaacaactct   4620
agtgagtatt atagattaat aaattgtaat acctcagcca taacacaagc atgtccaaag   4680
gtcagttttg atccaattcc tatacactat tgtgctccag ctggttatgc gattctaaag   4740
tgtaacaata agacattcaa tgggacagga ccatgcaata atgtcagcac agtacaatgt   4800
acacatggaa ttaagccagt ggtatcaact cagctattgt taaacggtag cctagcagaa   4860
ggagagataa taattagatc tgaaaatctg acagacaatg tcaaaacaat aatagtacat   4920
cttgatcaat ctgtagaaat tgtgtgtaca agacccaaca ataatacaag aaaaagtata   4980
aggatagggc caggacaaac attctatgca acaggaggca taatagggaa catacgacaa   5040
gcacattgta acattagtga agacaaatgg aatgaaactt tacaaagggt gggtaaaaaa   5100
ttagtagaac acttccctaa taagacaata aaatttgcac catcctcagg aggggaccta   5160
gaaattacaa cacatagctt taattgtaga ggagaatttt tctattgcag cacatcaaga   5220
ctgtttaata gtacatacat gcctaatgat acaaaaagta agtcaaacaa aaccatcaca   5280
atcccatgca gcataaaaca aattgtaaac atgtggcagg aggtaggacg agcaatgtat   5340
gcccctccca ttgaaggaaa cataacctgt agatcaaata tcacaggaat actattggta   5400
cgtgatggag gagtagattc agaagatcca gaaaataata agacagagac attccgacct   5460
ggaggaggag atatgaggaa caattggaga agtgaattat ataaatataa agcggcagaa   5520
```

```
attaagccat tgggagtagc acccactcca gcaaaaagga gagtggtgga gagagaaaaa   5580
agagcagtag gattaggagc tgtgttcctt ggattcttgg gagcagcagg aagcactatg   5640
ggcgcagcgt caataacgct gacggtacag gccagacaat tgttgtctgg tatagtgcaa   5700
cagcaaagca atttgctgag ggctatcgag gcgcaacagc atctgttgca actcacggtc   5760
tggggcatta agcagctcca gacaagagtc ctggctatcg aaagatacct aaaggatcaa   5820
cagctcctag ggctttgggg ctgctctgga aaactcatct gcaccactaa tgtaccttgg   5880
aactccagtt ggagtaacaa atctcaaaca gatatttggg aaaacatgac ctggatgcag   5940
tgggataaag aagttagtaa ttacacagac acaatataca ggttgcttga agactcgcaa   6000
acccagcagg aaagaaatga aaaggattta ttagcattgg acaattggaa aaatctgtgg   6060
aattggttta gtataacaaa ctggctgtgg tatataaaaa tattcataat gatagtagga   6120
ggcttgatag gcttaagaat aatttttgct gtgctttcta tagtgaatag agttaggcag   6180
ggatactcac ctttgtcgtt tcagaccctt accccaaacc caaggggacc cgacaggctc   6240
ggaagaatcg aagaagaagg tggagggcaa gacagagaca gatcgattcg attagtgaac   6300
ggattcttag cacttgcctg ggacgacctg tggagcctgt gcctcttcag ctaccaccga   6360
ttgagagact taatattggt gacagcgaga gcggtggaac ttctgggaca cagcagtctc   6420
aggggactac agagggggtg ggaagccctt aagtatctgg gaggtattgt gcagtattgg   6480
ggtctggaac taaaaaagag ggctattagt ctgcttgata ctgtagcaat agcagtagct   6540
gaaggcacag ataggattat agaattcctc caaagaattt gtagagctat ccgcaacata   6600
cctagaagga taagacaggg ctttgaagca gctttgcagt aaaatggcta gccccgggtg   6660
ataaacggac cgcgcaatcc ctaggctgtg ccttctagtt gccagccatc tgttgtttgc   6720
ccctcccccg tgccttcctt gaccctggaa ggtgccactc ccactgtcct ttcctaataa   6780
aatgaggaaa ttgcatcgca ttgtctgagt aggtgtcatt ctattctggg gggtggggtg   6840
gggcaggaca gcaaggggga ggattgggaa gacaatagca ggcatgctgg ggatgcggtg   6900
ggctctatat aaaaaacgcc cggcggcaac cgagcgttct gaacgctaga gtcgacaaat   6960
tcagaagaac tcgtcaagaa ggcgatagaa ggcgatgcgc tgcgaatcgg gagcggcgat   7020
accgtaaagc acgaggaagc ggtcagccca ttcgccgcca agctcttcag caatatcacg   7080
ggtagccaac gctatgtcct gatagcggtc tgccacaccc agccggccac agtcgatgaa   7140
tccagaaaag cggccatttt ccaccatgat attcggcaag caggcatcgc catgggtcac   7200
gacgagatcc tcgccgtcgg gcatgctcgc cttgagcctg gcgaacagtt cggctggcgc   7260
gagcccctga tgctcttcgt ccagatcatc ctgatcgaca agaccggctt ccatccgagt   7320
acgtgctcgc tcgatgcgat gtttcgcttg gtggtcgaat gggcaggtag ccggatcaag   7380
cgtatgcagc cgccgcattg catcagccat gatggatact ttctcggcag gagcaaggtg   7440
agatgacagg agatcctgcc ccggcacttc gcccaatagc agccagtccc ttcccgcttc   7500
agtgacaacg tcgagcacag ctgcgcaagg aacgcccgtc gtggccagcc acgatagccg   7560
cgctgcctcg tcttgcagtt cattcagggc accggacagg tcggtcttga caaaaagaac   7620
cgggcgcccc tgcgctgaca gccggaacac ggcggcatca gagcagccga ttgtctgttg   7680
tgcccagtca tagccgaata gcctctccac ccaagcggcc ggagaacctg cgtgcaatcc   7740
atcttgttca atcatgcgaa acgatcctca tcctgtctct tgatcagatc ttgatcccct   7800
gcgccatcag atccttggcg gcaagaaagc catccagttt actttgcagg gcttcccaac   7860
cttaccagag ggcgccccag ctggcaattc cggttcgctt gctgtccata aaaccgccca   7920
```

```
gtctagctat cgccatgtaa gcccactgca agctacctgc tttctctttg cgcttgcgtt   7980
ttcccttgtc cagatagccc agtagctgac attcatccgg ggtcagcacc gtttctgcgg   8040
actggctttc tacgtgaaaa ggatctaggt gaagatcctt tttgataatc tcatgaccaa   8100
aatcccttaa cgtgagtttt cgttccactg agcgtcagac cccgtagaaa agatcaaagg   8160
atcttcttga gatccttttt ttctgcgcgt aatctgctgc ttgcaaacaa aaaaaccacc   8220
gctaccagcg gtggtttgtt tgccggatca agagctacca actctttttc cgaaggtaac   8280
tggcttcagc agagcgcaga taccaaatac tgttcttcta gtgtagccgt agttaggcca   8340
ccacttcaag aactctgtag caccgcctac atacctcgct ctgctaatcc tgttaccagt   8400
ggctgctgcc agtggcgata agtcgtgtct taccgggttg gactcaagac gatagttacc   8460
ggataaggcg cagcggtcgg gctgaacggg gggttcgtgc acacagccca gcttggagcg   8520
aacgacctac accgaactga gatacctaca gcgtgagcta tgagaaagcg ccacgcttcc   8580
cgaagggaga aaggcggaca ggtatccggt aagcggcagg gtcggaacag gagagcgcac   8640
gagggagctt ccagggggaa acgcctggta tctttatagt cctgtcgggt ttcgccacct   8700
ctgacttgag cgtcgatttt tgtgatgctc gtcagggggg cggagcctat ggaaaaacgc   8760
cagcaacgcg gcctttttac ggttcctggc cttttgctgg ccttttgctc acatgttgtc   8820
gacaatattg gctattggcc attgcatacg ttgtatctat atcataatat gtacatttat   8880
attggctcat gtccaatatg accgccatgt tgacattgat tattgactag ttattaatag   8940
taatcaatta cgggttcatt agttcatagc ccatatatgg agttccgcgt tacataactt   9000
acggtaaatg gcccgcctgg ctgaccgccc aacgaccccc gcccattgac gtcaataatg   9060
acgtatgttc ccatagtaac gccaataggg actttccatt gacgtcaatg ggtggagtat   9120
ttacggtaaa ctgcccactt ggcagtacat caagtgtatc atatgccaag tccgccccct   9180
attgacgtca atgacggtaa atggcccgcc tggcattatg cccagtacat gaccttacgg   9240
gactttccta cttggcagta catctacggt attagtcatc ggctattacc atggtgatgc   9300
ggttttggca gtacaccaat gggcgtggat agcggtttga ctcacgggga tttccaagtc   9360
tccaccccat tgacgtcaat gggagtttgt tttggcacca aaatcaacgg gactttccaa   9420
aatgtcgtaa taaccccgcc ccgttgacgc aaatgggcgg taggcgtgta cggtgggagg   9480
tctatataag cagagctcgt ttagtgaacc gtcagatcgc ctggagacgc catccacgct   9540
gttttgacct ccatagaaga caccgggacc gatccagcct ccgcggccgg gaacggtgca   9600
ttggaacgcg gattccccgt gccaagagtg acgtaagtac cgcctataga ctctataggc   9660
acacccettt ggctcttatg catgctatac tgtttttggc ttggggccta tacacccccg   9720
cttccttatg ctataggtga tggtatagct tagcctatag gtgtgggtta ttgaccatta   9780
ttgaccactc ccctattggt gacgatactt tccattacta atccataaca tggctctttg   9840
ccacaactat ctctattggc tatatgccaa tactctgtcc ttcagagact gacacggact   9900
ctgtattttt acaggatggg gtcccattta ttatttacaa attcacatat acaacaacgc   9960
cgtcccccgt gcccgcagtt tttattaaac atagcgtggg atctccacgc gaatctcggg  10020
taccgtgttc cggacatggg ytcttctccg gtagcggcgg agcttccaca tccgagccct  10080
ggtcccatgc ctccagcggc tcatggtcgc tcggcagctc cttgctccta acagtggagg  10140
ccagacttag gcacagcaca atgcccacca ccaccagtgt gccgcacaag gccgtggcgg  10200
tagggtatgt gtctgaaaat gagctcggag attgggctcg caccgctgac gcagatggaa  10260
```

gacttaaggc agcggcagaa gaagatgcag gcagctgagt tgttgtattc tgataagagt 10320
cagaggtaac tcccgttgcg gtgctgttaa cggtggaggg cagtgtagtc tgagcagtac 10380
tcgttgctgc cgcgcgcgcc accagacata atagctgaca gactaacaga ctgttccttt 10440
ccatgggtct tttctgcagt caccat 10466

<210> SEQ ID NO 15
<211> LENGTH: 10466
<212> TYPE: DNA
<213> ORGANISM: Artificial Sequence
<220> FEATURE:
<223> OTHER INFORMATION: Synthetically generated vector sequence-pGA1/IN2

<400> SEQUENCE: 15
ggatccggct tgctgaagtg cactcggcaa gaggcgaggg gtggcggctg gtgagtacgc 60
caaattttat ttgactagcg gaggctagaa ggagagagat gggtgcgaga gcgtcaatat 120
taagaggggg aaaattagat aaatgggaaa agattaggtt aaggccaggg ggaaagaaac 180
actatatgct aaaacaccta gtatgggcaa gcagggagct ggaaagattt gcacttaacc 240
ctggcctttt agagacatca gaaggctgta aacaaataat aaaacagcta caaccagctc 300
ttcagacagg aacagaggaa cttaggtcat tattcaatgc agtagcaact ctctattgtg 360
tacatgcaga catagaggta cgagacacca aagaagcatt agacaagata gaggaagaac 420
aaaacaaaag tcagcaaaaa acgcagcagg caaaagaggc tgacaaaaag gtcgtcagtc 480
aaaattatcc tatagtgcag aatcttcaag ggcaaatggt acaccaggca ctatcaccta 540
gaactttgaa tgcatgggta aaagtaatag aagaaaaagc ctttagcccg gaggtaatac 600
ccatgttcac agcattatca gaaggagcca ccccacaaga tttaaacacc atgttaaata 660
ccgtgggggg acatcaagca gccatgcaaa tgttaaaaga taccatcaat gaggaggctg 720
cagaatggga tagattacat ccagtacatg cagggcctgt tgcaccaggc caaatgagag 780
aaccaagggg aagtgacata gcaggaacta ctagtaacct tcaggaacaa atagcatgga 840
tgacaagtaa cccacctatt ccagtgggag atatctataa aagatggata attctggggt 900
taaataaaat agtaagaatg tatagccctg tcagcatttt agacataaga caagggccaa 960
aggaaccctt tagagattat gtagaccggt tctttaaaac tttaagagct gaacaagctt 1020
cacaagatgt aaaaaattgg atggcagaca ccttgttggt ccaaaatgcg aacccagatt 1080
gtaagaccat tttaagagca ttaggaccag gagctacatt agaagaaatg atgacagcat 1140
gtcaaggagt gggaggacct agccacaaag caagagtgtt ggctgaggca atgagccaaa 1200
caggcagtac cataatgatg cagagaagca attttaaagg ctctaaaaga actgttaaat 1260
gcttcaactg tggcaaggaa gggcacatag ctagaaattg cagggcccct aggaaaaaag 1320
gctgttggaa atgtggaaag gaaggacacc aaatgaaaga ctgtgctgag aggcaggcta 1380
attttttagg gaaaatttgg ccttcccaca aggggaggcc agggaatttc cttcagaaca 1440
ggccagagcc aacagcccca ccagcagaga gcttcaggtt cgaggagaca acccctgctc 1500
cgaagcagga gctgaaagac agggaaccct taacctccct caaatcactc tttggcagcg 1560 acccettgtc tcaataaaaa tagggggcca gataaaggag gctctcttag acacaggagc 1620
agatgataca gtattagaag aaatgaattt gccaggaaaa tggaaaccaa aaatgatagg 1680
aggaattgga ggttttatca aagtaagaca gtatgatcaa atacttatag aaatttgtgg 1740
aaaaaaggct ataggtacag tattagtagg acccacacct gtcaacataa ttggaagaaa 1800

```
tatgctgact cagattggat gcacgctaaa ttttccaatt agtcccattg aaactgtacc   1860
agtaaaatta aagccaggaa tggatggccc aaaggttaaa caatggccat tgacagagga   1920
gaaaataaaa gcattaacag caatttgtga tgaaatggag aaggaaggaa aaattacaaa   1980
aattgggcct gaaaatccat ataacactcc aatattcgcc ataaaaaaga aggacagtac   2040
taagtggaga aaattagtag atttcagaga acttaataaa agaactcaag acttctggga   2100
agttcaatta ggaataccac acccagcagg gttaaaaaag aaaaaatcag tgacagtact   2160
agatgtgggg gatgcatatt tttcagttcc tttagatgaa agctttagga ggtatactgc   2220
attcaccata cctagtagaa acaatgaaac accagggatt agatatcaat ataatgtgct   2280
tccacaagga tggaaaggat caccagcaat attccagagt agcatgacaa aaatcttaga   2340
gccctttaga gcacaaaatc cagaaatagt catctatcaa tatatgaatg acttgtatgt   2400
aggatctgac ttagaaatag ggcaacatag agcaaagata gaggaattaa gagaacatct   2460
attaaggtgg ggatttacca caccagacaa gaaacatcag aaagaacccc catttctttg   2520
gatggggtat gaactccatc ctgacaaatg gacagtacag cctatacagc tgccagaaaa   2580
ggagagctgg actgtcaatg atatacagaa gttagtggga aaattaaaca cggcaagcca   2640
gatttaccca gggattaaag taagacaact ttgtagactc cttagagggg ccaaagcact   2700
aacagacata gtaccactaa ctgaagaagc agaattagaa ttggcagaga acagggaaat   2760
tctaaaagaa ccagtacatg gagtatatta tgacccttca aaagacttga tagctgaaat   2820
acagaaacag ggacatgacc aatggacata tcaaatttac caagaaccat tcaaaaatct   2880
gaaaacaggg aagtatgcaa aaatgaggac tgcccacact aatgatgtaa aacggttaac   2940
agaggcagtg caaaaaatag ccttagaaag catagtaata tggggaaaga ttcctaaact   3000
taggttaccc atccaaaaag aaacatggga gacatggtgg actgactatt ggcaagccac   3060
ctggattcct gagtgggaat ttgttaatac tcctccccta gtaaaattat ggtaccagct   3120
agagaaggaa cccataatag gagtagaaac tttctatgta gatggagcag ctaataggga   3180
aaccaaaata ggaaaagcag ggtatgttac tgacagagga aggcagaaaa ttgtttctct   3240
aactgaaaca acaaatcaga agactcaatt acaagcaatt tatctagctt tgcaagattc   3300
aggatcagaa gtaaacatag taacagactc acagtatgca ttaggaatta ttcaagcaca   3360
accagataag agtgaatcag ggttagtcaa ccaaataata gaacaattaa taaaaaagga   3420
aagggtctac ctgtcatggg taccagcaca taaaggtatt ggaggaaatg aacaagtaga   3480
caaattagta agtagtggaa tcaggagagt gctataataa gctcgagata cttggacagg   3540
agttgaaact atcataagaa tgctgcaaca actactgttt attcatttca gaattgggtg   3600
ccagcatagc agaataggca ttatgagaca gagaagagca agaaatggag ccagtagatc   3660
ctaacctaga gccctggaac catccaggaa gtcagcctga aactgcttgc aataactgtt   3720
attgtaaacg ctatagctac cattgtctag tttgctttca gagaaaaggc ttaggcattt   3780
cctatggcag gaagaagcgg agacagcgac gaagcgctcc tcagagcagt gaggatcatc   3840
agaattttgt atcaaagcag taagtatctg taatgttaga tttagattat aaattagcag   3900
taggagcatt tatagtagca ctactcatag caatagttgt gtggaccata gtatttatag   3960
aatataggaa attgttaaga caaagaaaaa tagactggtt aattaaaaga attagggaaa   4020
gagcagaaga cagtggcaat gagagtgaag ggggatactga ggaattatcg acaatggtgg   4080
atatggggca tcttaggctt ttggatgtta atgatttgta atggaaactt gtgggtcaca   4140
gtctattatg gggtacctgt gtggaaagaa gcaaaaacta ctctattctg tgcatcaaat   4200
```

```
gctaaagcat atgagaaaga agtacataat gtctgggcta cacatgcctg tgtacccaca   4260
gaccccaacc cacaagaaat ggttttggaa aacgtaacag aaaattttaa catgtggaaa   4320
aatgacatgg tgaatcagat gcatgaggat gtaatcagct tatgggatca aagcctaaag   4380
ccatgtgtaa agttgacccc actctgtgtc actttagaat gtagaaaggt taatgctacc   4440
cataatgcta ccaataatgg ggatgctacc cataatgtta ccaataatgg gcaagaaata   4500
caaaattgct ctttcaatgc aaccacagaa ataagagata ggaagcagag agtgtatgca   4560
ctttttata gacttgatat agtaccactt gataagaaca actctagtaa gaacaactct   4620
agtgagtatt atagattaat aaattgtaat acctcagcca taacacaagc atgtccaaag   4680
gtcagttttg atccaattcc tatacactat tgtgctccag ctggttatgc gattctaaag   4740
tgtaacaata agacattcaa tgggacagga ccatgcaata atgtcagcac agtacaatgt   4800
acacatggaa ttaagccagt ggtatcaact cagctattgt taaacggtag cctagcagaa   4860
ggagagataa taattagatc tgaaaatctg acagacaatg tcaaaacaat aatagtacat   4920
cttgatcaat ctgtagaaat tgtgtgtaca agacccaaca ataatacaag aaaaagtata   4980
aggatagggc caggacaaac attctatgca acaggaggca taataggaa catacgacaa   5040
gcacattgta acattagtga agacaaatgg aatgaaactt tacaaagggt gggtaaaaaa   5100
ttagtagaac acttccctaa taagacaata aaatttgcac catcctcagg aggggaccta   5160
gaaattacaa cacatagctt taattgtaga ggagaatttt tctattgcag cacatcaaga   5220
ctgtttaata gtacatacat gcctaatgat acaaaaagta agtcaaacaa aaccatcaca   5280
atcccatgca gcataaaaca aattgtaaac atgtggcagg aggtaggacg agcaatgtat   5340
gcccctccca ttgaaggaaa cataacctgt agatcaaata tcacaggaat actattggta   5400
cgtgatggag gagtagattc agaagatcca gaaaataata agacagagac attccgacct   5460
ggaggaggag atatgaggaa caattggaga agtgaattat ataaatataa agcggcagaa   5520
attaagccat tgggagtagc acccactcca gcaaaaagga gagtggtgga gagagaaaaa   5580
agagcagtag gattaggagc tgtgttcctt ggattcttgg gagcagcagg aagcactatg   5640
ggcgcagcgt caataacgct gacggtacag gccagacaat tgttgtctgg tatagtgcaa   5700
cagcaaagca atttgctgag ggctatcgag gcgcaacagc atctgttgca actcacggtc   5760
tggggcatta agcagctcca gacaagagtc ctggctatcg aaagatacct aaaggatcaa   5820
cagctcctag ggctttgggg ctgctctgga aaactcatct gcaccactaa tgtaccttgg   5880
aactccagtt ggagtaacaa atctcaaaca gatatttggg aaaacatgac ctggatgcag   5940
tgggataaag aagttagtaa ttacacagac acaatataca ggttgcttga agactcgcaa   6000
acccagcagg aaagaaatga aaaggattta ttagcattgg acaattggaa aaatctgtgg   6060
aattggttta gtataacaaa ctggctgtgg tatataaaaa tattcataat gatagtagga   6120
ggcttgatag gcttaagaat aatttttgct gtgctttcta tagtgaatag agttaggcag   6180
ggatactcac ctttgtcgtt tcagaccctt accccaaacc caaggggacc cgacaggctc   6240
ggaagaatcg aagaagaagg tggagggcaa gacagagaca gatcgattcg attagtgaac   6300
ggattcttag cacttgcctg ggacgacctg tggagcctgt gcctcttcag ctaccaccga   6360
ttgagagact taatattggt gacagcgaga gcggtggaac ttctgggaca cagcagtctc   6420
aggggactac agagggggtg ggaagccctt aagtatctgg gaggtattgt gcagtattgg   6480
ggtctggaac taaaaaagag ggctattagt ctgcttgata ctgtagcaat agcagtagct   6540
```

-continued

```
gaaggcacag ataggattat agaattcctc caaagaattt gtagagctat ccgcaacata   6600
cctagaagga taagacaggg ctttgaagca gctttgcagt aaaatggcta gccccgggtg   6660
ataaacggac cgcgcaatcc ctaggctgtg ccttctagtt gccagccatc tgttgtttgc   6720
ccctcccccg tgccttcctt gaccctggaa ggtgccactc ccactgtcct ttcctaataa   6780
aatgaggaaa ttgcatcgca ttgtctgagt aggtgtcatt ctattctggg gggtggggtg   6840
gggcaggaca gcaaggggga ggattgggaa gacaatagca ggcatgctgg ggatgcggtg   6900
ggctctatat aaaaaacgcc cggcggcaac cgagcgttct gaacgctaga gtcgacaaat   6960
tcagaagaac tcgtcaagaa ggcgatagaa ggcgatgcgc tgcgaatcgg gagcggcgat   7020
accgtaaagc acgaggaagc ggtcagccca ttcgccgcca agctcttcag caatatcacg   7080
ggtagccaac gctatgtcct gatagcggtc tgccacaccc agccggccac agtcgatgaa   7140
tccagaaaag cggccatttt ccaccatgat attcggcaag caggcatcgc catgggtcac   7200
gacgagatcc tcgccgtcgg gcatgctcgc cttgagcctg gcgaacagtt cggctggcgc   7260
gagcccctga tgctcttcgt ccagatcatc ctgatcgaca agaccggctt ccatccgagt   7320
acgtgctcgc tcgatgcgat gtttcgcttg gtggtcgaat gggcaggtag ccggatcaag   7380
cgtatgcagc cgccgcattg catcagccat gatggatact ttctcggcag gagcaaggtg   7440
agatgacagg agatcctgcc ccggcacttc gcccaatagc agccagtccc ttcccgcttc   7500
agtgacaacg tcgagcacag ctgcgcaagg aacgcccgtc gtggccagcc acgatagccg   7560
cgctgcctcg tcttgcagtt cattcagggc accggacagg tcggtcttga caaaaagaac   7620
cgggcgcccc tgcgctgaca gccggaacac ggcggcatca gagcagccga ttgtctgttg   7680
tgcccagtca tagccgaata gcctctccac ccaagcggcc ggagaacctg cgtgcaatcc   7740
atcttgttca atcatgcgaa acgatcctca tcctgtctct tgatcagatc ttgatcccct   7800
gcgccatcag atccttggcg gcaagaaagc catccagttt actttgcagg gcttcccaac   7860
cttaccagag ggcgccccag ctggcaattc cggttcgctt gctgtccata aaaccgccca   7920
gtctagctat cgccatgtaa gcccactgca agctacctgc tttctctttg cgcttgcgtt   7980
ttcccttgtc cagatagccc agtagctgac attcatccgg ggtcagcacc gtttctgcgg   8040
actggctttc tacgtgaaaa ggatctaggt gaagatcctt tttgataatc tcatgaccaa   8100
aatcccttaa cgtgagtttt cgttccactg agcgtcagac cccgtagaaa agatcaaagg   8160
atcttcttga gatccttttt ttctgcgcgt aatctgctgc ttgcaaacaa aaaaaccacc   8220
gctaccagcg gtggtttgtt tgccggatca agagctacca actctttttc cgaaggtaac   8280
tggcttcagc agagcgcaga taccaaatac tgttcttcta gtgtagccgt agttaggcca   8340
ccacttcaag aactctgtag caccgcctac atacctcgct ctgctaatcc tgttaccagt   8400
ggctgctgcc agtggcgata agtcgtgtct taccgggttg gactcaagac gatagttacc   8460
ggataaggcg cagcggtcgg gctgaacggg gggttcgtgc acacagccca gcttggagcg   8520
aacgacctac accgaactga gatacctaca gcgtgagcta tgagaaagcg ccacgcttcc   8580
cgaagggaga aaggcggaca ggtatccggt aagcggcagg gtcggaacag gagagcgcac   8640
gagggagctt ccagggggaa acgcctggta tctttatagt cctgtcgggt ttcgccacct   8700
ctgacttgag cgtcgatttt tgtgatgctc gtcagggggg cggagcctat ggaaaaacgc   8760
cagcaacgcg gcctttttac ggttcctggc cttttgctgg ccttttgctc acatgttgtc   8820
gacaatattg gctattggcc attgcatacg ttgtatctat atcataatat gtacatttat   8880
attggctcat gtccaatatg accgccatgt tgacattgat tattgactag ttattaatag   8940
```

```
taatcaatta cgggttcatt agttcatagc ccatatatgg agttccgcgt tacataactt   9000

acggtaaatg gcccgcctgg ctgaccgccc aacgaccccc gcccattgac gtcaataatg   9060

acgtatgttc ccatagtaac gccaataggg actttccatt gacgtcaatg ggtggagtat   9120

ttacggtaaa ctgcccactt ggcagtacat caagtgtatc atatgccaag tccgccccct   9180

attgacgtca atgacggtaa atggcccgcc tggcattatg cccagtacat gaccttacgg   9240

gactttccta cttggcagta catctacggt attagtcatc gctattacc atggtgatgc   9300

ggttttggca gtacaccaat gggcgtggat agcggtttga ctcacgggga tttccaagtc   9360

tccaccccat tgacgtcaat gggagtttgt tttggcacca aaatcaacgg gactttccaa   9420

aatgtcgtaa taaccccgcc ccgttgacgc aaatgggcgg taggcgtgta cggtgggagg   9480

tctatataag cagagctcgt ttagtgaacc gtcagatcgc ctggagacgc catccacgct   9540

gttttgacct ccatagaaga caccgggacc gatccagcct ccgcggccgg gaacggtgca   9600

ttggaacgcg gattccccgt gccaagagtg acgtaagtac cgcctataga ctctataggc   9660

acacccctt ggctcttatg catgctatac tgtttttggc ttggggccta tacacccccg   9720

cttccttatg ctataggtga tggtatagct tagcctatag gtgtgggtta ttgaccatta   9780

ttgaccactc ccctattggt gacgatactt tccattacta atccataaca tggctctttg   9840

ccacaactat ctctattggc tatatgccaa tactctgtcc ttcagagact gacacggact   9900

ctgtattttt acaggatggg gtcccattta ttatttacaa attcacatat acaacaacgc   9960

cgtcccccgt gcccgcagtt tttattaaac atagcgtggg atctccacgc gaatctcggg  10020

taccgtgttc cggacatggg ytcttctccg gtagcggcgg agcttccaca tccgagccct  10080

ggtcccatgc ctccagcggc tcatggtcgc tcggcagctc cttgctccta acagtggagg  10140

ccagacttag gcacagcaca atgcccacca ccaccagtgt gccgcacaag gccgtggcgg  10200

tagggtatgt gtctgaaaat gagctcggag attgggctcg caccgctgac gcagatggaa  10260

gacttaaggc agcggcagaa gaagatgcag gcagctgagt tgttgtattc tgataagagt  10320

cagaggtaac tcccgttgcg gtgctgttaa cggtggaggg cagtgtagtc tgagcagtac  10380

tcgttgctgc cgcgcgcgcc accagacata atagctgaca gactaacaga ctgttccttt  10440

ccatgggtct ttctgcagt caccat                                        10466
```

```
<210> SEQ ID NO 16
<211> LENGTH: 35
<212> TYPE: DNA
<213> ORGANISM: Artificial Sequence
<220> FEATURE:
<223> OTHER INFORMATION: Synthetically generated oligonucleotide

<400> SEQUENCE: 16

ataaaaaacg cccggcggca accgagcgtt ctgaa                                35


<210> SEQ ID NO 17
<211> LENGTH: 33
<212> TYPE: DNA
<213> ORGANISM: Artificial Sequence
<220> FEATURE:
<223> OTHER INFORMATION: Primer

<400> SEQUENCE: 17

gctgctgctg tgtggagaat tcttcgtttc ggc                                  33


<210> SEQ ID NO 18
```

<211> LENGTH: 33
<212> TYPE: DNA
<213> ORGANISM: Artificial Sequence
<220> FEATURE:
<223> OTHER INFORMATION: Primer

<400> SEQUENCE: 18
gccgaaacga agaattctcc acacagcagc agc 33

<210> SEQ ID NO 19
<211> LENGTH: 44
<212> TYPE: DNA
<213> ORGANISM: Artificial Sequence
<220> FEATURE:
<223> OTHER INFORMATION: Primer

<400> SEQUENCE: 19
ctgcagtcac catggatcct tgcactcgag gatgcaatga agag 44

<210> SEQ ID NO 20
<211> LENGTH: 44
<212> TYPE: DNA
<213> ORGANISM: Artificial Sequence
<220> FEATURE:
<223> OTHER INFORMATION: Primer

<400> SEQUENCE: 20
ctcttcattg catcctcgag tgcaaggatc catggtgact gcag 44

<210> SEQ ID NO 21
<211> LENGTH: 30
<212> TYPE: DNA
<213> ORGANISM: Artificial Sequence
<220> FEATURE:
<223> OTHER INFORMATION: Primer

<400> SEQUENCE: 21
ccgtcagatc gcatcgatac gccatccacg 30

<210> SEQ ID NO 22
<211> LENGTH: 30
<212> TYPE: DNA
<213> ORGANISM: Artificial Sequence
<220> FEATURE:
<223> OTHER INFORMATION: Primer

<400> SEQUENCE: 22
cgtggatggc gtatcgatgc gatctgacgg 30

<210> SEQ ID NO 23
<211> LENGTH: 44
<212> TYPE: DNA
<213> ORGANISM: Artificial Sequence
<220> FEATURE:
<223> OTHER INFORMATION: Primer

<400> SEQUENCE: 23
gaactcattc tatggatcct tgctcgagtg gatgcaatga agag 44

<210> SEQ ID NO 24
<211> LENGTH: 44
<212> TYPE: DNA
<213> ORGANISM: Artificial Sequence
<220> FEATURE:
<223> OTHER INFORMATION: Primer

<400> SEQUENCE: 24
ctcttcattg catccactcg agcaaggatc catagaatga gttc 44

<210> SEQ ID NO 25
<211> LENGTH: 29
<212> TYPE: DNA
<213> ORGANISM: Artificial Sequence
<220> FEATURE:
<223> OTHER INFORMATION: Primer

<400> SEQUENCE: 25
gagctctatc gatgcaggac tcggcttgc 29

<210> SEQ ID NO 26
<211> LENGTH: 31
<212> TYPE: DNA
<213> ORGANISM: Artificial Sequence
<220> FEATURE:
<223> OTHER INFORMATION: Primer

<400> SEQUENCE: 26
ggcaggtttt aatcgctagc ctatgctctc c 31

<210> SEQ ID NO 27
<211> LENGTH: 17
<212> TYPE: DNA
<213> ORGANISM: Artificial Sequence
<220> FEATURE:
<223> OTHER INFORMATION: Primer

<400> SEQUENCE: 27
gggcaggagt gctagcc 17

<210> SEQ ID NO 28
<211> LENGTH: 29
<212> TYPE: DNA
<213> ORGANISM: Artificial Sequence
<220> FEATURE:
<223> OTHER INFORMATION: Primer

<400> SEQUENCE: 28
ccacactact ttcggaccgc tagccaccc 29

<210> SEQ ID NO 29
<211> LENGTH: 32
<212> TYPE: DNA
<213> ORGANISM: Artificial Sequence
<220> FEATURE:
<223> OTHER INFORMATION: Primer

<400> SEQUENCE: 29
ggttaagagc ttcaatagcg gcaaagaagg gc 32

<210> SEQ ID NO 30
<211> LENGTH: 32
<212> TYPE: DNA
<213> ORGANISM: Artificial Sequence
<220> FEATURE:
<223> OTHER INFORMATION: Primer

<400> SEQUENCE: 30
gcccttcttt gccgctattg aagctcttaa cc 32

<210> SEQ ID NO 31
<211> LENGTH: 27
<212> TYPE: DNA

<213> ORGANISM: Artificial Sequence
<220> FEATURE:
<223> OTHER INFORMATION: Primer

<400> SEQUENCE: 31
gggcagctgg aaaagcggaa aggaagg 27

<210> SEQ ID NO 32
<211> LENGTH: 27
<212> TYPE: DNA
<213> ORGANISM: Artificial Sequence
<220> FEATURE:
<223> OTHER INFORMATION: Primer

<400> SEQUENCE: 32
ccttcctttc cgcttttcca gctgccc 27

<210> SEQ ID NO 33
<211> LENGTH: 44
<212> TYPE: DNA
<213> ORGANISM: Artificial Sequence
<220> FEATURE:
<223> OTHER INFORMATION: Primer

<400> SEQUENCE: 33
ccagacatag ttatctatca atacatgaac gatttgtatg tagg 44

<210> SEQ ID NO 34
<211> LENGTH: 44
<212> TYPE: DNA
<213> ORGANISM: Artificial Sequence
<220> FEATURE:
<223> OTHER INFORMATION: Primer

<400> SEQUENCE: 34
cctacataca aatcgttcat gtattgatag ataactatgt ctgg 44

<210> SEQ ID NO 35
<211> LENGTH: 33
<212> TYPE: DNA
<213> ORGANISM: Artificial Sequence
<220> FEATURE:
<223> OTHER INFORMATION: Primer

<400> SEQUENCE: 35
ggggaaattg aataccgcaa gtcagattta ccc 33

<210> SEQ ID NO 36
<211> LENGTH: 33
<212> TYPE: DNA
<213> ORGANISM: Artificial Sequence
<220> FEATURE:
<223> OTHER INFORMATION: Primer

<400> SEQUENCE: 36
gggtaaatct gacttgcggt attcaatttc ccc 33

<210> SEQ ID NO 37
<211> LENGTH: 40
<212> TYPE: DNA
<213> ORGANISM: Artificial Sequence
<220> FEATURE:
<223> OTHER INFORMATION: Primer

<400> SEQUENCE: 37
ccctaactaa cacaacaaat cagaaaactc agttacaagc 40

<210> SEQ ID NO 38
<211> LENGTH: 40
<212> TYPE: DNA
<213> ORGANISM: Artificial Sequence
<220> FEATURE:
<223> OTHER INFORMATION: Primer

<400> SEQUENCE: 38
gcttgtaact gagttttctg atttgttgtg ttagttaggg 40

<210> SEQ ID NO 39
<211> LENGTH: 29
<212> TYPE: DNA
<213> ORGANISM: Artificial Sequence
<220> FEATURE:
<223> OTHER INFORMATION: Primer

<400> SEQUENCE: 39
gagctctatc gatgcaggac tcggcttgc 29

<210> SEQ ID NO 40
<211> LENGTH: 37
<212> TYPE: DNA
<213> ORGANISM: Artificial Sequence
<220> FEATURE:
<223> OTHER INFORMATION: Primer

<400> SEQUENCE: 40
ctccaattac tgtgagaatt ctaatgttca tcttggg 37

<210> SEQ ID NO 41
<211> LENGTH: 34
<212> TYPE: DNA
<213> ORGANISM: Artificial Sequence
<220> FEATURE:
<223> OTHER INFORMATION: Primer

<400> SEQUENCE: 41
ggcaactaaa ggaagctcta ttagccacag gagc 34

<210> SEQ ID NO 42
<211> LENGTH: 34
<212> TYPE: DNA
<213> ORGANISM: Artificial Sequence
<220> FEATURE:
<223> OTHER INFORMATION: Primer

<400> SEQUENCE: 42
gctcctgtgg ctaatagagc ttcctttagt tgcc 34

<210> SEQ ID NO 43
<211> LENGTH: 32
<212> TYPE: DNA
<213> ORGANISM: Artificial Sequence
<220> FEATURE:
<223> OTHER INFORMATION: Synthetically generated oligonucleotide

<400> SEQUENCE: 43
gcagtaagta gtaaatctaa tccaaccttt ac 32

<210> SEQ ID NO 44
<211> LENGTH: 32
<212> TYPE: DNA
<213> ORGANISM: Artificial Sequence
<220> FEATURE:

<223> OTHER INFORMATION: Synthetically generated oligonucleotide

<400> SEQUENCE: 44
gtaaaggttg gattagattt actacttact gc 32

<210> SEQ ID NO 45
<211> LENGTH: 30
<212> TYPE: DNA
<213> ORGANISM: Artificial Sequence
<220> FEATURE:
<223> OTHER INFORMATION: Primer

<400> SEQUENCE: 45
aagatctatc gatgcaagga ctcggcttgc 30

<210> SEQ ID NO 46
<211> LENGTH: 37
<212> TYPE: DNA
<213> ORGANISM: Artificial Sequence
<220> FEATURE:
<223> OTHER INFORMATION: Primer

<400> SEQUENCE: 46
ttccaattgc tgtgagaatt ctcatgctct tcttggg 37

<210> SEQ ID NO 47
<211> LENGTH: 31
<212> TYPE: DNA
<213> ORGANISM: Artificial Sequence
<220> FEATURE:
<223> OTHER INFORMATION: Primer

<400> SEQUENCE: 47
aaggggttaa agctataata agaattctgc a 31

<210> SEQ ID NO 48
<211> LENGTH: 29
<212> TYPE: DNA
<213> ORGANISM: Artificial Sequence
<220> FEATURE:
<223> OTHER INFORMATION: Primer

<400> SEQUENCE: 48
cctttgctgc cctatctgat tcttctagg 29

<210> SEQ ID NO 49
<211> LENGTH: 40
<212> TYPE: DNA
<213> ORGANISM: Artificial Sequence
<220> FEATURE:
<223> OTHER INFORMATION: Primer

<400> SEQUENCE: 49
gccagagaat aataaagagc ttcaacagcg gcaaagaagg 40

<210> SEQ ID NO 50
<211> LENGTH: 40
<212> TYPE: DNA
<213> ORGANISM: Artificial Sequence
<220> FEATURE:
<223> OTHER INFORMATION: Primer

<400> SEQUENCE: 50
ccttctttgc cgctgttgaa gctctttatt attctctggc 40

<210> SEQ ID NO 51
<211> LENGTH: 38
<212> TYPE: DNA
<213> ORGANISM: Artificial Sequence
<220> FEATURE:
<223> OTHER INFORMATION: Primer

<400> SEQUENCE: 51
cctagaaaga gaggcagctg gaaaagcgga aaggaagg 38

<210> SEQ ID NO 52
<211> LENGTH: 38
<212> TYPE: DNA
<213> ORGANISM: Artificial Sequence
<220> FEATURE:
<223> OTHER INFORMATION: Primer

<400> SEQUENCE: 52
ccttcctttc cgcttttcca gctgcctctc tttctagg 38

<210> SEQ ID NO 53
<211> LENGTH: 34
<212> TYPE: DNA
<213> ORGANISM: Artificial Sequence
<220> FEATURE:
<223> OTHER INFORMATION: Primer

<400> SEQUENCE: 53
ccaatatatg aacgatttat atgtaggatc tgac 34

<210> SEQ ID NO 54
<211> LENGTH: 34
<212> TYPE: DNA
<213> ORGANISM: Artificial Sequence
<220> FEATURE:
<223> OTHER INFORMATION: Primer

<400> SEQUENCE: 54
gtcagatcct acatataaat cgttcatata ttgg 34

<210> SEQ ID NO 55
<211> LENGTH: 36
<212> TYPE: DNA
<213> ORGANISM: Artificial Sequence
<220> FEATURE:
<223> OTHER INFORMATION: Primer

<400> SEQUENCE: 55
gggaaaacta aataccgcaa gtcagattta tgcagg 36

<210> SEQ ID NO 56
<211> LENGTH: 36
<212> TYPE: DNA
<213> ORGANISM: Artificial Sequence
<220> FEATURE:
<223> OTHER INFORMATION: Primer

<400> SEQUENCE: 56
cctgcataaa tctgacttgc ggtatttagt tttccc 36

<210> SEQ ID NO 57
<211> LENGTH: 40
<212> TYPE: DNA
<213> ORGANISM: Artificial Sequence
<220> FEATURE:
<223> OTHER INFORMATION: Primer

<400> SEQUENCE: 57
ccctaattga gacaacaaat caaaagactc agttacatgc 40

<210> SEQ ID NO 58
<211> LENGTH: 40
<212> TYPE: DNA
<213> ORGANISM: Artificial Sequence
<220> FEATURE:
<223> OTHER INFORMATION: Primer

<400> SEQUENCE: 58
gcatgtaact gagtcttttg atttgttgtc tcaattaggg 40

<210> SEQ ID NO 59
<211> LENGTH: 30
<212> TYPE: DNA
<213> ORGANISM: Artificial Sequence
<220> FEATURE:
<223> OTHER INFORMATION: Primer

<400> SEQUENCE: 59
gccaatagaa gccctattaa acacaggagc 30

<210> SEQ ID NO 60
<211> LENGTH: 30
<212> TYPE: DNA
<213> ORGANISM: Artificial Sequence
<220> FEATURE:
<223> OTHER INFORMATION: Primer

<400> SEQUENCE: 60
gctcctgtgt ttaatagggc ttctattggc 30

<210> SEQ ID NO 61
<211> LENGTH: 26
<212> TYPE: DNA
<213> ORGANISM: Artificial Sequence
<220> FEATURE:
<223> OTHER INFORMATION: Synthetically generated oligonucleotide

<400> SEQUENCE: 61
cctccaattc ccactatcat ttttgg 26

<210> SEQ ID NO 62
<211> LENGTH: 26
<212> TYPE: DNA
<213> ORGANISM: Artificial Sequence
<220> FEATURE:
<223> OTHER INFORMATION: Synthetically generated oligonucleotide

<400> SEQUENCE: 62
cctccaattc ccactatcat ttttgg 26

<210> SEQ ID NO 63
<211> LENGTH: 27
<212> TYPE: DNA
<213> ORGANISM: Artificial Sequence
<220> FEATURE:
<223> OTHER INFORMATION: Synthetically generated oligonucleotide

<400> SEQUENCE: 63
ggacgaaata tgatgactca gattggt 27

<210> SEQ ID NO 64
<211> LENGTH: 27

<212> TYPE: DNA
<213> ORGANISM: Artificial Sequence
<220> FEATURE:
<223> OTHER INFORMATION: Synthetically generated oligonucleotide

<400> SEQUENCE: 64
accaatctga gtcatcatat ttcgtcc 27

<210> SEQ ID NO 65
<211> LENGTH: 22
<212> TYPE: DNA
<213> ORGANISM: Artificial Sequence
<220> FEATURE:
<223> OTHER INFORMATION: Primer

<400> SEQUENCE: 65
cgcaggatcc ggcttgctga ag 22

<210> SEQ ID NO 66
<211> LENGTH: 30
<212> TYPE: DNA
<213> ORGANISM: Artificial Sequence
<220> FEATURE:
<223> OTHER INFORMATION: Primer

<400> SEQUENCE: 66
tctactcgag cttattatag cactctcctg 30

<210> SEQ ID NO 67
<211> LENGTH: 24
<212> TYPE: DNA
<213> ORGANISM: Artificial Sequence
<220> FEATURE:
<223> OTHER INFORMATION: Primer

<400> SEQUENCE: 67
cctctcgaga tacttggaca ggag 24

<210> SEQ ID NO 68
<211> LENGTH: 27
<212> TYPE: DNA
<213> ORGANISM: Artificial Sequence
<220> FEATURE:
<223> OTHER INFORMATION: Primer

<400> SEQUENCE: 68
cacttgctag ccattttact gcaaagc 27

<210> SEQ ID NO 69
<211> LENGTH: 420
<212> TYPE: DNA
<213> ORGANISM: Artificial Sequence
<220> FEATURE:
<223> OTHER INFORMATION: Synthetically generated vector sequence-Plasmid pW-48

<400> SEQUENCE: 69
gaattcgttg gtggtcgcca tggatggtgt tattgtatac tgtctaaacg cgttagtaaa 60
acatggcgag gaaataaatc atataaaaaa tgatttcatg attaaaccat gttgtgaaaa 120
agtcaagaac gttcacattg gcggacaatc taaaaacaat acagtgattg cagatttgcc 180
atatatggat aatgcggtat ccgatgtatg caattcactg tataaaaaga atgtatcaag 240
aatatccaga tttgctaatt tgataaagat agatgacgat gacaagactc ctactggtgt 300
atataattat tttaaaccta aagatgccat tcctgttatt atatccatag gaaaggatag 360
agatgtttgt gaactattaa tctcatctga taaagcgtgt gcgtgtatag agttaaattc 420

<210> SEQ ID NO 70
<211> LENGTH: 44
<212> TYPE: DNA
<213> ORGANISM: Artificial Sequence
<220> FEATURE:
<223> OTHER INFORMATION: Primer

<400> SEQUENCE: 70
ctaaaagaac tgttaaatcc ttcaactctg gcaaggaagg gcac 44

<210> SEQ ID NO 71
<211> LENGTH: 44
<212> TYPE: DNA
<213> ORGANISM: Artificial Sequence
<220> FEATURE:
<223> OTHER INFORMATION: Primer

<400> SEQUENCE: 71
gtgcccttcc ttgccagagt tgaaggattt aacagttctt ttag 44

<210> SEQ ID NO 72
<211> LENGTH: 41
<212> TYPE: DNA
<213> ORGANISM: Artificial Sequence
<220> FEATURE:
<223> OTHER INFORMATION: Primer

<400> SEQUENCE: 72
ctaggaaaaa aggctcttgg aaatctggaa aggaaggaca c 41

<210> SEQ ID NO 73
<211> LENGTH: 41
<212> TYPE: DNA
<213> ORGANISM: Artificial Sequence
<220> FEATURE:
<223> OTHER INFORMATION: Primer

<400> SEQUENCE: 73
gtgtccttcc tttccagatt tccaagagcc tttttcccta g 41

<210> SEQ ID NO 74
<211> LENGTH: 34
<212> TYPE: DNA
<213> ORGANISM: Artificial Sequence
<220> FEATURE:
<223> OTHER INFORMATION: Primer

<400> SEQUENCE: 74
gtcatctatc aatatatgaa tgacttgtat gtag 34

<210> SEQ ID NO 75
<211> LENGTH: 34
<212> TYPE: DNA
<213> ORGANISM: Artificial Sequence
<220> FEATURE:
<223> OTHER INFORMATION: Primer

<400> SEQUENCE: 75
ctacatacaa gtcattcata tattgataga tgac 34

<210> SEQ ID NO 76
<211> LENGTH: 33
<212> TYPE: DNA

<213> ORGANISM: Artificial Sequence
<220> FEATURE:
<223> OTHER INFORMATION: Primer

<400> SEQUENCE: 76
gtgggaaaat taaacacggc aagccagatt tac 33

<210> SEQ ID NO 77
<211> LENGTH: 33
<212> TYPE: DNA
<213> ORGANISM: Artificial Sequence
<220> FEATURE:
<223> OTHER INFORMATION: Primer

<400> SEQUENCE: 77
gtaaatctgg cttgccgtgt ttaattttcc cac 33

<210> SEQ ID NO 78
<211> LENGTH: 33
<212> TYPE: DNA
<213> ORGANISM: Artificial Sequence
<220> FEATURE:
<223> OTHER INFORMATION: Primer

<400> SEQUENCE: 78
caaatcagaa gactcaatta caagcaattt atc 33

<210> SEQ ID NO 79
<211> LENGTH: 33
<212> TYPE: DNA
<213> ORGANISM: Artificial Sequence
<220> FEATURE:
<223> OTHER INFORMATION: Primer

<400> SEQUENCE: 79
gataaattgc ttgtaattga gtcttctgat ttg 33

<210> SEQ ID NO 80
<211> LENGTH: 29
<212> TYPE: DNA
<213> ORGANISM: Artificial Sequence
<220> FEATURE:
<223> OTHER INFORMATION: Primer

<400> SEQUENCE: 80
ggaggctctc ttagccacag gagcagatg 29

<210> SEQ ID NO 81
<211> LENGTH: 29
<212> TYPE: DNA
<213> ORGANISM: Artificial Sequence
<220> FEATURE:
<223> OTHER INFORMATION: Primer

<400> SEQUENCE: 81
catctgctcc tgtggctaag agagcctcc 29

<210> SEQ ID NO 82
<211> LENGTH: 420
<212> TYPE: DNA
<213> ORGANISM: Artificial Sequence
<220> FEATURE:
<223> OTHER INFORMATION: Synthetically generated vector sequence-plasmid pLW-48

<400> SEQUENCE: 82

```
gaatttaact ctatacacgc acacgcttta tcagatgaga ttaatagttc acaaacatct      60

ctatcctttc ctatggatat aataacagga atggcatctt taggtttaaa ataattatat     120

acaccagtag gagtcttgtc atcgtcatct atctttatca aattagcaaa tctggatatt     180

cttgatacat tctttttata cagtgaattg catacatcgg ataccgcatt atccatatat     240

ggcaaatctg caatcactgt attgttttta gattgtccgc caatgtgaac gttcttgact     300

ttttcacaac atggtttaat catgaaatca ttttttatat gatttatttc ctcgccatgt     360

tttactaacg cgtttagaca gtatacaata acaccatcca tggcgaccac caacgaattc     420


<210> SEQ ID NO 83
<211> LENGTH: 12224
<212> TYPE: DNA
<213> ORGANISM: Artificial Sequence
<220> FEATURE:
<223> OTHER INFORMATION: Synthetically generated plasmid sequence-pLW-48

<400> SEQUENCE: 83

gaattcgttg gtggtcgcca tggatggtgt tattgtatac tgtctaaacg cgttagtaaa      60

acatggcgag gaaataaatc atataaaaaa tgatttcatg attaaaccat gttgtgaaaa     120

agtcaagaac gttcacattg gcggacaatc taaaaacaat acagtgattg cagatttgcc     180

atatatggat aatgcggtat ccgatgtatg caattcactg tataaaaaga atgtatcaag     240

aatatccaga tttgctaatt tgataaagat agatgacgat gacaagactc ctactggtgt     300

atataattat tttaaaccta aagatgccat tcctgttatt atatccatag gaaaggatag     360

agatgtttgt gaactattaa tctcatctga taaagcgtgt gcgtgtatag agttaaattc     420

atataaagta gccattcttc ccatggatgt ttcctttttt accaaaggaa atgcatcatt     480

gattattctc ctgtttgatt tctctatcga tgcggcacct ctcttaagaa gtgtaaccga     540

taataatgtt attatatcta gacaccagcg tctacatgac gagcttccga gttccaattg     600

gttcaagttt tacataagta taaagtccga ctattgttct atattatata tggttgttga     660

tggatctgtg atgcatgcaa tagctgataa tagaacttac gcaaatatta gcaaaaatat     720

attagacaat actacaatta acgatgagtg tagatgctgt tattttgaac cacagattag     780

gattcttgat agagatgaga tgctcaatgg atcatcgtgt gatatgaaca gacattgtat     840

tatgatgaat ttacctgatg taggcgaatt tggatctagt atgttgggga aatatgaacc     900

tgacatgatt aagattgctc tttcggtggc tgggtaccag gcgcgccttt cattttgttt     960

ttttctatgc tataaatggt acgtcctgta gaaaccccaa cccgtgaaat caaaaaactc    1020

gacggcctgt gggcattcag tctggatcgc gaaaactgtg gaattgatca gcgttggtgg    1080

gaaagcgcgt tacaagaaag ccgggcaatt gctgtgccag gcagttttaa cgatcagttc    1140

gccgatgcag atattcgtaa ttatgcgggc aacgtctggt atcagcgcga agtctttata    1200

ccgaaaggtt gggcaggcca gcgtatcgtg ctgcgtttcg atgcggtcac tcattacggc    1260

aaagtgtggg tcaataatca ggaagtgatg gagcatcagg gcggctatac gccatttgaa    1320

gccgatgtca cgccgtatgt tattgccggg aaaagtgtac gtatcaccgt ttgtgtgaac    1380

aacgaactga actggcagac tatcccgccg ggaatggtga ttaccgacga aaacggcaag    1440

aaaaagcagt cttacttcca tgatttcttt aactatgccg gaatccatcg cagcgtaatg    1500

ctctacacca cgccgaacac ctgggtggac gatatcaccg tggtgacgca tgtcgcgcaa    1560

gactgtaacc acgcgtctgt tgactggcag gtggtggcca atggtgatgt cagcgttgaa    1620

ctgcgtgatg cggatcaaca ggtggttgca actggacaag gcactagcgg gactttgcaa    1680
```

```
gtggtgaatc cgcacctctg gcaaccgggt gaaggttatc tctatgaact gtgcgtcaca   1740
gccaaaagcc agacagagtg tgatatctac ccgcttcgcg tcggcatccg gtcagtggca   1800
gtgaagggcg aacagttcct gattaaccac aaaccgttct actttactgg ctttggtcgt   1860
catgaagatg cggacttgcg tggcaaagga ttcgataacg tgctgatggt gcacgaccac   1920
gcattaatgg actggattgg ggccaactcc taccgtacct cgcattaccc ttacgctgaa   1980
gagatgctcg actgggcaga tgaacatggc atcgtggtga ttgatgaaac tgctgctgtc   2040
ggctttaacc tctctttagg cattggtttc gaagcgggca acaagccgaa agaactgtac   2100
agcgaagagg cagtcaacgg ggaaactcag caagcgcact tacaggcgat taaagagctg   2160
atagcgcgtg acaaaaacca cccaagcgtg gtgatgtgga gtattgccaa cgaaccggat   2220
acccgtccgc aaggtgcacg ggaatatttc gcgccactgg cggaagcaac gcgtaaactc   2280
gacccgacgc gtccgatcac ctgcgtcaat gtaatgttct gcgacgctca caccgatacc   2340
atcagcgatc tctttgatgt gctgtgcctg aaccgttatt acggatggta tgtccaaagc   2400
ggcgatttgg aaacggcaga gaaggtactg gaaaaagaac ttctggcctg gcaggagaaa   2460
ctgcatcagc cgattatcat caccgaatac ggcgtggata cgttagccgg gctgcactca   2520
atgtacaccg acatgtggag tgaagagtat cagtgtgcat ggctggatat gtatcaccgc   2580
gtctttgatc gcgtcagcgc cgtcgtcggt gaacaggtat ggaatttcgc cgattttgcg   2640
acctcgcaag gcatattgcg cgttggcggt aacaagaaag ggatcttcac tcgcgaccgc   2700
aaaccgaagt cggcggcttt tctgctgcaa aaacgctgga ctggcatgaa cttcggtgaa   2760
aaaccgcagc agggaggcaa acaatgagag ctcggttgtt gatggatctg tgatgcatgc   2820
aatagctgat aatagaactt acgcaaatat tagcaaaaat atattagaca atactacaat   2880
taacgatgag tgtagatgct gttattttga accacagatt aggattcttg atagagatga   2940
gatgctcaat ggatcatcgt gtgatatgaa cagacattgt attatgatga atttacctga   3000
tgtaggcgaa tttggatcta gtatgttggg gaaatatgaa cctgacatga ttaagattgc   3060
tctttcggtg gctggcggcc cgctcgagta aaaaatgaaa aaatattcta atttatagga   3120
cggttttgat tttctttttt tctatgctat aaataataaa tagcggccgc accatgaaag   3180
tgaaggggat caggaagaat tatcagcact tgtggaaatg gggcatcatg ctccttggga   3240
tgttgatgat ctgtagtgct gtagaaaatt tgtgggtcac agtttattat ggggtacctg   3300
tgtggaaaga agcaaccacc actctatttt gtgcatcaga tgctaaagca tatgatacag   3360
aggtacataa tgtttgggcc acacatgcct gtgtacccac agaccccaac ccacaagaag   3420
tagtattgga aaatgtgaca gaaaatttta acatgtggaa aaataacatg gtagaacaga   3480
tgcatgagga tataatcagt ttatgggatc aaagcctaaa gccatgtgta aaattaaccc   3540
cactctgtgt tactttaaat tgcactgatt tgaggaatgt tactaatatc aataatagta   3600
gtgagggaat gagaggagaa ataaaaaact gctctttcaa tatcaccaca agcataagag   3660
ataaggtgaa gaaagactat gcacttttct atagacttga tgtagtacca atagataatg   3720
ataatactag ctataggttg ataaattgta atacctcaac cattacacag gcctgtccaa   3780
aggtatcctt tgagccaatt cccatacatt attgtacccc ggctggtttt gcgattctaa   3840
agtgtaaaga caagaagttc aatggaacag ggccatgtaa aaatgtcagc acagtacaat   3900
gtacacatgg aattaggcca gtagtgtcaa ctcaactgct gttaaatggc agtctagcag   3960
aagaagaggt agtaattaga tctagtaatt tcacagacaa tgcaaaaaac ataatagtac   4020
```

```
agttgaaaga atctgtagaa attaattgta caagacccaa caacaataca aggaaaagta   4080

tacatatagg accaggaaga gcattttata caacaggaga aataatagga gatataagac   4140

aagcacattg caacattagt agaacaaaat ggaataacac tttaaatcaa atagctacaa   4200

aattaaaaga acaatttggg aataataaaa caatagtctt taatcaatcc tcaggagggg   4260

acccagaaat tgtaatgcac agttttaatt gtggagggga attcttctac tgtaattcaa   4320

cacaactgtt taatagtact tggaatttta atggtacttg gaatttaaca caatcgaatg   4380

gtactgaagg aaatgacact atcacactcc catgtagaat aaaacaaatt ataaatatgt   4440

ggcaggaagt aggaaaagca atgtatgccc ctcccatcag aggacaaatt agatgctcat   4500

caaatattac agggctaata ttaacaagag atggtggaac taacagtagt gggtccgaga   4560

tcttcagacc tgggggagga gatatgaggg acaattggag aagtgaatta tataaatata   4620

aagtagtaaa aattgaacca ttaggagtag cacccaccaa ggcaaaaaga agagtggtgc   4680

agagagaaaa aagagcagtg ggaacgatag gagctatgtt ccttgggttc ttgggagcag   4740

caggaagcac tatgggcgca gcgtcaataa cgctgacggt acaggccaga ctattattgt   4800

ctggtatagt gcaacagcag aacaatttgc tgagggctat tgaggcgcaa cagcatctgt   4860

tgcaactcac agtctggggc atcaagcagc tccaggcaag agtcctggct gtggaaagat   4920

acctaaggga tcaacagctc ctagggattt ggggttgctc tggaaaactc atctgcacca   4980

ctgctgtgcc ttggaatgct agttggagta ataaaactct ggatatgatt tgggataaca   5040

tgacctggat ggagtgggaa agagaaatcg aaaattacac aggcttaata tacaccttaa   5100

ttgaggaatc gcagaaccaa caagaaaaga atgaacaaga cttattagca ttagataagt   5160

gggcaagttt gtggaattgg tttgacatat caaattggct gtggtatgta aaaatcttca   5220

taatgatagt aggaggcttg ataggtttaa gaatagtttt tactgtactt tctatagtaa   5280

atagagttag gcagggatac tcaccattgt catttcagac ccacctccca gccccgaggg   5340

gacccgacag gcccgaagga atcgaagaag aaggtggaga cagagactaa tttttatgcg   5400

gccgctggta cccaacctaa aaattgaaaa taaatacaaa ggttcttgag ggttgtgtta   5460

aattgaaagc gagaaataat cataaataag cccggggatc ctctagagtc gacaccatgg   5520

gtgcgagagc gtcagtatta agcgggggag aattagatcg atgggaaaaa attcggttaa   5580

ggccaggggg aaagaaaaaa tataaattaa aacatatagt atgggcaagc agggagctag   5640

aacgattcgc agttaatcct ggcctgttag aaacatcaga aggctgtaga caaatactgg   5700

gacagctaca accatccctt cagacaggat cagaagaact tagatcatta tataatacag   5760

tagcaaccct ctattgtgtg catcaaagga tagagataaa agacaccaag gaagctttag   5820

acaagataga ggaagagcaa aacaaaagta agaaaaaagc acagcaagca gcagctgaca   5880

caggacacag caatcaggtc agccaaaatt accctatagt gcagaacatc caggggcaaa   5940

tggtacatca ggccatatca cctagaactt taaatgcatg ggtaaaagta gtagaagaga   6000

aggctttcag cccagaagtg atacccatgt tttcagcatt atcagaagga gccaccccac   6060

aagatttaaa caccatgcta aacacagtgg ggggacatca agcagccatg caaatgttaa   6120

aagagaccat caatgaggaa gctgcagaat gggatagagt gcatccagtg catgcagggc   6180

ctattgcacc aggccagatg agagaaccaa ggggaagtga catagcagga actactagta   6240

cccttcagga acaaatagga tggatgacaa ataatccacc tatcccagta ggagaaattt   6300

ataaaagatg gataatcctg ggattaaata aaatagtaag aatgtatagc cctaccagca   6360

ttctggacat aagacaagga ccaaaagaac cctttagaga ctatgtagac cggttctata   6420
```

```
aaactctaag agccgagcaa gcttcacagg aggtaaaaaa ttggatgaca gaaaccttgt   6480
tggtccaaaa tgcgaaccca gattgtaaga ctattttaaa agcattggga ccagcggcta   6540
cactagaaga aatgatgaca gcatgtcagg gagtaggagg acccggccat aaggcaagag   6600
ttttggctga agcaatgagc caagtaacaa attcagctac cataatgatg cagagaggca   6660
attttaggaa ccaaagaaag attgttaagt gtttcaattg tggcaaagaa gggcacacag   6720
ccagaaattg cagggcccct aggaaaaagg gctgttggaa atgtggaaag gaaggacacc   6780
aaatgaaaga ttgtactgag agacaggcta attttttagg gaagatctgg ccttcctaca   6840
agggaaggcc agggaatttt cttcagagca gaccagagcc aacagcccca ccagaagaga   6900
gcttcaggtc tggggtagag acaacaactc cccctcagaa gcaggagccg atagacaagg   6960
aactgtatcc tttaacttcc ctcagatcac tctttggcaa cgacccctcg tcacaataaa   7020
gataggggg caactaaagg aagctctatt agatacagga gcagatgata cagtattaga   7080
agaaatgagt ttgccaggaa gatggaaacc aaaaatgata gggggaattg gaggttttat   7140
caaagtaaga cagtatgatc agatactcat agaaatctgt ggacataaag ctataggtac   7200
agtattagta ggacctacac ctgtcaacat aattggaaga aatctgttga ctcagattgg   7260
ttgcacttta aattttccca ttagccctat tgagactgta ccagtaaaat taaagccagg   7320
aatggatggc ccaaaagtta aacaatggcc attgacagaa gaaaaaataa aagcattagt   7380
agaaatttgt acagaaatgg aaaaggaagg gaaaatttca aaaattgggc ctgagaatcc   7440
atacaatact ccagtatttg ccataaagaa aaaagacagt actaaatgga ggaaattagt   7500
agatttcaga gaacttaata agagaactca agacttctgg gaagttcaat taggaatacc   7560
acatcccgca gggttaaaaa agaaaaaatc agtaacagta ctggatgtgg gtgatgcata   7620
tttttcagtt cccttagatg aagacttcag gaagtatact gcatttacca tacctagtat   7680
aaacaatgag acaccaggga ttagatatca gtacaatgtg cttccacagg gatggaaagg   7740
atcaccagca atattccaaa gtagcatgac aaaaatctta gagcctttta aaaaacaaaa   7800
tccagacata gttatctatc aatacatgaa cgatttgtat gtaggatctg acttagaaat   7860
agggcagcat agaacaaaaa tagaggagct gagacaacat ctgttgaggt ggggacttac   7920
cacaccagac aaaaaacatc agaaagaacc tccattcctt tggatgggtt atgaactcca   7980
tcctgataaa tggacagtac agcctatagt gctgccagaa aaagacagct ggactgtcaa   8040
tgacatacag aagttagtgg ggaaattgaa taccgcaagt cagatttacc caggattaa    8100
agtaaggcaa ttatgtaaac tccttagagg aaccaaagca ctaacagaag taataccact   8160
aacagaagaa gcagagctag aactggcaga aaacagagag attctaaaag aaccagtaca   8220
tggagtgtat tatgacccat caaaagactt aatagcagaa atacagaagc aggggcaagg   8280
ccaatggaca tatcaaattt atcaagagcc atttaaaaat ctgaaaacag gaaaatatgc   8340
aagaatgagg ggtgcccaca ctaatgatgt aaaacaatta acagaggcag tgcaaaaaat   8400
aaccacagaa agcatagtaa tatggggaaa gactcctaaa tttaaactac ccatacaaaa   8460
ggaaacatgg gaaacatggt ggacagagta ttggcaagcc acctggattc ctgagtggga   8520
gtttgttaat acccctcctt tagtgaaatt atggtaccag ttagagaaag aacccatagt   8580
aggagcagaa accttctatg tagatggggc agctaacagg gagactaaat taggaaaagc   8640
aggatatgtt actaacaaag gaagacaaaa ggttgtcccc ctaactaaca caacaaatca   8700
gaaaactcag ttacaagcaa tttatctagc tttgcaggat tcaggattag aagtaaacat   8760
```

```
agtaacagac tcacaatatg cattaggaat cattcaagca caaccagata aaagtgaatc   8820
agagttagtc aatcaaataa tagagcagtt aataaaaaag gaaaaggtct atctggcatg   8880
ggtaccagca cacaaaggaa ttggaggaaa tgaacaagta gataaattag tcagtgctgg   8940
aatcaggaaa atactatttt tagatggaat agataaggcc caagatgaac attagttttt   9000
atgtcgacct gcagggaaag ttttataggt agttgataga acaaaataca taattttgta   9060
aaaataaatc actttttata ctaatatgac acgattacca atacttttgt tactaatatc   9120
attagtatac gctacacctt ttcctcagac atctaaaaaa ataggtgatg atgcaacttt   9180
atcatgtaat cgaaataata caaatgacta cgttgttatg agtgcttggt ataaggagcc   9240
caattccatt attcttttag ctgctaaaag cgacgtcttg tattttgata attataccaa   9300
ggataaaata tcttacgact ctccatacga tgatctagtt acaactatca caattaaatc   9360
attgactgct agagatgccg gtacttatgt atgtgcattc tttatgacat cgcctacaaa   9420
tgacactgat aaagtagatt atgaagaata ctccacagag ttgattgtaa atacagatag   9480
tgaatcgact atagacataa tactatctgg atctacacat tcaccagaaa ctagttaagc   9540
ttgtctccct atagtgagtc gtattagagc ttggcgtaat catggtcata gctgtttcct   9600
gtgtgaaatt gttatccgct cacaattcca cacaacatac gagccggaag cataaagtgt   9660
aaagcctggg gtgcctaatg agtgagctaa ctcacattaa ttgcgttgcg ctcactgccc   9720
gctttcgagt cgggaaacct gtcgtgccag ctgcattaat gaatcggcca acgcgcgggg   9780
agaggcggtt tgcgtattgg gcgctcttcc gcttcctcgc tcactgactc gctgcgctcg   9840
gtcgttcggc tgcggcgagc ggtatcagct cactcaaagg cggtaatacg gttatccaca   9900
gaatcagggg ataacgcagg aaagaacatg tgagcaaaag gccagcaaaa ggccaggaac   9960
cgtaaaaagg ccgcgttgct ggcgtttttc gataggctcc gcccccctga cgagcatcac  10020
aaaaatcgac gctcaagtca gaggtggcga aacccgacag gactataaag ataccaggcg  10080
tttccccctg gaagctccct cgtgcgctct cctgttccga ccctgccgct taccggatac  10140
ctgtccgcct ttctcccttc gggaagcgtg gcgctttctc atagctcacg ctgtaggtat  10200
ctcagttcgg tgtaggtcgt tcgctccaag ctgggctgtg tgcacgaacc ccccgttcag  10260
cccgaccgct gcgccttatc cggtaactat cgtcttgagt ccaacccggt aagacacgac  10320
ttatcgccac tggcagcagc cactggtaac aggattagca gagcgaggta tgtaggcggt  10380
gctacagagt tcttgaagtg gtggcctaac tacggctaca ctagaaggac agtatttggt  10440
atctgcgctc tgctgaagcc agttaccttc ggaaaaagag ttggtagctc ttgatccggc  10500
aaacaaacca ccgctggtag cggtggtttt tttgtttgca agcagcagat tacgcgcaga  10560
aaaaaaggat ctcaagaaga tcctttgatc ttttctacgg ggtctgacgc tcagtggaac  10620
gaaaactcac gttaagggat tttggtcatg agattatcaa aaaggatctt cacctagatc  10680
cttttaaatt aaaaatgaag ttttaaatca atctaaagta tatatgagta aacttggtct  10740
gacagttacc aatgcttaat cagtgaggca cctatctcag cgatctgtct atttcgttca  10800
tccatagttg cctgactccc cgtcgtgtag ataactacga tacgggaggg cttaccatct  10860
ggccccagtg ctgcaatgat accgcgagac ccacgctcac cggctccaga tttatcagca  10920
ataaaccagc cagccggaag ggccgagcgc agaagtggtc ctgcaacttt atccgcctcc  10980
atccagtcta ttaattgttg ccgggaagct agagtaagta gttcgccagt taatagtttg  11040
cgcaacgttg ttggcattgc tacaggcatc gtggtgtcac gctcgtcgtt tggtatggct  11100
tcattcagct ccggttccca acgatcaagg cgagttacat gatcccccat gttgtgcaaa  11160
```

```
aaagcggtta gctccttcgg tcctccgatc gttgtcagaa gtaagttggc cgcagtgtta  11220

tcactcatgg ttatggcagc actgcataat tctcttactg tcatgccatc cgtaagatgc  11280

ttttctgtga ctggtgagta ctcaaccaag tcattctgag aatagtgtat gcggcgaccg  11340

agttgctctt gcccggcgtc aatacgggat aataccgcgc cacatagcag aactttaaaa  11400

gtgctcatca ttggaaaacg ttcttcgggg cgaaaactct caaggatctt accgctgttg  11460

agatccagtt cgatgtaacc cactcgtgca cccaactgat cttcagcatc ttttactttc  11520

accagcgttt ctgggtgagc aaaaacagga aggcaaaatg ccgcaaaaaa gggaataagg  11580

gcgacacgga aatgttgaat actcatactc ttcctttttc aatattattg aagcatttat  11640

cagggttatt gtctcatgag cggatacata tttgaatgta tttagaaaaa taaacaaata  11700

ggggttccgc gcacattccc cgaaaagtgc cacctgacgt ctaagaaacc attattatca  11760

tgacattaac ctataaaaat aggcgtatca cgaggccctt tcgtctcgcg cgtttcggtg  11820

atgacggtga aaacctctga cacatgcagc tcccggagac ggtcacagct tgtctgtaag  11880

cggatgccgg gagcagacaa gcccgtcagg gcgcgtcagc gggtgttggc gggtgtcggg  11940

gctggcttaa ctatgcggca tcagagcaga ttgtactgag agtgcaccat atgcggtgtg  12000

aaataccgca cagatgcgta aggagaaaat accgcatcag gcgccattcg ccattcaggc  12060

tgcgcaactg ttgggaaggg cgatcggtgc gggcctcttc gctattacgc cagctggcga  12120

aagggggatg tgctgcaagg cgattaagtt gggtaacgcc agggttttcc cagtcacgac  12180

gttgtaaaac gacggccagt gaattggatt taggtgacac tata                  12224
```

<210> SEQ ID NO 84
<211> LENGTH: 74
<212> TYPE: DNA
<213> ORGANISM: Artificial Sequence
<220> FEATURE:
<223> OTHER INFORMATION: New Psyn II Promoter which controls ADA envelope expression

<400> SEQUENCE: 84

```
taaaaaatga aaaaatattc taatttatag gacggttttg attttctttt tttctatgct     60

ataaataata aata                                                       74
```

<210> SEQ ID NO 85
<211> LENGTH: 2214
<212> TYPE: DNA
<213> ORGANISM: Artificial Sequence
<220> FEATURE:
<223> OTHER INFORMATION: ADA envelope truncated

<400> SEQUENCE: 85

```
atgaaagtga aggggatcag gaagaattat cagcacttgt ggaaatgggg catcatgctc     60

cttgggatgt tgatgatctg tagtgctgta gaaaatttgt gggtcacagt ttattatggg    120

gtacctgtgt ggaaagaagc aaccaccact ctattttgtg catcagatgc taaagcatat    180

gatacagagg tacataatgt ttgggccaca catgcctgtg tacccacaga ccccaaccca    240

caagaagtag tattggaaaa tgtgacagaa aattttaaca tgtggaaaaa taacatggta    300

gaacagatgc atgaggatat aatcagttta tgggatcaaa gcctaaagcc atgtgtaaaa    360

ttaaccccac tctgtgttac tttaaattgc actgatttga ggaatgttac taatatcaat    420

aatagtagtg agggaatgag aggagaaata aaaaactgct ctttcaatat caccacaagc    480

ataagagata aggtgaagaa agactatgca cttttctata gacttgatgt agtaccaata    540
```

```
gataatgata atactagcta taggttgata aattgtaata cctcaaccat tacacaggcc    600

tgtccaaagg tatcctttga gccaattccc atacattatt gtaccccggc tggttttgcg    660

attctaaagt gtaaagacaa gaagttcaat ggaacagggc catgtaaaaa tgtcagcaca    720

gtacaatgta cacatggaat taggccagta gtgtcaactc aactgctgtt aaatggcagt    780

ctagcagaag aagaggtagt aattagatct agtaatttca cagacaatgc aaaaaacata    840

atagtacagt tgaaagaatc tgtagaaatt aattgtacaa gacccaacaa caatacaagg    900

aaaagtatac atataggacc aggaagagca ttttatacaa caggagaaat aataggagat    960

ataagacaag cacattgcaa cattagtaga acaaaatgga ataacacttt aaatcaaata   1020

gctacaaaat taaaagaaca atttgggaat aataaaacaa tagtctttaa tcaatcctca   1080

ggaggggacc cagaaattgt aatgcacagt tttaattgtg gaggggaatt cttctactgt   1140

aattcaacac aactgtttaa tagtacttgg aattttaatg gtacttggaa tttaacacaa   1200

tcgaatggta ctgaaggaaa tgacactatc acactcccat gtagaataaa acaaattata   1260

aatatgtggc aggaagtagg aaaagcaatg tatgcccctc ccatcagagg acaaattaga   1320

tgctcatcaa atattacagg gctaatatta acaagagatg gtggaactaa cagtagtggg   1380

tccgagatct tcagacctgg gggaggagat atgagggaca attggagaag tgaattatat   1440

aaatataaag tagtaaaaat tgaaccatta ggagtagcac ccaccaaggc aaaaagaaga   1500

gtggtgcaga gagaaaaaag agcagtggga acgataggag ctatgttcct tgggttcttg   1560

ggagcagcag gaagcactat gggcgcagcg tcaataacgc tgacggtaca ggccagacta   1620

ttattgtctg gtatagtgca acagcagaac aatttgctga gggctattga ggcgcaacag   1680

catctgttgc aactcacagt ctggggcatc aagcagctcc aggcaagagt cctggctgtg   1740

gaaagatacc taagggatca acagctccta gggatttggg gttgctctgg aaaactcatc   1800

tgcaccactg ctgtgccttg gaatgctagt tggagtaata aaactctgga tatgatttgg   1860

gataacatga cctggatgga gtgggaaaga gaaatcgaaa attacacagg cttaatatac   1920

accttaattg aggaatcgca gaaccaacaa gaaaagaatg aacaagactt attagcatta   1980

gataagtggg caagtttgtg gaattggttt gacatatcaa attggctgtg gtatgtaaaa   2040

atcttcataa tgatagtagg aggcttgata ggtttaagaa tagtttttac tgtactttct   2100

atagtaaata gagttaggca gggatactca ccattgtcat ttcagaccca cctcccagcc   2160

ccgaggggac ccgacaggcc cgaaggaatc gaagaagaag gtggagacag agac         2214
```

<210> SEQ ID NO 86
<211> LENGTH: 70
<212> TYPE: DNA
<213> ORGANISM: Artificial Sequence
<220> FEATURE:
<223> OTHER INFORMATION: PnH5 promoter (which controls HXB2 gag pol expression)

<400> SEQUENCE: 86

```
aaaaattgaa aataaataca aaggttcttg agggttgtgt taaattgaaa gcgagaaata     60

atcataaata                                                            70
```

<210> SEQ ID NO 87
<211> LENGTH: 3477
<212> TYPE: DNA
<213> ORGANISM: Artificial Sequence
<220> FEATURE:
<223> OTHER INFORMATION: HXB2 gag pol (with safety mutations, delta integrase)

<400> SEQUENCE: 87

```
atgggtgcga gagcgtcagt attaagcggg ggagaattag atcgatggga aaaaattcgg      60
ttaaggccag ggggaaagaa aaaatataaa ttaaaacata tagtatgggc aagcagggag     120
ctagaacgat tcgcagttaa tcctggcctg ttagaaacat cagaaggctg tagacaaata     180
ctgggacagc tacaaccatc ccttcagaca ggatcagaag aacttagatc attatataat     240
acagtagcaa ccctctattg tgtgcatcaa aggatagaga taaaagacac caaggaagct     300
ttagacaaga tagaggaaga gcaaaacaaa agtaagaaaa aagcacagca agcagcagct     360
gacacaggac acagcaatca ggtcagccaa aattacccta tagtgcagaa catccagggg     420
caaatggtac atcaggccat atcacctaga actttaaatg catgggtaaa agtagtagaa     480
gagaaggctt tcagcccaga agtgataccc atgttttcag cattatcaga aggagccacc     540
ccacaagatt taaacaccat gctaaacaca gtggggggac atcaagcagc catgcaaatg     600
ttaaaagaga ccatcaatga ggaagctgca gaatgggata gagtgcatcc agtgcatgca     660
gggcctattg caccaggcca gatgagagaa ccaaggggaa gtgacatagc aggaactact     720
agtacccttc aggaacaaat aggatggatg acaaataatc cacctatccc agtaggagaa     780
atttataaaa gatggataat cctgggatta aataaaatag taagaatgta tagccctacc     840
agcattctgg acataagaca aggaccaaaa gaacccttta gagactatgt agaccggttc     900
tataaaactc taagagccga gcaagcttca caggaggtaa aaaattggat gacagaaacc     960
ttgttggtcc aaaatgcgaa cccagattgt aagactattt taaaagcatt gggaccagcg    1020
gctacactag aagaaatgat gacagcatgt cagggagtag gaggacccgg ccataaggca    1080
agagttttgg ctgaagcaat gagccaagta acaaattcag ctaccataat gatgcagaga    1140
ggcaatttta ggaaccaaag aaagattgtt aagtgtttca attgtggcaa agaagggcac    1200
acagccagaa attgcagggc ccctaggaaa aagggctgtt ggaaatgtgg aaaggaagga    1260
caccaaatga aagattgtac tgagagacag gctaattttt tagggaagat ctggccttcc    1320
tacaagggaa ggccagggaa ttttcttcag agcagaccag agccaacagc cccaccagaa    1380
gagagcttca ggtctggggt agagacaaca actccccctc agaagcagga gccgatagac    1440
aaggaactgt atcctttaac ttccctcaga tcactctttg gcaacgaccc ctcgtcacaa    1500
taaagatagg ggggcaacta aaggaagctc tattagatac aggagcagat gatacagtat    1560
tagaagaaat gagtttgcca ggaagatgga aaccaaaaat gataggggga attggaggtt    1620
ttatcaaagt aagacagtat gatcagatac tcatagaaat ctgtggacat aaagctatag    1680
gtacagtatt agtaggacct acacctgtca acataattgg aagaaatctg ttgactcaga    1740
ttggttgcac tttaaatttt cccattagcc ctattgagac tgtaccagta aaattaaagc    1800
caggaatgga tggcccaaaa gttaaacaat ggccattgac agaagaaaaa ataaaagcat    1860
tagtagaaat ttgtacagaa atggaaaagg aagggaaaat ttcaaaaatt gggcctgaga    1920
atccatacaa tactccagta tttgccataa agaaaaaaga cagtactaaa tggaggaaat    1980
tagtagattt cagagaactt aataagagaa ctcaagactt ctgggaagtt caattaggaa    2040
taccacatcc cgcagggtta aaaaagaaaa aatcagtaac agtactggat gtgggtgatg    2100
catatttttc agttccctta gatgaagact tcaggaagta tactgcattt accataccta    2160
gtataaacaa tgagacacca gggattagat atcagtacaa tgtgcttcca cagggatgga    2220
aaggatcacc agcaatattc caaagtagca tgacaaaaat cttagagcct tttaaaacaa    2280
```

```
aatccagaca tagttatcta tcaatacatg aacgatttgt atgtaggatc tgacttagaa   2340

atagggcagc atagaacaaa aatagaggag ctgagacaac atctgttgag gtggggactt   2400

accacaccag acaaaaaaca tcagaaagaa cctccattcc tttggatggg ttatgaactc   2460

catcctgata aatggacagt acagcctata gtgctgccag aaaaagacag ctggactgtc   2520

aatgacatac agaagttagt ggggaaattg aataccgcaa gtcagattta cccagggatt   2580

aaagtaaggc aattatgtaa actccttaga ggaaccaaag cactaacaga agtaatacca   2640

ctaacagaag aagcagagct agaactggca gaaaacagag agattctaaa agaaccagta   2700

catggagtgt attatgaccc atcaaaagac ttaatagcag aaatacagaa gcaggggcaa   2760

ggccaatgga catatcaaat ttatcaagag ccatttaaaa atctgaaaac aggaaaatat   2820

gcaagaatga ggggtgccca cactaatgat gtaaaacaat taacagaggc agtgcaaaaa   2880

ataaccacag aaagcatagt aatatgggga aagactccta aatttaaact acccatacaa   2940

aaggaaacat gggaaacatg gtggacagag tattggcaag ccacctggat tcctgagtgg   3000

gagtttgtta atacccctcc tttagtgaaa ttatggtacc agttagagaa agaacccata   3060

gtaggagcag aaaccttcta tgtagatggg gcagctaaca gggagactaa attaggaaaa   3120

gcaggatatg ttactaacaa aggaagacaa aaggttgtcc ccctaactaa cacaacaaat   3180

cagaaaactc agttacaagc aatttatcta gctttgcagg attcaggatt agaagtaaac   3240

atagtaacag actcacaata tgcattagga atcattcaag cacaaccaga taaaagtgaa   3300

tcagagttag tcaatcaaat aatagagcag ttaataaaaa aggaaaaggt ctatctggca   3360

tgggtaccag cacacaaagg aattggagga aatgaacaag tagataaatt agtcagtgct   3420

ggaatcagga aaatactatt tttagatgga atagataagg cccaagatga acattag      3477


<210> SEQ ID NO 88
<211> LENGTH: 36
<212> TYPE: DNA
<213> ORGANISM: Artificial Sequence
<220> FEATURE:
<223> OTHER INFORMATION: Psyn II Promoter: Early part

<400> SEQUENCE: 88

taaaaaatga aaaaatattc taatttatag gacggt                                36


<210> SEQ ID NO 89
<211> LENGTH: 38
<212> TYPE: DNA
<213> ORGANISM: Artificial Sequence
<220> FEATURE:
<223> OTHER INFORMATION: Psyn II promoter (Late part)

<400> SEQUENCE: 89

tttgattttc ttttttcta tgctataaat aataaata                               38
```